(12) United States Patent
Cook et al.

(10) Patent No.: US 11,078,269 B2
(45) Date of Patent: Aug. 3, 2021

(54) IL-11Rα ANTIBODIES

(71) Applicants: Singapore Health Services PTE LTD., Singapore (SG); National University of Singapore, Singapore (SG)

(72) Inventors: Stuart Alexander Cook, Singapore (SG); Sebastian Schaefer, Singapore (SG)

(73) Assignees: Singapore Health Services PTE LTD, Singapore (SG); National University of Singapore, Singapore (SG)

( * ) Notice: Subject to any disclaimer, the term of this patent is extended or adjusted under 35 U.S.C. 154(b) by 0 days.

(21) Appl. No.: 16/726,190

(22) Filed: Dec. 23, 2019

(65) Prior Publication Data

US 2020/0207847 A1 Jul. 2, 2020

Related U.S. Application Data

(63) Continuation of application No. 15/843,212, filed on Dec. 15, 2017, now abandoned.

(30) Foreign Application Priority Data

Dec. 16, 2016 (GB) ...................... 1621439

(51) Int. Cl.
| | |
|---|---|
| C07K 16/24 | (2006.01) |
| C07K 14/54 | (2006.01) |
| A61P 17/02 | (2006.01) |
| C07K 14/715 | (2006.01) |
| C07K 16/28 | (2006.01) |
| A61P 43/00 | (2006.01) |
| A61K 39/00 | (2006.01) |
| A61P 35/00 | (2006.01) |
| G01N 33/68 | (2006.01) |

(52) U.S. Cl.
CPC ............ *C07K 16/244* (2013.01); *A61P 17/02* (2018.01); *A61P 35/00* (2018.01); *A61P 43/00* (2018.01); *C07K 14/5431* (2013.01); *C07K 14/7155* (2013.01); *C07K 16/2866* (2013.01); *G01N 33/6854* (2013.01); *G01N 33/6869* (2013.01); *A61K 2039/505* (2013.01); *C07K 2317/24* (2013.01); *C07K 2317/76* (2013.01); *C07K 2317/92* (2013.01); *C07K 2319/32* (2013.01); *C07K 2319/75* (2013.01); *G01N 2333/7155* (2013.01)

(58) Field of Classification Search
None
See application file for complete search history.

(56) References Cited

U.S. PATENT DOCUMENTS

| | | |
|---|---|---|
| 5,679,339 A | 10/1997 | Keith et al. |
| 6,126,933 A | 10/2000 | Warne et al. |
| 6,540,993 B1 | 4/2003 | Warne et al. |
| 6,846,907 B1 | 1/2005 | Shaughnessy et al. |
| 6,953,777 B2 | 10/2005 | Keith et al. |
| 6,998,123 B1 | 2/2006 | Shaughnessy et al. |
| 7,993,637 B2 | 8/2011 | Baca |
| 8,182,814 B2 | 5/2012 | Baca et al. |
| 8,361,966 B2 | 1/2013 | Azuma et al. |
| 8,518,888 B2 | 8/2013 | Jenkins et al. |
| 8,540,977 B2 | 9/2013 | Baca |
| 9,340,618 B2 | 5/2016 | Edwards et al. |
| 10,035,852 B2 | 7/2018 | Cook et al. |
| 10,106,603 B2 | 10/2018 | Cook et al. |
| 2003/0147849 A1 | 8/2003 | Warne et al. |
| 2004/0126358 A1 | 7/2004 | Warne et al. |
| 2004/0142871 A1 | 7/2004 | Shaughnessy et al. |
| 2006/0062760 A1 | 3/2006 | Keith et al. |
| 2007/0160577 A1 | 7/2007 | Damle et al. |
| 2009/0191147 A1 | 7/2009 | Keith et al. |
| 2009/0202533 A1 | 8/2009 | Baca et al. |
| 2010/0062058 A1 | 3/2010 | Warne et al. |
| 2010/0093976 A1 | 4/2010 | Azuma et al. |
| 2010/0183544 A1 | 7/2010 | Jenkins et al. |
| 2013/0302277 A1 | 11/2013 | Jenkins et al. |
| 2014/0219919 A1 | 8/2014 | Edwards et al. |
| 2016/0031999 A1 | 2/2016 | Edwards et al. |
| 2017/0174759 A1 | 6/2017 | Cook et al. |
| 2018/0186871 A1 | 7/2018 | Cook et al. |
| 2018/0186872 A1 | 7/2018 | Cook et al. |
| 2018/0265579 A1 | 9/2018 | Cook et al. |
| 2018/0362633 A1 | 12/2018 | Cook et al. |
| 2018/0362634 A1 | 12/2018 | Cook et al. |
| 2018/0362635 A1 | 12/2018 | Cook et al. |
| 2018/0362636 A1 | 12/2018 | Cook et al. |
| 2018/0362637 A1 | 12/2018 | Cook et al. |
| 2018/0362638 A1 | 12/2018 | Cook et al. |

(Continued)

FOREIGN PATENT DOCUMENTS

| | | |
|---|---|---|
| CN | 105497893 A | 4/2016 |
| EP | 1630232 A2 | 3/2006 |

(Continued)

OTHER PUBLICATIONS

International Search Report and Written Opinion for PCT/EP2016/081430 dated Apr. 18, 2017.
Chapter II Demand filed Aug. 14, 2017 for International Patent Application No. PCT/EP2016/081430.
International Preliminary Report on Patentability (Chapter II) for International Patent Application No. PCT/EP2016/081430, dated Nov. 6, 2017.
International Search Report and Written Opinion for Application No. PCT/EP2017/083043 dated Jul. 23, 2018.

(Continued)

*Primary Examiner* — Gary B Nickol
*Assistant Examiner* — Jegatheesan Seharaseyon
(74) *Attorney, Agent, or Firm* — Wolf, Greenfield & Sacks, P.C.

(57) ABSTRACT

IL-11Rα antibodies are disclosed. Also disclosed are compositions comprising the IL-11Rα antibodies, and methods using the IL-11Rα antibodies.

15 Claims, 61 Drawing Sheets

Specification includes a Sequence Listing.

(56) References Cited

U.S. PATENT DOCUMENTS

| | | |
|---|---|---|
| 2018/0362639 A1 | 12/2018 | Cook et al. |
| 2018/0362640 A1 | 12/2018 | Cook et al. |
| 2018/0362641 A1 | 12/2018 | Cook et al. |
| 2018/0371077 A1 | 12/2018 | Cook et al. |
| 2018/0371078 A1 | 12/2018 | Cook et al. |
| 2019/0002553 A1 | 1/2019 | Cook et al. |
| 2019/0389957 A1 | 12/2019 | Cook et al. |
| 2020/0031918 A1 | 1/2020 | Cook et al. |

FOREIGN PATENT DOCUMENTS

| | | |
|---|---|---|
| KR | 20110047179 A | 5/2011 |
| RU | 2016 125 115 A | 12/2017 |
| RU | 2016 151 730 A | 6/2018 |
| WO | WO 1996/019574 A1 | 6/1996 |
| WO | WO 1998/36061 A2 | 8/1998 |
| WO | WO 1999/020755 A2 | 4/1999 |
| WO | WO 2000/078336 A1 | 12/2000 |
| WO | WO 2002/020609 A2 | 3/2002 |
| WO | WO 2005/058956 A1 | 6/2005 |
| WO | WO 2005/070446 A1 | 8/2005 |
| WO | WO 2005/098041 A2 | 10/2005 |
| WO | WO 2009/052588 A1 | 4/2009 |
| WO | WO 2014/121325 A1 | 8/2014 |
| WO | WO 2017/103108 A1 | 6/2017 |
| WO | WO 2018/109170 A2 | 6/2018 |
| WO | WO 2018/109174 A2 | 6/2018 |

OTHER PUBLICATIONS

International Search Report and Written Opinion for Application No. PCT/EP2017/083051 dated Aug. 13, 2018.

[No Author Listed] Human IL-11 Antibody. Monoclonal Mouse IgG2A. Clone No. 22626. Cat. No. MAB218. R& D Systems: A Biotechne Brand. Rev. Feb. 7, 2018. 1 page.

[No Author Listed] Human Il-11 Rα Antibody. Monoclonal Mouse IgGl. Clone No. 473143. Cat. No. MAB1977. R& D Systems: A Biotechne Brand. Rev. Feb. 7, 2018. 1 page.

[No Author Listed] Recombinant Human anti-human IL11 antibody. 2 pages. May 8, 2018.

[No Author Listed] Section 2, Definition, Pathophsiology and Pathogenesis of Asthma, and Natural History of Asthma. Aug. 28, 2007. 24 pages.

Ancey et al., A fusion protein of the gp130 and interleukin-6Ralpha ligand-binding domains acts as a potent interleukin-6 inhibitor. J Biol Chem. May 9, 2003;278(19):16968-72.

Blanc et al., Monoclonal antibodies against the human interleukin-11 receptor alpha-chain (IL-11Ralpha) and their use in studies of human mononuclear cells. J Immunol Methods. Jul. 31, 2000;241(1-2):43-59.

Bravo et al., Crystal structure of a cytokine-binding region of gp130. EMBO J. Mar. 16, 1998;17(6):1665-74.

Carr et al., Asthma heterogeneity and severity. World Allergy Organ J. 2016; 9(1): 41. EPub Nov. 29, 2016. doi: 10.1186/s40413-016-0131-2. 8 pages.

Chen et al., Enhancement and destruction of antibody function by somatic mutation: unequal occurrence is controlled by V gene combinatorial associations. The EMBO Journal. 1995;14(12):2784-94.

Chen et al., IL-11 receptor alpha in the pathogenesis of IL-13-induced inflammation and remodeling. J Immunol. Feb. 15, 2005;174(4):2305-13.

Cheng et al., Cross-reactivity of antibody against SARS-coronavirus nucleocapsid protein with IL-11. Biochem Biophys Res Commun. Dec. 23, 2005;338(3):1654-60. Epub Oct. 25, 2005.

Chow et al., Structure of an extracellular gp130 cytokine receptor signaling complex. Science. Mar. 16, 2001;291(5511):2150-5.

Colman, Effects of Amino Acid Sequence Changes on Antibody-Antigen Interactions. Research in Immunology. 1994;145:33-6.

Deguchi et al., Generation of and characterization of anti-IL-11 antibodies using newly established in Il11-deficient mice. Biochem Biophys Res Commun. Oct. 28, 2018;505(2):453-459. doi: 10.1016/j.bbrc.2018.09.128. Epub Sep. 26, 2018.

Du et al., A bone marrow stromal-derived growth factor, interleukin-11, stimulates recovery of small intestinal mucosal cells after cytoablative therapy. Blood. Jan. 1, 1994;83(1):33-7.

Du et al., Interleukin-11: review of molecular, cell biology, and clinical use. Blood. Jun. 1, 1997;89(11):3897-908.

Forth, et al., Allgemeine und spezielle Pharmakologie und Toxikologie. 11th Edition. Aktories et al., Editors. Urban & Fischer. Sep. 17, 2013;Chapter 16:362-4.

Friedlander, Fibrosis and diseases of the eye. J Clin Invest. Mar. 2007;117(3):576-86.

Garbers et al., Interleukin-6 and interleukin-11: same same but different. Biol Chem. Sep. 2013;394(9):1145-61. doi: 10.1515/hsz-2013-0166.

Gu et al., Anti-gp130 transducer monoclonal antibodies specifically inhibiting ciliary neurotrophic factor, interleukin-6, interleukin-11, leukemia inhibitory factor or oncostatin M. J Immunol Methods. Mar. 28, 1996;190(1):21-7.

Halwani et al., Airway remodeling in asthma. Curr Opin Pharmacol. Jun. 2010;10(3):236-45. doi: 10.1016/j.coph.2010.06.004.

Ham et al., Critical role of interleukin-11 in isoflurane-mediated protection against ischemic acute kidney injury in mice. Anesthesiology. Dec. 2013:119(6):1389-401. doi: 10.1097/ALN.0b013e3182a950da.

Hennersdorf, et al., Das Herz bei arterieller Hypertonie. Internist. 2007;48(3): 236-45. https://doi.org/10.1007/s00108-006-1762-0.

Hermann et al., Important immunoregulatory role of interleukin-11 in the inflammatory process in rheumatoid arthritis. Arthritis Rheum. Aug. 1998;41(8):1388-97.

Johnstone et al., Emerging roles for Il-11 signaling in cancer development and progression: Focus on breast cancer. Cytokine Growth Factor Rev. Oct. 2015;26(5):489-98. doi: 10.1016/j.cytogfr.2015.07.015. Epub Jul. 14, 2015.

Kapina et al., Interleukin-11 drives early lung inflammation during *Mycobacterium tuberculosis* infection in genetically susceptible mice. PLoS One. 2011;6(7):e21878. doi: 10.1371/journal.pone.0021878.

Keith et al., IL-11, a pleiotropic cytokine: exciting new effects of IL-11 on gastrointestinal mucosal biology. Stem Cells. 1994;12 Suppl 1:79-89; discussion 89-90.

Khan et al., Fibrosis in heart disease: understanding the role of transforming growth factor-beta in cardiomyopathy, valvular disease and arrhythmia. Immunology. May 2006;118(1):10-24.

Kimura et al., Identification of cardiac myocytes as the target of interleukin 11, a cardioprotective cytokine. Cytokine. May 2007;38(2):107-15.

King, A scar-y movie, starring IL-11. Science Translational Medicine. Nov. 29, 2017;9(418):eaar2443. doi: 10.1126/scitranslmed.aar2443.

Kussie et al., A single engineered amino acid substitution changes antibody fine specificity. J Immunol. Jan. 1, 1994;152(1):146-52.

Lee et al., Cysteinyl leukotriene upregulates IL-11 expression in allergic airway disease of mice. J Allergy Clin Immunol. Jan. 2007;119(1):141-9. Epub Oct. 27, 2006.

Lee et al., Endogenous IL-11 signaling is essential in Th2- and IL-13-induced inflammation and mucus production. Am J Respir Cell Mol Biol. Dec. 2008;39(6):739-46. doi: 10.1165/rcmb.2008-0053OC. Epub Jul. 10, 2008.

Lemoli et al., Interleukin-11 (IL-11) acts as a synergistic factor for the proliferation of human myeloid leukaemic cells. Br J Haematol. Oct. 1995;91(2):319-26.

Lindahl et al., Microarray profiling reveals suppressed interferon stimulated gene program in fibroblasts from scleroderma-associated interstitial lung disease. Respir Res. Aug. 2, 2012;14:80. doi: 10.1186/1465-9921-14-80.

Lokau et al., Generation of soluble interleukin-11 and interleukin-6 receptors: a crucial function for proteases during inflammation. Mediators of Inflammation. 2016. Article ID:1785021.10 pages.

Lokau et al., Proteolytic Cleavage Governs Interleukin-11 Trans-signaling. Cell Rep. 2016; 14(7):1761-1773.

Lokau et al., Signal transduction of Interleukin-11 and Interleukin-6 α-Receptors. Recep Clin Investigation. 2016;3.

(56) References Cited

OTHER PUBLICATIONS

McCoy et al., IL-11 produced by breast cancer cells augments osteoclastogenesis by sustaining the pool of osteoclast progenitor cells. BMC Cancer. Jan. 11, 2013;13:16. doi: 10.1186/1471-2407-13-16. 11 pages.
Metz et al., Characterization of the Interleukin (IL)-6 Inhibitor IL-6-RFP: fused receptor domains act as high affinity cytokine-binding proteins. J Biol Chem. Jan. 12, 2007;282(2):1238-48. Epub Nov. 3, 2006.
Minshall et al., IL-11 expression is increased in severe asthma: association with epithelial cells and eosinophils. J Allergy Clin Immunol. Feb. 2000;105(2 Pt 1):232-8.
Molet et al., IL-11 and IL-17 expression in nasal polyps: relationship to collagen deposition and suppression by intranasal fluticasone propionate. Laryngoscope. Oct. 2003;113(10):1803-12.
Murray et al., Targeting Interleukin-13 with Tralokinumab Attenuates Lung Fibrosis and Epithelial Damage in a Humanized SCID Idiopathic Pulmonary Fibrosis Model Am. J. Resp. Cell Mol. Biol. 2014; 50(5): 985-994, & Data Suppl.
Obana et al., Therapeutic activation of signal transducer and activator of transcription 3 by interleukin-11 ameliorates cardiac fibrosis after myocardial infarction. Circulation. Feb. 9, 2010;121(5):684-91. doi: 10.1161/CIRCULATIONAHA.109.893677. Epub Jan. 25, 2010.
Obana et al., Therapeutic administration of IL-11 exhibits the postconditioning effects against ischemia-reperfusion injury via STAT3 in the heart. Am J Physiol Heart Circ Physiol. Sep. 1, 2012;303(5):H569-77. doi: 10.1152/ajpheart.00060.2012.
Panka et al., Variable region framework differences result in decreased or increased affinity of variant anti-digoxin antibodies. Proc. Natl. Acad. Sci. USA. 1988; 85(9): 3080-3084.
Park et al., Monoclonal antibody therapy. Advances in Protein Chemistry. 2001;56:369-421. https://doi.org/10.1016/S0065-3233(01)56010-6.
Putoczki et al., IL-11 signaling as a therapeutic target for cancer. Immunotherapy. 2015;7(4):441-53. doi: 10.2217/imt.15.17.
Putoczki et al., Interleukin-11 is the dominant IL-6 family cytokine during gastrointestinal tumorigenesis and can be targeted therapeutically. Cancer Cell. Aug. 12, 2013;24(2):257-71. doi: 10.1016/j.ccr.2013.06.017.
Ray et al., Regulated overexpression of interleukin 11 in the lung. Use to dissociate development-dependent and -independent phenotypes. J Clin Invest. Nov. 15, 1997;100(10):2501-11.
Redlich et al., IL-11 enhances survival and decreases TNF production after radiation-induced thoracic injury. J Immunol. Aug. 15, 1996;157(4):1705-10.
Relevance of third-party observation dated Aug. 5, 2018. 3 pages.
Rudikoff et al., Single amino acid substitution altering antigen-binding specificity. Proc Natl Acad Sci U S A. Mar. 1982; 79(6): 1979-1983. doi: 10.1073/pnas.79.6.1979.
Schafer et al., IL-11 is a crucial determinant of cardiovascular fibrosis. Nature. 2017; 552(7683): 110-115.
Shepelkova et al., Therapeutic Effect of Recombinant Mutated Interleukin 11 in the Mouse Model of Tuberculosis. J Infect Dis. Aug. 1, 2016;214(3):496-501. doi: 10.1093/infdis/jiw176.
Sommer et al., Constitutively active mutant gp130 receptor protein from inflammatory hepatocellular adenoma is inhibited by an anti-gp130 antibody that specifically neutralizes interleukin 11 signaling. J Biol Chem. Apr. 20, 2012;287(17):13743-51. doi: 10.1074/jbc.M111.349167.
Stangou et al., Effect of IL-11 on glomerular expression of TGF-beta and extracellular matrix in nephrotoxic nephritis in Wistar Kyoto rats. J Nephrol. Jan.-Feb. 2011;24(1):106-11. Author Manuscript.
Tang et al., Targeted expression of IL-11 in the murine airway causes lymphocytic inflammation, bronchial remodeling, and airways obstruction. J Clin Invest. Dec. 15, 1996;98(12):2845-53.
Tang et al., Transforming Growth Factor-b Stimulates Interleukin-11 Transcription via Complex Activating Protein-1-dependent Pathways. J. Biol. Chem. 1998; 273(10): 5506-5513.

Third Party Observations for application No. EP20160822941, dated Aug. 5, 2018. 3 pages.
Third Party Submission Under 37 C.F.R. § 1.290 for U.S. Appl. No. 15/381,622, filed Apr. 30, 2018.
Toda et al., Polarized in vivo expression of IL-11 and IL-17 between acute and chronic skin lesions. J Allergy Clin Immunol. Apr. 2003;111(4):875-81.
Trepicchio et al., The therapeutic utility of Interleukin-11 in the treatment of inflammatory disease. Expert Opin Investig Drugs. Sep. 1998;7(9):1501-4.
Winship et al., Targeting Interleukin-11 Receptor-α Impairs Human Endometrial Cancer Cell Proliferation and Invasion In Vitro and Reduces Tumor Growth and Metastasis In Vivo. Mol Cancer Ther. Apr. 2016;15(4):720-30. doi: 10.1158/1535-7163.MCT-15/0677. Epub Feb. 4, 2016.
Wong et al., Endogenous IL-11 is pro-inflammatory in acute methylated bovine serum albumin/interleukin-1-induced (mBSA/IL-1)arthritis. Cytokine. Jan. 21, 2005;29(2):72-6.
Wynn, Cellular and molecular mechanisms of fibrosis. J Pathol. Jan. 2008;214(2):199-210. Author Manuscript.
Wynn, Fibrotic Disease and the TH1/TH2 Paradigm. Nat Rev Immunol. Aug. 2004; 4(8):583-594. doi: 10.1038/nri1412.
Yashiro et al., Transforming growth factor-beta stimulates interleukin-11 production by human periodontal ligament and gingival fibroblasts. J Clin Periodontol. Mar. 2006;33(3):165-71.
Zheng et al., IL-11: insights in asthma from overexpression transgenic modeling. J Allergy Clin Immunol. Oct. 2001;108(4):489-96.
Zhu et al., IL-11 Attenuates Liver Ischemia/Reperfusion Injury (IRI) through STAT3 Signaling Pathway in Mice. PLoS One. May 6, 2015;10(5):e0126296. doi: 10.1371/journal.pone.0126296.
Zong-Jiang et al., Anti-gp 130 transducer monoclonal antibodies specifically inhibiting ciliary neurotrophic factor, interleukin-6, interleukin-11, leukemia inhibitory factor or oncostatin M. J. Immunol. Methods. 1996; 190(1): 21-27.
Affo et al., The Role of Cancer-Associated Fibroblasts and Fibrosis in Liver Cancer. Annu Rev Pathol. Jan. 24, 2017;12:153-186. Author manuscript, 39 pgs.
Barbas et al., In vitro evolution of a neutralizing human antibody to human immunodeficiency virus type 1 to enhance affinity and broaden strain cross-reactivity. Proc Natl Acad Sci U S A. 1994;91(9):3809-3813.
Better et al., *Escherichia coli* secretion of an active chimeric antibody fragment. Science. 1988;240(4855):1041-1043.
Bird et al., Single-chain antigen-binding proteins [published correction appears in Science Apr. 28, 1989;244(4903):409]. Science. 1988;242(4877):423-426.
Buck et al., Detection of S-phase cell cycle progression using 5-ethynyl-2?-deoxyuridine incorporation with click chemistry, an alternative to using 5-bromo-2?-deoxyuridine antibodies. BioTechniques. Jun. 2008;44(7):927-929.
Ciliberto et al. Cytokine Inhibitors: Chapter 8. Marcel Dekker, Inc. 2001.
Concepcion et al., Label-free detection of biomolecular interactions using BioLayer interferometry for kinetic characterization. Comb Chem High Throughput Screen. Sep. 2009;12(8):791-800. doi: 10.2174/138620709789104915.
Curtis et al., Recombinant Soluble interleukin-11 (IL-11) Receptor Alpha-Chain Can Act as an IL-11 Antagonist. Blood. Dec. 1, 1997;90(11):4403-12.
Daba et al., Drug-induced pulmonary fibrosis. Saudi Medical Journal. 2004;25(6):700-706.
Dotti et al., Design and Development of Therapies using Chimeric Antigen Receptor-Expressing T cells. Immunol Rev. Jan. 2014;257(1)107-26, Author Manuscript. 35 pages.
Elias et al., IL-1 and transforming growth factor-beta regulation of fibroblast-derived IL-11. J Immunol. Mar. 1, 1994;152(5):2421-9.
Ernst et al., STAT3 and STAT1 mediate IL-11-dependent and inflammation-associated gastric tumorigenesis in gp130 receptor mutant mice. The Journal of Clinical Investigation. May 2008;118(5):1727-1738.
French R., How to Make Bispecific Antibodies, Diagnostic and Therapeutic Antibodies, Methods in Molecular Medicine. 2008;40:333-339.

(56) References Cited

OTHER PUBLICATIONS

Fulcher et al., Carboxyfluorescein succinimidyl ester-based proliferative assays for assessment of T cell function in the diagnostic laboratory. Immunology and Cell Biology. 1999;77:559-564.
Gourdie et al., Novel therapeutic strategies targeting fibroblasts and fibrosis in heart disease. Nat Rev Drug Discov. Sep. 2016;15(9):620-638. Author Manuscript, 38 pages.
Grivennikov et al., Autocrine IL-6 Signaling: A Key Event in Tumorigenesis? Cancer Cell. Jan. 2008;13:7-9.
GTEX Consortium, The Genotype-Tissue Expression (GTEx) pilot analysis: Multitissue gene regulation in humans. Science. 8 May 2015;348(6235):648-660.
Guo et al., Signaling cross-talk between TGF-beta/BMP and other pathways. Cell Res. 2009;19(1):71-88.
Haverick et al., Separation of mAbs molecular variants by analytical hydrophobic interaction chromatography HPLC. mAbs. 2014;6(4):852-858. Epub Apr. 1, 2014.
Hawkins et al., Selection of Phage Antibodies by Binding Affinity Mimicking Affinity Maturation. Journal of Molecular Biology. 1992;226:889-896.
Hearty et al., Measuring antibody-antigen binding kinetics using surface plasmon resonance. Methods Mol Biol. 2012;907:411-42. doi: 10.1007/978-1-61779-974-7_24.
Hilton et al., Cloning of a murine IL-11 receptor ?-chain; requirement for gp130 for high affinity binding and signal transduction. The EMBO Journal. 1994;13(20):4765-4775.
Hinz et al., Biological Perspectives. The Myofibroblast. On Function, Multiple Origins. Am J Pathol. Jun. 2007;170(60):1807-1816. doi: 10.2353/ajpath.2007.070112.
Hornbeck, Enzyme-Linked Immunosorbent Assays. Curr Protoc Immunol. 2015;110:2.1.1-2.1.23.
Hornig et al., Chapter 40: Production of bispecific antibodies: diabodies and tandem scFv. Methods Mol Biol. 2012;907:713-727. doi:10.1007/978-1-61779-974-7_40.
Hsu et al., Whole Genome Expression Differences in Human Left and Right Atria Ascertained by RNA Sequencing. Circulation Cardiovascular Genetics. Jun. 2012;5(3):327-335.
Hunter et al., IL-6 as a keystone cytokine in helath and disease. Nature Immunology. May 2015;16(5)448-457. Epub Apr. 21, 2015.
Hurrell, Monoclonal Hybridoma Antibodies: Techniques and Applications. CRC Press. 1982.
Huston et al., Protein engineering of antibody binding sites: Recovery of specific activity in an anti-digoxin single-chain Fv analogue produced in *Escherichia coli*. Proceedings of the National Academy of Sciences of the United States of America. Aug. 1988;85:5879-5883.
Jackson et al., In vitro antibody maturation. Improvement of a high affinity, neutralizing antibody against IL-1 beta. J Immunol. 1995;154(7):3310-3319.
Jerabek-Willemsen et al., Molecular interaction studies using microscale thermophoresis Assay and Drug Development Technologies. Aug. 2011;9(4):342-353.
Karpovich et al., Expression and Function of interleukin-11 and Its Receptor Alpha in the Human Endometrium. Mol Hum Reprod. Feb. 2003;9(2):75-80. doi: 10.1093/molehr/gag012.
Khaw et al., Modulation of wound healing after glaucoma surgery. Curr Opin Ophthalmol. Apr. 2001;12(2):143-8.
Kontermann, Dual tergeting strategies with bispecific antibodies. mAbs. 2012;4(2):182-197.
Kurahar er al., Significant contribution of TRPC6 channel-mediated Ca2+ influx to the pathogenesis of Crohn's disease fibrotic stenosis. Journal of Smooth Muscle Research. 2016;52:78-92. Epub Nov. 3, 2016.
Lacob et al., Investigating monoclonal antibody aggregation using a combination of H/DX-MS and other biophysical measurements. J Pharm Sci., Dec. 2013;102(12):4315-4329, Author Manuscript, 25 pages.
Lad et al., High-Throughput Kinetic Screening of Hybridomas to Identify High-Affinity Antibodies Using Bio-Layer Interferometry. Journal of Biomolecular Screening. 2015;20(4):498-507.

Leask et al., TGF?? signaling and the fibrotic response. The FASEB Journal. 2004;18:816-827.
Liang et al., In vitro scratch assay: a convenient and inexpensive method for analysis of cell migration in vitro. Nature Protocols. 2007;2(2):329-333. Epub Mar. 1, 2007.
Marks et al., By-passing immunization: building high affinity human antibodies by chain shuffling. Biotechnology. Jul. 1992;10(7):779-783.
Marks J.D., Antibody Affinity Maturation by Chain Shuffling. Antibody Engineering: Methods and Protocols. Methods in Molecular Biology 2004;248:327-343.
Martineau P., Affinity Measurements by Competition ELISA. Antibody Engineering. 2010;1:657-665.
Mead et al., Evaluation of Anti-TGF-2 Antibody as a New Postoperative Anti-scarring Agent in Glaucoma Surgery. IOVS. Aug. 2003;44(8):3394-3401.
Menzen et al., High-Throughput Melting-Temperature Analysis of a Monoclonal Antibody by Differential Scanning Fluorimetry in the Presence of Surfactants. Journal of Pharmaceutical Sciences. Feb. 2013;10(2):415-428.
Morrison et al., Chimeric human antibody molecules: mouse antigen-binding domains with human constant region domains. Proc Natl Acad Sci U S A. 1984;81(21):6851-6855.
Nandurkar et al., The human IL-11 receptor requires gp130 for signalling: demonstration by molecular cloning of the receptor. Oncogene. 1996;12:585-593.
Nanthakumar et al., Dissecting fibrosis: therapeutic insights from the small-molecule toolbox. Nature Reviews. Oct. 2015;14:693-720. Epub Sep. 4, 2105.
Neuberger et al. Antibody Engineering. 8th International Biotechnology Symposium Part 2. 1988:792-799.
Pflanz et al., A Fusion Protein of interleukin-11 and Soluble interleukin-11 Receptor Acts as a Superagonist on Cells Expressing gp130. FEBS Lett. Apr. 30, 1999;450(1-2):117-22. doi: 10.1016/s0014-5793(99)00477-9.
Putoczki et al., More than a sidekick: the IL-6 family cytokine IL-11 links inflammation to cancer. Journal of Leukocyte Biology. Dec. 2010;88:1109-1117.
Retter et al., VBASE2, an integrative V gene database. Nucleic Acids Research. 2005;33:D671-D674.
Rich et al., Extracting kinetic rate constants from surface plasmon resonance array systems. Analytical Biochemistry. 2008;373(1):112-120. Epub Aug. 19, 2007.
Rockey et al., Fibrosis—a common pathway to organ injury and failure. N Engl J Med. Mar. 19, 2015;372(12):1138-49. doi: 10.1056/NEJMra1300575.
Sadelain et al., The basic principles of chimeric antigen receptor (CAR) design. Cancer Discov. Apr. 2013;3(4):388-398. Author Manuscript, 21 pages.
Salic et al., A chemical method for fast and sensitive detection of DNA synthesis in vivo. PNAS. Feb. 19, 2008;105(7):2415-2420.
Schier et al., Identification of functional and structural amino-acid residues by parsimonious mutagenesis. Gene. 1996;169:147-155.
Seet et al., Validation of the Glaucoma Filtration Surgical Mouse Model for Antifibrotic Drug Evaluation. Mol Med. 2011;17(5-6):557-567. Epub Jan. 11, 2011.
Segal et al., Production of Bispecific Antibodies. Current Protocols in Immunology. 1995:2.13(1-16).
Sittampalam et al., Assay Guidance Manual, Eli Lilly & Company and the National Center for Advancing Translational Sciences. 2004 (last updated Jul. 1, 2016), 10 pages.
Skerra et al., Assembly of a functional immunoglobulin Fv fragment in *Escherichia coli*. Science. 1988;240(4855):1038-1041.
Szendroi et al., Polarization colours of collagen fibres: a sign of collagen production activity in fibrotic processes. Acta Morphol Hung. 1984;32(1):47-55.
Tarnavski et al., Mouse cardiac surgery: comprehensive techniques for the generation of mouse models of human diseases and their application for genomic studies. Physiol Genomics. 2004;16:349-360. Epub Dec. 16, 2003.
Unverdorben et al., Pharmacokinetic properties of IgG and various Fc fusion proteins in mice. mAbs. Jan. 2016;8(1):120-128.

(56) References Cited

OTHER PUBLICATIONS

Walia et al., TGF-B down-regulates IL-6 signaling in intestinal epithelial cells: Critical role of SMAD-2. The FASEB Journal. Nov. 2003;17(14):20 Pages. Epub Sep. 18, 2003.
Ward et al., Binding activities of a repertoire of single immunoglobulin variable domains secreted from *Escherichia coli*. Nature. 1989;341(6242):544-546.
Winter et al., Man-made antibodies. Nature. 1991;349(6307):293-299.
Wong et al., Matrix Metalloproteinase Inhibition Modulates Postoperative Scarring after Experimental Glaucoma Filtration Surgery. Investigative Ophthalmology & Visual Science. Mar. 2003;44(3):1097-1103.
Wong et al., Prolonged Antiscarring Effects of Ilomastat and MMC after Experimental Glaucoma Filtration Surgery. Investigative Ophthalmology & Visual Science. Jun. 2005;46(6):2018-2022.
Wynn et al., Mechanisms of fibrosis: therapeutic translation for fibrotic disease. Nat Med. Jul. 6, 2012;18(7):1028-1041. Author Manuscript, 28 pages.
Xu et al., The role of IL-11 in immunity and cancer. Cancer Letters. 2016;373:156-163.
Yelton et al., Affinity Maturation of the BR96 Anti-Carcinoma Antibody by Codon-Based Mutagenesis. The Journal of Immunology. 1995;155:1994-2004.
Zhang et al., IL-11 in multiple sclerosis. Oncotarget. Oct. 7, 2015;6(32):32297-32298.
Zola, Monoclonal Antibodies: A Manual of Techniques. CRC Press. 1988.
U.S. Appl. No. 16/055,245, filed Aug. 6, 2018, Cook et al.
U.S. Appl. No. 16/055,251, filed Aug. 6, 2018, Cook et al.
U.S. Appl. No. 16/055,261, filed Aug. 6, 2018, Cook et al.
U.S. Appl. No. 16/055,270, filed Aug. 6, 2018, Cook et al.
U.S. Appl. No. 16/055,283, filed Aug. 6, 2018, Cook et al.
U.S. Appl. No. 16/055,295, filed Aug. 6, 2018, Cook et al.
U.S. Appl. No. 16/055,304, filed Aug. 6, 2018, Cook et al.
U.S. Appl. No. 16/055,319, filed Aug. 6, 2018, Cook et al.
U.S. Appl. No. 16/106,041, filed Aug. 21, 2018, Cook et al.
U.S. Appl. No. 16/106,044, filed Aug. 21, 2018, Cook et al.
U.S. Appl. No. 16/106,047, filed Aug. 21, 2018, Cook et al.
U.S. Appl. No. 16/106,050, filed Aug. 21, 2018, Cook et al.
U.S. Appl. No. 16/726,173, filed Dec. 23, 2019, Cook et al.
U.S. Appl. No. 16/440,840, filed Jun. 13, 2019, Cook et al.
U.S. Appl. No. 16/440,876, filed Jun. 13, 2019, Cook et al.
U.S. Appl. No. 16/748,698, filed Jan. 21, 2020, Cook et al.
U.S. Appl. No. 16/798,101, filed Feb. 21, 2020, Cook et al.
PCT/EP2016/081430, Apr. 18, 2017, International Search Report and Written Opinion.
PCT/EP2016/081430, Aug. 14, 2017, Chapter II Demand.
PCT/EP2016/081430, Nov. 6, 2017, International Preliminary Report on Patentability.
PCT/EP2017/083043, Jul. 20, 2018, International Search Report and Written Opinion.
PCT/EP2017/083051, Aug. 13, 2018, International Search Report and Written Opinion.

BSO-1E3_1

DVVMTQIPLSLSVSMKFQASISCRSSQSLVHSNGNTYLHWYLQKPGQSPKLLIYKVSNRFS
GVPDRFSGSGSGTDFTLKISRVEAEDLGVYFCSQSTHVPLTFGAGTKLELK (SEQ ID NO:1)

LC-CDR1:    QSLVHSNGNTY    (SEQ ID NO:19)
    LC-CDR2:    KVS    (SEQ ID NO:20)
    LC-CDR3:    SQSTHVPLT    (SEQ ID NO:21)

BSO-1E3_2

NIVMTQSPKSMSMSVGERVTLSCKASENVGTYVSWYQQKPEQSPKLLIYGASNRYTGVPD
RFTGSGSATDFTLTISSVQAEDLADYHCGQGYSYPYTFGGGTKLEIK (SEQ ID NO:2)

LC-CDR1:    ENVGTY    (SEQ ID NO:22)
    LC-CDR2:    GAS    (SEQ ID NO:23)
    LC-CDR3:    GQGYSYPYT    (SEQ ID NO:24)

BSO-2E5

DIQMTQSPSSLSASLGERVSLTCRASQDIGSSLNWLQQEPDGTIKRLIYATASLESGVPKRF
SGSRSGSDYSLTISRLESEDFVDYYCQQYASSPPTFGAGTKLELK (SEQ ID NO:3)

LC-CDR1:    QDIGSS    (SEQ ID NO:25)
    LC-CDR2:    ATA    (SEQ ID NO:26)
    LC-CDR3:    QQYASSPPT    (SEQ ID NO:27)

BSO-4G3

DIVLTQSPASLAVSLGQSVTISCRASESVEYSGTTLMQWYQQKPGQPPKLLIYGASNVESG
VPARFSGSGSGTDFSLNIHPVEEDDIAMYFCQQSRKVPYTFGSGTKLEIK (SEQ ID NO:4)

LC-CDR1:    ESVEYSGTTL    (SEQ ID NO:28)
    LC-CDR2:    GAS    (SEQ ID NO:23)
    LC-CDR3:    QQSRKVPYT    (SEQ ID NO:29)

FIG. 16

BSO-5E5

DIVMSQSPSSLPVSVGENVTMSCKSS<u>QSLLYGSNQKNY</u>LAWYQQKPGQSPKLLIY<u>WAS</u>TR
ESGVPDRFTGSGSGTDFTLTISSVKAEDLAVYFC<u>QQYYSYPRT</u>FGGGTKLEIK (SEQ ID
NO:5)

LC-CDR1:    QSLLYGSNQKNY    (SEQ ID NO:30)
    LC-CDR2:    WAS    (SEQ ID NO:31)
    LC-CDR3:    QQYYSYPRT    (SEQ ID NO:32)

BSO-7G9

DVVMTQTPLSLPVSLGDQASISCRSS<u>QSLVHSNGNTY</u>LHWYLQKPGQSPKLLIY<u>KVS</u>NRFS
GVPDRFSGSGSGTDFTLKISRVEAEDLGVYFC<u>SQSTHVPLT</u>FGAGTKLELK (SEQ ID NO:6)

LC-CDR1:    QSLVHSNGNTY    (SEQ ID NO:19)
    LC-CDR2:    KVS    (SEQ ID NO:20)
    LC-CDR3:    SQSTHVPLT    (SEQ ID NO:21)

BSO-9A7

DIVLTQSPATLSMTPGDSVSLSCRAS<u>QSISNN</u>LHWYQQKSHESPRLLIKYASQSISGIPSRFS
GSGSGTDFTLSFNSVETEDFGVYFC<u>QQRYSWPLT</u>FGAGTKLEMK (SEQ ID NO:7)

LC-CDR1:    QSISNN    (SEQ ID NO:33)
    LC-CDR2:    YAS    (SEQ ID NO:34)
    LC-CDR3:    QQRYSWPLT    (SEQ ID NO:35)

BSO-10D11

DIQMTQSPSSLSASLGERVSLTCRAS<u>QEISAY</u>LSWLQQKPDGTIKRLIY<u>STS</u>TLDSGVPKRF
SGSRSGSDYSLTISSLESEDFADYFC<u>LQYASSPLT</u>FGAGTKLELK (SEQ ID NO:8)

LC-CDR1:    QEISAY    (SEQ ID NO:36)
    LC-CDR2:    STS    (SEQ ID NO:37)
    LC-CDR3:    LQYASSPLT    (SEQ ID NO:38)

FIG. 16 (Cont.)

BSO-13B10

DIVMTQSQKFMSTSVGDRVSVTCKAS<u>QNVGSN</u>VAWYQQKAGQSPKALIY<u>SAS</u>YRYSGVP
DRFTGSGSGTDFTLTISNVQSEDLAEYFC<u>QQYNSYPLT</u>FGAGTKLELK (SEQ ID NO:9)

|  |  |  |
|---|---|---|
| LC-CDR1: | QNVGSN | (SEQ ID NO:39) |
| LC-CDR2: | SAS | (SEQ ID NO:40) |
| LC-CDR3: | QQYNSYPLT | (SEQ ID NO:41) |

FIG. 16 (Cont.)

BSO-1E3_1

QVQLQQPGAELVTPGASVKLSCKAS<u>GFTFTNNW</u>MHWVKQRPGQGLEWIGM<u>IHPNSGIT</u>NI
NEKFKNKATVTVDKSSSTVYIQLSSLTSEDSAVYYC<u>RSDGTYEGYFDY</u>WGQGTPLTVSS
(SEQ ID NO:10)

HC-CDR1:    GFTFTNNW    (SEQ ID NO:42)
    HC-CDR2:    IHPNSGIT    (SEQ ID NO:43)
    HC-CDR3:    RSDGTYEGYFDY    (SEQ ID NO:44)

BSO-1E3_2

QVQLQQSGPELVKPGASVKISCKAS<u>GYNFNDYY</u>INWVNQRPGQGLEWIGW<u>IFPGRIIT</u>YYN
EKFKGKATLTVDTSSNTAYMLLSSLTSEDSAVYFC<u>ARGVGEGFDY</u>WGQGTTLTVSS (SEQ
ID NO:11)

HC-CDR1:    GYNFNDYY    (SEQ ID NO:45)
    HC-CDR2:    IFPGRIIT    (SEQ ID NO:46)
    HC-CDR3:    ARGVGEGFDY    (SEQ ID NO:47)

BSO-2E5

QGQVQQSGAELVKPGASVKLSCKTS<u>GFTFSTSY</u>ISWLKQKPRQSLEWIAW<u>IYAGTGST</u>SYN
QKFTGKAQLTVDTSSSTAYMQLSSLTSEDSAIYYC<u>ARHWAY</u>WGQGTLVTVSA (SEQ ID
NO:12)

HC-CDR1:    GFTFSTSY    (SEQ ID NO:48)
    HC-CDR2:    IYAGTGST    (SEQ ID NO:49)
    HC-CDR3:    ARHWAY    (SEQ ID NO:50)

BSO-4G3

EVQLVESGGGLVKPGGSLKLSCAAS<u>GFTFSTYA</u>MSWVRQTPEKRLEWVAA<u>IKSNGGST</u>YY
PDTVKDRFTISRDNAKNTLYLQMSSLRPEDTALYYC<u>AHGLLFAH</u>WGQGTLVTVSA (SEQ ID
NO:13)

HC-CDR1:    GFTFSTYA    (SEQ ID NO:51)
    HC-CDR2:    IKSNGGST    (SEQ ID NO:52)
    HC-CDR3:    AHGLLFAH    (SEQ ID NO:53)

FIG. 17

BSO-5E5

DVQLQESGPGLVKPSQSLSLTCSVT<u>GYSITSDYY</u>WNWIRQFPGNKLEWMGY<u>ISYDSSN</u>NY
NPSLKNRISITRDTSKNQFFLKLNSVTTEDTATYYC<u>ASVGYYYVSDWYFDV</u>WGTGTTVTVS
S (SEQ ID NO:14)

HC-CDR1:    GYSITSDYY    (SEQ ID NO:54)
    HC-CDR2:    ISYDSSN    (SEQ ID NO:55)
    HC-CDR3:    ASVGYYYVSDWYFDV    (SEQ ID NO:56)

BSO-7G9

QVQLQQPGAELVKPGASVRLSCKAS<u>GYTFTSYW</u>MHWVKQRPGQGLEWIGM<u>IHPNSGYT</u>N
YNEKFKIKATLTVDKSSSTAHMQLSSLTSEDSAVYHC<u>ARGGYDGSYGPWFAY</u>WGQGTLVT
VSA (SEQ ID NO:15)

HC-CDR1:    GYTFTSYW    (SEQ ID NO:57)
    HC-CDR2:    IHPNSGYT    (SEQ ID NO:58)
    HC-CDR3:    ARGGYDGSYGPWFAY    (SEQ ID NO:59)

BSO-9A7

QVQLQQPGAELVRPGSSVKLSCKAS<u>GYTFTNYW</u>MHWLKQRPVQGLEWIGN<u>IGPSDSKT</u>H
YNQKFKDKATLTVDKSSSTAYMQLNSLTSEDSAVYYC<u>ARGDYVLFTY</u>WGQGTLVTVSA
(SEQ ID NO:16)

HC-CDR1:    GYTFTNYW    (SEQ ID NO:60)
    HC-CDR2:    IGPSDSKT    (SEQ ID NO:61)
    HC-CDR3:    ARGDYVLFTY    (SEQ ID NO:62)

BSO-10D11

QVQLQQSGTELVRPGTSVKMSCKAA<u>GYTFTDYW</u>IGWIKQRPGHGLEWIGD<u>IFPGGDYTKC</u>
SERFKGKAKLTADTSSSTAYMQLSRLTSEDSAIYYC<u>ARRSTTIRFGAMDN</u>WGQGTSVTVSS
(SEQ ID NO:17)

HC-CDR1:    GYTFTDYW    (SEQ ID NO:63)
    HC-CDR2:    IFPGGDYT    (SEQ ID NO:64)
    HC-CDR3:    ARRSTTIRFGAMDN    (SEQ ID NO:65)

FIG. 17 (Cont.)

BSO-13B10

QVQLKESGPGLVAPSQSLSITCTVS<u>GFSLTSFS</u>ISWVRQPPGKGLEWLGG<u>IWTGGGT</u>NYN
SALKPRLSISKDNSKSQVFLKMNSLQTDDTARYYC<u>ARNSNYPSGFAY</u>WGQGTLVTVSA
(SEQ ID NO:18)

| | | |
|---|---|---|
| HC-CDR1: | GFSLTSFS | (SEQ ID NO:66) |
| HC-CDR2: | IWTGGGT | (SEQ ID NO:67) |
| HC-CDR3: | ARNSNYPSGFAY | (SEQ ID NO:68) |

FIG. 17 (Cont.)

| Clone | CDR 1 | CDR 2 | CDR 3 |
|---|---|---|---|
| Light Chain | | | |
| BSO-1E3_1 | QSLVHSNGNTY (SEQ ID NO:19) | KVS (SEQ ID NO:20) | SQSTHVPLT (SEQ ID NO:21) |
| BSO-1E3_2 | ENVGTY (SEQ ID NO:22) | GAS (SEQ ID NO:23) | GQGYSYPYT (SEQ ID NO:24) |
| BSO-2E5 | QDIGSS (SEQ ID NO:25) | ATA (SEQ ID NO:26) | QQYASSPPT (SEQ ID NO:27) |
| BSO-4G3 | ESVEYSGTTL (SEQ ID NO:28) | GAS (SEQ ID NO:23) | QQSRKVPYT (SEQ ID NO:29) |
| BSO-5E5 | QSLLYGSNQKNY (SEQ ID NO:30) | WAS (SEQ ID NO:31) | QQYYSYPRT (SEQ ID NO:32) |
| BSO-7G9 | QSLVHSNGNTY (SEQ ID NO:19) | KVS (SEQ ID NO:20) | SQSTHVPLT (SEQ ID NO:21) |
| BSO-9A7 | QSISNN (SEQ ID NO:33) | YAS (SEQ ID NO:34) | QQRYSWPLT (SEQ ID NO:35) |
| BSO-10D11 | QEISAY (SEQ ID NO:36) | STS (SEQ ID NO:37) | LQYASSPLT (SEQ ID NO:38) |
| BSO-13B10 | QNVGSN (SEQ ID NO:39) | SAS (SEQ ID NO:40) | QQYNSYPLT (SEQ ID NO:41) |

FIG. 18

| Clone | CDR 1 | CDR 2 | CDR 3 |
|---|---|---|---|
| Heavy Chain | | | |
| BSO-1E3_1 | GFTFTNNW (SEQ ID NO:42) | IHPNSGIT (SEQ ID NO:43) | RSDGTYEGYFDY (SEQ ID NO:44) |
| BSO-1E3_2 | GYNFNDYY (SEQ ID NO:45) | IFPGRIIT (SEQ ID NO:46) | ARGVGEGFDY (SEQ ID NO:47) |
| BSO-2E5 | GFTFSTSY (SEQ ID NO:48) | IYAGTGST (SEQ ID NO:49) | ARHWAY (SEQ ID NO:50) |
| BSO-4G3 | GFTFSTYA (SEQ ID NO:51) | IKSNGGST (SEQ ID NO:52) | AHGLLFAH (SEQ ID NO:53) |
| BSO-5E5 | GYSITSDYY (SEQ ID NO:54) | ISYDSSN (SEQ ID NO:55) | ASVGYYYVSDWYFDV (SEQ ID NO:56) |
| BSO-7G9 | GYTFTSYW (SEQ ID NO:57) | IHPNSGYT (SEQ ID NO:58) | ARGGYDGSYGPWFAY (SEQ ID NO:59) |
| BSO-9A7 | GYTFTNYW (SEQ ID NO:60) | IGPSDSKT (SEQ ID NO:61) | ARGDYVLFTY (SEQ ID NO:62) |
| BSO-10D11 | GYTFTDYW (SEQ ID NO:63) | IFPGDYT (SEQ ID NO:64) | ARRSTTIRFGAMDN (SEQ ID NO:65) |
| BSO-13B10 | GFSLTSFS (SEQ ID NO:66) | IWTGGGT (SEQ ID NO:67) | ARNSNYPSGFAY (SEQ ID NO:68) |

FIG. 19

| Clone(s) | LC-CDR1 | Sequence family | Family Consensus |
|---|---|---|---|
| BSO-9A7 | QSISNN (SEQ ID NO:33) | LC-CDR1-1 | $QX_1X_2X_3X_4X_5$ (SEQ ID NO:69)<br><br>$X_1$ = N, S, E or D<br>$X_2$ = I or V<br>$X_3$ = G or S<br>$X_4$ = S, N or A<br>$X_5$ = N, Y or S |
| BSO-10D11 | QEISAY (SEQ ID NO:36) | | |
| BSO-13B10 | QNVGSN (SEQ ID NO:39) | | |
| BSO-2E5 | QDIGSS (SEQ ID NO:25) | | |
| BSO-5E5 | QSLLYGSNQKNY (SEQ ID NO:30) | LC-CDR1-2 | $QSLX_6X_7X_8SNX_9X_{10}X_{11}Y$ (SEQ ID NO:70)<br><br>$X_6$ = Absent or L<br>$X_7$ = V or Y<br>$X_8$ = H or G<br>$X_9$ = G or Q<br>$X_{10}$ = N or K<br>$X_{11}$ = T or N |
| BSO-1E3_1, BSO-7G9 | QSLVHSNGNTY (SEQ ID NO:19) | | |
| BSO-4G3 | ESVEYSGTTL (SEQ ID NO:28) | LC-CDR1-3 | ESVEYSGTTL (SEQ ID NO:28) |
| BSO-1E3_2 | ENVGTY (SEQ ID NO:22) | LC-CDR1-4 | ENVGTY (SEQ ID NO:22) |

FIG. 20A

| Clone(s) | LC-CDR2 | Sequence family | Family Consensus |
|---|---|---|---|
| BSO-4G3, BSO-1E3_2 | GAS (SEQ ID NO:23) | LC-CDR2-1 | $X_{12}AS$ (SEQ ID NO:71)<br><br>$X_{12}$ = G, W, Y or S |
| BSO-5E5 | WAS (SEQ ID NO:31) | | |
| BSO-9A7 | YAS (SEQ ID NO:34) | | |
| BSO-13B10 | SAS (SEQ ID NO:40) | | |
| BSO-10D11 | STS (SEQ ID NO:37) | LC-CDR2-2 | $X_{13}X_{14}S$ (SEQ ID NO:72)<br><br>$X_{13}$ = S or K<br>$X_{14}$ = T or V |
| BSO-1E3_1, BSO-7G9 | KVS (SEQ ID NO:20) | | |
| BSO-2E5 | ATA (SEQ ID NO:26) | LC-CDR2-3 | ATA (SEQ ID NO:26) |

FIG. 20B

| Clone(s) | LC-CDR3 | Sequence family | Family Consensus |
|---|---|---|---|
| BSO-1E3_1, BSO-7G9 | SQSTHVPLT (SEQ ID NO:21) | LC-CDR3-1 | $X_{15}QX_{16}X_{17}X_{18}X_{19}PX_{20}T$ (SEQ ID NO:73) $X_{15}$ = Q, S, G or L $X_{16}$ = Y, S, G or R $X_{17}$ = Y, A, T, N or R $X_{18}$ = S, H or K $X_{19}$ = V, Y, S or W $X_{20}$ = L, Y, R or P |
| BSO-1E3_2 | GQGYSYPYT (SEQ ID NO:24) | | |
| BSO-2E5 | QQYASSPPT (SEQ ID NO:27) | | |
| BSO-4G3 | QQSRKVPYT (SEQ ID NO:29) | | |
| BSO-5E5 | QQYYSYPRT (SEQ ID NO:32) | | |
| BSO-9A7 | QQRYSWPLT (SEQ ID NO:35) | | |
| BSO-10D11 | LQYASSPLT (SEQ ID NO:38) | | |
| BSO-13B10 | QQYNSYPLT (SEQ ID NO:41) | | |

FIG. 20C

| Clone(s) | HC-CDR1 | Sequence family | Family Consensus |
|---|---|---|---|
| BSO-7G9 | GYTFTSYW (SEQ ID NO:57) | HC-CDR1-1 | $GYTFTX_{21}YW$ (SEQ ID NO:74) $X_{21}$ = S, N or D |
| BSO-9A7 | GYTFTNYW (SEQ ID NO:60) | | |
| BSO-10D11 | GYTFTDYW (SEQ ID NO:63) | | |
| BSO-2E5 | GFTFSTSY (SEQ ID NO:48) | HC-CDR1-2 | $GFTFX_{22}X_{23}X_{24}X_{25}$ (SEQ ID NO:75) $X_{22}$ = S or T $X_{23}$ = T or N $X_{24}$ = S, Y or N $X_{25}$ = Y, A or W |
| BSO-4G3 | GFTFSTYA (SEQ ID NO:51) | | |
| BSO-1E3_1 | GFTFTNNW (SEQ ID NO:42) | | |
| BSO-5E5 | GYSITSDYY (SEQ ID NO:54) | HC-CDR1-3 | $GYX_{26}X_{27}X_{28}X_{29}DYY$ (SEQ ID NO:76) $X_{26}$ = S or N $X_{27}$ = I or F $X_{28}$ = T or N $X_{29}$ = Absent or S |
| BSO-1E3_2 | GYNFNDYY (SEQ ID NO:45) | | |
| BSO-13B10 | GFSLTSFS (SEQ ID NO:66) | HC-CDR1-4 | GFSLTSFS (SEQ ID NO:66) |

FIG. 21A

| Clone(s) | HC-CDR2 | Sequence family | Family Consensus |
|---|---|---|---|
| BSO-1E3_1 | IHPNSGIT (SEQ ID NO:43) | HC-CDR2-1 | I$X_{30}X_{31}X_{32}X_{33}GX_{34}$T (SEQ ID NO:77) |
| BSO-4G3 | IKSNGGST (SEQ ID NO:52) | | |
| BSO-2E5 | IYAGTGST (SEQ ID NO:49) | | $X_{30}$ = H, K or Y |
| BSO-7G9 | IHPNSGYT (SEQ ID NO:58) | | $X_{31}$ = P, S or A |
| | | | $X_{32}$ = N or G |
| | | | $X_{33}$ = S, G or T |
| | | | $X_{34}$ = S, I or Y |
| BSO-1E3_2 | IFPGRIIT (SEQ ID NO:46) | HC-CDR2-2 | IFPG$X_{35}X_{36}X_{37}$T (SEQ ID NO:78) |
| BSO-10D11 | IFPGGDYT (SEQ ID NO:64) | | |
| | | | $X_{35}$ = R or G |
| | | | $X_{36}$ = I or D |
| | | | $X_{37}$ = I or Y |
| BSO-5E5 | ISYDSSN (SEQ ID NO:55) | HC-CDR2-3 | ISYDSSN (SEQ ID NO:55) |
| BSO-9A7 | IGPSDSKT (SEQ ID NO:61) | HC-CDR2-4 | IGPSDSKT (SEQ ID NO:61) |
| BSO-13B10 | IWTGGGT (SEQ ID NO:67) | HC-CDR2-5 | IWTGGGT (SEQ ID NO:67) |

FIG. 21B

| Clone(s) | HC-CDR3 | Sequence family | Family Consensus |
|---|---|---|---|
| BSO-7G9 | ARGGYDGSYGPWFAY (SEQ ID NO:59) | HC-CDR3-1 | ARG$X_{38}X_{39}X_{40}X_{41}X_{42}X_{43}X_{44}X_{45}X_{46}FX_{47}$Y (SEQ ID NO:79) |
| BSO-1E3_2 | ARGVGEGFDY (SEQ ID NO:47) | | |
| BSO-9A7 | ARGDYVLFTY (SEQ ID NO:62) | | $X_{38}$ = Absent, D or G |
| | | | $X_{39}$ = Absent or Y |
| | | | $X_{40}$ = V or D |
| | | | $X_{41}$ = G or L |
| | | | $X_{42}$ = Absent, E or S |
| | | | $X_{43}$ = Absent or Y |
| | | | $X_{44}$ = Absent or G |
| | | | $X_{45}$ = Absent or P |
| | | | $X_{46}$ = Absent or W |
| | | | $X_{47}$ = D, T or A |
| BSO-5E5 | ASVGYYYVSDWYFDV (SEQ ID NO:56) | HC-CDR3-2 | ASVGYYYVSDWYFDV (SEQ ID NO:56) |
| BSO-2E5 | ARHWAY (SEQ ID NO:50) | HC-CDR3-3 | ARHWAY (SEQ ID NO:50) |
| BSO-4G3 | AHGLLFAH (SEQ ID NO:53) | HC-CDR3-4 | AHGLLFAH (SEQ ID NO:53) |
| BSO-1E3_1 | RSDGTYEGYFDY (SEQ ID NO:44) | HC-CDR3-5 | RSDGTYEGYFDY (SEQ ID NO:44) |
| BSO-13B10 | ARNSNYPSGFAY (SEQ ID NO:68) | HC-CDR3-6 | ARNSNYPSGFAY (SEQ ID NO:68) |
| BSO-10D11 | ARRSTTIRFGAMDN (SEQ ID NO:65) | HC-CDR3-7 | ARRSTTIRFGAMDN (SEQ ID NO:65) |

FIG. 21C

BSO-1E3_1

GATGTTGTGATGACCCAAATTCCACTCTCCCTGTCTGTCAGTATGAAGTTCCAAGCCTC
CATCTCTTGCAGATCTAGTCAGAGCCTTGTACACAGTAATGGAAACACCTATTTACATTG
GTACCTGCAGAAGCCAGGCCAGTCTCCAAAGCTCCTGATCTACAAAGTTTCCAACCGAT
TTTCTGGGGTCCCAGACAGGTTCAGTGGCAGTGGATCAGGGACAGATTTCACACTCAA
GATCAGCAGAGTGGAGGCTGAGGATCTGGGAGTTTATTTCTGCTCTCAAAGTACACATG
TTCCGCTCACGTTCGGTGCTGGGACCAAGCTGGAGCTGAAA (SEQ ID NO:80)

BSO-1E3_2

AACATTGTAATGACCCAATCTCCCAAATCCATGTCCATGTCAGTAGGAGAGAGGGTCAC
CTTGAGCTGCAAGGCCAGTGAGAATGTGGGTACTTATGTATCCTGGTATCAACAGAAAC
CAGAGCAGTCTCCTAAACTGCTGATATACGGGGCATCCAACCGGTACACTGGGGTCCC
CGATCGCTTCACAGGCAGTGGATCTGCAACAGATTTCACTCTGACCATCAGCAGTGTG
CAGGCTGAAGACCTTGCAGATTATCACTGTGGACAGGGTTACAGCTATCCGTACACGTT
CGGAGGGGGGACCAAGCTGGAAATAAAA (SEQ ID NO:81)

BSO-2E5

GACATCCAGATGACCCAGTCTCCATCCTCCTTATCTGCCTCTCTGGGAGAAAGAGTCAG
TCTCACTTGTCGGGCAAGTCAGGACATTGGTAGTAGCTTAAACTGGCTTCAGCAGGAAC
CAGATGGAACTATTAAACGCCTGATCTACGCCACAGCCAGTTTAGAATCTGGTGTCCCC
AAAAGGTTCAGTGGCAGTAGGTCTGGGTCAGACTATTCTCTCACCATCAGCAGACTTGA
GTCTGAAGATTTTGTAGACTATTACTGTCAACAATATGCTAGCTCTCCTCCCACGTTCGG
TGCTGGGACCAAGCTGGAGCTGAAA (SEQ ID NO:82)

BSO-4G3

GACATTGTGCTCACCCAATCTCCAGCTTCTTTGGCTGTGTCTCTAGGGCAGAGTGTCAC
CATCTCCTGCAGAGCCAGTGAAAGTGTTGAATATTCTGGCACTACTTTAATGCAGTGGT
ACCAACAGAAACCAGGACAGCCACCCAAACTCCTCATCTATGGTGCATCCAACGTAGAA
TCTGGGGTCCCTGCCAGGTTTAGTGGCAGTGGGTCTGGGACAGACTTCAGCCTCAACA
TCCATCCTGTGGAGGAGGATGATATTGCAATGTATTTCTGTCAGCAAAGTAGGAAGGTT
CCGTATACGTTCGGATCGGGGACCAAGCTGGAAATAAAA (SEQ ID NO:83)

FIG. 22A

BSO-5E5

GACATTGTGATGTCACAGTCTCCATCCTCCCTACCTGTGTCAGTTGGAGAGAATGTTAC
TATGAGCTGCAAGTCCAGTCAGAGCCTTTTATATGGTAGCAATCAAAAGAACTACTTGG
CCTGGTACCAGCAGAAACCAGGGCAGTCTCCTAAACTGCTGATTTACTGGGCATCCAC
TAGGGAATCTGGGGTCCCTGATCGCTTCACAGGCAGTGGATCTGGGACAGATTTCACT
CTCACCATCAGCAGTGTGAAGGCTGAAGACCTGGCAGTTTATTTCTGTCAGCAATATTA
TAGCTATCCTCGGACGTTCGGTGGAGGCACCAAGCTGGAAATCAAA (SEQ ID NO:84)

BSO-7G9

GATGTTGTGATGACCCAAACTCCACTCTCCTGCCTGTCAGTCTTGGAGATCAAGCCTC
CATCTCTTGCAGATCTAGTCAGAGCCTTGTACACAGTAATGGAAACACCTATTTACATTG
GTACCTGCAGAAGCCAGGCCAGTCTCCAAAGCTCCTGATCTACAAAGTTTCCAACCGAT
TTTCTGGGGTCCCAGACAGGTTCAGTGGCAGTGGATCAGGGACAGATTTCACACTCAA
GATCAGCAGAGTGGAGGCTGAGGATCTGGGAGTTTATTTCTGCTCTCAAAGTACACATG
TTCCGCTCACGTTCGGTGCTGGGACCAAGCTGGAGCTGAAA (SEQ ID NO:85)

BSO-9A7

GATATTGTGCTAACTCAGTCTCCAGCCACCCTGTCTATGACTCCAGGAGATAGCGTCAG
TCTTTCCTGCAGGGCCAGCCAAAGTATTAGCAACAACCTACACTGGTATCAACAAAAAT
CACATGAGTCTCCAAGGCTTCTCATCAAGTATGCTTCCCAGTCCATCTCTGGGATCCCC
TCCAGGTTCAGTGGCAGTGGATCGGGGACAGATTTCACTCTCAGTTTCAACAGTGTGG
AGACTGAAGATTTTGGAGTGTATTTCTGTCAACAGAGATACAGCTGGCCTCTCACGTTC
GGTGCTGGGACCAAGCTGGAAATGAAA (SEQ ID NO:86)

BSO-10D11

GACATCCAGATGACCCAGTCTCCATCCTCCTTATCTGCCTCTCTGGGAGAAAGAGTCAG
TCTCACTTGTCGGGCAAGTCAGGAATTAGTGCTTACTTAAGCTGGCTTCAGCAGAAAC
CAGATGGAACTATTAAACGCCTGATCTACAGCACATCCACTTTAGATTCTGGTGTCCCA
AAAAGGTTCAGTGGCAGTAGGTCTGGGTCAGATTATTCTCTCACCATCAGCAGCCTTGA
GTCTGAAGATTTTGCAGACTATTTCTGTCTCCAATATGCTAGTTCTCCGCTCACGTTCGG
TGCTGGGACCAAGCTGGAGCTGAAA (SEQ ID NO:87)

FIG. 22A (Cont.)

BSO-13B10

GACATTGTGATGACCCAGTCTCAAAAATTCATGTCCACATCAGTAGGAGACAGGGTCAG
CGTCACCTGCAAGGCCAGTCAGAATGTGGGTAGTAATGTAGCCTGGTATCAACAGAAA
GCAGGGCAATCTCCTAAAGCACTGATTTACTCGGCATCCTACCGGTACAGTGGAGTCC
CTGATCGCTTCACAGGCAGTGGATCTGGGACAGATTTCACTCTCACCATCAGCAATGTG
CAGTCTGAAGACTTGGCAGAGTATTTCTGTCAGCAATATAACAGCTATCCGCTCACGTT
CGGTGCTGGGACCAAGCTGGAGCTGAAA (SEQ ID NO:88)

FIG. 22A (Cont.)

BSO-1E3_1

CAGGTCCAACTGCAGCAGCCTGGGGCTGAACTGGTCACGCCTGGGGCTTCAGTGAAG
TTGTCCTGCAAGGCTTCTGGCTTCACTTTCACCAACAACTGGATGCACTGGGTGAAGCA
GAGACCTGGACAAGGCCTTGAGTGGATTGGAATGATTCATCCTAATAGTGGGATTACTA
ACATCAATGAGAAGTTCAAGAACAAGGCCACAGTGACTGTAGACAAATCCTCCAGCACA
GTCTACATACAACTCAGCAGCCTGACATCTGAGGACTCTGCGGTCTATTACTGTCGCTC
CGATGGTACCTACGAGGGCTACTTTGACTACTGGGGCCAAGGCACCCCTCTCACAGTC
TCCTCA (SEQ ID NO:89)

BSO-1E3_2

CAGGTCCAACTACAGCAGTCTGGACCTGAACTGGTGAAGCCTGGGGCTTCAGTGAAGA
TATCCTGCAAGGCTTCTGGCTACAATTTCAATGACTACTATATAAACTGGGTGAACCAGA
GGCCTGGACAGGGACTTGAGTGGATTGGATGGATTTTTCCTGGAAGAATTATTACTTAC
TACAATGAGAAATTCAAGGGCAAGGCCACACTTACTGTAGACACATCCTCCAACACAGC
CTACATGTTGCTCAGCAGCCTGACCTCTGAGGACTCTGCGGTCTATTTCTGTGCAAGAG
GGGTAGGAGAGGGCTTTGACTACTGGGGCCAAGGCACCACTCTCACAGTCTCCTCA
(SEQ ID NO:90)

BSO-2E5

CAGGGTCAGGTGCAGCAGTCTGGAGCTGAGCTGGTGAAGCCTGGGGCTTCAGTGAAG
CTGTCCTGCAAGACTTCTGGCTTCACCTTCAGTACTAGTTATATAAGTTGGTTGAAGCA
GAAGCCTCGACAGAGTCTTGAGTGGATTGCATGGATTTATGCTGGAACTGGTAGTACTA
GCTATAATCAGAAATTCACAGGCAAGGCCCAACTGACTGTAGACACATCCTCCAGCACA
GCCTACATGCAACTCAGCAGCCTGACATCTGAGGACTCTGCCATCTATTACTGTGCAAG
ACACTGGGCTTACTGGGGCCAAGGGACTCTGGTCACTGTCTCTGCA (SEQ ID NO:91)

BSO-4G3

GAGGTGCAGCTGGTGGAGTCTGGGGGAGGCTTAGTGAAGCCTGGCGGGTCCCTGAAA
CTCTCCTGTGCAGCCTCTGGATTCACTTTCAGTACCTATGCCATGTCTTGGGTTCGCCA
GACTCCAGAGAAGAGGCTGGAGTGGGTCGCAGCCATTAAAAGTAATGGTGGTAGCACC
TACTATCCAGACACTGTGAAGGACCGATTCACCATTTCCAGAGACAATGCCAAGAACAC
CCTGTACCTGCAAATGAGCAGTCTGAGGCCTGAGGACACAGCCTTGTATTACTGTGCA
CATGGTCTCCTGTTTGCTCACTGGGGCCAAGGGACTCTGGTCACTGTCTCTGCA (SEQ
ID NO:92)

FIG. 22B

BSO-5E5

GATGTACAGCTTCAGGAGTCAGGACCTGGCCTCGTGAAACCTTCTCAGTCTCTGTCTCT
CACCTGCTCTGTCACTGGCTACTCCATCACCAGTGATTATTACTGGAACTGGATCCGGC
AGTTTCCAGGAAACAAACTGGAATGGATGGGCTACATAAGCTACGATAGTAGCAATAAC
TACAACCCATCTCTCAAAAATCGAATCTCCATCACTCGTGACACATCTAAGAACCAGTTT
TTCCTGAAGTTGAATTCTGTGACTACTGAGGACACAGCCACATATTACTGTGCTTCAGT
GGGTTATTACTACGTTAGTGACTGGTACTTCGATGTCTGGGGCACAGGGACCACGNTC
ACCGTCTCCTCA (SEQ ID NO:93)

BSO-7G9

CAGGTCCAACTGCAGCAGCCTGGGGCTGAGCTGGTAAAGCCTGGGGCTTCAGTGAGG
TTGTCCTGCAAGGCTTCTGGCTACACTTTCACCAGCTACTGGATGCACTGGGTGAAGCA
GAGGCCTGGACAAGGCCTTGAGTGGATTGGAATGATTCATCCTAATAGTGGTTATACTA
ATTACAATGAGAAGTTCAAGATCAAGGCCACACTGACTGTAGACAAATCCTCCAGCACA
GCCCACATGCAACTCAGCAGCCTGACATCTGAGGATTCTGCGGTCTATCACTGTGCAA
GAGGGGGTATGATGGTTCCTACGGGCCCTGGTTTGCTTACTGGGGCCAAGGGACTC
TGGTCACTGTCTCTGCA (SEQ ID NO:94)

BSO-9A7

CAGGTCCAACTGCAGCAGCCTGGGGCTGAGCTGGTGAGGCCTGGGTCTTCAGTGAAG
CTGTCCTGCAAGGCTTCTGGCTACACCTTCACCAACTACTGGATGCATTGGTTGAAGCA
GAGGCCTGTACAAGGCCTTGAGTGGATTGGTAACATTGGCCTTCTGATAGTAAAACTC
ACTACAATCAAAAATTCAAGGACAAGGCCACATTGACTGTAGACAAATCCTCCAGCACA
GCCTACATGCAACTCAACAGCCTGACATCTGAGGACTCTGCGGTCTATTACTGTGCAAG
GGGTGATTACGTCCTGTTTACTTACTGGGGCCAAGGGACTCTGGTCACTGTCTCTGCA
(SEQ ID NO:95)

BSO-10D11

CAGGTCCAGCTGCAGCAGTCTGGAACTGAGCTGGTAAGGCCTGGGACTTCAGTGAAGA
TGTCCTGCAAGGCTGCTGGATACACCTTCACTGACTACTGGATAGGTTGGATAAAGCAG
AGGCCTGGACATGGCCTTGAGTGGATTGGAGATATTTTCCCTGGAGGTGATTATACTAA
GTGCAGTGAGAGGTTCAAGGGCAAGGCCAAACTGACTGCAGACACATCCTCCAGCACT
GCCTACATGCAGCTCAGCAGACTGACATCTGAGGACTCTGCCATCTATTACTGTGCAAG
AAGGAGTACTACGATACGCTTCGGGGCTATGGACAACTGGGGTCAAGGAACCTCAGTC
ACCGTCTCCTCA (SEQ ID NO:96)

FIG. 22B (Cont.)

BSO-13B10

CAGGTGCAGCTGAAGGAGTCAGGACCTGGCCTGGTGGCGCCCTCACAGAGCCTGTCC
ATCACATGCACTGTCTCTGGGTTCTCATTAACCAGCTTTTCTATAAGCTGGGTTCGCCA
GCCACCAGGAAAGGGTCTGGAGTGGCTTGGAGGAATATGGACTGGTGGAGGCACAAA
TTATAATTCAGCTCTCAAACCCAGACTGAGCATCAGCAAAGACAACTCCAAGAGTCAAG
TTTTCTTAAAAATGAACAGTCTGCAAACTGATGACACAGCCAGGTACTACTGTGCCAGA
AATAGTAACTACCCTTCCGGGTTTGCTTACTGGGGCCAAGGGACTCTGGTCACTGTCTC
TGCA (SEQ ID NO:97)

FIG. 22B (Cont.)

| ID | Clone |
|---|---|
| RA1 | BSO-1E3 |
| RA2 | BSO-2C1 |
| RA3 | BSO-2E5 |
| RA4 | BSO-4G3 |
| RA5 | BSO-5E5 |
| RA6 | BSO-7G9 |
| RA7 | BSO-9A7 |
| RA8 | BSO-10D11 |
| RA9 | BSO-13B10 |
| RA10 | BSW-1D3 |
| RA11 | BSW-1F6 |
| RA12 | BSW-4G5 |
| RA13 | BSW-6H3 |
| RA14 | BSW-7E9 |
| RA15 | BSW-7G8 |
| RA16 | BSW-7H8 |
| RA17 | BSW-8B7 |

| Antibody Candidate | Human IL11 activated fibroblasts (norm.) | Mouse IL11 activated fibroblasts (norm.) | Trans IL11 MMP2 (norm.) |
|---|---|---|---|
| Unstimulated | 1 | 1 | 1 |
| Stimulated | 1.58 | 2.24 | 2.34 |
| Industry Standard | 0.69 | 1.44 | 1.32 |
| RA1 | 0.66 | 1.24 | 1.00 |
| RA2 | 1.12 | 1.26 | 2.41 |
| RA3 | 1.35 | 2.03 | 1.29 |
| RA4 | 1.30 | 1.93 | 1.69 |
| RA5 | 0.62 | 1.11 | 1.02 |
| RA6 | 1.05 | 2.12 | 1.97 |
| RA7 | 0.95 | 1.31 | 1.11 |
| RA8 | 1.09 | 1.89 | 1.61 |
| RA9 | 0.62 | 1.09 | 1.07 |
| RA10 | 1.54 | 1.77 | 1.67 |
| RA11 | 1.10 | 2.07 | 1.66 |
| RA12 | 1.00 | 2.15 | 1.13 |
| RA13 | 1.50 | 1.82 | 1.39 |
| RA14 | 1.19 | 1.54 | 2.03 |
| RA15 | 1.70 | 1.54 | 1.93 |
| RA16 | 1.37 | 2.28 | 2.09 |
| RA17 | 1.32 | 1.73 | 1.90 |

| No | Clone | GMFI | % positive | isotype |
|---|---|---|---|---|
| 1 | BSO-1E3 | 4697 | 15% | n.d./kappa |
| 2 | BSO-2C1 | 44127 | 140% | IgG1/kappa |
| 3 | BSO-2E5 | 9545 | 30% | IgG2b/kappa |
| 4 | BSO-4G3 | 9302 | 30% | IgG1/kappa |
| 5 | BSO-5E5 | 8780 | 28% | IgG1/IgG2b/kappa |
| 6 | BSO-7G9 | 18649 | 59% | IgG2a&2c /kappa |
| 7 | BSO-9A7 | 34771 | 111% | IgG1/kappa |
| 8 | BSO-10D11 | 13139 | 42% | IgG1/kappa |
| 9 | BSO-13B10 | 10931 | 35% | IgG1/kappa |
| | positive control | 31429 | 100% | |
| | negative control | 930 | 3% | |

*incubated on cells transfected with pB1-IL11-hum.FL, flow cytometry (Attunes), Results of subcloning*

IL-11Rα ANTIBODIES

CROSS-REFERENCE TO RELATED APPLICATIONS

The present application is a continuation of U.S. patent application Ser. No. 15/843,212, filed Dec. 15, 2017, which claims priority under 35 USC § 119(a)-(d) to United Kingdom Application No. 1621439.7, filed Dec. 16, 2016, the entire contents of which are incorporated by reference herein.

FIELD OF THE INVENTION

The present invention relates to antibodies that bind to interleukin 11 Receptor alpha (IL-11Ra).

BACKGROUND TO THE INVENTION

Many fatal and incurable diseases are caused by organ failure due to excessive and maladaptive fibrosis (Rockey et al., 2015 Journal of Infectious Diseases 214, jiw176). Fibrotic disorders include both rare, genetically-driven diseases such as scleroderma, idiopathic pulmonary fibrosis and hypertrophic cardiomyopathy, dilated cardiomyopathy (DCM), and common diseases like atrial fibrillation, ventricular fibrillation, non-alcoholic fatty liver disease and diabetic kidney disease. Due to the significant impact on world-wide morbidity and mortality, there is a need to develop therapeutics to inhibit the fibrotic response (Nanthakumar et al., 2015 Nat Rev Drug Discov 14, 693-720).

A major hallmark of fibrosis is the pathologic activation of resident fibroblasts that drives their transition from a quiescent state to proliferating, secretory and contractile myofibroblasts (Hinz et al., 2010 Am J Pathology 170, 1807-1816). Stimuli such as mechanical stress and pro-fibrotic cytokines can activate fibroblasts. The TGFβ1 pathway is considered to be of central importance for the fibrotic response (Leask and Abraham, 2004 The FASEB Journal 18, 816-827) and its inhibition is a therapeutic strategy that is under investigation (Gourdie et al., 2016 Nature Reviews Drug Discovery 15, 620-638). However, direct inhibition of multi-functional TGFβ1 is associated with severe side effects such as inflammation and cancer susceptibility.

SUMMARY OF THE INVENTION

In one aspect, the present invention provides an antibody or antigen binding fragment, optionally isolated, which is capable of binding to IL-11Rα, wherein the antibody or antigen binding fragment is capable of inhibiting IL-11 trans signalling.

In another aspect, the present invention provides an antibody or antigen binding fragment, optionally isolated, which is capable of binding to IL-11Rα, comprising the amino acid sequences i) to vi):

i) LC-CDR1:

$QX_1X_2X_3X_4X_5$; (SEQ ID NO: 69)

$QSLX_6X_7X_8SNX_9X_{10}X_{11}Y$; (SEQ ID NO: 70)

ENVGTY; (SEQ ID NO: 22)

or

ESVEYSGTTL; (SEQ ID NO: 28)

ii) LC-CDR2:

$X_{12}AS$; (SEQ ID NO: 71)

$X_{13}X_{14}S$; (SEQ ID NO: 72)

or

ATA; (SEQ ID NO: 26)

iii) LC-CDR3:

$X_{15}QX_{16}X_{17}X_{18}X_{19}PX_{20}T$; (SEQ ID NO: 73)

iv) HC-CDR1:

$GYTFTX_{21}YW$; (SEQ ID NO: 74)

$GFTFX_{22}X_{23}X_{24}X_{25}$; (SEQ ID NO: 75)

$GYX_{26}X_{27}X_{28}X_{29}DYY$; (SEQ ID NO: 76)

or

GFSLTSFS; (SEQ ID NO: 66)

v) HC-CDR2:

$IX_{30}X_{31}X_{32}X_{33}GX_{34}T$; (SEQ ID NO: 77)

$IFPGX_{35}X_{36}X_{37}T$; (SEQ ID NO: 78)

ISYDSSN; (SEQ ID NO: 55)

IGPSDSKT; (SEQ ID NO: 61)

or

IWTGGGT (SEQ ID NO: 67)

vi) HC-CDR3:

$ARGX_{38}X_{39}X_{40}X_{41}X_{42}X_{43}X_{44}X_{45}X_{46}FX_{47}Y$; (SEQ ID NO: 79)

ASVGYYYVSDWYFDV; (SEQ ID NO: 56)

ARHWAY; (SEQ ID NO: 50)

AHGLLFAH; (SEQ ID NO: 53)

RSDGTYEGYFDY; (SEQ ID NO: 44)

ARNSNYPSGFAY; (SEQ ID NO: 68)

or

ARRSTTIRFGAMDN; (SEQ ID NO: 65)

or a variant thereof in which one or two or three amino acids in one or more of the sequences i) to vi) are replaced with another amino acid;

wherein $X_1$=N, S, E or D, $X_2$=I or V, $X_3$=G or S, $X_4$=S, N or A, $X_5$=N, Y or S, $X_6$=Absent or L, $X_7$=V or Y, $X_8$=H or G, $X_9$=G or Q, $X_{10}$=N or K, $X_{11}$=T or N, $X_{12}$=G, W, Y or S, $X_{13}$=S or K, $X_{14}$=T or V, $X_{15}$=Q, S, G or L, $X_{16}$=Y, S, G or R, $X_{17}$=Y, A, T, N or R, $X_{18}$=S, H or K, $X_{19}$=V, Y, S or W, $X_{20}$=L, Y, R or P, $X_{21}$=S, N or D, $X_{22}$=S or T, $X_{23}$=T or N, $X_{24}$=S, Y or N, $X_{25}$=Y, A or W, $X_{26}$=S or N, $X_{27}$=I or F, $X_{28}$=T or N, $X_{29}$=Absent or S, $X_{30}$=H, K or Y, $X_{31}$=P, S or A, $X_{32}$=N or G, $X_{33}$=S, G or T, $X_{34}$=S, I or Y, $X_{35}$=R or G, $X_{36}$=I or D, $X_{37}$=I or Y, $X_{38}$=Absent, D or G, $X_{39}$=Absent or Y, $X_{40}$=V or D, $X_{41}$=G or L, $X_{42}$=Absent, E or S, $X_{43}$=Absent or Y, $X_{44}$=Absent or G, $X_{45}$=Absent or P, $X_{46}$=Absent or W, $X_{47}$=D, T or A.

In some embodiments, HC-CDR1 is one of GFTFTNNW (SEQ ID NO:42), GYNFNDYY (SEQ ID NO:45), GFTFSTSY (SEQ ID NO:48), GFTFSTYA (SEQ ID NO:51), GYSITSDYY (SEQ ID NO:54), GYTFTSYW (SEQ ID NO:57), GYTFTNYW (SEQ ID NO:60), GYTFTDYW (SEQ ID NO:63) or GFSLTSFS (SEQ ID NO:66).

In some embodiments, HC-CDR2 is one of IHPNSGIT (SEQ ID NO:43), IFPGRIIT (SEQ ID NO:46), IYAGTGST (SEQ ID NO:49), IKSNGGST (SEQ ID NO:52), ISYDSSN (SEQ ID NO:55), IHPNSGYT (SEQ ID NO:58), IGPSDSKT (SEQ ID NO:61), IFPGGDYT (SEQ ID NO:64) or IWTGGGT (SEQ ID NO:67).

In some embodiments, HC-CDR3 is one of RSDGTYEGYFDY (SEQ ID NO:44), ARGVGEGFDY (SEQ ID NO:47), ARHWAY (SEQ ID NO:50), AHGLLFAH (SEQ ID NO:53), ASVGYYYVSDWYFDV (SEQ ID NO:56), ARGGYDGSYGPWFAY (SEQ ID NO:59), ARGDYVLFTY (SEQ ID NO:62), ARRSTTIRFGAMDN (SEQ ID NO:65) or ARNSNYPSGFAY (SEQ ID NO:68).

In some embodiments, LC-CDR1 is one of QSLVHSNGNTY (SEQ ID NO:19), ENVGTY (SEQ ID NO:22), QDIGSS (SEQ ID NO:25), ESVEYSGTTL (SEQ ID NO:28), QSLLYGSNQKNY (SEQ ID NO:30), QSISNN (SEQ ID NO:33), QEISAY (SEQ ID NO:36) or QNVGSN (SEQ ID NO:39).

In some embodiments, LC-CDR2 is one of KVS (SEQ ID NO:20), GAS (SEQ ID NO:23), ATA (SEQ ID NO:26), WAS (SEQ ID NO:31), YAS (SEQ ID NO:34), STS (SEQ ID NO:37) or SAS (SEQ ID NO:40).

In some embodiments, LC-CDR3 is one of SQSTHVPLT (SEQ ID NO:21), GQGYSYPYT (SEQ ID NO:24), QQYASSPPT (SEQ ID NO:27), QQSRKVPYT (SEQ ID NO:29), QQYYSYPRT (SEQ ID NO:32), QQRYSWPLT (SEQ ID NO:35), LQYASSPLT (SEQ ID NO:38) or QQYNSYPLT (SEQ ID NO:41).

In some embodiments, the antibody or antigen binding fragment has at least one heavy chain variable region incorporating the following CDRs:

```
                            (SEQ ID NO: 42)
    HC-CDR1: GFTFTNNW (SEQ ID NO: 43)
    HC-CDR2: IHPNSGIT (SEQ ID NO: 44)
    HC-CDR3: RSDGTYEGYFDY;
or (SEQ ID NO: 45)
    HC-CDR1: GYNFNDYY (SEQ ID NO: 46)
    HC-CDR2: IFPGRIIT (SEQ ID NO: 47)
    HC-CDR3: ARGVGEGFDY;
or (SEQ ID NO: 48)
    HC-CDR1: GFTFSTSY (SEQ ID NO: 49)
    HC-CDR2: IYAGTGST (SEQ ID NO: 50)
    HC-CDR3: ARHWAY;
or (SEQ ID NO: 51)
    HC-CDR1: GFTFSTYA (SEQ ID NO: 52)
    HC-CDR2: IKSNGGST (SEQ ID NO: 53)
    HC-CDR3: AHGLLFAH;
or (SEQ ID NO: 54)
    HC-CDR1: GYSITSDYY (SEQ ID NO: 55)
    HC-CDR2: ISYDSSN (SEQ ID NO: 56)
    HC-CDR3: ASVGYYYVSDWYFDV;
or (SEQ ID NO: 57)
    HC-CDR1: GYTFTSYW (SEQ ID NO: 58)
    HC-CDR2: IHPNSGYT (SEQ ID NO: 59)
    HC-CDR3: ARGGYDGSYGPWFAY;
or (SEQ ID NO: 60)
    HC-CDR1: GYTFTNYW (SEQ ID NO: 61)
    HC-CDR2: IGPSDSKT (SEQ ID NO: 62)
    HC-CDR3: ARGDYVLFTY;
or (SEQ ID NO: 63)
    HC-CDR1: GYTFTDYW (SEQ ID NO: 64)
    HC-CDR2: IFPGGDYT (SEQ ID NO: 65)
    HC-CDR3: ARRSTTIRFGAMDN;
or (SEQ ID NO: 66)
    HC-CDR1: GFSLTSFS (SEQ ID NO: 67)
    HC-CDR2: IWTGGGT (SEQ ID NO: 68)
    HC-CDR3: ARNSNYPSGFAY.
```

In some embodiments, the antibody or antigen binding fragment has at least one light chain variable region incorporating the following CDRs:

```
                            (SEQ ID NO: 19)
LC-CDR1: QSLVHSNGNTY (SEQ ID NO: 20)
LC-CDR2: KVS (SEQ ID NO: 21)
LC-CDR3: SQSTHVPLT;
or (SEQ ID NO: 22)
LC-CDR1: ENVGTY (SEQ ID NO: 23)
LC-CDR2: GAS (SEQ ID NO: 24)
LC-CDR3: GQGYSYPYT;
or (SEQ ID NO: 25)
LC-CDR1: QDIGSS (SEQ ID NO: 26)
LC-CDR2: ATA (SEQ ID NO: 27)
LC-CDR3: QQYASSPPT;
or (SEQ ID NO: 28)
LC-CDR1: ESVEYSGTTL (SEQ ID NO: 23)
LC-CDR2: GAS (SEQ ID NO: 29)
LC-CDR3: QQSRKVPYT;
or (SEQ ID NO: 30)
LC-CDR1: QSLLYGSNQKNY (SEQ ID NO: 31)
LC-CDR2: WAS (SEQ ID NO: 32)
LC-CDR3: QQYYSYPRT;
or (SEQ ID NO: 19)
LC-CDR1: QSLVHSNGNTY (SEQ ID NO: 20)
LC-CDR2: KVS (SEQ ID NO: 21)
LC-CDR3: SQSTHVPLT;
or (SEQ ID NO: 33)
LC-CDR1: QSISNN (SEQ ID NO: 34)
LC-CDR2: YAS (SEQ ID NO: 35)
LC-CDR3: QQRYSWPLT;
or (SEQ ID NO: 36)
LC-CDR1: QEISAY (SEQ ID NO: 37)
LC-CDR2: STS (SEQ ID NO: 38)
LC-CDR3: LQYASSPLT;
or (SEQ ID NO: 39)
LC-CDR1: QNVGSN (SEQ ID NO: 40)
LC-CDR2: SAS (SEQ ID NO: 41)
LC-CDR3: QQYNSYPLT.
```

In another aspect, the present invention provides an antibody or antigen binding fragment, optionally isolated, which is capable of binding to IL-11Rα, comprising a light chain and a heavy chain variable region sequence, wherein:
the light chain comprises a LC-CDR1, LC-CDR2, LC-CDR3, having at least 85% overall sequence identity to LC-CDR: one of $QX_1X_2X_3X_4X_5$ (SEQ ID NO:69), $QSLX_6X_7X_8SNX_9X_{10}X_{11}Y$ (SEQ ID NO:70), ENVGTY (SEQ ID NO:22), or ESVEYSGTTL (SEQ ID NO:28); LC-CDR2: one of $X_{12}AS$ (SEQ ID NO:71), $X_{13}X_{14}S$ (SEQ ID NO:72), or ATA (SEQ ID NO:26); LC-CDR3: $X_{15}QX_{16}X_{17}X_{18}X_{19}PX_{20}T$ (SEQ ID NO:73); and
the heavy chain comprises a HC-CDR1, HC-CDR2, HC-CDR3, having at least 85% overall sequence identity to HC-CDR1: one of $GYTFTX_{21}YW$ (SEQ ID NO:74), $GFTFX_{22}X_{23}X_{24}X_{25}$ (SEQ ID NO:75), $GYX_{26}X_{27}X_{28}X_{29}DYY$ (SEQ ID NO:76), or GFSLT-SFS (SEQ ID NO:66); HC-CDR2: one of $IX_{30}X_{31}X_{32}X_{33}GX_{34}T$ (SEQ ID NO:77), $IFPGX_{35}X_{36}X_{37}T$ (SEQ ID NO:78), ISYDSSN (SEQ ID NO:55), IGPSDSKT (SEQ ID NO:61), or IWTGGGT (SEQ ID NO:67); HC-CDR3: one of $ARGX_{38}X_{39}X_{40}X_{41}X_{42}X_{43}X_{44}X_{45}X_{46}FX_{47}Y$ (SEQ ID NO:79), ASVGYYYVSDWYFDV (SEQ ID NO:56), ARHWAY (SEQ ID NO:50), AHGLLFAH (SEQ ID NO:53), RSDGTYEGYFDY (SEQ ID NO:44), ARNSNYPSGFAY (SEQ ID NO:68), or ARRSTTIRFGAMDN (SEQ ID NO:65);
wherein $X_1$=N, S, E or D, $X_2$=I or V, $X_3$=G or S, $X_4$=S, N or A, $X_5$=N, Y or S, $X_6$=Absent or L, $X_7$=V or Y, $X_8$=H or G, $X_9$=G or Q, $X_{10}$=N or K, $X_{11}$=T or N, $X_{12}$=G, W, Y or S, $X_{13}$=S or K, $X_{14}$=T or V, $X_{15}$=Q, S, G or L, $X_{16}$=Y, S, G or R, $X_{17}$=Y, A, T, N or R, $X_{18}$=S, H or K, $X_{19}$=V, Y, S or W, $X_{20}$=L, Y, R or P, $X_{21}$=S, N or D, $X_{22}$=S or T, $X_{23}$=T or N, $X_{24}$=S, Y or N, $X_{25}$=Y, A or W, $X_{26}$=S or N, $X_{27}$=I or F, $X_{28}$=T or N, $X_{29}$=Absent or S, $X_{30}$=H, K or Y, $X_{31}$=P, S or A, $X_{32}$=N or G, $X_{33}$=S, G or T, $X_{34}$=S, I or Y, $X_{35}$=R or G, $X_{36}$=I or D, $X_{37}$=I or Y, $X_{38}$=Absent, D or G, $X_{39}$=Absent or Y, $X_{40}$=V or D, $X_{41}$=G or L, $X_{42}$=Absent, E or S, $X_{43}$=Absent or Y, $X_{44}$=Absent or G, $X_{45}$=Absent or P, $X_{46}$=Absent or W, $X_{47}$=D, T or A.

In another aspect, the present invention provides an antibody or antigen binding fragment, optionally isolated, which is capable of binding to IL-11Rα, comprising a light chain and a heavy chain variable region sequence, wherein:
the light chain sequence has at least 85% sequence identity to the light chain sequence of one of SEQ ID NOs:1 to 9, and;
the heavy chain sequence has at least 85% sequence identity to the heavy chain sequence of one of SEQ ID NOs:10 to 18.

In some embodiments in accordance with the various aspects of the present invention, the antibody or antigen binding fragment is capable of inhibiting IL-11 trans signalling.

In some embodiments, the antibody or antigen binding fragment is conjugated to a drug moiety or a detectable moiety.

In another aspect, the present invention provides a complex, optionally in vitro and/or optionally isolated, comprising an antibody or antigen binding fragment according to the present invention bound to IL-11Rα.

In another aspect, the present invention provides a composition comprising the antibody or antigen binding fragment according to the present invention, and at least one pharmaceutically-acceptable carrier.

In another aspect, the present invention provides an isolated nucleic acid encoding the antibody or antigen binding fragment according to the present invention.

In another aspect, the present invention provides a vector comprising the nucleic acid according to the present invention.

In another aspect, the present invention provides a host cell comprising the vector according to the present invention.

In another aspect, the present invention provides a method for making an antibody or antigen binding fragment according to the present invention, comprising culturing the host cell according to the present invention under conditions suitable for the expression of the antibody or antigen binding fragment, and recovering the antibody or antigen binding fragment.

In another aspect, the present invention provides an antibody, antigen binding fragment or composition according to the present invention for use in therapy, or in a method of medical treatment.

In another aspect, the present invention provides an antibody, antigen binding fragment or composition according to the present invention for use in the treatment or prevention of fibrosis, or a disease/disorder characterised by fibrosis.

In another aspect, the present invention provides an antibody, antigen binding fragment or composition according to the present invention for use in the treatment of a cancer.

In another aspect, the present invention provides the use of an antibody, antigen binding fragment or composition according to the present invention in the manufacture of a medicament for use in the treatment or prevention of fibrosis or a disease/disorder characterised by fibrosis.

In another aspect, the present invention provides the use of an antibody, antigen binding fragment or composition according to the present invention in the manufacture of a medicament for use in the treatment or prevention of a cancer.

In another aspect, the present invention provides a method of treating fibrosis comprising administering an antibody, antigen binding fragment or composition according to the present invention to a subject suffering from fibrosis or a disease/disorder characterised by fibrosis.

In another aspect, the present invention provides a method of treating cancer comprising administering an antibody, antigen binding fragment or composition according to the present invention to a subject suffering from a cancer.

In another aspect, the present invention provides an antibody or antigen binding fragment for use in a method of treating a disease in which IL-11/IL-11R signalling is implicated in the pathology of the disease, wherein the antibody or antigen binding fragment is capable of inhibiting IL-11 trans signalling.

In another aspect, the present invention provides the use of an antibody or antigen binding fragment in the manufacture of a medicament for use in the treatment of a disease in which IL-11/IL-11R signalling is implicated in the pathology of the disease, wherein the antibody or antigen binding fragment is capable of inhibiting IL-11 trans signalling.

In another aspect, the present invention provides a method of treating a disease in which IL-11/IL-11R signalling is implicated in the pathology of the disease, comprising administering an antibody or antigen binding fragment to a subject suffering from the disease, wherein the antibody or antigen binding fragment is capable of inhibiting IL-11 trans signalling.

In another aspect, the present invention provides a method comprising contacting a sample containing, or suspected to contain, IL-11Rα with an antibody or antigen binding fragment according to the present invention and detecting the formation of a complex of the antibody or antigen binding fragment with IL-11Rα.

In another aspect, the present invention provides a method of diagnosing a disease or condition in a subject, the method comprising contacting, in vitro, a sample from the subject with an antibody or antigen binding fragment according to the present invention and detecting the formation of a complex of the antibody or antigen binding fragment with IL-11Rα.

In another aspect, the present invention provides a method of selecting or stratifying a subject for treatment with an IL-11Rα-targeted agent, the method comprising contacting, in vitro, a sample from the subject with the antibody or antigen binding fragment according to the present invention and detecting the formation of a complex of the antibody or antigen binding fragment with IL-11Rα.

In another aspect, the present invention provides the use of an antibody or antigen binding fragment according to the present invention for the detection of IL-11Rα in vitro or in vivo.

In another aspect, the present invention provides the use of an antibody or antigen binding fragment according to the present invention as an in vitro or in vivo diagnostic or prognostic agent.

DESCRIPTION

The present invention relates to antibodies with specificity for interleukin-11 receptor alpha (IL-11Rα). The present disclosure describes the identification of IL-11/IL-11R signalling as a key mediator of fibrosis, and the generation and functional characterisation of anti-IL-11Rα antibodies. Therapeutic and diagnostic uses of the antibodies is also described.

IL-11 and IL-11/IL-11R Mediated Signalling

The antibodies and fragments of the present invention bind to interleukin 11 receptor alpha (IL-11Rα).

Interleukin 11 (IL-11), also known as adipogenesis inhibitory factor, is a pleiotropic cytokine and a member of the IL-6 family of cytokines that includes IL-6, IL-11, IL-27, IL-31, oncostatin M (OSM), leukemia inhibitory factor (LIF), cardiotrophin-1 (CT-1), cardiotrophin-like cytokine (CLC), ciliary neurotrophic factor (CNTF) and neuropoetin (NP-1).

IL-11 is transcribed with a canonical signal peptide that ensures efficient secretion from cells. The immature form of human IL-11 is a 199 amino acid polypeptide whereas the mature form of IL-11 encodes a protein of 178 amino acid residues (Garbers and Scheller., Biol. Chem. 2013; 394(9): 1145-1161). The human IL-11 amino acid sequence is available under UniProt accession no. P20809 (P20809.1 GI:124294). Recombinant human IL-11 (oprelvekin) is also commercially available. IL-11 from other species, including mouse, rat, pig, cow, several species of bony fish and primates, have also been cloned and sequenced.

In this specification "IL-11" refers to an IL-11 from any species and includes isoforms, fragments, variants or homologues of an IL-11 from any species. Similarly, in this specification "IL-11Rα" refers to an IL-11Rα from any species and includes isoforms, fragments, variants or homologues of an IL-11Rα from any species.

IL-11 signals through a homodimer of the ubiquitously expressed β-receptor glycoprotein 130 (gp130; also known as glycoprotein 130, IL-6ST, IL-6-beta or CD130). Gp130 is a transmembrane protein that forms one subunit of the type I cytokine receptor with the IL-6 receptor family. Specificity is gained through an individual IL-11 α-receptor (IL-11Rα), which does not directly participate in signal transduction, although the initial cytokine binding event to the α-receptor leads to the final complex formation with the β-receptors. IL-11 activates a downstream signalling pathway, which is predominantly the mitogen-activated protein kinase (MAPK)-cascade and the Janus kinase/signal transducer and activator of transcription (Jak/STAT) pathway (Garbers and Scheller, supra).

Human IL-11Rα is a 422 amino acid polypeptide (Genbank accession no. NP_001136256.1 GI:218505839; UniProt Q14626) and shares 85% nucleotide and amino acid sequence identity with the murine IL-11Rα (Du and Williams., Blood Vol, 89, No, 11, Jun. 1, 1997). Two isoforms of IL-11Rα have been reported, which differ in the cytoplasmic domain (Du and Williams, supra). In some embodiments as used herein, the IL-11Rα may be IL-11Rα isoform 1 or IL-11Rα isoform 2.

The IL-11 receptor α-chain (IL-11Rα) shares many structural and functional similarities with the IL-6 receptor α-chain (IL-6Rα). The extracellular domain shows 24% amino acid identity including the characteristic conserved Trp-Ser-X-Trp-Ser (WSXWS) motif. The short cytoplasmic domain (34 amino acids) lacks the Box 1 and 2 regions that are required for activation of the JAK/STAT signalling pathway.

IL-11Rα binds its ligand with a low affinity (Kd ~10 nmol/L) and alone is insufficient to transduce a biological signal. The generation of a high affinity receptor (Kd ~400 to 800 pmol/L) capable of signal transduction requires co-expression of the IL-11Rα and gp130 (Curtis et al (Blood 1997 Dec. 1; 90 (11):4403-12; Hilton et al., EMBO J 13:4765, 1994; Nandurkar et al., Oncogene 12:585, 1996). Binding of IL-11 to cell-surface IL-11Rα induces heterodimerization, tyrosine phosphorylation, activation of gp130 and MAPK and/or Jak/STAT signalling as described above.

The receptor binding sites on murine IL-11 have been mapped and three sites—sites I, II and III—identified. Binding to gp130 is reduced by substitutions in the site II region and by substitutions in the site III region. Site III mutants show no detectable agonist activity and have IL-11Rα antagonist activity (Cytokine Inhibitors Chapter 8; edited by Gennaro Ciliberto and Rocco Savino, Marcel Dekker, Inc. 2001).

In principle, a soluble IL-11Rα can also form biologically active soluble complexes with IL-11 (Pflanz et al., 1999 FEBS Lett, 450, 117-122) raising the possibility that, similar to IL-6, IL-11 may in some instances bind soluble IL-11Rα prior to binding cell-surface gp130 (Garbers and Scheller, supra). Curtis et al (Blood 1997 Dec. 1; 90 (11):4403-12) describe expression of a soluble murine IL-11 receptor alpha chain (sIL-11Rα) and examined signalling in cells expressing gp130. In the presence of gp130 but not transmembrane IL-11R the sIL-11R mediated IL-11 dependent differentiation of M1 leukemic cells and proliferation in Ba/F3 cells and early intracellular events including phosphorylation of gp130, STAT3 and SHP2 similar to signalling through transmembrane IL-11R.

As used herein, 'IL-11/IL-11R signalling' refers to signalling mediated by IL-11 and/or IL-11Rα, fragments of IL-11 and/or IL-11Rα and polypeptide complexes comprising IL-11, IL-11Rα and/or fragments thereof. IL-11/IL-11R signalling involves binding of IL-11 and/or IL-11Rα to gp130, and consequent activation of signalling through gp130.

Activation of signalling through cell-membrane bound gp130 by IL-11 bound to soluble IL-11Rα has recently been demonstrated (Lokau et al., 2016 Cell Reports 14, 1761-1773). This so-called IL-11 trans signalling may be a very important component of IL-11/IL-11R signalling, and may even be the most common form of IL-11/IL-11R signalling, because whilst the expression of IL-11Rα is restricted to a relatively small subset of cell types, gp130 is expressed on a wide range of cell types.

As used herein, 'IL-11 trans signalling' is used to refer to signalling which is triggered by binding of IL-11 bound to IL-11Rα, to gp130. The IL-11 may be bound to IL-11Rα as a non-covalent complex. The gp130 is membrane-bound and expressed by the cell in which signalling occurs following binding of the IL-11:IL-11Rα complex to gp130. In some embodiments the IL-11Rα may be a soluble IL-11Rα. In some embodiments, the soluble IL-11Rα is a soluble (secreted) isoform of IL-11Rα (e.g. lacking a transmembrane domain). In some embodiments, the soluble IL-11Rα is the liberated product of proteolytic cleavage of the extracellular domain of cell membrane bound IL-11Rα. In some embodiments, the IL-11Rα may be cell membrane-bound, and signalling through gp130 may be triggered by binding of IL-11 bound to cell-membrane-bound IL-11Rα.

In this specification an IL-11 receptor (IL-11R) refers to a polypeptide capable of binding IL-11 and inducing signal transduction in cells expressing gp130. An IL-11 receptor may be from any species and includes isoforms, fragments, variants or homologues of an IL-11 receptor from any species. In preferred embodiments the species is human (*Homo sapiens*). In some embodiments the IL-11 receptor may be IL-11Rα. Isoforms, fragments, variants or homologues of an IL-11Rα may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of IL-11Rα from a given species, e.g. human. Isoforms, fragments, variants or homologues of an IL-11Rα may optionally be characterised by ability to bind IL-11 (preferably from the same species) and stimulate signal transduction in cells expressing IL-11Rα and gp130 (e.g. as described in Curtis et al. Blood, 1997, 90(11) or Karpovich et al. Mol. Hum. Reprod. 2003 9(2): 75-80). A fragment of an IL-11 receptor may be of any length (by number of amino acids), although may optionally be at least 25% of the length of the mature IL-11Rα and have a maximum length of one of 50%, 75%, 80%, 85%, 90%, 91%, 92%, 93%, 94%, 95%, 96%, 97%, 98%, or 99% of the length of the mature IL-11Rα. A fragment of an IL-11 receptor fragment may have a minimum length of 10 amino acids, and a maximum length of one of 15, 20, 25, 30, 40, 50, 100, 110, 120, 130, 140, 150, 160, 170, 180, 190, 200, 250, 300, 400, or 415 amino acids.

In some embodiments, the IL-11Rα may comprise, or consist of, the extracellular domain of IL-11Rα, which corresponds to amino acids 24 to 370 of the amino acid sequence of UniProt Q14626. In some embodiments, the IL-11Rα may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of the extracellular domain of IL-11Rα from a given species.

In some embodiments, the IL-11 is mammalian IL-11 (e.g. cynomolgous, human and/or rodent (e.g. rat and/or murine) IL-11). Isoforms, fragments, variants or homologues of an IL-11 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of immature or mature IL-11 from a given species, e.g. human. Isoforms, fragments, variants or homologues of an IL-11 may optionally be characterised by ability to bind IL-11Rα (preferably from the same species) and stimulate signal transduction in cells expressing IL-11Rα and gp130 (e.g. as described in Curtis et al. Blood, 1997, 90(11); or Karpovich et al. Mol. Hum. Reprod. 2003 9(2): 75-80). A fragment of IL-11 may be of any length (by number of amino acids), although may optionally be at least 25% of the length of mature IL-11 and may have a maximum length of one of 50%, 75%, 80%, 85%, 90%, 91%, 92%, 93%, 94%, 95%, 96%, 97%, 98%, or 99% of the length of mature IL-11. A fragment of IL-11 may have a minimum length of 10 amino acids, and a maximum length of one of 15, 20, 25, 30, 40, 50, 100, 110, 120, 130, 140, 150, 160, 170, 180, 190 or 195 amino acids IL-11 has been proposed to function mainly as a thrombopoietic growth factor, which underpinned the use of recombinant IL-11 (Neumega (Oprelvekin)) as a therapeutic agent to increase platelet count. TGFβ1 has been shown to induce IL-11 expression in fibroblasts (Elias et al., 1994 J. Immunol. 152, 2421-2429).

The role of IL-11/IL-11R signalling in fibrosis is not clear. The majority of studies suggest an anti-fibrotic function for IL-11/IL-11R signalling in the heart (Obana et al., 2010 Circulation 121, 684-691; Obana et al., 2012 Heart and Circulatory Physiology 303, H569-77) and kidney (Ham et al., 2013 Anesthesiology 119, 1389-1401; Stangou et al., 2011 J. Nephrol. 24, 106-111). Kurahara et al., J. Smooth Muscle Res. 2016; 52: 78-92 describes IL-11 as an anti-fibrotic cytokine, and suggests that IL-11/IL-11R signalling supresses αSMA expression.

IL-11 has also been suggested to be an anti-inflammatory factor in several tissues and chronic inflammatory diseases (Trepicchio and Dorner, 1998 Expert Opin Investig Drugs 7, 1501-1504; Zhu et al., 2015 PLoS ONE 10, e0126296). These studies suggest that the observed secretion of IL-11 in response to TGFβ1 is a protective mechanism.

On the other hand, it has been suggested that IL-11/IL-11R signalling may be involved in pathology of diseases of the lung. Inhibition of IL-11/IL-11R signalling either via antibodies or a mutated recombinant IL-11 in a model of tuberculosis revealed a positive feedback loop in vivo and diminished histopathology of the lung (Kapina et al., 2011 PLoS ONE 6, e21878; Shepelkova et al., 2016 Journal of Infectious Diseases 214, jiw176), fibrosis of the murine airway has been associated with IL-11 expression (Tang et al., 1996 The Journal of Clinical Investigation 98, 2845-2853). When the pro-fibrotic function of IL-13 in lung tissue was investigated in IL-11RA-/- mice, IL-11/IL-11R signalling was implicated in the mechanism (Chen et al., 2005 J. Immunol. 174, 2305-2313).

IL-11 was also found to be elevated in the airway of patients with severe asthma (Minshall et al., 2000 Respiratory Research 14, 1-14), is overexpressed in the lungs of IPF patients (Lindahl et al., 2013 Respiratory Research 14, 1-14) and is elevated in skin lesions in atopic dermatitis patients (Toda et al., 2003 J Allergy Clin Immun 111, 875-881). It is uncertain whether these associations are due to increased IL-11 gene/protein expression as a response to disease processes, or whether IL-11 is an effector of disease processes.

Antibodies and Antigen-Binding Fragments

Antibodies and antigen-binding fragments according to the present invention bind to IL-11Rα (interleukin 11 receptor alpha). In some embodiments, the antibody/fragment binds to human IL-11Rα. In some embodiments, the antibody/fragment binds to non-human primate IL-11Rα. In some embodiments, the antibody/fragment binds to murine IL-11Rα.

By "antibody" we include fragments and derivatives thereof, or a synthetic antibody or synthetic antibody fragment. As used herein, an antibody is a polypeptide capable of binding specifically to the relevant target molecule (i.e. the antigen for which the antibody is specific). Antibodies according to the present invention may be provided in isolated form.

In view of contemporary techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimeric antibodies are discussed by Neuberger et al (1988, 8th International Biotechnology Symposium Part 2, 792-799).

Monoclonal antibodies (mAbs) are useful in the methods of the invention and are a homogenous population of antibodies specifically targeting a single epitope on an antigen.

Antigen binding fragments of antibodies, such as Fab and Fab2 fragments may also be used/provided as can genetically engineered antibodies and antibody fragments. The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parent antibody (Morrison et al (1984) Proc. Natl. Acad. Sd. USA 81, 6851-6855).

In some embodiments, the antibody/fragment is a fully human antibody/fragment. A fully human antibody/fragment is encoded by human nucleic acid sequence(s). Fully human antibodies/fragments are devoid of non-human amino acid sequences.

The two most commonly employed techniques to the production of fully human antibodies are (i) phage display, in which human antibody genes are expressed in phage display libraries, and (ii) production of antibodies in transgenic mice engineered to have human antibody genes (described in Park and Smolen Advances in Protein Chemistry (2001) 56: 369-421). Briefly, in the human antibody gene-phage display technique, genes encoding the VH and VL chains are generated by PCR amplification and cloning from "naive" human lymphocytes, and assembled into a library from which they can be expressed either as disulfide-linked Fab fragments or as single-chain Fv (scFv) fragments. The Fab- or scFv-encoding genes are fused to a surface coat protein of filamentous bacteriophage and Fab or scFv capable of binding to the target of interest can then be identified by screening the library with antigen. Molecular evolution or affinity maturation procedures can be employed to enhance the affinity of the Fab/scFv fragment. In the transgenic mouse technique, mice in which the endogenous murine Ig gene loci have been replaced by homologous recombination with their human homologues are immunized with antigen, and monoclonal antibody is prepared by conventional hybridoma technology, to yield fully human monoclonal antibody.

The antibody/fragment may be prepared by phage display using a human naïve antibody gene library.

In some embodiments, the antibody/fragment according to the present invention is a murine antibody/fragment. In some embodiments, the antibody/fragment is a mouse/human chimeric antibody/fragment (e.g., an antibody/antigen binding fragment comprising murine variable domains and human constant regions). In some embodiments, the antibody/fragment is a humanised antibody/fragment (e.g., an antibody/antigen binding fragment comprising murine CDRs and human framework and constant regions).

A mouse/human chimeric antibody/antigen binding fragment can be prepared from a mouse monoclonal antibody by the process of chimerisation, e.g. as described in Human Monoclonal Antibodies: Methods and Protocols, Michael Steinitz (Editor), Methods in Molecular Biology 1060, Springer Protocols, Humana Press (2014), in Chapter 8 thereof, in particular section 3 of Chapter 8.

A humanised antibody/antigen binding fragment can be prepared from a mouse antibody by the process of chimerisation, e.g. as described in Human Monoclonal Antibodies: Methods and Protocols, Michael Steinitz (Editor), Methods in Molecular Biology 1060, Springer Protocols, Humana Press (2014), in Chapter 7 thereof, in particular section 3.1 of Chapter 7 entitled 'Antibody Humanization'.

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sd. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are covalently linked, e.g. by a flexible oligopeptide.

Fab, Fv, ScFv and dAb antibody fragments can all be expressed in and secreted from E. coli, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site.

The present invention provides an antibody or antigen binding fragment which is capable of binding to IL-11Rα. In some embodiments, the antibody or antigen binding fragment may be isolated.

An antigen-binding fragment according to the present invention may be any fragment of a polypeptide which is capable of binding to an antigen.

In some embodiments, an antigen binding fragment comprises at least three light chain CDRs (i.e. LC-CDR1, LC-CDR2 and LC-CDR3; also referred to herein as LC-CDRs 1-3) and three heavy chain CDRs (i.e. HC-CDR1, HC-CDR2 and HC-CDR3; also referred to herein as HC-CDRs 1-3) which together define the antigen binding region of an antibody or antigen binding fragment. In some embodiments, an antigen binding fragment may comprise the light chain variable domain and heavy chain variable domain of an antibody or antigen binding fragment. In some embodiments, an antigen binding fragment may comprise the light chain polypeptide and heavy chain polypeptide of an antibody or antigen binding fragment.

The present invention also provides a chimeric antigen receptor (CAR) capable of binding to IL-11Rα, comprising one or more antigen binding fragments or polypeptides according to the present invention. Chimeric Antigen Receptors (CARs) are recombinant receptors that provide both antigen-binding and T cell activating functions. CAR structure and engineering is reviewed, for example, in Dotti et al., Immunol Rev (2014) 257(1), hereby incorporated by reference in its entirety. Antigen-binding fragments according to the present invention are provided herein as the antigen-binding domain of a chimeric antigen receptor (CAR). In some embodiments, the CAR comprises a VL domain and a VH domain according to any embodiment of an antibody, antigen binding fragment or polypeptide described herein. CARs may be combined with costimulatory ligands, chimeric costimulatory receptors or cytokines to further enhance T cell potency, specificity and safety (Sadelain et al., The basic principles of chimeric antigen receptor (CAR) design. Cancer Discov. 2013 April; 3(4): 388-398. doi:1 0.1158/2159-8290.CD-12-0548, specifically incorporated herein by reference). Also provided is a cell comprising a CAR according to the invention. The CAR according to the present invention may be used to generate T cells. Engineering of CARs into T cells may be performed during culture, in vitro, for transduction and expansion, such as happens during expansion of T cells for adoptive T cell therapy.

Also provided in the present invention are bispecific antibodies and bispecific antigen binding fragments comprising an antibody or antigen binding fragment according to the present invention. The bispecific antibodies or bispecific antigen binding fragments may comprise (i) an antibody or antigen binding fragment according to the present invention, and (ii) an antibody or antigen binding fragment specific for a target other than IL-11Rα.

Bispecific antibodies/fragments may be provided in any suitable format, such as those formats described in Kontermann MAbs 2012, 4(2): 182-197, which is hereby incorporated by reference in its entirety. For example, a bispecific antibody or bispecific antigen binding fragment may be a bispecific antibody conjugate (e.g. an IgG2, F(ab')$_2$ or CovX-Body), a bispecific IgG or IgG-like molecule (e.g. an IgG, scFv$_4$-Ig, IgG-scFv, scFv-IgG, DVD-Ig, IgG-sVD, sVD-IgG, 2 in 1-IgG, mAb$^2$, or Tandemab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (Db), dsDb, DART, scDb, tandAbs, tandem scFv (taFv), tandem dAb/VHH, triple body, triple head, Fab-scFv, or F(ab')$_2$-scFv$_2$), a bispecific Fc and $C_H^3$ fusion protein (e.g. a taFv-Fc, Di-diabody, scDb-$C_H$3, scFv-Fc-scFv, HCAb-VHH, scFv-kih-Fc, or scFv-kih-$C_H$3), or a bispecific fusion protein (e.g. a scFv$_2$-albumin, scDb-albumin, taFv-toxin, DNL-Fab$_3$, DNL-Fab$_4$-IgG, DNL-Fab$_4$-IgG-cytokine$_2$). See in particular FIG. 2 of Kontermann MAbs 2012, 4(2): 182-19.

Methods for producing bispecific antibodies include chemically crosslinking of antibodies or antibody fragments, e.g. with reducible disulphide or non-reducible thioether bonds, for example as described in Segal and Bast, 2001. Production of Bispecific Antibodies. Current Protocols in Immunology. 14:IV:2.13:2.13.1-2.13.16, which is hereby incorporated by reference in its entirety. For example, N-succinimidyl-3-(−2-pyridyldithio)-propionate (SPDP) can be used to chemically crosslink e.g. Fab fragments via hinge region SH-groups, to create disulfide-linked bispecific F(ab)$_2$ heterodimers. Other methods include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16. Bispecific antibodies and bispecific antigen binding fragments can also be produced recombinantly, by expression from e.g. a nucleic acid construct encoding polypeptides for the antigen binding molecules, for example as described in Antibody Engineering: Methods and Protocols, Second Edition (Humana Press, 2012), at Chapter 40: Production of Bispecific Antibodies: Diabodies and Tandem scFv (Hornig and Farber-Schwarz), or French, How to make bispecific antibodies, Methods Mol. Med. 2000; 40:333-339, the entire contents of both of which are hereby incorporated by reference.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., *Rio/Technology* 10:779-783 (1992); Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):331 0-15 9 (1995); and Hawkins et al, *J. Mol. Biol.* 226:889-896 (1992).

The present invention provides antibodies described herein which have further undergone the process of chain shuffling, e.g. light chain shuffling and/or heavy chain shuffling. Chain shuffling to improve antibody affinity is described in detail in Marks, Antibody Affinity Maturation by Chain Shuffling, Antibody Engineering Methods and Protocols, Humana Press (2004) Vol. 248, pp 327-343, which is hereby incorporated by reference in its entirety—in particular, light chain shuffling is described in detail at sections 3.1 and 3.2 thereof. In light chain shuffling, heavy chain variable regions of antibodies are combined with a repertoire of light chain variable region partners to identify new VL/VH combinations having high affinity for the target protein of interest.

In some aspects, the antibody/fragment of the present invention comprises the CDRs (i.e. CDRs 1-3) of the VH and/or VL domains of an IL-11Rα-binding antibody clone described herein, or a variant thereof. In some embodiments, the antibody/fragment of the present invention comprises HC-CDRs 1-3 of an IL-11Rα-binding antibody clone described herein, or a variant thereof. In some embodiments, the antibody/fragment of the present invention comprises LC-CDRs 1-3 of an IL-11Rα-binding antibody clone described herein, or a variant thereof.

HC-CDRs 1-3 and LC-CDRs 1-3 of the antibody clones of the present disclosure are defined according to VBASE2, as described in Retter et al., Nucl. Acids Res. (2005) 33 (suppl 1): D671-D674, which is hereby incorporated by reference in its entirety.

As used herein, a variant of a CDR may comprise e.g. 1 or 2 or 3 substitutions in the amino acid sequence of the CDR. As used herein, a variant of a VL or VH domain may comprise e.g. 1, 2, 3, 4, 5, 6, 7, 8, 9 or 10 substitutions in the amino acid sequence of the domain.

In some embodiments, the antibody/fragment of the present invention comprises HC-CDRs 1-3 of an IL-11Rα-binding antibody clone described herein, or a variant thereof, and LC-CDRs 1-3 of an IL-11Rα-binding antibody clone described herein, or a variant thereof.

In some aspects, the antibody/fragment of the present invention comprises the CDRs of the VH and/or VL domains of an IL-11Rα-binding antibody clone described herein, or a variant thereof. In some aspects, the antibody/fragment of the present invention comprises the VH and/or VL domains of an IL-11Rα-binding antibody clone described herein, or a variant thereof.

In some aspects, the antibody/fragment of the present invention comprises the CDRs of the VH and/or VL domains of a clone, or a variant thereof, selected from BSO-1E3_1, BSO-1E3_2, BSO-2E5, BSO-4G3, BSO-5E5, BSO-7G9, BSO-9A7, BSO-10D11 and BSO-13B10; e.g. selected from BSO-2E5, BSO-4G3, BSO-5E5, BSO-7G9, BSO-9A7, BSO-10D11 and BSO-13B10; e.g. selected from BSO-1E3_1, BSO-1E3_2, BSO-5E5, BSO-9A7 and BSO-13B10; e.g. selected from BSO-2C1, BSO-5E5, BSO-9A7 and BSO-13B10; e.g. selected from BSO-5E5 and BSO-13B10; e.g. selected from BSO-2C1 and BSO-9A7.

In some aspects, the antibody/fragment of the present invention comprises the VH and/or VL domains of a clone, or a variant thereof, selected from BSO-1E3_1, BSO-1E3_2, BSO-2E5, BSO-4G3, BSO-5E5, BSO-7G9, BSO-9A7, BSO-10D11 and BSO-13B10; e.g. selected from BSO-2E5, BSO-4G3, BSO-5E5, BSO-7G9, BSO-9A7, BSO-10D11 and BSO-13B10; e.g. selected from BSO-1E3_1, BSO-1E3_2, BSO-5E5, BSO-9A7 and BSO-13B10; e.g. selected from BSO-2C1, BSO-5E5, BSO-9A7 and BSO-13B10; e.g. selected from BSO-5E5 and BSO-13B10; e.g. selected from BSO-2C1 and BSO-9A7.

In some aspects, the antibody/fragment of the present invention comprises HC-CDRs 1-3 of the VH domain of an IL-11Rα-binding antibody clone described herein, or a variant thereof. In some aspects, the antibody/fragment of the present invention comprises the VH domain of a clone, or a variant thereof.

In some aspects, the antibody/fragment of the present invention comprises LC-CDRs 1-3 of the VL domain of an IL-11Rα-binding antibody clone described herein, or a variant thereof. In some aspects, the antibody/fragment of the present invention comprises the VL domain of a clone, or a variant thereof.

In some embodiments the antibody/fragment of the present invention comprises HC-CDRs 1-3 of the VH domain, or the VH domain, of an IL-11Rα-binding antibody clone selected from BSO-1E3_1, BSO-1E3_2, BSO-2E5, BSO-4G3, BSO-5E5, BSO-7G9, BSO-9A7, BSO-10D11 and BSO-13B10; e.g. selected from BSO-2E5, BSO-4G3, BSO-5E5, BSO-7G9, BSO-9A7, BSO-10D11 and BSO-13B10; or selected from BSO-1E3_1, BSO-1E3_2, BSO-5E5 and BSO-9A7 and BSO-13B10; or selected from BSO-2C1, BSO-5E5, BSO-9A7 and BSO-13B10; or selected from BSO-5E5 and BSO-13B10; or selected from BSO-2C1 and BSO-9A7.

In some embodiments, the antibody/fragment comprises a VL domain which is arrived at following light chain shuffling.

In some embodiments the antibody/fragment of the present invention comprises LC-CDRs 1-3 of the VL domain, or the VL domain, of an IL-11Rα-binding antibody clone selected from BSO-1E3_1, BSO-1E3_2, BSO-2E5, BSO-4G3, BSO-5E5, BSO-7G9, BSO-9A7, BSO-10D11 and BSO-13B10; e.g. selected from BSO-2E5, BSO-4G3, BSO-5E5, BSO-7G9, BSO-9A7, BSO-10D11 and BSO-13B10; or selected from BSO-1E3_1, BSO-1E3_2, BSO-5E5, BSO-9A7 and BSO-13B10; or selected from BSO-2C1, BSO-5E5, BSO-9A7 and BSO-13B10; or selected from BSO-5E5 and BSO-13B10; or selected from BSO-2C1 and BSO-9A7. In some embodiments, the antibody/fragment comprises a VH domain which is arrived at following heavy chain shuffling.

The amino acid sequences of the VL domains of the anti-human IL-11Rα-binding antibody clones BSO-1E3_1, BSO-1E3_2, BSO-2E5, BSO-4G3, BSO-5E5, BSO-7G9, BSO-9A7, BSO-10D11 and BSO-13B10 are shown in FIG. 16, as are the LC-CDRs 1-3, defined using VBASE2 (described in Retter et al., Nucl. Acids Res. (2005) 33 (suppl 1): D671-D674). The amino acid sequences of the VH domains for these anti-human IL-11Rα-binding antibody clones are shown in FIG. 17, as are the HC-CDRs 1-3, defined using VBASE2.

Antibodies according to the present invention may comprise VL and/or VH chains comprising an amino acid sequence that has a high percentage sequence identity to one or more of the VL and/or VH amino acid sequences described herein. For example, antibodies according to the present invention include antibodies that bind IL-11Rα and have a VL chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the VL chain amino acid sequence of one of SEQ ID NOs:1 to 9. Antibodies according to the present invention include antibodies that bind IL-11Rα and have VH chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the VH chain amino acid sequence of one of SEQ ID NOs:10 to 18.

Antibodies according to the present invention may comprise VL and/or VH chains encoded by a nucleic acid sequence that has a high percentage sequence identity to one or more of the VL and/or VH nucleic acid sequences described herein, or nucleic acid sequence encoding the same amino acid sequence as a result of codon degeneracy. For example, antibodies according to the present invention include antibodies that bind IL-11Rα and have a VL chain encoded by a nucleic acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the VL chain nucleic acid sequence of one of SEQ ID NOs:80 to 88 or nucleic acid sequence encoding the same amino acid sequence as one of SEQ ID NOs:80 to 88 as a result of codon degeneracy. Antibodies according to the present invention include antibodies that bind IL-11Rα and have a VH chain encoded by a nucleic acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the VH chain nucleic acid sequence of one of SEQ ID NOs:89 to 97 or nucleic acid sequence encoding the same amino acid sequence as one of SEQ ID NOs:89 to 97 as a result of codon degeneracy.

The light and heavy chain CDRs disclosed herein may also be particularly useful in conjunction with a number of different framework regions. Accordingly, light and/or heavy chains having LC-CDR1-3 or HC-CDR1-3 may possess an alternative framework region. Suitable framework regions are well known in the art and are described for example in M. Lefranc & G. Le:franc (2001) "The Immunoglobulin FactsBook", Academic Press, incorporated herein by reference.

Antibodies according to the present invention may be detectably labelled or, at least, capable of detection. For example, the antibody may be labelled with a radioactive atom or a coloured molecule or a fluorescent molecule or a molecule which can be readily detected in any other way. Suitable detectable molecules include fluorescent proteins, luciferase, enzyme substrates, radiolabels and binding moieties. Labelling may be by conjugation to the antibody/fragment. The antigen binding molecule may be directly labelled with a detectable label or it may be indirectly labelled. In some embodiments, the label may be selected from: a radio-nucleotide, positron-emitting radionuclide (e.g. for positron emission tomography (PET)), MRI contrast agent or fluorescent label.

Antibodies and antigen binding fragments according to the present invention may be conjugated to a drug moiety, e.g. a cytotoxic small molecule. Such conjugates are useful for the targeted killing of cells expressing the antigen molecule.

Also provided by the present invention are isolated heavy chain variable region polypeptides, and isolated light chain variable region polypeptides.

In some aspects an isolated heavy chain variable region polypeptide is provided, comprising the HC-CDRs 1-3 of any one of the anti-IL-11Rα antibody clones described herein. In some aspects an isolated heavy chain variable region polypeptide is provided, comprising an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100% sequence identity to the amino acid sequence of the heavy chain variable region of any one of the anti-IL-11Rα antibody clones described herein.

In some aspects an isolated light chain variable region polypeptide is provided, comprising the LC-CDRs 1-3 of any one of the anti-IL-11Rα antibody clones described herein. In some aspects an isolated light chain variable region polypeptide is provided, comprising an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100% sequence identity to the amino acid sequence of the light chain variable region of any one of the anti-IL-11Rα antibody clones described herein.

Functional Properties of the Antibodies/Fragments

The anti-IL-11Rα antibodies and fragments of the present invention may be characterised by reference to certain functional properties. In particular, an anti-IL-11Rα antibody or antigen binding fragment according to the present invention may possess one or more of the following properties:

a) Specific binding to IL-11Rα (e.g. human IL-11Rα and/or mouse IL-11Rα);
b) Binding to IL-11Rα (e.g. human IL-11Rα) with an affinity of binding of EC50=less than 1000 ng/ml, e.g. as determined by ELISA;
c) Inhibition of interaction between IL-11Rα and IL-11;
d) Inhibition of interaction between IL-11Rα and gp130;
e) Inhibition of interaction between IL-11Rα:gp130 receptor complex and IL-11;
f) Inhibition of interaction between IL-11:IL-11Rα complex and gp130;
g) Inhibition of IL-11/IL-11R signalling;
h) Inhibition of signalling mediated by binding of IL-11 to IL-11Rα:gp130 receptor complex;
i) Inhibition of signalling mediated by binding of IL-11:IL-11Rα complex to gp130 (i.e. IL-11 trans signalling);
j) Inhibition of fibroblast proliferation;
k) Inhibition of myofibroblast generation from fibroblasts;
l) Inhibition of a pathological process mediated by IL-11/IL-11R signalling;
m) Inhibition of fibrosis;
n) Inhibition of gene or protein expression in fibroblasts of one or more of collagen, fibronectin, periostin, IL-6, IL-11, αSMA, TIMP1, MMP2, e.g. following stimulation with a profibrotic factor;
o) Inhibition of extracellular matrix production by fibroblasts
p) Inhibition of proliferation and/or survival of cells of a cancer;
q) Inhibition of tumour growth.

Herein, 'inhibition' refers to a reduction, decrease or lessening relative to a control condition. For example, inhibition of a process by an antibody/fragment refers to a reduction, decrease or lessening of the extent/degree of that process in the absence of the antibody/fragment, and/or in the presence of an appropriate control antibody/fragment.

Inhibition may herein also be referred to as neutralisation or antagonism. That is, an IL-11Rα binding antibody/fragment which is capable of inhibiting a function or process (e.g. interaction, signalling or other activity mediated by IL-11Rα or an IL-11Rα-containing complex) may be said to be a 'neutralising' or 'antagonist' antibody/fragment with respect to the relevant function or process. For example, antibody/fragment which is capable of inhibiting IL-11/IL-11R signalling may be referred to as an antibody/fragment which is capable of neutralising IL-11/IL-11R signalling, or may be referred to as an antagonist of IL-11/IL-11R signalling.

The skilled person is able to identify an appropriate control condition for a given assay. For example, a control antibody/fragment may be an antibody/fragment directed against a target protein which is known not to have a role involved in the property being investigated in the assay. A control antibody/fragment may be of the same isotype as the ant-IL-11Rα antibody/fragment being analysed, and may e.g. have the same constant regions.

An antibody/fragment that specifically binds to a target molecule preferably binds the target with greater affinity, and/or with greater duration than it binds to other, non-target molecules. In some embodiments the present antibodies/fragments may bind with greater affinity to IL-11Rα than to one or more members of the IL-6 receptor family. In some embodiments the present antibodies/fragments may bind with greater affinity to IL-11Rα than to one or more of IL-6Rα, leukemia inhibitory factor receptor (LIFR), oncostatin M receptor (OSMR) and ciliary neurotrophic factor receptor alpha (CNTFRα).

In some embodiments, the extent of binding of an antibody to an non-target is less than about 10% of the binding of the antibody to the target as measured, e.g., by ELISA, SPR, Bio-Layer Interferometry (BLI), MicroScale Thermophoresis (MST), or by a radioimmunoassay (RIA). Alternatively, the binding specificity may be reflected in terms of binding affinity, where the anti-IL-11Rα antibody/fragment of the present invention binds to IL-11Rα with a $K_D$ that is at least 0.1 order of magnitude (i.e. $0.1 \times 10^n$, where n is an integer representing the order of magnitude) greater than the $K_D$ towards another, non-target molecule. This may optionally be one of at least 0.2, 0.3, 0.4, 0.5, 0.6, 0.7, 0.8, 0.9, 1.0, 1.5, or 2.0.

Binding affinity of an antibody or antigen-binding fragment for its target is often described in terms of its dissociation constant ($K_D$). Binding affinity can be measured by methods known in the art, such as by ELISA, Surface Plasmon Resonance (SPR; see e.g. Hearty et al., Methods Mol Biol (2012) 907:411-442; or Rich et al., Anal Biochem. 2008 Feb. 1; 373(1):112-20), Bio-Layer Interferometry (see e.g. Lad et al., (2015) J Biomol Screen 20(4): 498-507; or Concepcion et al., Comb Chem High Throughput Screen. 2009 September; 12(8):791-800), MicroScale Thermophoresis (MST) analysis (see e.g. Jerabek-Willemsen et al., Assay Drug Dev Technol. 2011 August; 9(4): 342-353), or by a radiolabelled antigen binding assay (RIA) performed with the Fab version of the antibody and antigen molecule.

In some embodiments, the antibody/fragment according to the present invention binds to IL-11Rα with a $K_D$ of 5 µM or less, preferably one of ≤1 µM, ≤500 nm, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM ≤3 nM, ≤2 nM, ≤1 nM, ≤500 µM.

In some embodiments, the antibody/fragment according to the present invention binds to IL-11Rα with an affinity of binding (e.g. as determined by ELISA) of EC50=1000 ng/ml or less, preferably one of ≤900 ng/ml, ≤800 ng/ml, ≤700 ng/ml, ≤600 ng/ml, ≤500 ng/ml, ≤400 ng/ml, ≤300 ng/ml, ≤200 ng/ml, ≤100 ng/ml, ≤90 ng/ml, ≤80 ng/ml, ≤70 ng/ml, ≤60 ng/ml, ≤50 ng/ml, ≤40 ng/ml, ≤30 ng/ml, ≤20 ng/ml, ≤15 ng/ml, ≤10 ng/ml, ≤7.5 ng/ml, ≤5 ng/ml, ≤2.5 ng/ml, or ≤1 ng/ml.

Affinity of binding to IL-11Rα by an antibody/fragment may be analysed in vitro by ELISA assay. Suitable assays are well known in the art and can be performed by the skilled person, for example, as described in Antibody Engineering, vol. 1 ($2^{nd}$ Edn), Springer Protocols, Springer (2010), Part V, pp 657-665. For example, the affinity of binding to IL-11Rα by an antibody/fragment may be analysed according to the methodology described herein in the experimental examples.

The ability of an antibody/fragment to inhibit interaction between two proteins can be determined for example by analysis of interaction in the presence of, or following incubation of one or both of the interaction partners with, the antibody/fragment. An example of a suitable assay to determine whether a given antibody/fragment is capable of inhibiting interaction between two interaction partners is a competition ELISA assay.

An antibody/fragment which is capable of inhibiting a given interaction (e.g. between IL-11Rα and IL-11, or between IL-11Rα and gp130, or between IL-11Rα:gp130 and IL-11, or between IL-11:IL-11Rα and gp130) is identified by the observation of a reduction/decrease in the level of interaction between the interaction partners in the presence of—or following incubation of one or both of the interaction partners with—the antibody/fragment, as compared to the level of interaction in the absence of the antibody/fragment (or in the presence of an appropriate control antibody/fragment). Suitable analysis can be performed in vitro, e.g. using recombinant interaction partners or using cells expressing the interaction partners. Cells expressing interaction partners may do so endogenously, or may do so from nucleic acid introduced into the cell. For the purposes of such assays, one or both of the interaction partners and/or the antibody/fragment may be labelled or used in conjunction with a detectable entity for the purposes of detecting and/or measuring the level of interaction.

Ability of an antibody/fragment to inhibit interaction between two binding partners can also be determined by analysis of the downstream functional consequences of such interaction, e.g. receptor signalling. For example, downstream functional consequences of interaction between IL-11Rα:gp130 and IL-11 or between IL-11:IL-11Rα and gp130 may include proliferation of fibroblasts, myofibroblast generation from fibroblasts, or gene or protein expression of one or more of collagen, fibronectin, periostin, IL-6, IL-11, αSMA, TIMP1, MMP2.

Fibroblasts according to the present disclosure may be derived from any tissue, including liver, lungs, kidney, heart, blood vessels, eye, skin, pancreas, spleen, bowel (e.g. large or small intestine), brain, and bone marrow. In particular embodiments, for the purposes of analysis of the antibody/fragment, the fibroblasts may be cardiac fibroblasts (e.g. atrial fibroblasts), skin fibroblasts, lung fibroblasts, kidney fibroblasts or liver fibroblasts. Fibroblasts may be characterised by gene or protein expression of one or more of COL1A, ACTA2, prolyl-4-hydroxylase, MAS516, and FSP1.

Gene expression can be measured by various means known to those skilled in the art, for example by measuring levels of mRNA by quantitative real-time PCR (qRT-PCR), or by reporter-based methods. Similarly, protein expression can be measured by various methods well known in the art, e.g. by antibody-based methods, for example by western blot, immunohistochemistry, immunocytochemistry, flow cytometry, ELISA, ELISPOT, or reporter-based methods.

In some embodiments, the antibody/fragment according to the present invention may inhibit protein expression of one or more markers of fibrosis, e.g. protein expression of one or more of collagen, fibronectin, periostin, IL-6, IL-11, αSMA, TIMP1, MMP2.

The ability of an antibody/fragment to inhibit interaction between IL-11Rα:gp130 and IL-11 can, for example, be analysed by stimulating fibroblasts with TGFβ1, incubating the cells in the presence of the antibody/fragment and analysing the proportion of cells having αSMA-positive phenotype after a defined period of time. In such example, inhibition of interaction between IL-11Rα:gp130 and IL-11 can be identified by observation of a lower proportion of cells having an αSMA-positive phenotype as compared to positive control condition in which cells are treated with TGFβ1 in the absence of the antibody/fragment (or in the presence of an appropriate control antibody/fragment), or in the presence of an appropriate control antibody/fragment.

Such assays are also suitable for analysing the ability of antibody/fragment to inhibit IL-11/IL-11R signalling.

In some embodiments, the antibody/fragment according to the present invention is capable of inhibiting interaction between IL-11Rα and IL-11 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11Rα and IL-11 in the absence of the antibody/fragment (or in the presence of an appropriate control antibody/fragment). In some embodiments, the antibody/fragment according to the present invention is capable of inhibiting interaction between IL-11Rα and IL-11 to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11Rα and IL-11 in the absence of the antibody/fragment (or in the presence of an appropriate control antibody/fragment).

In some embodiments, the antibody/fragment according to the present invention is capable of inhibiting interaction between IL-11Rα and gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11Rα and gp130 in the absence of the antibody/fragment (or in the presence of an appropriate control antibody/fragment). In some embodiments, the antibody/fragment according to the present invention is capable of inhibiting interaction between IL-11Rα and gp130 to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11Rα and gp130 in the absence of the antibody/fragment (or in the presence of an appropriate control antibody/fragment).

In some embodiments, the antibody/fragment according to the present invention is capable of inhibiting interaction between IL-11Rα:gp130 and IL-11 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11Rα:gp130 and IL-11 in the absence of the antibody/fragment (or in the presence of an appropriate control antibody/fragment). In some embodiments, the antibody/fragment according to the present invention is capable of inhibiting interaction between IL-11Rα:gp130 and IL-11 to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11Rα:gp130 and IL-11 in the absence of the antibody/fragment (or in the presence of an appropriate control antibody/fragment).

In some embodiments, the antibody/fragment according to the present invention is capable of inhibiting interaction between IL-11:IL-11Rα complex and gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11:IL-11Rα complex and gp130 in the absence of the antibody/fragment (or in the presence of an appropriate control antibody/fragment). In some embodiments, the antibody/fragment is capable of inhibiting interaction between IL-11:IL-11Rα complex and gp130 to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11:IL-11Rα complex and gp130 in the absence of the antibody/fragment.

Inhibition of IL-11/IL-11R signalling can also be analysed using $^3$H-thymidine incorporation and/or Ba/F3 cell proliferation assays such as those described in e.g. Curtis et al. Blood, 1997, 90(11) and Karpovich et al. Mol. Hum. Reprod. 2003 9(2): 75-80. Ba/F3 cells co-express IL-11Rα and gp130.

As used herein, IL-11/IL-11R signalling and/or processes mediated by IL-11/IL-11R signalling includes signalling mediated by fragments of IL-11 or IL-11Rα and polypeptide complexes comprising IL-11, IL-11Rα or fragments thereof. IL-11/IL-11R signalling may be signalling mediated by human IL-11 or IL-11Rα and/or mouse IL-11 or IL-11Rα. IL-11/IL-11R signalling may occur following binding of IL-11 or an IL-11 containing complex to a receptor to which IL-11 or said complex binds.

In some embodiments, antibodies and fragments according to the present invention are capable of inhibiting the biological activity of IL-11, IL-11Rα or an IL-11- or IL-11Rα-containing complex. In some embodiments, the antibody/fragment binds IL-11Rα in a region which is important for binding to IL-11 or gp130, and thereby disrupts binding to and/or IL-11/IL-11R signalling.

In some embodiments, the antibody/fragment according to the present invention is an antagonist of one or more signalling pathways which are activated by signal transduction through receptors comprising IL-11Rα and/or gp130, e.g. IL-11Rα:gp130. In some embodiments, the antibody/fragment is capable of inhibiting signalling through one or more immune receptor complexes comprising IL-11Rα and/or gp130, e.g. IL-11Rα:gp130.

In some embodiments, the antibody/fragment according to the present invention is capable of inhibiting IL-11/IL-11R signalling to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of signalling in the absence of the antibody/fragment (or in the presence of an appropriate control antibody/fragment). In some embodiments, the antibody/fragment is capable of reducing IL-11/IL-11R signalling to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of signalling in the absence of the antibody/fragment (or in the presence of an appropriate control antibody/fragment).

In some embodiments, the IL-11/IL-11R signalling may be signalling mediated by binding of IL-11 to IL-11Rα: gp130 receptor. Such signalling can be analysed e.g. by treating cells expressing IL-11Rα and gp130 with IL-11, or by stimulating IL-11 production in cells which express IL-11Rα and gp130.

The IC$_{50}$ for antibody/fragment for inhibition of IL-11/IL-11R signalling may be determined, e.g. by culturing Ba/F3 cells expressing IL-11Rα and gp130 in the presence of human IL-11 and the IL-11Rα binding agent, and measuring $^3$H-thymidine incorporation into DNA.

In some embodiments, the antibody/fragment of the present invention may exhibit an IC$_{50}$ of 10 µg/ml or less, preferably one of ≤5 µg/ml, ≤4 µg/ml, ≤3.5 µg/ml, ≤3 µg/ml, ≤2 µg/ml, ≤1 µg/ml, ≤0.9 µg/ml, ≤0.8 µg/ml, ≤0.7 µg/ml, ≤0.6 µg/ml, or ≤0.5 µg/ml in such an assay.

In some embodiments, the IL-11/IL-11R signalling may be signalling mediated by binding of IL-11:IL-11Rα complex to gp130. In some embodiments, the IL-11:IL-11Rα complex may be soluble, e.g. complex of extracellular domain of IL-11Rα and IL-11, or complex of soluble IL-11Rα isoform/fragment, and IL-11. In some embodiments, the soluble IL-11Rα is a soluble (secreted) isoform of IL-11Rα, or is the liberated product of proteolytic cleavage of the extracellular domain of cell membrane bound IL-11Rα.

In some embodiments, the IL-11:IL-11Rα complex may be cell-bound, e.g. complex of cell-membrane bound IL-11Rα and IL-11. Signalling mediated by binding of IL-11:IL-11Rα complex to gp130 can be analysed by treating cells expressing gp130 with IL-11:IL-11Rα complex, e.g. recombinant fusion protein comprising IL-11 joined by a peptide linker to the extracellular domain of IL-11Rα (e.g. hyper IL-11 as described herein).

In some embodiments, the antibody/fragment according to the present invention is capable of inhibiting signalling mediated by binding of IL-11:IL-11Rα complex to gp130, and is also capable of inhibiting signalling mediated by binding of IL-11 to IL-11Rα:gp130 receptor.

In some embodiments, the antibody/fragment is capable of inhibiting fibroblast proliferation. Proliferation of fibroblasts can be determined by analysing cell division over a period of time. Cell division for a given population of fibroblasts can be analysed, for example, by in vitro analysis of incorporation of $^3$H-thymidine or by CFSE dilution assay, e.g. as described in Fulcher and Wong, Immunol Cell Biol (1999) 77(6): 559-564, hereby incorporated by reference in entirety. Proliferating cells (e.g. proliferating fibroblasts) may also be identified by analysis of incorporation of 5-ethynyl-2'-deoxyuridine (EdU) by an appropriate assay, as described e.g. in Buck et al., Biotechniques. 2008 June; 44(7):927-9, and Sali and Mitchison, PNAS USA 2008 Feb. 19; 105(7): 2415-2420, both hereby incorporated by reference in their entirety.

Fibroblasts according to the present disclosure may be derived from any tissue, including liver, lungs, kidney, heart, blood vessels, eye, skin, pancreas, spleen, bowel (e.g. large or small intestine), brain, and bone marrow. In particular embodiments, for the purposes of analysis of the antibody/fragment, the fibroblasts may be cardiac fibroblasts (e.g. atrial fibroblasts), skin fibroblasts, lung fibroblasts, kidney fibroblasts or liver fibroblasts.

In some embodiments, the antibody/fragment according to the present invention is capable of inhibiting fibroblast proliferation to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of fibroblast proliferation in the absence of the antibody/fragment (or in the presence of an appropriate control antibody/fragment). In some embodiments, the antibody/fragment is capable of reducing fibroblast proliferation to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of fibroblast proliferation in the absence of the antibody/fragment (or in the presence of an appropriate control antibody/fragment).

In some embodiments, the antibody/fragment according to the present invention is capable of inhibiting a pathological process mediated by IL-11/IL-R signalling, e.g. following stimulation with a profibrotic factor (e.g. TGFβ1). Pathological processes mediated by IL-11/IL-R signalling include fibrosis, and can be evaluated either in vitro or in vivo.

In some embodiments, the antibody/fragment according to the present invention is capable of inhibiting fibrosis. Fibrosis may be of a particular tissue or several tissues, e.g. liver, lung, kidney, heart, blood vessel, eye, skin, pancreas, spleen, bowel (e.g. large or small intestine), brain, or bone marrow. Fibrosis may be measured by means well known to the skilled person, for example by analysing gene or protein expression of one or more myofibroblast markers and/or gene or protein expression of one or more markers of fibrosis in a given tissue or tissues.

Myofibroblast markers may include one or more of increased αSMA, vimentin, palladin, cofilin or desmin. Markers of fibrosis include increased level of collagen, fibronectin, periostin, IL-6, IL-11, αSMA, TIMP1 and MMP2, extracellular matrix components, number/proportion of myofibroblasts, and organ weight.

Inhibition of fibrosis can be measured in vitro or in vivo. For example, whether an antibody/fragment is capable of inhibiting fibrosis in a given tissue can be analysed in vitro by treating fibroblasts derived from that tissue with a profibrotic stimulus, and then analysing whether the antibody can reduce myofibroblast generation from the fibroblasts (or e.g. some other marker of fibrosis). Whether an antibody/fragment is capable of inhibiting fibrosis can be analysed in vivo, for example, by administering the antibody/fragment to a subject (e.g. a subject that has been exposed to a profibrotic stimulus), and analysing tissue(s) for one or more markers of fibrosis.

In some embodiments, the antibody/fragment according to the present invention is capable of inhibiting fibrosis to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of fibrosis in the absence of the antibody/fragment (or in the presence of an appropriate control antibody/fragment). In some embodiments, the antibody/fragment is capable of reducing fibrosis to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of fibrosis in the absence of the antibody/fragment (or in the presence of an appropriate control antibody/fragment).

In some embodiments, the antibody/fragment according to the present invention is capable of inhibiting myofibroblast generation from fibroblasts, e.g. following exposure of the fibroblasts to profibrotic factor. Myofibroblast generation from fibroblasts can be investigated by analysis for myofibroblast markers. A profibrotic factor according to the present disclosure may be e.g. TGFβ1, IL-11, IL-13, PDGF, ET-1, oncostatin M (OSM) or ANG2 (AngII).

In some embodiments, the antibody/fragment is capable of inhibiting gene or protein expression in fibroblasts, or fibroblast-derived cells (e.g. myofibroblasts), of one or more of collagen, fibronectin, periostin, IL-6, IL-11, αSMA, TIMP1, MMP2, e.g. following stimulation with a profibrotic factor. In some embodiments, the antibody/fragment is capable of inhibiting gene or protein expression in fibroblasts, or fibroblast-derived cells (e.g. myofibroblasts), of one or more extracellular matrix components, e.g. following stimulation with a profibrotic factor.

In the experimental examples herein, myofibroblast generation from fibroblasts is analysed by measuring αSMA protein expression levels using Operetta High-Content Imaging System following stimulation of the fibroblasts with TGFβ1.

In some embodiments, the antibody/fragment according to the present invention is capable of inhibiting myofibroblast generation from fibroblasts to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of myofibroblast generation from fibroblasts in the absence of the antibody/fragment (or in the presence of an appropriate control antibody/fragment). In some embodiments, the antibody/fragment is capable of reducing myofibroblast generation from fibroblasts to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of myofibroblast generation from fibroblasts in the absence of the antibody/fragment (or in the presence of an appropriate control antibody/fragment).

In some embodiments, the antibody/fragment according to the present invention is capable of inhibiting gene or protein expression in fibroblasts of one or more of collagen, fibronectin, periostin, IL-6, IL-11, αSMA, TIMP1, MMP2, e.g. following stimulation with a profibrotic factor (e.g. TGFβ1). In some embodiments, the antibody/fragment according to the present invention is capable of inhibiting gene or protein expression to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of gene or protein expression in the absence of the antibody/fragment (or in the presence of an appropriate control antibody/fragment). In some embodiments, the antibody/fragment is capable of reducing gene or protein expression to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of gene or protein expression in the absence of the antibody/fragment (or in the presence of an appropriate control antibody/fragment).

In some embodiments, the antibody/fragment according to the present invention is capable of inhibiting extracellular matrix production by fibroblasts, e.g. following stimulation with a profibrotic factor (e.g. TGFβ1). Extracellular matrix production can be evaluated, for example, by measuring the level of an extracellular matrix component. Extracellular matrix components according to the present invention include e.g. proteoglycan, heparan sulphate, chondroitin sulphate, keratan sulphate, hyaluronic acid, collagen, periostin, fibronectin, vitronectin, elastin, fibronectin, laminin, nidogen, gelatin and aggrecan.

In some embodiments, the antibody/fragment according to the present invention is capable of inhibiting extracellular matrix production by fibroblasts to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of extracellular matrix production by fibroblasts in the absence of the antibody/fragment (or in the presence of an appropriate control antibody/fragment). In some embodiments, the antibody/fragment is capable of reducing extracellular matrix production by fibroblasts to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of extracellular matrix production in the absence of the antibody/fragment (or in the presence of an appropriate control antibody/fragment).

In some embodiments, the antibody/fragment according to the present invention is capable of inhibiting proliferation and/or survival of cells of a cancer. The skilled person is able to determine whether an antibody/fragment is capable of inhibiting proliferation and/or survival of cells of a cancer for example by analysing the effect of the antibody/fragment on cells of the cancer. For example, proliferation of cells can be measured as described herein, e.g. by $^3$H thymidine incorporation or CFSE dilution assays. Cell survival can be analysed by measuring cells for markers of cell viability/cell death following treatment with the antibody/fragment.

In some embodiments, the antibody/fragment according to the present invention is capable of inhibiting proliferation and/or survival of cells of a cancer to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of proliferation and/or survival of cells of a cancer in the absence of the antibody/fragment (or in the presence of an appropriate control antibody/fragment). In some embodiments, the antibody/fragment is capable of reducing proliferation and/or survival of cells of a cancer to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of proliferation and/or survival of cells of a cancer in the absence of the antibody/fragment (or in the presence of an appropriate control antibody/fragment).

In some embodiments, the antibody/fragment according to the present invention is capable of inhibiting tumour growth to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of tumour growth in the absence of the antibody/fragment (or in the presence of an appropriate control antibody/fragment). In some embodiments, the antibody/fragment is capable of reducing tumour growth to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of tumour growth in the absence of the antibody/fragment (or in the presence of an appropriate control antibody/fragment).

In some embodiments, the antibody/fragment according to the present invention has one or more improved properties as compared to a prior art anti-IL-11Rα antibody/fragment. In some embodiments, the antibody/fragment according to the present invention has one or more improved properties as compared to a prior art antibody capable of inhibiting IL-11/IL-11R signalling. In some embodiments the prior art antibody may be, or may comprise the CDRs and/or VL and VH sequences of, monoclonal mouse anti-human IL-11 antibody clone #22626; Catalog No. MAB218 (R&D Systems, MN, USA).

In some embodiments, the antibody/fragment of the present invention displays one or more of the following properties as compared to a prior art antibody/antigen binding fragment which is capable of binding to IL-11Rα:

(i) binds to IL-11Rα with greater specificity relative to one or more of IL-6Rα, LIFR, OSMR, and CNTFRα (i.e. reduced cross-reactivity for proteins of the IL-6 cytokine receptor family other than IL-11Rα);
(ii) binds to IL-11Rα (e.g. human IL-11Rα and/or mouse IL-11Rα) with greater affinity (e.g. has lower EC50 as determined by ELISA);
(iii) inhibits interaction between IL-11Rα and IL-11 to a greater extent;
(iv) inhibits interaction between IL-11Rα and gp130 to a greater extent;
(v) inhibits interaction between IL-11Rα:gp130 receptor complex and IL-11 to a greater extent;
(vi) inhibits interaction between IL-11:IL-11Rα complex and gp130 to a greater extent;
(vii) inhibits IL-11/IL-11R signalling to a greater extent;
(viii) inhibits signalling mediated by binding of IL-11 to IL-11Rα:gp130 receptor complex to a greater extent;
(ix) inhibits signalling mediated by binding of IL-11:IL-11Rα complex to gp130 (i.e. IL-11 trans signalling) to a greater extent;
(x) inhibits fibroblast proliferation to a greater extent;
(xi) inhibits myofibroblast generation from fibroblasts to a greater extent;
(xii) inhibits a pathological process mediated by IL-11/IL-11R signalling to a greater extent;
(xiii) inhibits fibrosis to a greater extent;
(xiv) inhibits gene or protein expression in fibroblasts of one or more of collagen, fibronectin, periostin, IL-6, IL-11, αSMA, TIMP1, MMP2, e.g. following stimulation with a profibrotic factor to a greater extent;
(xv) inhibits extracellular matrix production by fibroblasts to a greater extent;
(xvi) inhibits proliferation and/or survival of cells of a cancer to a greater extent; or
(xvii) inhibits tumour growth to a greater extent.

In some embodiments, "greater specificity" or "greater affinity" or "inhibition to a greater extent" herein is, respectively, a level of specificity, affinity or inhibition which is greater than 1 times, e.g. ≥1.01 times, ≥1.02 times, ≥1.03 times, ≥1.04 times, ≥1.05 times, ≥1.06 times, ≥1.07 times, ≥1.08 times, ≥1.09 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥2.1 times, ≥2.2 times, ≥2.3 times, ≥2.4 times, ≥2.5 times, ≥2.6 times, ≥2.7 times, ≥2.8 times, ≥2.9 times, ≥3 times, ≥3.5 times, ≥4 times, ≥4.5 times, ≥5 times, ≥6 times, ≥7 times, ≥8 times, ≥9 times, ≥10 times, ≥15 times, ≥20 times, ≥25 times, ≥30 times, ≥35 times, ≥40 times, ≥45 times, ≥50 times, ≥60 times, ≥70 times, ≥80 times, ≥90 times, ≥100 times, ≥200 times, ≥300 times, ≥400 times, ≥500 times, ≥600 times, ≥700 times, ≥800 times, ≥900 times, ≥1000 times the specificity or affinity or level of inhibition displayed by the prior art antibody/antigen binding fragment in a comparable assay.

Therapeutic Applications

Antibodies and antigen binding fragments according to the present invention and compositions comprising such agents may be provided for use in methods of medical treatment or prevent of a disease/disorder, or alleviation of the symptoms of a disease/disorder. The antibodies/fragments of the present invention may be administered to subjects having a disease/condition in need of treatment, and/or to subjects at risk of such developing or contracting the disease/disorder.

Treatment, prevention or alleviation of fibrosis according to the present invention may be of fibrosis that is associated with an upregulation of IL-11 and/or IL-11Rα, e.g. an upregulation of IL-11 in cells or tissue in which the disease/disorder occurs or may occur, or upregulation of extracellular IL-11 or IL-11Rα. In some embodiments, IL-11 or IL-11R expression is locally or systemically upregulated in the subject.

Treatment or alleviation of a disease/disorder may be effective to prevent progression of the disease/disorder, e.g. to prevent worsening of the condition or to slow the rate of development. In some embodiments treatment or alleviation may lead to an improvement in the disease/disorder, e.g. a reduction in the symptoms of the disease/disorder or reduction in some other correlate of the severity/activity of the disease/disorder.

Prevention of a disease/disorder may refer to prevention of a worsening of the condition or prevention of the development of the disease/disorder, e.g. preventing an early stage disease/disorder developing to a later, chronic, stage.

The antibodies/fragments of the present invention are preferably able to bind to and inhibit the biological activity of IL-11Rα and IL-11Rα-containing molecules/complexes (e.g. IL-11:IL-11Rα complex). Accordingly, the antibodies/fragments of the present invention find use in the treatment or prevention of diseases and disorders in which IL-11 and/or IL-11Rα is implicated in the pathology of the disease/disorder. That is, the antibodies/fragments of the present invention find use in the treatment or prevention of diseases and disorders associated with IL-11/IL-11R signalling.

In some embodiments, the disease/disorder may be associated with increased IL-11, IL-11Rα and/or gp130 gene or protein expression, e.g. as compared to the control (i.e. non-diseased) state. In some embodiments, the disease/disorder may be associated with an increased level of IL-11/IL-11R signalling as compared to the control state. In some embodiments, the disease/disorder may be associated with an increased level of signalling through ERK and/or STAT3 pathways as compared to the control state. In some embodiments, the increased expression/activity of IL-11, IL-11Rα and/or gp130, and/or the increased level of IL-11/IL-11R signalling, may be observed in effector cells of the disease/disorder (e.g. for a cancer, the cancerous cells). In some embodiments, the increased expression/activity of IL-11, IL-11α and/or gp130, and/or the increased level of IL-11/IL-11R signalling, may be observed in cells other than the effector cells.

Signaling through ERK can be measured e.g. using an assay for ERK phosphorylation such as an assay described in Assay Guidance Manual: Phospho-ERK Assays, Kim E. Garbison, Beverly A. Heinz, Mary E. Lajiness, Jeffrey R. Weidner, and G. Sitta Sittampalam, Eli Lilly & Company, Sittampalam G S, Coussens N P, Nelson H, et al., editors Bethesda (Md.): Eli Lilly & Company and the National Center for Advancing Translational Sciences; 2004. Signalling through STAT3 can be measured e.g. using an assay for phosphorylation of STAT3, such as the Phospho-STAT3 (Tyr705) Cellular Assay Kit (Cisbio Assays).

In some embodiments, the treatment is of a disease/disorder for which a reduction in IL-1/IL-11R signalling is therapeutic. In some embodiments, the treatment is of a disease/disorder associated with excess ERK and/or STAT3 signalling. In some embodiments, the treatment is of a disease/disorder associated with excess proliferation or hyperactivation of fibroblasts, or associated with an excess of myofibroblasts.

In some embodiments, the treatment may be aimed at preventing or treating a disease/disorder by decreasing the number or proportion of myofibroblasts or αSMA-positive fibroblasts.

In some embodiments, the disease/disorder may be fibrosis, a fibrotic condition, or a disease/disorder characterised by fibrosis. As used herein, "fibrosis" refers to the formation of excess fibrous connective tissue as a result of the excess deposition of extracellular matrix components, for example collagen. Fibrous connective tissue is characterised by having extracellular matrix (ECM) with a high collagen content. The collagen may be provided in strands or fibers, which may be arranged irregularly or aligned. The ECM of fibrous connective tissue may also include glycosaminoglycans.

As used herein, "excess fibrous connective tissue" refers to an amount of connective tissue at a given location (e.g. a given tissue or organ, or part of a given tissue or organ) which is greater than the amount of connective tissue present at that location in the absence of fibrosis, e.g. under normal, non-pathological conditions. As used herein, "excess deposition of extracellular matrix components" refers to a level of deposition of one or more extracellular matrix components which is greater than the level of deposition in the absence of fibrosis, e.g. under normal, non-pathological conditions.

The cellular and molecular mechanisms of fibrosis are described in Wynn, J. Pathol. (2008) 214(2): 199-210, and Wynn and Ramalingam, Nature Medicine (2012) 18:1028-1040, which are hereby incorporated by reference in their entirety. The main cellular effectors of fibrosis are myofibroblasts, which produce a collagen-rich extracellular matrix.

In response to tissue injury, damaged cells and leukocytes produce pro-fibrotic factors such as TGFβ, IL-13 and PDGF, which activate fibroblasts to αSMA-expressing myofibroblasts, and recruit myofibroblasts to the site of injury. Myofibroblasts produce a large amount of extracellular matrix, and are important mediators in aiding contracture and closure of the wound. However, under conditions of persistent infection or during chronic inflammation there can be overactivation and recruitment of myofibroblasts, and thus over-production of extracellular matrix components, resulting in the formation of excess fibrous connective tissue.

In some embodiments fibrosis may be triggered by pathological conditions, e.g. conditions, infections or disease states that lead to production of pro-fibrotic factors such as TGFβ1. In some embodiments, fibrosis may be caused by physical injury/stimuli, chemical injury/stimuli or environmental injury/stimuli. Physical injury/stimuli may occur during surgery, e.g. iatrogenic causes. Chemical injury/stimuli may include drug induced fibrosis, e.g. following chronic administration of drugs such as bleomycin, cyclophosphamide, amiodarone, procainamide, penicillamine, gold and nitrofurantoin (Daba et al., Saudi Med J 2004 June; 25(6): 700-6). Environmental injury/stimuli may include exposure to asbestos fibres or silica.

Fibrosis can occur in many tissues of the body. For example, fibrosis can occur in the lung, liver (e.g. cirrhosis), kidney, heart, blood vessels, eye, skin, pancreas, spleen, bowel (e.g. large or small intestine), brain, and bone marrow. Fibrosis may also occur in multiple organs at once.

In embodiments herein, fibrosis may involve an organ of the gastrointestinal system, e.g. of the liver, small intestine, large intestine, or pancreas. In some embodiments, fibrosis may involve an organ of the respiratory system, e.g. the lungs. In embodiments, fibrosis may involve an organ of the cardiovascular system, e.g. of the heart or blood vessels. In some embodiments, fibrosis may involve the skin. In some embodiments, fibrosis may involve an organ of the nervous system, e.g. the brain. In some embodiments, fibrosis may involve an organ of the urinary system, e.g. the kidneys. In some embodiments, fibrosis may involve an organ of the musculoskeletal system, e.g. muscle tissue.

In some preferred embodiments, the fibrosis is cardiac or myocardial fibrosis, hepatic fibrosis, or renal fibrosis. In some embodiments cardiac or myocardial fibrosis is associated with dysfunction of the musculature or electrical properties of the heart, or thickening of the walls or valves of the heart. In some embodiments fibrosis is of the atrium and/or ventricles of the heart. Treatment or prevention of atrial or ventricular fibrosis may help reduce risk or onset of atrial fibrillation, ventricular fibrillation, or myocardial infarction.

In some preferred embodiments hepatic fibrosis is associated with chronic liver disease or liver cirrhosis. In some preferred embodiments renal fibrosis is associated with chronic kidney disease.

Diseases/disorders characterised by fibrosis in accordance with the present invention include but are not limited to: respiratory conditions such as pulmonary fibrosis, cystic fibrosis, idiopathic pulmonary fibrosis, progressive massive fibrosis, scleroderma, obliterative bronchiolitis, Hermansky-Pudlak syndrome, asbestosis, silicosis, chronic pulmonary hypertension, AIDS associated pulmonary hypertension, sarcoidosis, tumor stroma in lung disease, and asthma chronic liver disease, primary biliary cirrhosis (PBC), schistosomal liver disease, liver cirrhosis; cardiovascular conditions such as hypertrophic cardiomyopathy, dilated cardiomyopathy (DCM), fibrosis of the atrium, atrial fibrillation, fibrosis of the ventricle, ventricular fibrillation, myocardial fibrosis, Brugada syndrome, myocarditis, endomyocardial fibrosis, myocardial infarction, fibrotic vascular disease, hypertensive heart disease, arrhythmogenic right ventricular cardiomyopathy (ARVC), tubulointerstitial and glomerular fibrosis, atherosclerosis, varicose veins, cerebral infarcts; neurological conditions such as gliosis and Alzheimer's disease; muscular dystrophy such as Duchenne muscular dystrophy (DMD) or Becker's muscular dystrophy (BMD); gastrointestinal conditions such as Chron's disease, microscopic colitis and primary sclerosing cholangitis (PSC); skin conditions such as scleroderma, nephrogenic systemic fibrosis and cutis keloid; arthrofibrosis; Dupuytren's contracture; mediastinal fibrosis; retroperitoneal fibrosis; myelofibrosis; Peyronie's disease; adhesive capsulitis; kidney disease (e.g., renal fibrosis, nephritic syndrome, Alport's syndrome, HIV associated nephropathy, polycystic kidney disease, Fabry's disease, diabetic nephropathy, chronic glomerulonephritis, nephritis associated with systemic lupus); progressive systemic sclerosis (PSS): chronic graft versus host disease: diseases/disorders of the eye and associated processes, such as Grave's ophthalmopathy, epiretinal fibrosis (e.g. diabetic retinopathy (DR)), glaucoma, subretinal fibrosis (e.g. associated with macular degeneration (e.g. wet age-related macular degeneration (AMD macular edema, drusen formation, post-surgical fibrosis (e.g. of the posterior capsule following cataract surgery, or of the bleb following trabeculectomy for glaucoma), conjunctival fibrosis, subconjunctival fibrosis; arthritis; fibrotic pre-neoplastic and fibrotic neoplastic disease; and fibrosis induced by chemical or environmental insult (e.g., cancer chemotherapy, pesticides, radiation/cancer radiotherapy).

It will be appreciated that many of the diseases/conditions listed above are interrelated. For example, fibrosis of the ventricle may occur post myocardial infarction, and is associated with DCM, HCM and myocarditis.

In particular embodiments, the disease/disorder may be one of pulmonary fibrosis, atrial fibrillation, ventricular fibrillation, hypertrophic cardiomyopathy (HCM), dilated cardiomyopathy (DCM), non-alcoholic steatohepatitis (NASH), cirrhosis, chronic kidney disease, scleroderma, systemic sclerosis, keloid, cystic fibrosis, Chron's disease, post-surgical fibrosis or retinal fibrosis, e.g. associated with wet age-related macular degeneration (AMD).

Fibrosis can lead directly or indirectly to, and/or increase susceptibility to development of, diseases/disorders. For example, more than 80% of hepatocellular carcinomas (HCCs) develop in fibrotic or cirrhotic livers (Affo et al. 2016, Annu Rev Pathol.), suggesting an important role for liver fibrosis in the premalignant environment (PME) of the liver.

Accordingly, the antibodies/fragments of the present invention find use in methods for the treatment and prevention of diseases/disorders associated with fibrosis, and/or for which fibrosis is a risk factor. In some embodiments, the disease/disorder associated with fibrosis, or for which fibrosis is a risk factor, is a cancer, e.g. cancer of the liver (e.g. hepatocellular carcinoma).

IL-11/IL-11R signaling is also implicated in the pathology of other diseases/disorders, and the anti-IL-1 Ra antibodies and fragments of the present invention accordingly find use in methods to treat, prevent and/or alleviate the symptoms of these diseases/disorders also.

IL-11/IL-1R signalling has been implicated in the development and progression of various cancers. Studies suggest that IL-11/IL-11R signalling is important for promoting chronic gastric inflammation and associated gastric, colonic, hepatocellular and breast cancer tumorogenesis through excessive activation of STAT3 (Ernst M, et al. J Clin Invest. (2008); 118:1727-1738), that IL-11/IL-11R signalling may promote tumorigenesis by triggering the JAK-STAT intracellular signalling pathway, and may also promote metastasis via signalling through the PI3K-AKT-mTORC1 pathway (Xu et al., Cancer Letters (2016) 373(2): 156-163). Through STAT3, IL-11 promotes survival, proliferation, invasion angiogenesis and metastasis, the IL-11/GP130/JAK/STAT3 signalling axis may be rate-limiting for the progression of gastrointestinal tumors, and elevated IL-1 expression is associated with poor prognosis of breast cancer patients (Johnstone et al., Cytokine & Growth Reviews (2015) 26(5): 489-498). IL-11/IL-11R signalling has also been shown to influence breast cancer stem cell dynamics and tumor heterogeneity (Johnstone et al., Cytokine & Growth Reviews (2015) 26(5): 489-498). Recently, IL-11 signaling has been implicated in chemoresistance of lung adenocarcinoma: cancer associated fibroblasts were found to upregulate IL-11, and confer chemoresistance to lung cancer cells through activation of the IL-11/IL-11R/STAT3 anti-apoptotic signalling pathway (Tao et al. 2016, Sci Rep. 6; 6:38408). IL-11 signalling may promote the fibroblast-to-myofibroblast transition and extracellular matrix production by fibroblasts in the pre-malignant environment (PME) and tumour micro-environment (TME).

In some embodiments, the antibodies/fragments of the present invention are provided for use in methods to treat/prevent a cancer. In some embodiments, the cancer may be a cancer which leads directly or indirectly to inflammation and/or fibrosis.

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue.

In some embodiments, the antibodies/fragments of the present invention are provided for use in methods to treat/prevent a cancer, e.g. an epithelial cell cancer, breast cancer, gastrointestinal cancer (e.g. esophageal cancer, stomach cancer, pancreatic cancer, liver cancer, gallbladder cancer, colorectal cancer, anal cancer, gastrointestinal carcinoid tumor), and lung cancer (e.g. non-small cell lung cancer (NSCLC) or small cell lung cancer (SCLC))). In some embodiments, the cancer is a cancer for which acute and/or chronic inflammation is a risk factor.

In some embodiments, the cancer may be associated with increased IL-11, IL-11Rα and/or gp130 gene or protein expression. For example, cells of the cancer may have increased expression of IL-11, IL-11Rα and/or gp130 as compared to comparable, non-cancerous cells, or may be associated with increased expression of IL-11, IL-11Rα and/or gp130 by other cells (e.g. non-cancerous cells) as compared to the level of expression by comparable cells in the absence of a cancer (e.g. in a healthy control subject). In some embodiments, cells of the cancer may be determined to have an increased level of signalling through ERK and/or STAT3 pathways as compared to comparable non-cancerous cells.

In some embodiments, the cancer may be associated with a mutation in IL-11, IL-11Rα and/or gp130. In some embodiments, such mutation may be associated with increased level of gene or protein expression, or may be associated with an increased level of IL-11/IL-11R signalling relative to the level of expression/signalling observed in the absence of the mutation.

IL-11/IL-11R signalling has also been implicated in diseases/disorders characterised by inflammation. Intra-articular injection of IL-11 has been shown to cause joint inflammation (Wong et al., Cytokine (2005) 29:72-76), and IL-11 has been shown to be proinflammatory at sites of IL-13-mediated tissue inflammation (Chen et al., J Immunol (2005) 174:2305-2313). IL-11 expression has also been observed to be significantly increased in chronic skin lesions in atopic dermatitis, and is known to be involved in bronchial inflammation (Toda et al., J Allergy Clin Immunol (2003) 111: 875-881). IL-11/IL-11R signalling is implicated in inflammatory bowel disease (IBD) and asthma (Putoczki and Ernst, J Leuko Biol (2010) 88(6)1109-1117). IL-11 has also been identified as a risk factor for multiple sclerosis; IL-11 is elevated in the cerebrospinal fluid of patients with clinically isolated syndrome (CIS) as compared to control subjects, and serum levels of IL-11 are higher during relapses for patients with relapsing-remitting multiple sclerosis, and IL-11 may promote differentiation of CD4+ T cells to a $T_H17$ phenotype—$T_H17$ cells are important cells in the pathogenesis of multiple sclerosis (Zhang et al., Oncotarget (2015) 6(32): 32297-32298).

In some embodiments, the antibodies/fragments of the present invention are provided for use in methods to treat/prevent a disease/disorder characterised by inflammation. In some embodiments, a disease or disorder characterised by inflammation may be a disease/disorder which leads directly or indirectly to a cancer and/or fibrosis. Diseases characterised by inflammation include e.g. allergic inflammation such as allergic asthma and bronchial inflammation, atopic dermatitis, allergic rhinitis and ocular allergic diseases, and autoimmune diseases such as multiple sclerosis, systemic lupus erythematosus, rheumatoid arthritis, chronic active hepatitis, type 1 diabetes mellitus, celiac disease, Grave's disease, uveitis, pemphigus, psoriasis, Crohn's disease, ulcerative colitis, inflammatory bowel disease, anaemia and autoimmune thyroiditis.

In some embodiments, the antibodies/fragments of the present invention are provided for use in methods to treat/prevent a disease/disorder associated with infection, in particular where infection leads directly or indirectly to fibrosis, cancer or inflammation. A disease associated with infection may be a disease which is caused or exacerbated by infection with the relevant infectious agent, or may be a disease for which infection with the relevant infectious agent is a risk factor.

An infection may be any infection or infectious disease, e.g. bacterial, viral, fungal, or parasitic infection. In particular embodiments, the disease/disorder may be associated with a viral infection. In some embodiments it may be particularly desirable to treat chronic/persistent infections, e.g. where such infections are associated with inflammation, cancer and/or fibrosis.

The infection may be chronic, persistent, latent or slow, and may be the result of bacterial, viral, fungal or parasitic infection. As such, treatment may be provided to patients having a bacterial, viral or fungal infection. Examples of bacterial infections include infection with *Helicobacter pylori*, and *Mycobacterium tuberculosis* infection of the lung. Examples of viral infections include infection with EBV, HPV, HIV, hepatitis B or hepatitis C.

The treatment may involve ameliorating, treating, or preventing the disease/disorder by inhibiting the biological activity of IL-11Rα or an IL-11Rα-containing complex. Such methods may include the administration of the antibodies/fragments/compositions according to the present invention to bind to and inhibit the biological activity of IL-11Rα or an IL-11Rα-containing complex. Herein, inhibiting the biological activity of IL-11Rα or an IL-11Rα-containing complex may be referred to as 'neutralising'.

Methods of treatment may optionally include the co-administration of biological adjuvants (e.g., interleukins, cytokines, *Bacillus* Comette-Guerin, monophosphoryl lipid A, etc.) in combination with conventional therapies for treating cancer such as treatment with an agent for treating cancer (e.g. chemotherapy), radiation, or surgery. Methods of treatment may involve administering a composition according to the present invention as a vaccine that works by activating the immune system to prevent or destroy cancer cell growth. Methods of medical treatment may also involve in vivo, ex vivo, and adoptive immunotherapies, including those using autologous and/or heterologous cells or immortalized cell lines.

The treatment may be aimed at prevention of a disease/disorder associated with overactive/elevated IL-11/IL-11R mediated signalling. As such, the antibodies, antigen binding fragments and polypeptides may be used to formulate pharmaceutical compositions or medicaments and subjects may be prophylactically treated against development of a disease state. This may take place before the onset of symptoms of the disease state, and/or may be given to subjects considered to be at greater risk of the disease or disorder.

Treatment may comprise co-therapy with a vaccine, which may involve simultaneous, separate or sequential therapy, or combined administration of vaccine and the antibody, antigen binding fragment or composition according to the invention.

Administration of an antibody, antigen binding fragment or polypeptide is preferably in a "therapeutically effective amount", this being sufficient to show benefit to the individual. The actual amount administered, and rate and time-course of administration, will depend on the nature and severity of the disease being treated.

Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Formulating Pharmaceutically Useful Compositions and Medicaments

Antibodies and antigen binding fragments according to the present invention may be formulated as pharmaceutical compositions or medicaments for clinical use and may comprise a pharmaceutically acceptable carrier, diluent, excipient or adjuvant.

The composition may be formulated for topical, parenteral, systemic, intracavitary, intravenous, intra-arterial, intramuscular, intrathecal, intraocular, intraconjunctival, intratumoral, subcutaneous, oral or transdermal routes of administration which may include injection or infusion. Suitable formulations may comprise the antibody/fragment in a sterile or isotonic medium. Medicaments and pharmaceutical compositions may be formulated in fluid, including gel, form. Fluid formulations may be formulated for administration by injection or via catheter to a selected region of the human or animal body.

In accordance with the present invention methods are also provided for the production of pharmaceutically useful compositions, such methods of production may comprise one or more steps selected from: isolating an antibody or antigen binding fragment as described herein; and/or mixing an isolated antibody or antigen binding fragment as described herein with a pharmaceutically acceptable carrier, adjuvant, excipient or diluent.

For example, a further aspect of the present invention relates to a method of formulating or producing a medicament or pharmaceutical composition for use in a method of medical treatment, the method comprising formulating a pharmaceutical composition or medicament by mixing an antibody or antigen binding fragment as described herein with a pharmaceutically acceptable carrier, adjuvant, excipient or diluent.

Methods of Detection

Antibodies, or antigen binding fragments, described herein may be used in methods that involve the binding of the antibody or antigen binding fragment to IL-11Rα. Such methods may involve detection of the bound complex of antibody, or antigen binding fragment, and IL-11Rα. As such, in one embodiment a method is provided, the method comprising contacting a sample containing, or suspected to contain, IL-11Rα with an antibody or antigen binding fragment as described herein and detecting the formation of a complex of antibody, or antigen binding fragment, and IL-11Rα.

Suitable method formats are well known in the art, including immunoassays such as sandwich assays, e.g. ELISA. The method may involve labelling the antibody/antigen binding fragment or IL-11Rα, or both, with a detectable label, e.g. fluorescent, luminescent or radio-label. IL-11Rα expression may be measured by immunohistochemistry (IHC), for example of a tissue sample obtained by biopsy. In some embodiments, the label may be selected from: a radio-nucleotide, positron-emitting radionuclide (e.g. for positron emission tomography (PET)), MRI contrast agent or fluorescent label.

Analysis in vitro or in vivo of processes mediated by IL-11 may involve analysis by positron emission tomography (PET), magnetic resonance imaging (MRI), or fluorescence imaging, e.g. by detection of appropriately labelled species.

Methods of this kind may provide the basis of a method of diagnosis of a disease or condition requiring detection and or quantitation of IL-11Rα or an IL-11Rα-containing complex. Such methods may be performed in vitro on a subject sample, or following processing of a subject sample. Once the sample is collected, the subject is not required to be present for the in vitro method of diagnosis to be performed and therefore the method may be one which is not practiced on the human or animal body.

Such methods may involve determining the amount of IL-11Rα or IL-11Rα-containing complex present in a subject sample. The method may further comprise comparing the determined amount against a standard or reference value as part of the process of reaching a diagnosis. Other diagnostic tests may be used in conjunction with those described here to enhance the accuracy of the diagnosis or prognosis or to confirm a result obtained by using the tests described here.

The level of IL-11Rα or IL-11Rα-containing complex present in a subject sample may be indicative that a subject may respond to treatment with an anti-IL-11Rα antibody/fragment, e.g. an anti-IL-11Rα antibody/fragment or composition according to the present invention. The presence of a high level of IL-11Rα or IL-11Rα-containing complex in a sample may be used to select a subject for treatment with an anti-IL-11Rα antibody/fragment or composition described herein. The antibodies of the present invention may therefore be used to select a subject for treatment with anti-IL-11Rα therapy.

Detection in a sample of IL-11Rα or IL-11Rα-containing complex may be used for the purpose of diagnosis of an infectious disease, autoimmune disorder or a cancerous condition in the subject, diagnosis of a predisposition to an infectious disease, autoimmune disorder or a cancerous condition or for providing a prognosis (prognosticating) of an infectious disease, autoimmune disorder or a cancerous condition. The diagnosis or prognosis may relate to an existing (previously diagnosed) infectious, inflammatory or autoimmune disease/disorder or cancerous condition.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; pleural fluid; cerebrospinal fluid (CSF); or cells isolated from said individual. In some embodiments, the sample may be obtained or derived from a tissue or tissues which are affected by the disease/disorder (e.g. tissue or tissues in which symptoms of the disease manifest, or which are involved in the pathogenesis of the disease/disorder).

Methods according to the present invention may preferably be performed in vitro. The term "in vitro" is intended to encompass experiments with cells in culture whereas the term "in vivo" is intended to encompass experiments with and/or treatment of intact multi-cellular organisms.

Combination Therapies

Antibodies, antigen binding fragments and compositions according to the present invention may be administered alone or in combination with other treatments. Administration of such combination may be simultaneous or sequential, depending on the disease/disorder to be treated. The other treatment with which the antibody/fragment or composition is administered may be aimed at treating or preventing the disease/disorder. In some embodiments, the other treatment with which the antibody/fragment or composition is administered may be aimed at treating or preventing e.g. infection, inflammation and/or cancer.

Simultaneous administration refers to administration of the antibody, antigen binding fragment or polypeptide and therapeutic agent together, for example as a pharmaceutical composition containing both agents (combined preparation), or immediately after each other and optionally via the same route of administration, e.g. to the same artery, vein or other blood vessel.

Sequential administration refers to administration of one of the antibody, antigen binding fragment or polypeptide or therapeutic agent followed after a given time interval by separate administration of the other agent. It is not required that the two agents are administered by the same route, although this is the case in some embodiments. The time interval may be any time interval.

In some embodiments, treatment with an antibody, antigen binding fragment or composition of the present invention may be accompanied by an agent for treating or preventing infection (e.g. an antibiotic, anti-viral, anti-fungal or anti-parasitic agent). In some embodiments, treatment with an antibody, antigen binding fragment or composition of the present invention may be accompanied by an agent for treating or preventing inflammation (e.g. a non-steroidal anti-inflammatory drug (NSAID). In some embodiments, treatment with an antibody, antigen binding fragment or composition of the present invention may be accompanied by radiotherapy (i.e. treatment with ionising radiation, e.g. X-rays or γ-rays) and/or an agent for treating or preventing cancer (e.g. a chemotherapeutic agent). In some embodiments, the antibody, antigen binding fragment or composition of the present invention may be administered as part of a combination treatment with an immunotherapy.

A treatment may involve administration of more than one drug. A drug may be administered alone or in combination with other treatments, either simultaneously or sequentially dependent upon the condition to be treated.

Routes of Administration

Antibodies, antigen binding fragments, medicaments and pharmaceutical compositions according to aspects of the present invention may be formulated for administration by a number of routes, including but not limited to, parenteral, intravenous, intra-arterial, intraocular, intraconjunctival, intramuscular, subcutaneous, intradermal, intratumoral injection or infusion, and oral administration. Antibodies, antigen binding fragments, polypeptides and other therapeutic agents, may be formulated in fluid or solid form. Fluid formulations may be formulated for administration by injection or infusion to a selected region of the human or animal body.

Kits

In some aspects of the present invention a kit of parts is provided. In some embodiments the kit may have at least one container having a predetermined quantity of the antibody, fragment, or composition. The kit may provide the antibody/fragment in the form of a medicament or pharmaceutical composition, and may be provided together with instructions for administration to a subject in order to treat a specified disease/disorder. The antibody, fragment or composition may be formulated so as to be suitable for injection or infusion to a tumor or to the blood.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Subjects

The subject to be treated may be any animal or human. The subject is preferably mammalian, more preferably human. The subject may be a non-human mammal, but is more preferably human. The subject may be male or female. The subject may be a patient. A subject may have been diagnosed with a disease or condition requiring treatment, or be suspected of having such a disease or condition.

In some embodiments the subject may be at risk of developing/contracting a disease or disorder.

Protein Expression

Molecular biology techniques suitable for producing the proteins (e.g. the antibodies/fragments) according to the invention in cells are well known in the art, such as those set out in Sambrook et al., Molecular Cloning: A Laboratory Manual, New York: Cold Spring Harbor Press, 1989

The polypeptide may be expressed from a nucleotide sequence. The nucleotide sequence may be contained in a vector present in a cell, or may be incorporated into the genome of the cell.

A "vector" as used herein is an oligonucleotide molecule (DNA or RNA) used as a vehicle to transfer exogenous genetic material into a cell. The vector may be an expression vector for expression of the genetic material in the cell. Such vectors may include a promoter sequence operably linked to the nucleotide sequence encoding the gene sequence to be expressed. A vector may also include a termination codon and expression enhancers. Any suitable vectors, promoters, enhancers and termination codons known in the art may be used to express polypeptides from a vector according to the invention. Suitable vectors include plasmids, binary vectors, viral vectors and artificial chromosomes (e.g. yeast artificial chromosomes).

In this specification the term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein or polypeptide.

Any cell suitable for the expression of polypeptides may be used for producing polypeptides according to the invention. The cell may be a prokaryote or eukaryote. Suitable prokaryotic cells include E. coli. Examples of eukaryotic cells include a yeast cell, a plant cell, insect cell or a mammalian cell (e.g. Chinese Hamster Ovary (CHO) cells). In some cases the cell is not a prokaryotic cell because some prokaryotic cells do not allow for the same post-translational modifications as eukaryotes. In addition, very high expression levels are possible in eukaryotes and proteins can be easier to purify from eukaryotes using appropriate tags. Specific plasmids may also be utilised which enhance secretion of the protein into the media.

Methods of producing a polypeptide of interest may involve culture or fermentation of a cell modified to express the polypeptide. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide. Culture, fermentation and separation techniques are well known to those of skill in the art.

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express the polypeptide of interest, that polypeptide is preferably isolated. Any suitable method for separating polypeptides from cell culture known in the art may be used. In order to isolate a polypeptide of interest from a culture, it may be necessary to first separate the cultured cells from media containing the polypeptide of interest. If the polypeptide of interest is secreted from the cells, the cells may be separated from the culture media that contains the secreted polypeptide by centrifugation. If the polypeptide of interest collects within the cell, it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the polypeptide of interest.

It may then be desirable to isolate the polypeptide of interest from the supernatant or culture medium, which may contain other protein and non-protein components. A common approach to separating polypeptide components from a supernatant or culture medium is by precipitation. Polypeptides/proteins of different solubility are precipitated at different concentrations of precipitating agent such as ammonium sulfate. For example, at low concentrations of precipitating agent, water soluble proteins are extracted. Thus, by adding increasing concentrations of precipitating agent, proteins of different solubility may be distinguished. Dialysis may be subsequently used to remove ammonium sulfate from the separated proteins.

Other methods for distinguishing different polypeptides/proteins are known in the art, for example ion exchange chromatography and size chromatography. These may be used as an alternative to precipitation, or may be performed subsequently to precipitation.

Once the polypeptide of interest has been isolated from culture it may be necessary to concentrate the protein. A number of methods for concentrating a protein of interest are known in the art, such as ultrafiltration or lyophilisation.

Sequence Identity

Alignment for purposes of determining percent amino acid or nucleotide sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures, in which:

(FIG. 2A) PECAM1, (FIG. 2B) MYH6 (FIG. 2C) TNNT2, (FIG. 2D) COL1A2, and (FIG. 2E) ACTA2.

(FIG. 3A and FIG. 3B) Graphs showing fold change in gene expression in fibrosis; IL-11 is the most upregulated gene in response to TGFβ1 treatment. (FIG. 3C) IL-11 secretion by fibroblasts in response to stimulation with TGFβ1. (FIG. 3D) Comparison of IL-11 gene expression in tissues of healthy individuals and in atrial fibroblasts, with or without TGFβ1 stimulation. (FIG. 3E) Correspondence of fold change in IL-11 expression as determined by RNA-seq vs. qPCR.

(FIG. 4A) TGFβ1, ET-1, AngII, PDGF, OSM and IL-13 induce IL-11 secretion, and IL-11 also induces IL-11 expression in a positive feedback loop. (FIG. 4B) Graph showing that the ELISA only detects native IL-11 secreted from cells, and does not detect recombinant IL-11 used for the IL-11 stimulation condition. (FIG. 4C) and (FIG. 4D) Cells were stimulated with recombinant IL-11, IL-11RNA was measured, and the native IL-11 protein level was measured in the cell culture supernatant by ELISA at the indicated time points.

(FIG. 5A) myofibroblast generation and ECM production by primary atrial fibroblasts following stimulation with TGFβ1 or IL-11, as measured by fluorescence microscopy following staining for a α-SMA, collagen or periostin. (FIG. 5B) Collagen content of cell culture supernatant as determined by Sirius Red staining. Secretion of the fibrosis markers (FIG. 5C) IL-6, (FIG. 5D) TIMP1 and (FIG. 5E) MMP2 as measured by ELISA. (FIG. 5F) Activation of murine fibroblasts by stimulation with human or mouse recombinant IL-11. * $P<0.05$,  $P<0.01$, * $P<0.001$, **** $P<0.0001$ [Mean±SD, Dunnett].

(FIG. 6A) Mouse fibroblasts from different tissues of origin can be activated by IL-11 and display increased ECM production. [Mean±SD, Dunnett]. Injection of mice with recombinant IL-11 or AngII results in (FIG. 6B) an increase in organ weight [Mean±SEM], and (FIG. 6C) an increase in collagen content (as determined by HPA assay). * $P<0.05$,  $P<0.01$, * $P<0.001$, **** $P<0.0001$ [Mean±SD, Dunnett].

(FIG. 7A) myofibroblast generation and ECM production by primary atrial fibroblasts, with or without stimulation with TGFβ1, and in the presence/absence of neutralising anti-IL-11 antibody or isotype control IgG, as measured by fluorescence microscopy following staining for (FIG. 7A) α-SMA, (FIG. 7B) EdU or (FIG. 7C) Periostin. (FIGS. 7D to 7F) Secretion of the fibrosis markers (FIG. 7D) IL-6, (FIG. 7E) TIMP1, and (FIG. 7F) MMP2 was analysed by ELISA. Fluorescence was normalized to the control group without stimulation. [Mean±SD, Dunnett]*$P<0.05$,  $P<0.01$, * $P<0.001$ or **** $P<0.0001$.

(FIG. 10A) Percentage of myofibroblasts as determined by analysis αSMA content, (FIG. 10B) Percentage proliferating cells as determined by staining for EdU, (FIG. 10C) Collagen content and (FIG. 10D) ECM production as measured by detection of periostin [Mean±SD].

(FIG. 12A) Collagen content, as measured by hydroxyproline assay. (FIG. 12B) Collagen (Col1A2) expression. (FIG. 12C) αSMA (ACTA2) expression. (FIG. 12D) Fibronectin (Fn1) expression.

(FIG. 14A) Fold changes in gene expression in fibroblasts following stimulation with TGFβ1, IL-11 or TGFβ1 and IL-11. (FIG. 14B) Fold changes in gene expression in fibroblasts obtained from IL-11RA+/+ and IL-11RA−/− mice following stimulation with TGFβ1.

FIG. 16. Light chain variable domain sequences for anti-IL-11Rα antibody clones. CDRs are underlined and shown separately.

FIG. 17. Heavy chain variable domain sequences for anti-IL-11Rα antibody clones. CDRs are underlined and shown separately.

FIG. 18. Table showing light chain CDR sequences for anti-IL-11Rα antibody clones.

FIG. 19. Table showing heavy chain CDR sequences for anti-IL-11Rα antibody clones.

FIGS. 20A to 20C. Tables showing light chain CDR sequences for anti-IL-11Rα antibody clones and consensus sequences, for (FIG. 20A) LC-CDR1, (FIG. 20B) LC-CDR2 and (FIG. 20C) LC-CDR3.

FIGS. 21A to 21C. Tables showing heavy chain CDR sequences for anti-IL-11Rα antibody clones and consensus sequences, for (FIG. 21A) HC-CDR1, (FIG. 21B) HC-CDR2 and (FIG. 21C) HC-CDR3.

FIGS. 22A and 22B. Nucleotide sequences for the anti-IL-11Rα antibody clones. (FIG. 22A) Nucleotide sequences encoding VL regions. (FIG. 22B) Nucleotide sequences encoding VH regions.

(FIG. 28A) Eye sections of IL-11RA+/+(WT) and IL-11RA−/− (KO) animals 7 days after filtration surgery. (FIG. 28B) Maturation of collagen fibres as evaluated by picro-sirius red/polarization light technique (Szendröi et al. 1984, Acta Morphol Hung 32, 47-55); more fibrosis is observed in WT mice than KO mice.

(FIG. 32A) and (FIG. 32B) present the results of two different experiments.

(FIG. 34B) Bar chart showing strength of binding relative to the positive control anti-FLAG antibody (100%); numbers correspond to the clones as indicated in FIG. 23.

(FIG. 35A) Images of Masson's Trichrome stained kidney sections. Fibrotic areas containing collagen appear darker as compared to healthy areas that appear lighter. (FIG. 35B) Graph showing semi-quantitative analysis of collagen area as a percentage (%) of the total kidney area. ***, P<0.001 compared to FA+IgG, ANOVA.

(FIG. 37A[[36A]]) Mice were treated by sham operation or ureteric obstruction of one ureter. Mice received IgG, anti-IL-11Rα antibody (20 mg/kg on surgical days −1, 1, 3, 5) and injured kidneys (UUO IgG, IL-11Rα) or contralateral (Con) uninjured kidneys (Con IgG, IL-11) were harvested on day 7 post surgery. (FIG. 37B) Semi-quantitative assessment of tubular injury was determined by histological analysis of casts, tubular atrophy or tubular expansion blinded to experimental conditions (Tubular injury score: 0, none; 1, minimal; 2, mild; 3, moderate; 4, severe). *, P<0.05 compared to UUO IgG, ANOVA.

(FIG. 40B) shows the amount of total collagen in the heart as determined by colourimetric detection of hydroxyproline using a QUICKZYME™ Total Collagen assay kit (Quickzyme Biosciences). **, P<0.01; ns, not significant vs SHAM. #, P<0.05, TAC+IgG control vs TAC+ anti-IL11RA. Ab, antibody.

EXAMPLES

In the following Examples, the inventors identify a role for IL-11/IL-11R signalling in fibrosis in a variety of tissues, and described the generation of anti-human IL-11Rα antibodies, and in vitro and in vivo functional characterisation of the antibodies.

Figure 1:
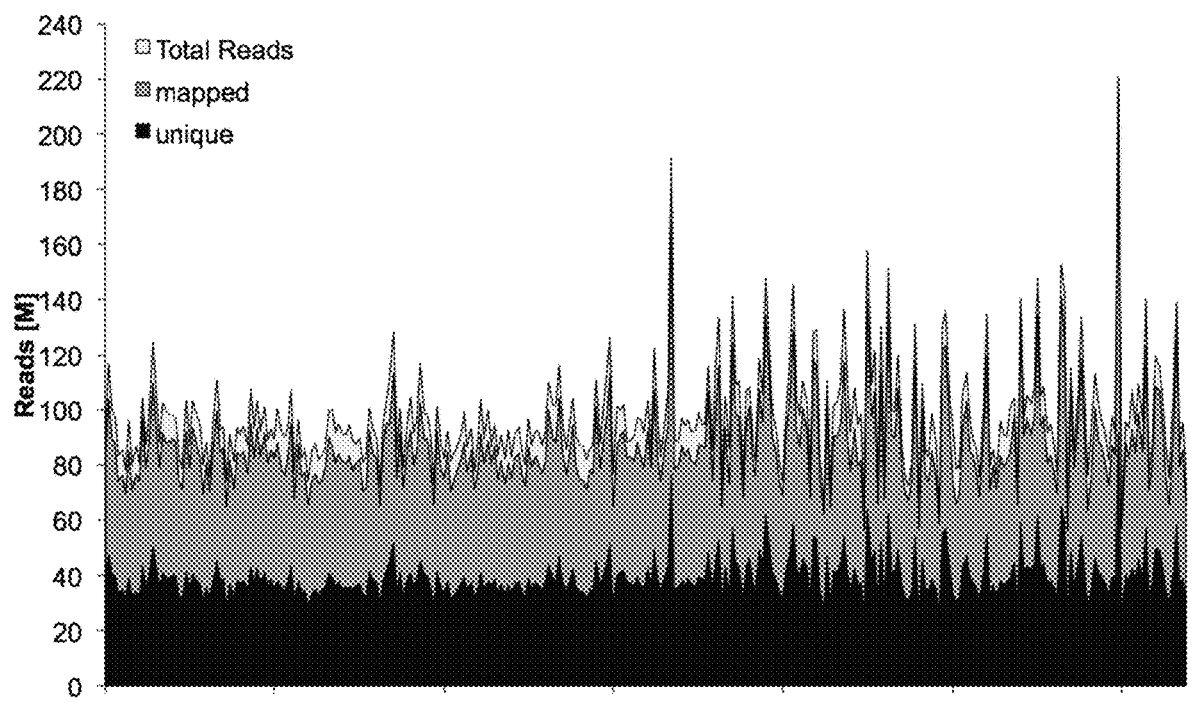
FIG. 1. Graph showing read depth for whole transcriptome sequencing of human atrial fibroblasts from 160 individuals with and without stimulation with TGFβ1.
Figure 2A:
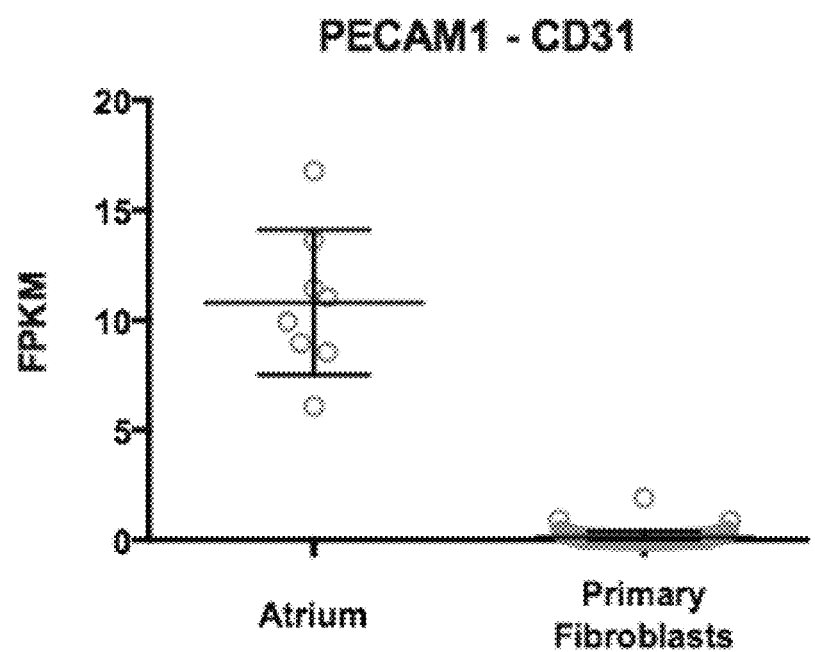
FIGS. 2A to 2E. Graphs showing expression of endothelial, cardiomyocyte and fibroblast marker genes as determined by RNA-seq of the tissue of origin (human atrial tissues samples, n=8) and primary, unstimulated fibroblast cultures.
Figure 2B:
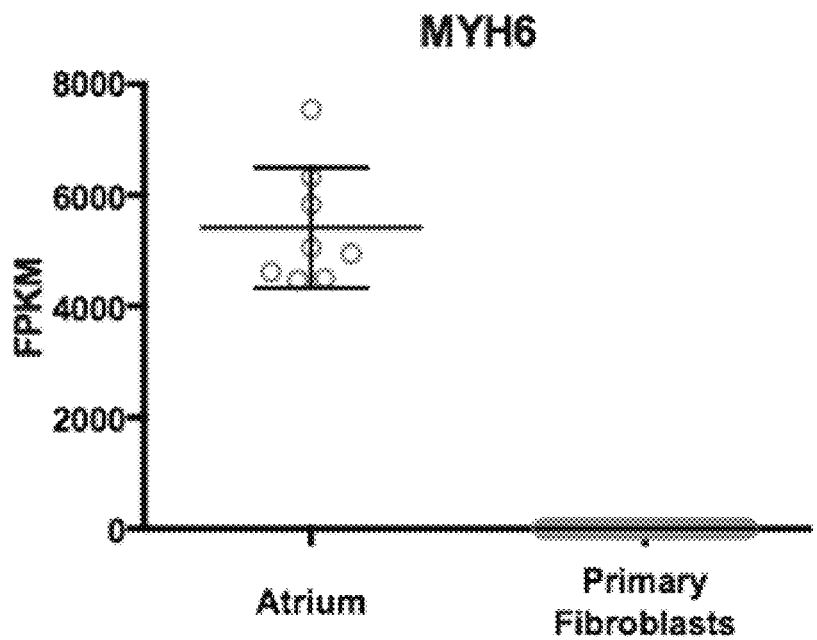
Figure 2C:
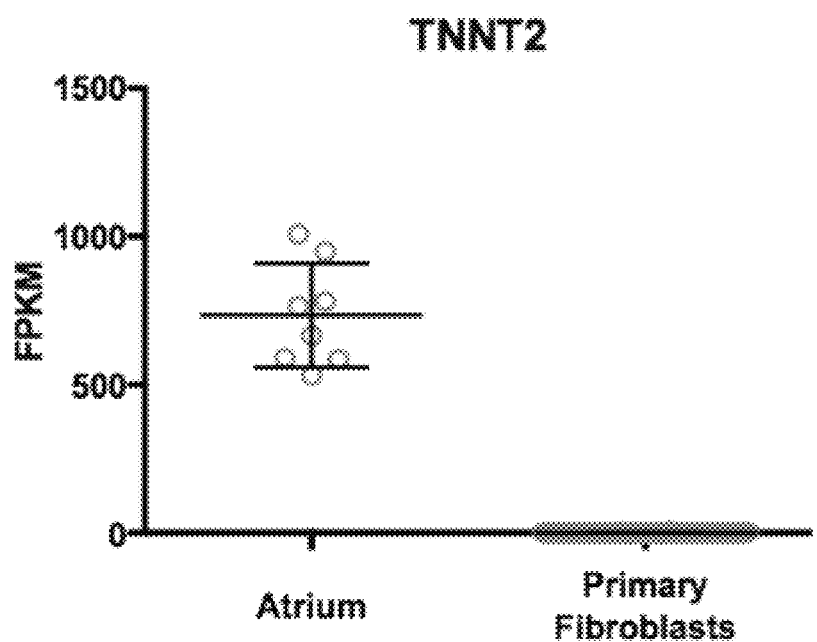
Figure 2D:
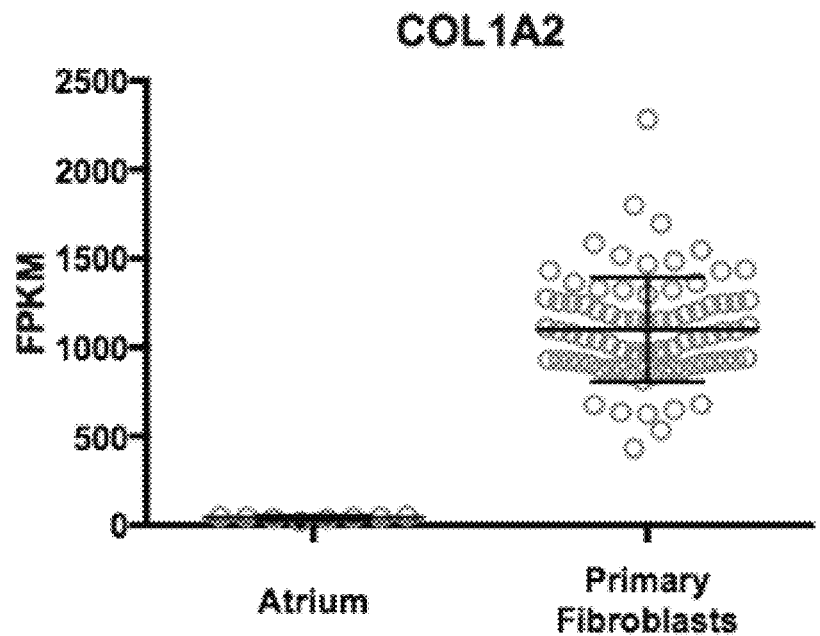
Figure 2E:
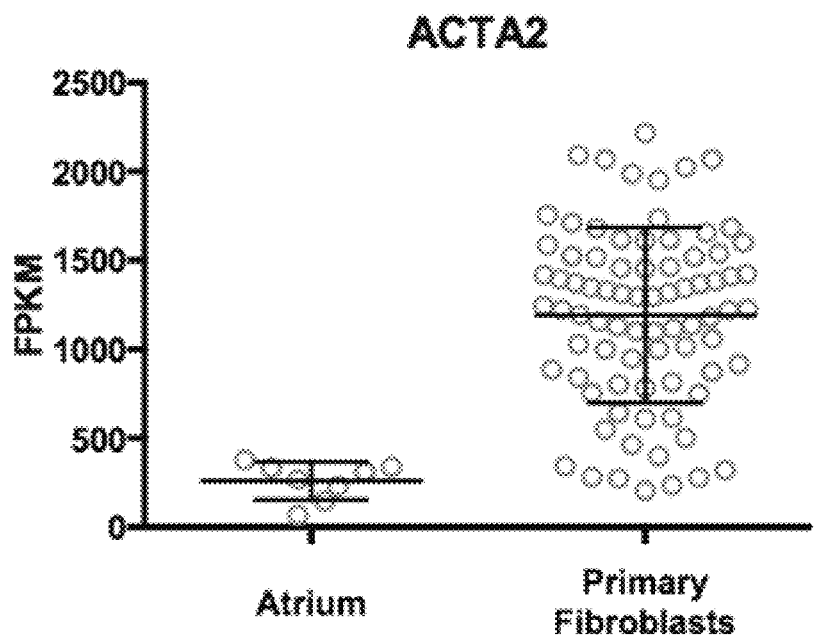

Example 1: A Role for IL-11/IL-11R Signalling in Fibrosis 1.1 IL-11 is Upregulated in Fibrosis To understand the molecular processes underlying the transition of fibroblasts to activated myofibroblasts, atrial tissue was obtained from more than 200 patients that underwent cardiac bypass surgery at the National Heart Centre Singapore. Cells were cultured in vitro at low passage (passage <4), and either not stimulated or stimulated with TGFβ1 for 24 h. We subsequently performed high-throughput RNA sequencing (RNA-seq) analysis of unstimulated fibroblasts and cells stimulated with the prototypic profibrotic stimulus TGFβ1 across 160 individuals; average read depth was ~70M reads per sample (paired-end 100 bp; FIG. 1).

To ensure the purity of the atrial fibroblast cell cultures, we analysed expression of endothelial cell, cardiomyocyte and fibroblast cell type marker genes from the atrium (Hsu et al., 2012 Circulation Cardiovasc Genetics 5, 327-335) in the RNA-seq dataset.

The results are shown in FIGS. 2A to 2E, and confirm the purity of the atrial fibroblast cultures.

Gene expression was assessed by RNA-seq of the tissue of origin (human atrial tissues samples, n=8) and primary, unstimulated fibroblast cultures. No/very low expression of the endothelial cell marker PECAM1 (FIG. 2A), and the cardiomyocyte markers MYH6 (FIG. 2B) and TNNT2 (FIG. 2C) was detected in the fibroblast cell culture samples. Markers for fibroblasts COL1A2 (FIG. 2D) and ACTA2 (FIG. 2E) were highly expressed compared to the tissue of origin.

Next, the RNA-seq data was analysed to identify genes whose expression was increased or decreased upon stimulation with TGFβ1, and this information was integrated with the large RNA-seq dataset across 35+ human tissues provided by the GTEx project (The GTEx Consortium, 2015 Science 348, 648-660). This enabled the identification of gene expression signatures that were specific to the fibroblast-myofibroblast transition.

Figure 3A:
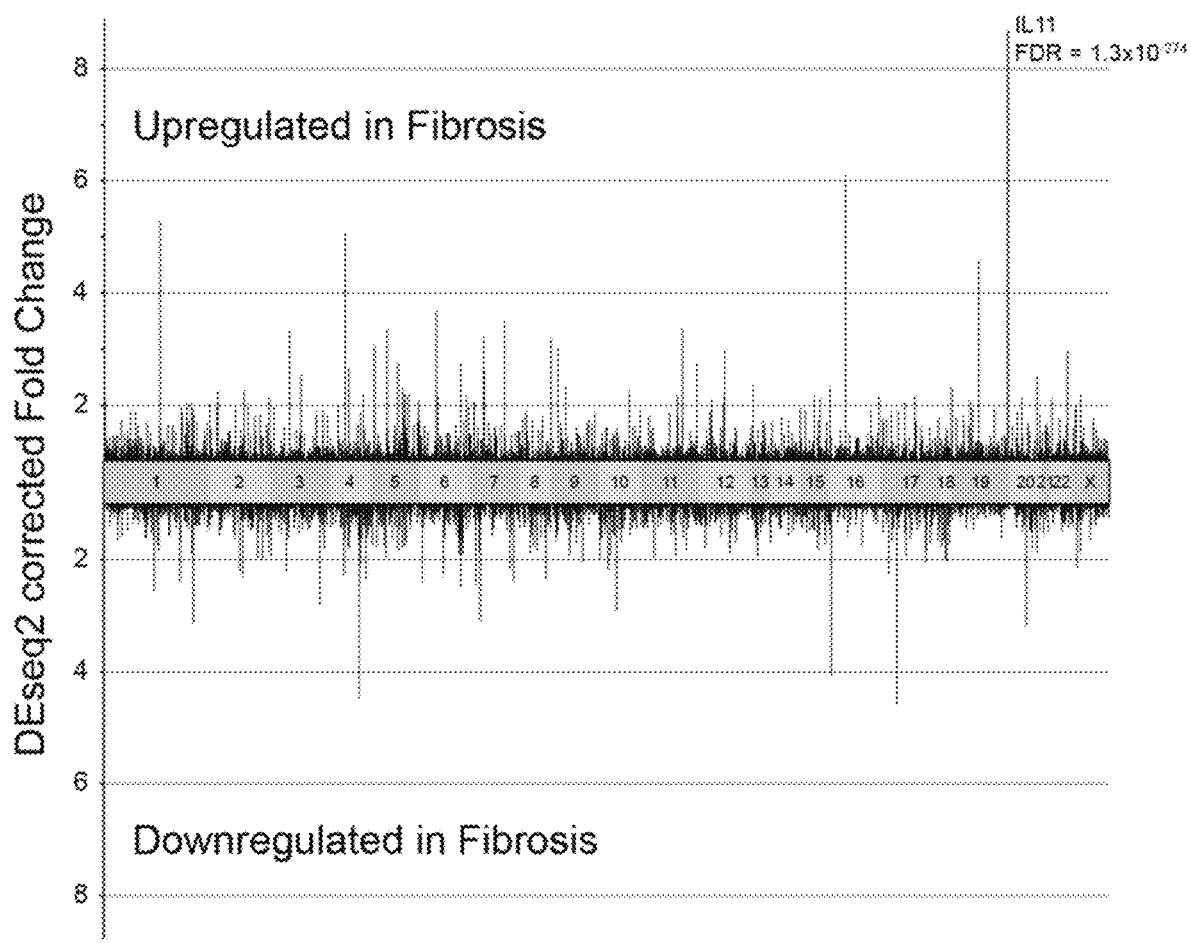
FIGS. 3A to 3E. Graphs showing upregulation of IL-11 expression in fibroblasts in response to stimulation with TGFβ1.
Figure 3B:
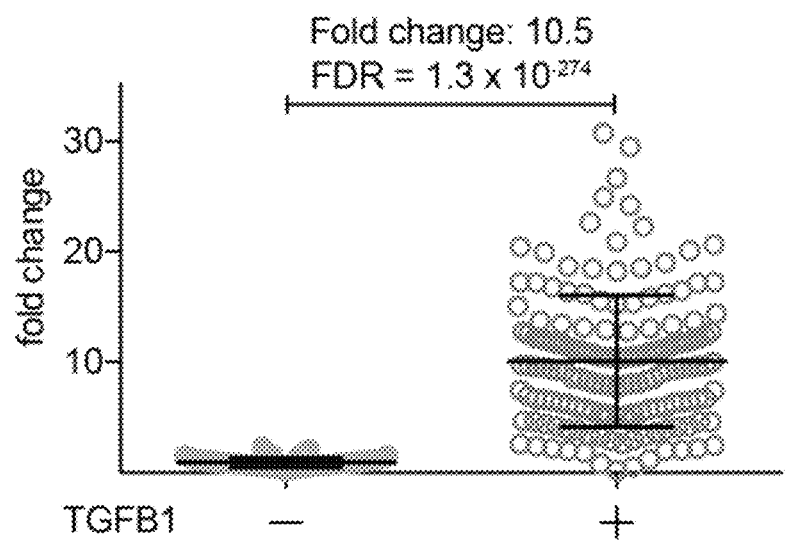

The results are shown in FIGS. 3A to 3E. Across the 10000+ genes expressed in the fibroblasts, IL-11 was the most strongly upregulated gene in response to stimulation with TGFβ1, and on average across the 160 individuals was upregulated more than 10-fold (FIG. 3B).

Figure 3C:
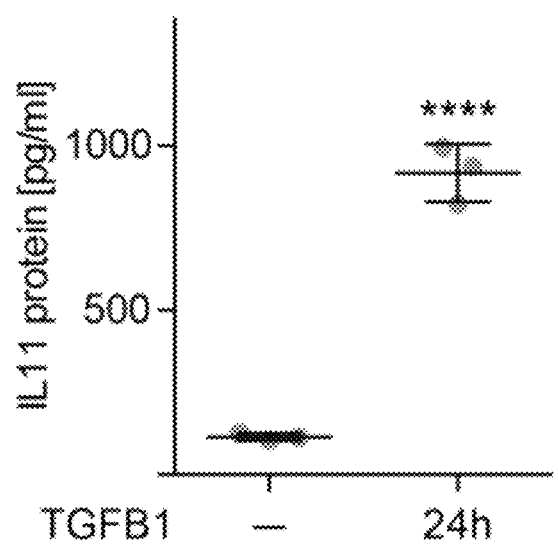
Figure 3D:
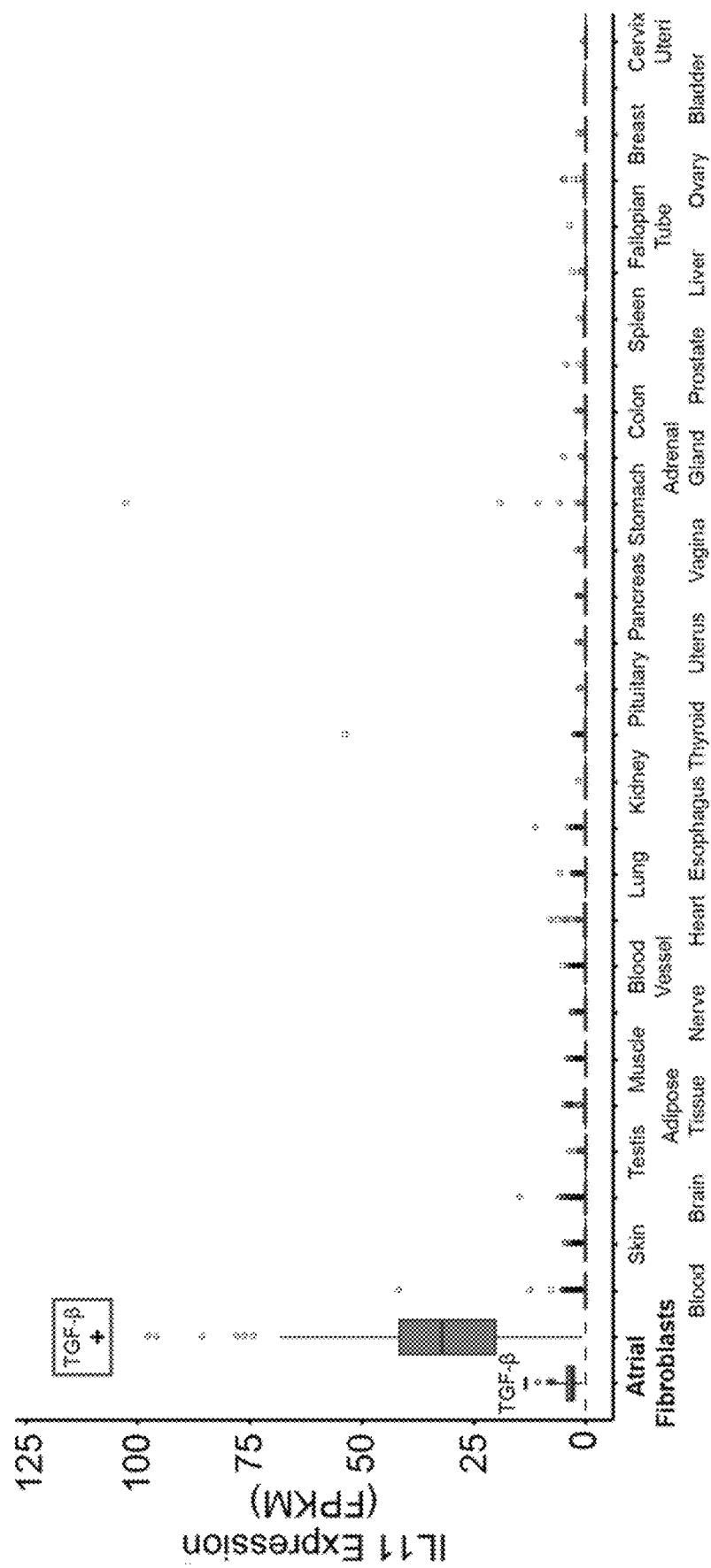
Figure 3E:
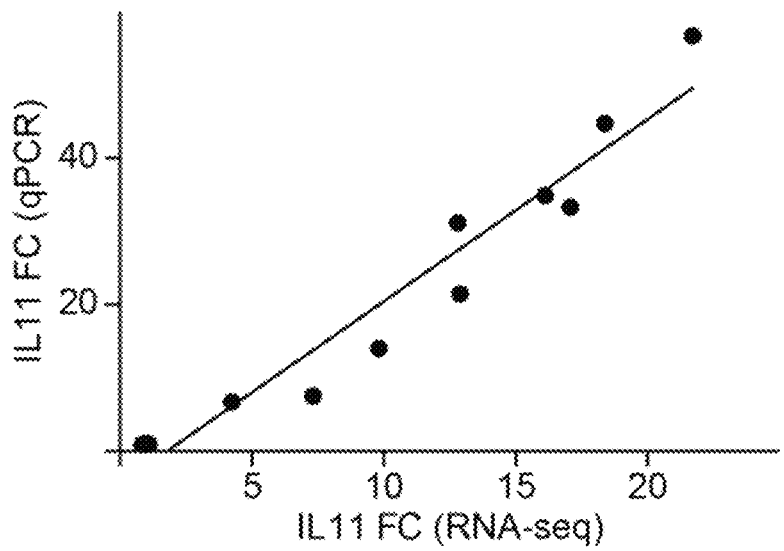

Upregulation of IL-11 expression was confirmed by ELISA analysis of the cell culture supernatant of TGFβ1 stimulated fibroblasts (FIG. 3C). As compared to the level of expression level of IL-11 in other tissues of healthy individuals, this response was observed to be highly specific to activated fibroblasts (FIG. 3D). Various fold changes of IL-11RNA expression were also confirmed by qPCR analysis (FIG. 3E).

Next, fibroblasts were cultured in vitro and stimulated with several other known pro-fibrotic factors: ET-1, ANGII, PDGF, OSM and IL-13, and also with human recombinant IL-11. For analysing upregulation of IL-11 produced in response to stimulation with IL-11, it was confirmed that the ELISA was only able to detect native IL-11 secreted from cells and does not detect recombinant IL-11 used for the stimulations (FIG. 4B).

Figure 4A:
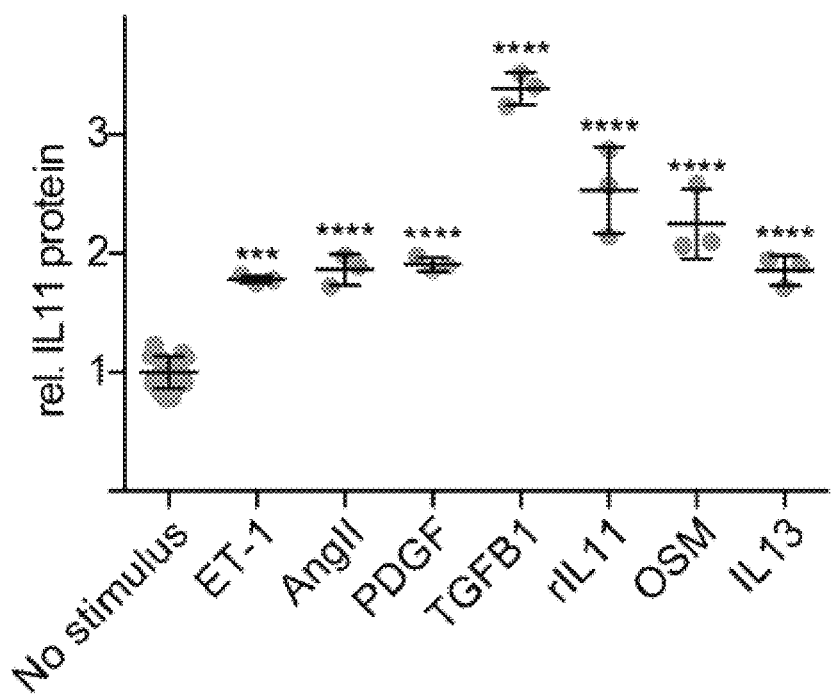
FIGS. 4A to 4D. Graphs showing induction of IL-11 secretion in primary fibroblasts by various profibrotic cytokines, as determined by ELISA.
Figure 4B:
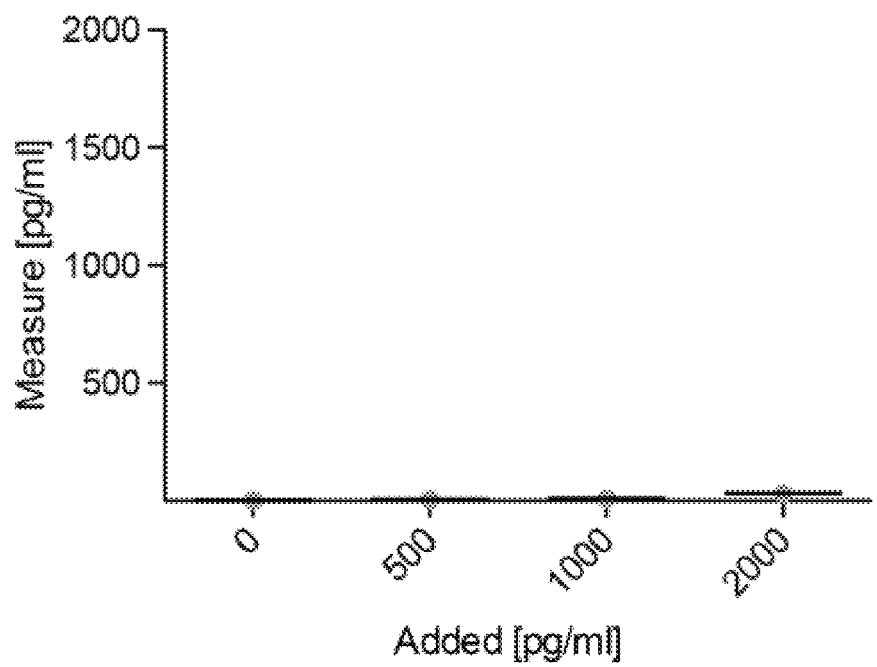
Figure 4C:
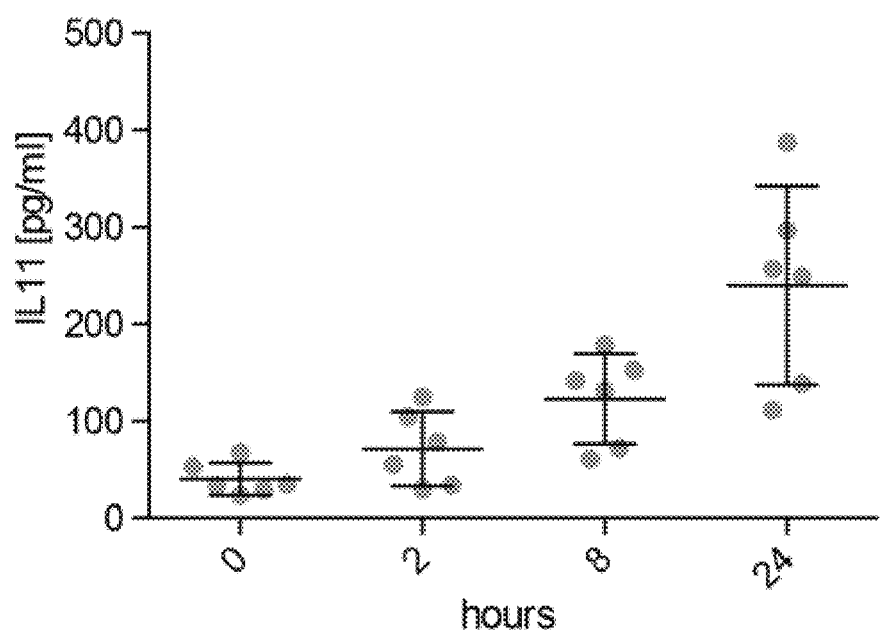

The results are shown in FIG. 4A. Each factor was found to significantly induce IL-11 secretion from fibroblasts. IL-11 is shown to act in an autocrine loop in fibroblasts, which can result in an upregulation of IL-11 protein as much as 100-fold after 72 hours (FIG. 4D).

Interestingly, this autocrine loop for IL-11 is similar to the autocrine production of IL-6. IL-6 is from the same cytokine family and also signals via the gp130 receptor (Garbers and Scheller, 2013 Biol Chem 394, 1145-1161), which is proposed to ensure the continued survival and growth of lung and breast cancer cells (Grivennikov and Karin, 2008 Cancer Cell 13, 7-9).

Figure 4D:
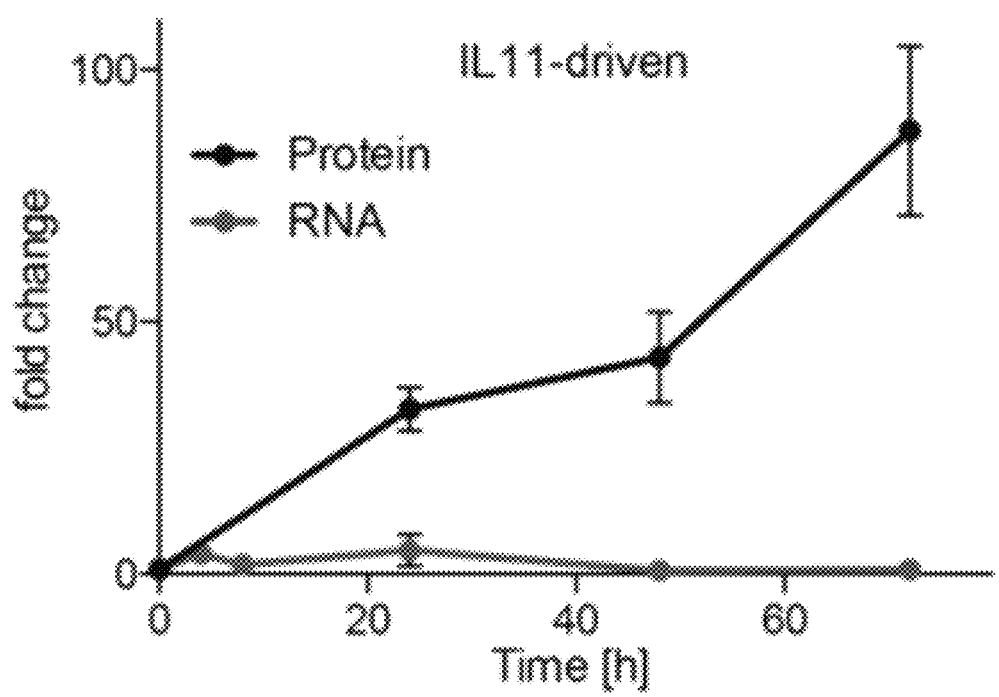

No increase in IL-11RNA level was detected in response to stimulation with IL-11 (FIG. 4D). Unlike TGFβ1, which increases IL-11 expression at both the RNA and protein level, therefore IL-11 seems to upregulate IL-11 expression only at the post-transcriptional level.

1.2 IL-11 has a Profibrotic Role in Fibrosis of Heart Tissue

To explore whether the autocrine production of IL-11 is pro- or anti-fibrotic, fibroblasts were cultured in vitro with recombinant IL-11, and the fraction of myofibroblasts (αSMA-positive cells) and extracellular matrix production was analysed.

The expression of αSMA, collagen and periostin was monitored with the Operetta High-Content Imaging System in an automated, high-throughput fashion. In parallel, secretion of fibrosis marker proteins such as MMP2, TIMP1 and IL-6 was analysed by ELISA assays, and the levels of collagen were confirmed by calorimetric Sirius Red analysis of the cell culture supernatant.

Briefly, atrial fibroblasts derived from 3 individuals were incubated in 2 wells each for 24 h without stimulation, with TGFβ1 (5 ng/ml), or with IL-11 (5 ng/ml). Following incubation, cells were stained to analyse α-SMA content to estimate the fraction of myofibroblasts, and for collagen and periostin to estimate ECM production. Fluorescence was measured in 7 fields per well. The supernatant of 2 wells per individual was also assessed for collagen content by Sirius Red staining. The signal was normalized to the control group without stimulation. Secretion of the fibrosis markers IL-6, TIMP1 and MMP2 was analysed via ELISA.

Figure 5A:
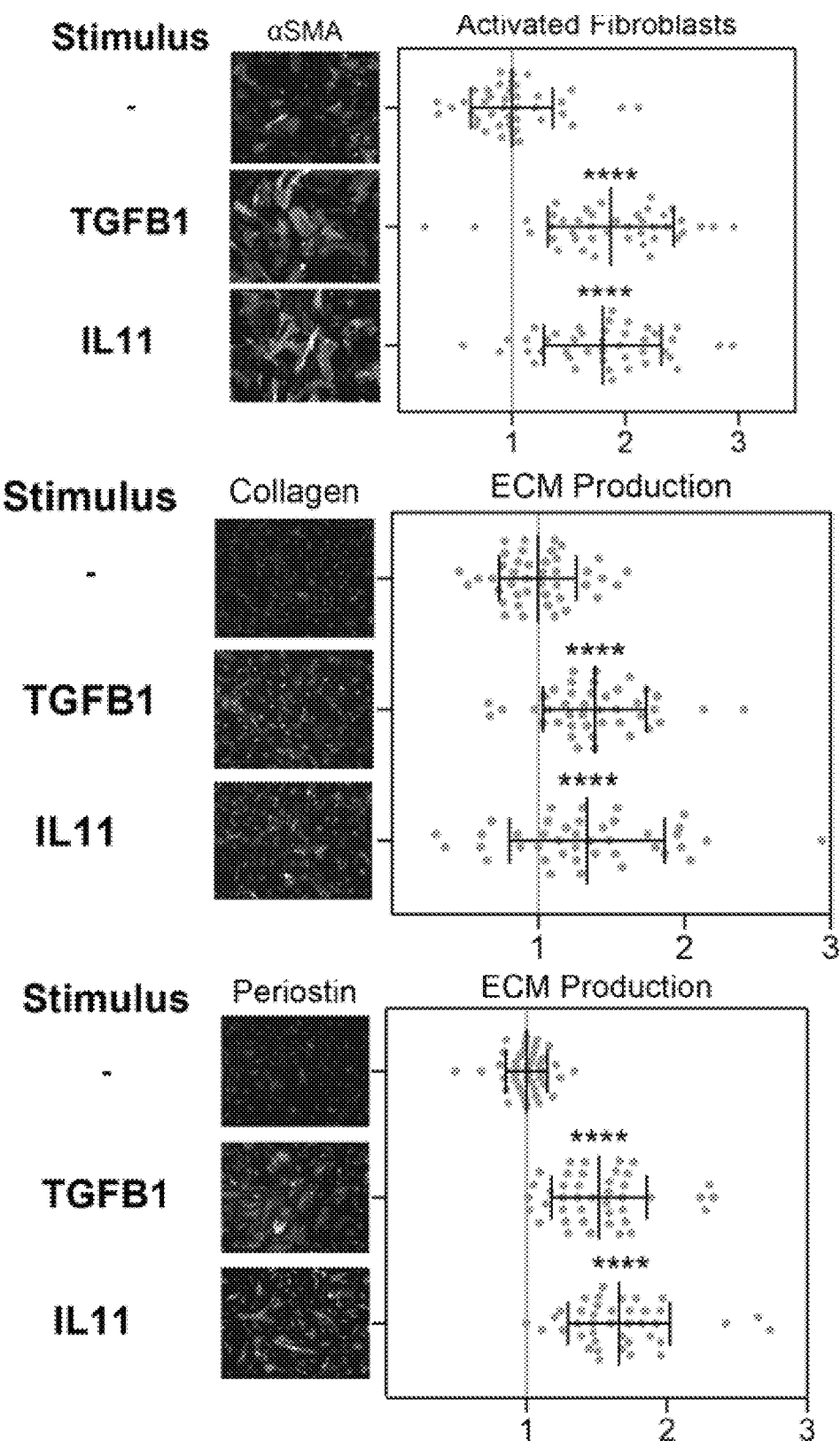
FIGS. 5A to 5F. Graphs and images showing myofibroblast generation from, and production of ECM and cytokine expression by, atrial fibroblasts in response to stimulation with TGFβ1 or IL-11.
Figure 5B:
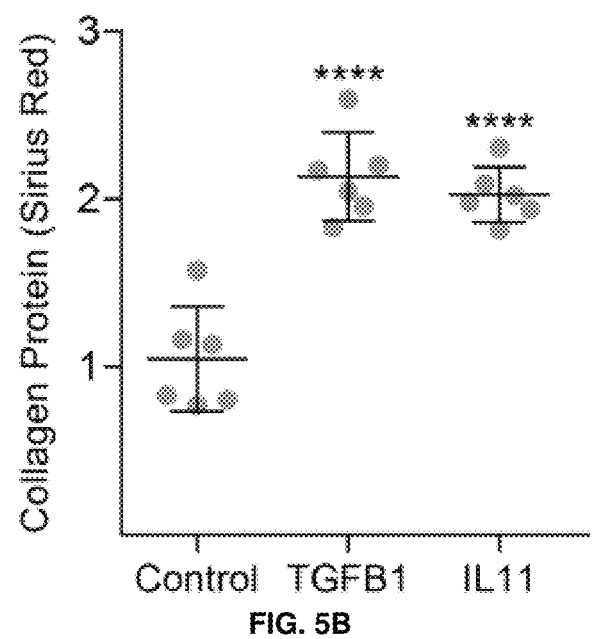
Figure 5C:
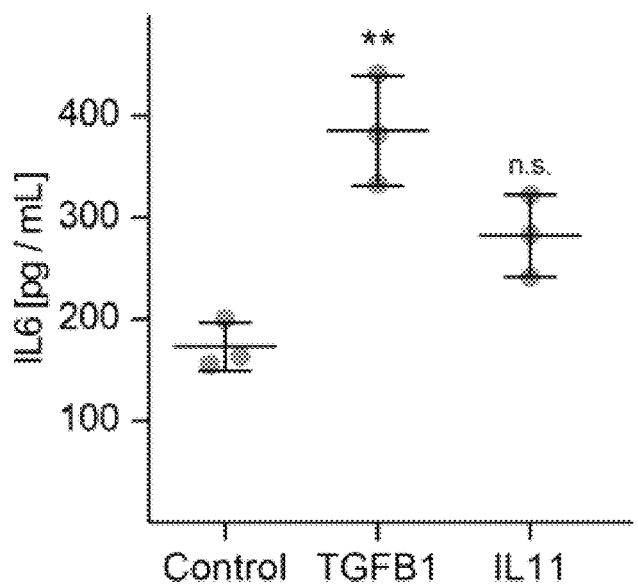
Figure 5D:
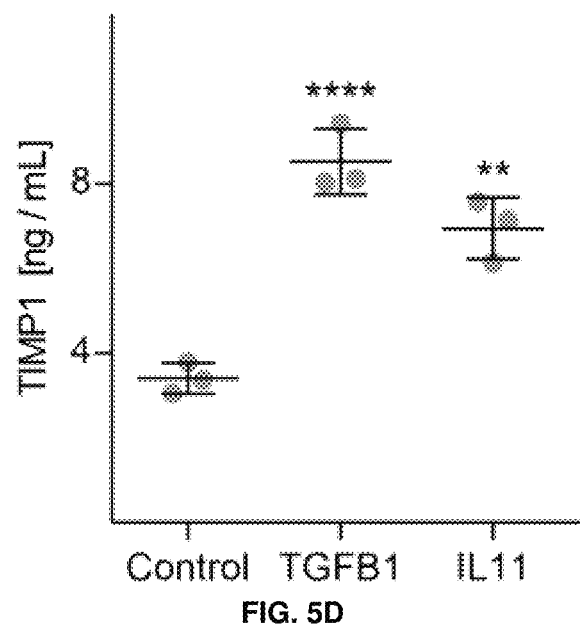
Figure 5E:
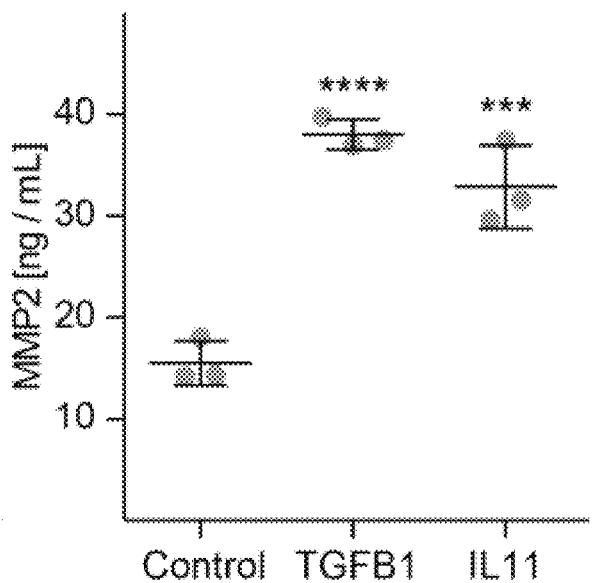

The results are shown in FIGS. 5A to 5F. TGFβ1 activated fibroblasts and increased ECM production (FIG. 5A). Unexpectedly, and in contrast with the anti-fibrotic role described for IL-11 in heart tissue in the scientific literature, recombinant IL-11 caused an increase in the fraction of myofibroblasts in fibroblast cultures, and also promoted the production of extracellular matrix proteins collagen and periostin to the same extent as TGFβ1 (FIG. 5A). Both of IL-11 and TGFβ1 cytokines also significantly increased the secretion of pro-fibrotic markers IL-6, TIMP1 and MMP2 (FIGS. 5B to 5E), and to a similar level.

The inventors hypothesized that the contradiction between the present finding that IL-11 is profibrotic in heart tissue and the antifibrotic role described in the literature might be related to the use of human IL-11 in rodents in those previous studies (Obana et al., 2010, 2012; Stangou et al., 2011; Trepicchio and Dorner, 1998).

Figure 5F:
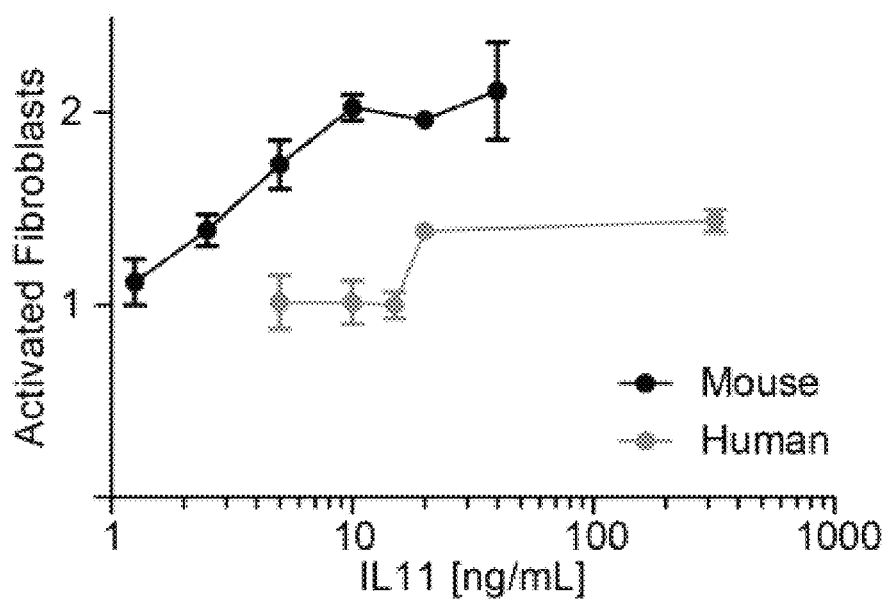

To investigate this hypothesis, serial dilutions of both human and mouse IL-11 were performed, and the activation of human atrial fibroblasts was monitored (FIG. 5F). No activation of fibroblasts was observed at low concentrations of human IL-11 on mouse cells, suggesting that previous insights into IL-11 function may in part be due to IL-11-non-specific observations.

1.3 IL-11/IL-11R Signalling has a Profibrotic Role in Fibrosis of a Variety of Tissues To test whether the profibrotic action of IL-11/IL-11R signalling was specific to atrial fibroblasts, human fibroblasts derived from several different tissues (heart, lung, skin, kidney and liver) were cultured in vitro, stimulated with human IL-11, and fibroblast activation and ECM production was analysed as described above. Increased fibroblast activation and production of ECM was observed as compared to non-stimulated cultures in fibroblasts derived from each of the tissues analysed.

1.3.1 Liver Fibrosis

To test whether IL-11 signalling is important in liver fibrosis, human primary liver fibroblasts (Cell Biologics, Cat #: H-6019) were cultured at low passage in wells of 96-well plates and either not stimulated, stimulated with TGFβ1 (5 ng/ml, 24 h), IL-11 (5 ng/ml, 24 h) or incubated with both TGFβ1 (5 ng/ml) and a neutralising IL-11 antibody (2 μg/ml), or TGFβ1 (5 ng/ml) and an Isotype control antibody. Fibroblast activation (αSMA positive cells), cell proliferation (EdU positive cells) and ECM production (Periostin and Collagen) was analysed using the Operetta platform.

The results of the experiments with primary human liver fibroblasts are shown in FIGS. 29A to 29D. IL-11 was found to activate liver fibroblasts, and IL-11 signalling was found to be necessary for the profibrotic action of TGFβ1 in liver fibroblasts. Both activation and proliferation of fibroblasts was inhibited by neutralising anti-IL-11 antibody.

1.3.2 Skin Fibrosis

To test whether IL-11 signalling is important in skin fibrosis, primary mouse skin fibroblasts were cultured at low passage in wells of 96-well plates and either not stimulated, stimulated with TGFβ1 (5 ng/ml, 24 h) or incubated for 24 h with both TGFβ1 (5 ng/ml) and a neutralising IL-11 antibody (2 μg/ml). Fibroblast activation (αSMA positive cells) was then analysed using the Operetta platform.

Figure 30:
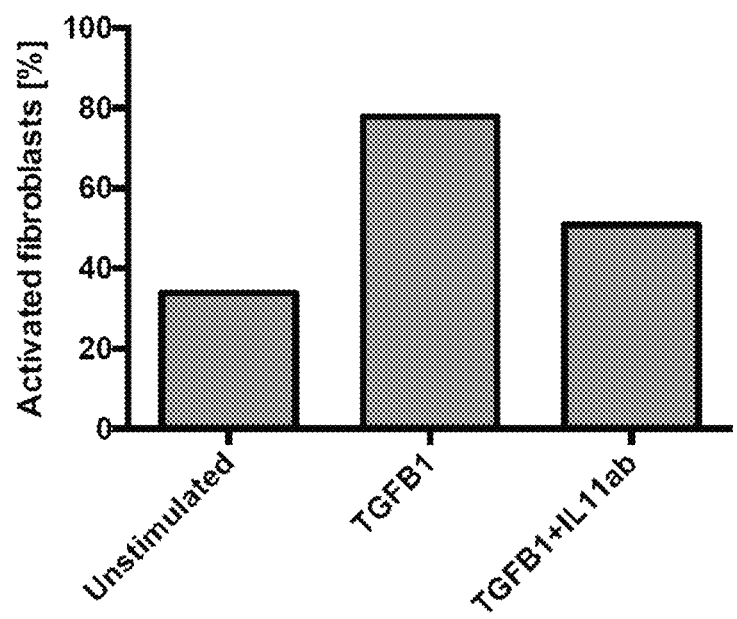
FIG. 30. Bar chart showing that IL-11 is required for the pro-fibrotic effects of TGFβ1 in skin fibroblasts. Activation of mouse skin fibroblasts, with or without stimulation with TGFβ1, and in the presence/absence of neutralising anti-IL-11 antibody, as measured by analysis of the percentage of α-SMA positive cells (activated fibroblasts).

The results are shown in FIG. 30. TGFβ1-mediated activation of skin fibroblasts was inhibited by neutralising anti-IL-11 antibody.

1.3.3 Fibrosis in Multiple Organs

Next, mouse recombinant IL-11 was injected (100 μg/kg, 3 days/week, 28 days) into mice to test whether IL-11 can drive global tissue fibrosis in vivo.

Figure 6A:
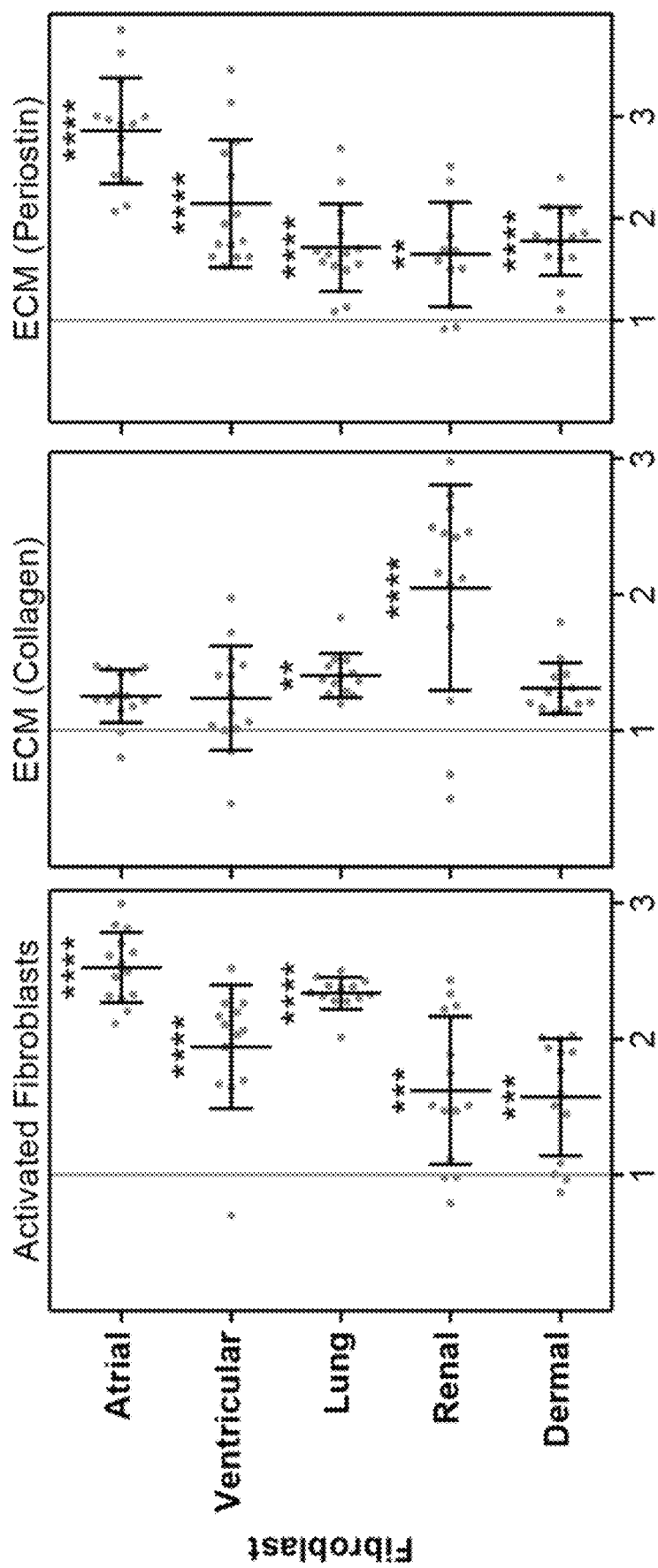
FIGS. 6A to 6C. Graphs showing the profibrotic effect of IL-11.
Figure 6B:
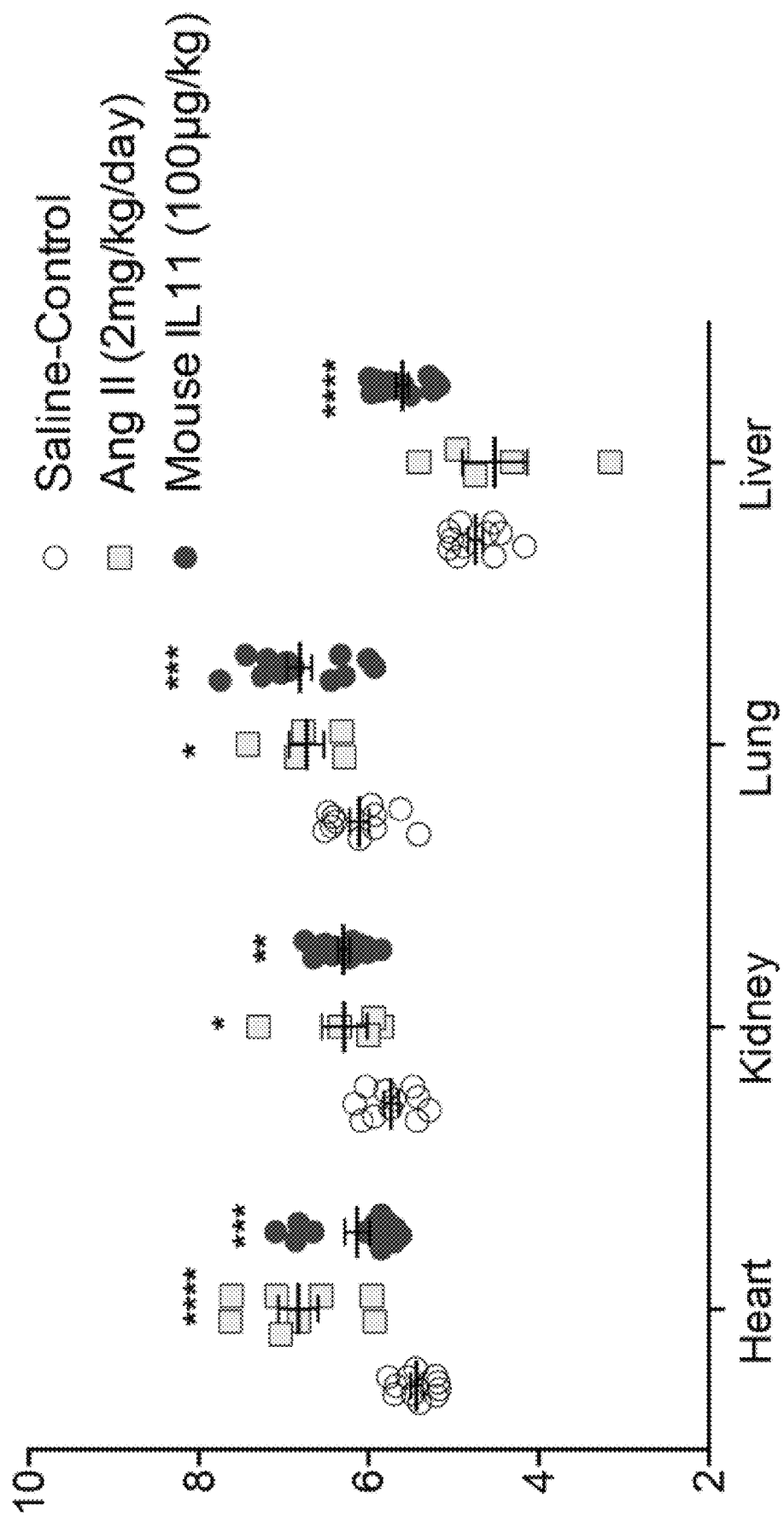
Figure 6C:
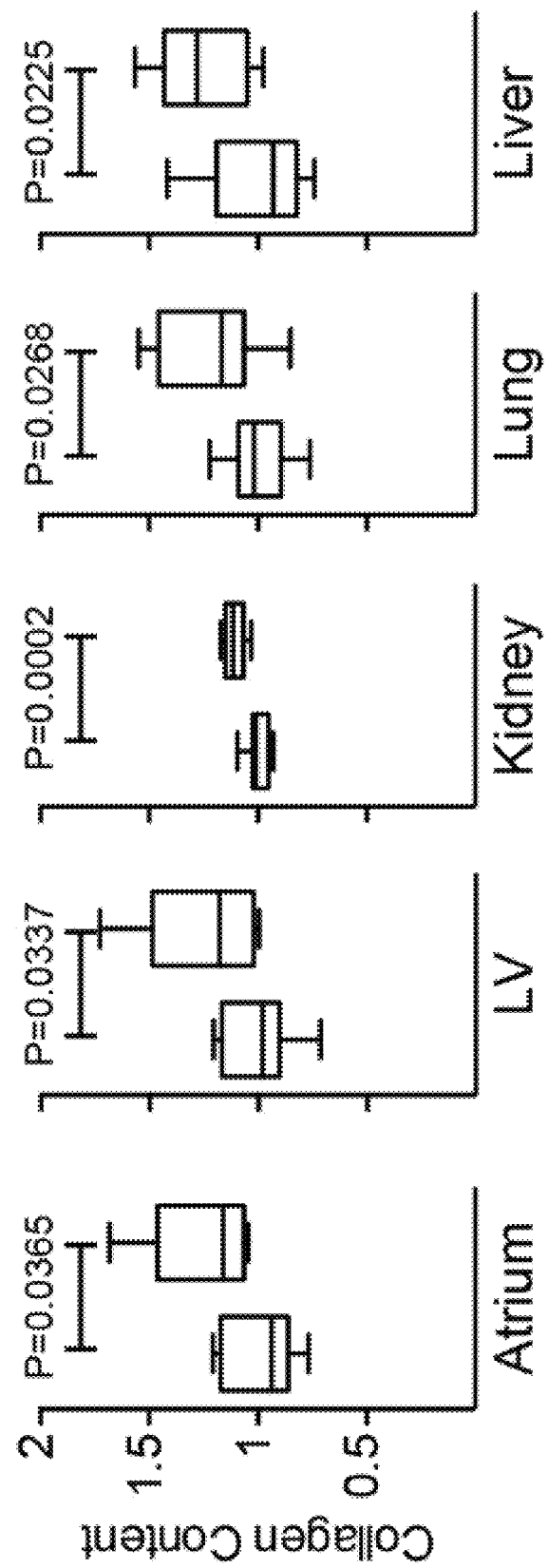
Figure 7A:
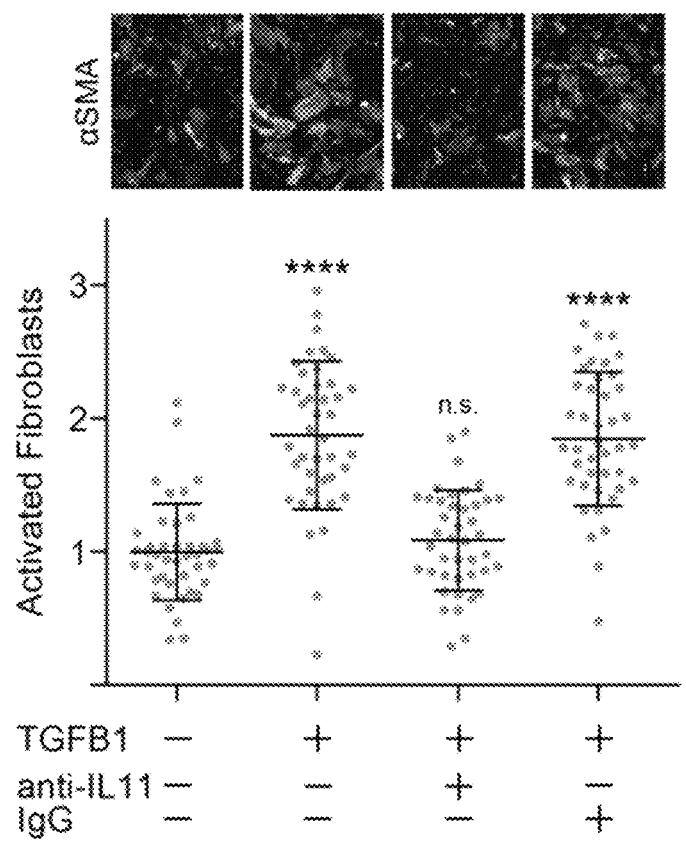
FIGS. 7A to 7F. Graphs and images showing that IL-11 is required the pro-fibrotic effects of TGFβ1 on fibroblasts.
Figure 7B:
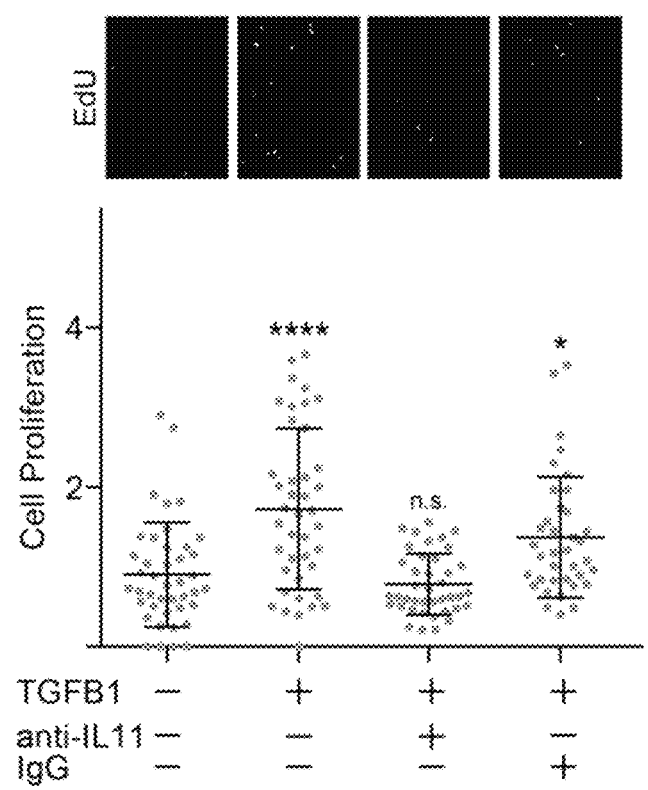
Figure 7C:
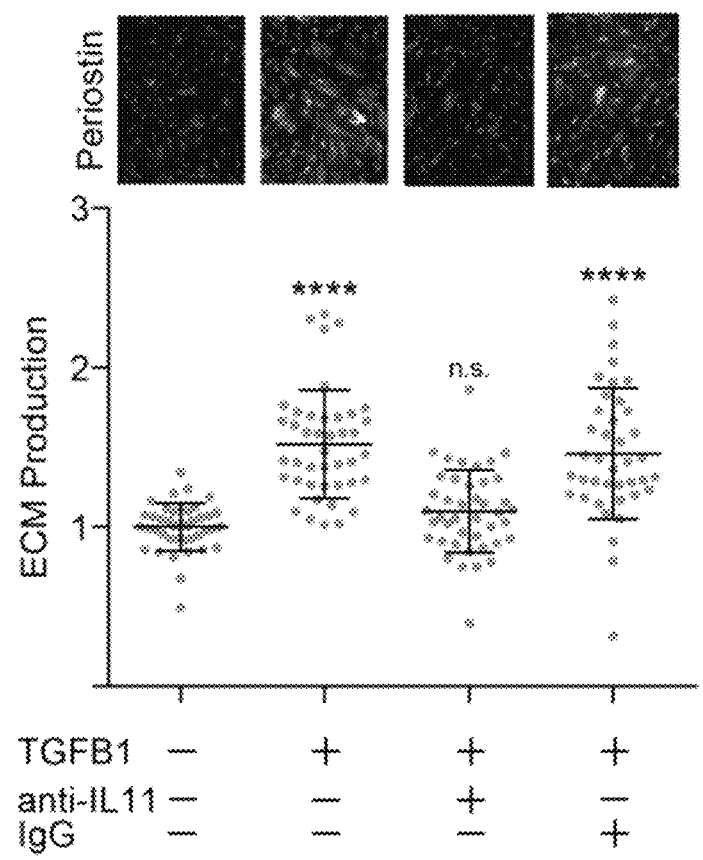
Figure 7D:
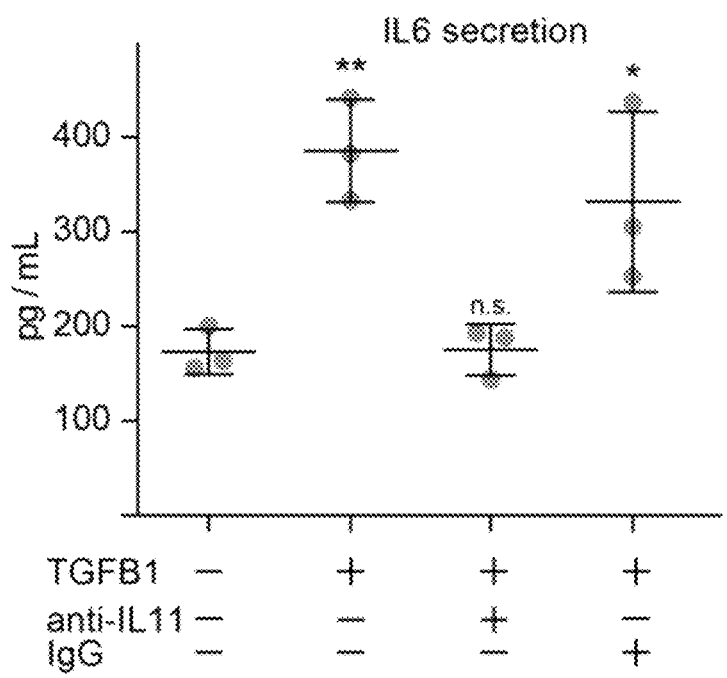
Figure 7E:
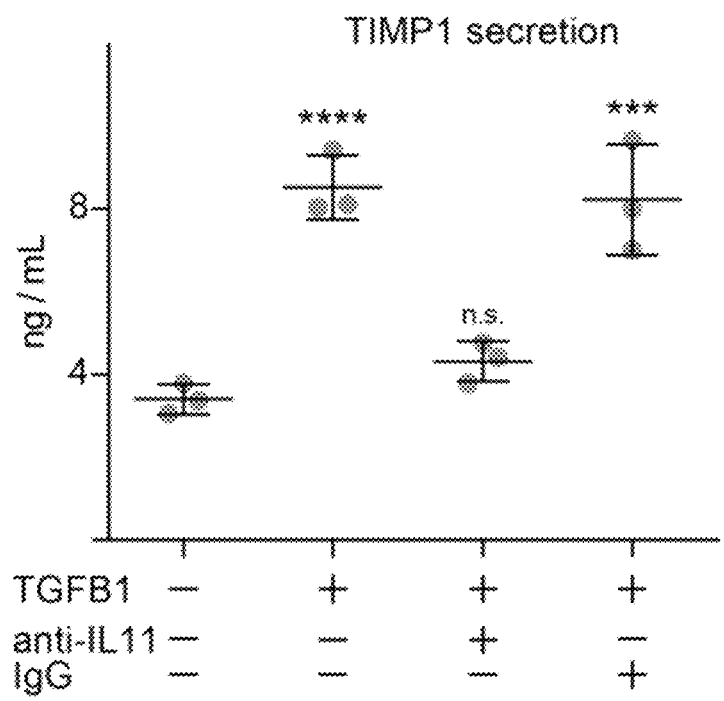
Figure 7F:
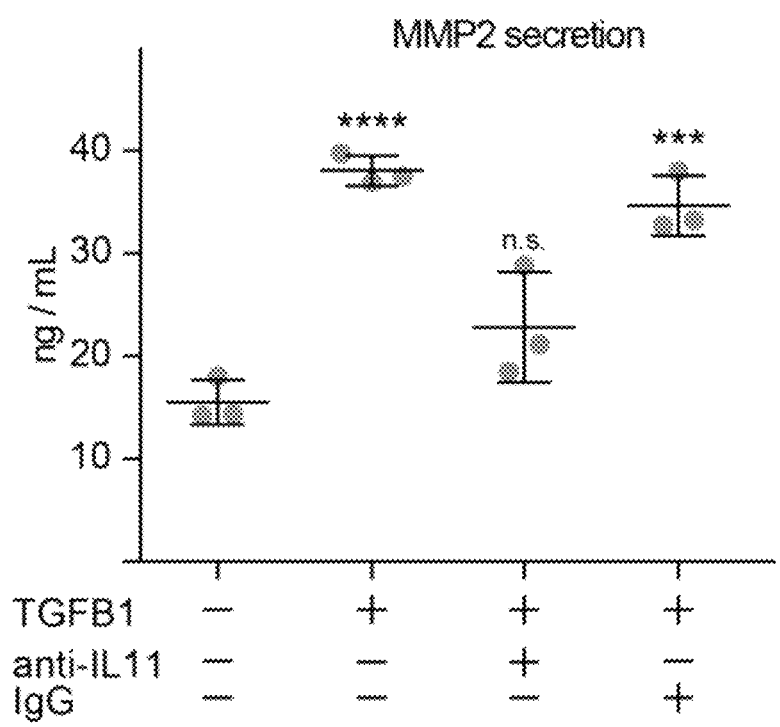

The results are shown in FIGS. 6A to 6C. Compared to injection of AngII (a cytokine that causes an elevation in blood pressure and hypertrophy of the heart), IL-11 also increased the heart weight but also kidney, lung and liver weight indexed to body weight (FIG. 6B). Assessing collagen content in these issues by hydroxyproline assay revealed an upregulation of collagen production in these tissues, indicating fibrosis as the likely cause for the increase in organ weight (FIG. 6C). Expression of fibrosis marker genes ACTA2 (=αSMA), Col1a1, Col3a1, Fn1, Mmp2 and Timp1 was also detected by qPCR analysis of RNA isolated from heart, kidney, lung and liver tissues of these animals Example 2: Therapeutic Potential of IL-11/IL-11R Antagonism 2.1 Inhibition of the Fibrotic Response Using Neutralising Antagonists of IL-11/IL-11R Next it was investigated whether the autocrine loop of IL-11 secretion was required for the pro-fibrotic effect of TGFβ1 on fibroblasts.

IL-11/IL-11R signalling was inhibited using a commercially available neutralizing antibody (Monoclonal Mouse IgG2A; Clone #22626; Catalog No. MAB218; R&D Systems, MN, USA). Fibroblasts were treated with TGFβ1 in the presence or absence of the antibody, and fibroblast activation, the proportion of proliferating cells and ECM production and markers of the fibrotic response were measured.

Briefly, atrial fibroblasts derived from 3 individuals were incubated for 24 h with TGFβ1 (5 ng/ml) or TGFβ1 in the presence of neutralising anti-IL-11 antibody or isotype control antibody. Following incubation, cells were stained for αSMA to determine the fraction of myofibroblasts, the proportion of proliferating cells was determined by analysing the cells for EdU incorporation, and periostin was measured to determine ECM production. Fluorescence was measured with the Operetta platform for 14 fields across 2 wells for each individual. Secretion of the fibrosis markers IL-6, TIMP1 and MMP2 was also analysed by ELISA. Fluorescence was normalized to the control group without stimulation.

The results are shown in FIGS. 7A to 7F. IL-11 inhibition was found to ameliorate TGFβ1-induced fibrosis, and it was shown that IL-11/IL-11R signalling is essential for the pro-fibrotic effect of TGFβ1. Inhibition of IL-11/IL-11R signalling was found to 'rescue' the TGFβ1 phenotype at the protein level.

Collagen production was also analysed. Cardiac fibroblasts derived from 3 individuals were incubated for 24 h with TGFβ1 (5 ng/ml) or TGFβ1 and a neutralizing anti-IL-11 antibody. Following incubation the cells were stained for collagen using the Operetta assay and florescence was quantified as described above. Secreted collagen levels in the cell culture supernatant were assessed by Sirius Red staining.

Figure 8A:
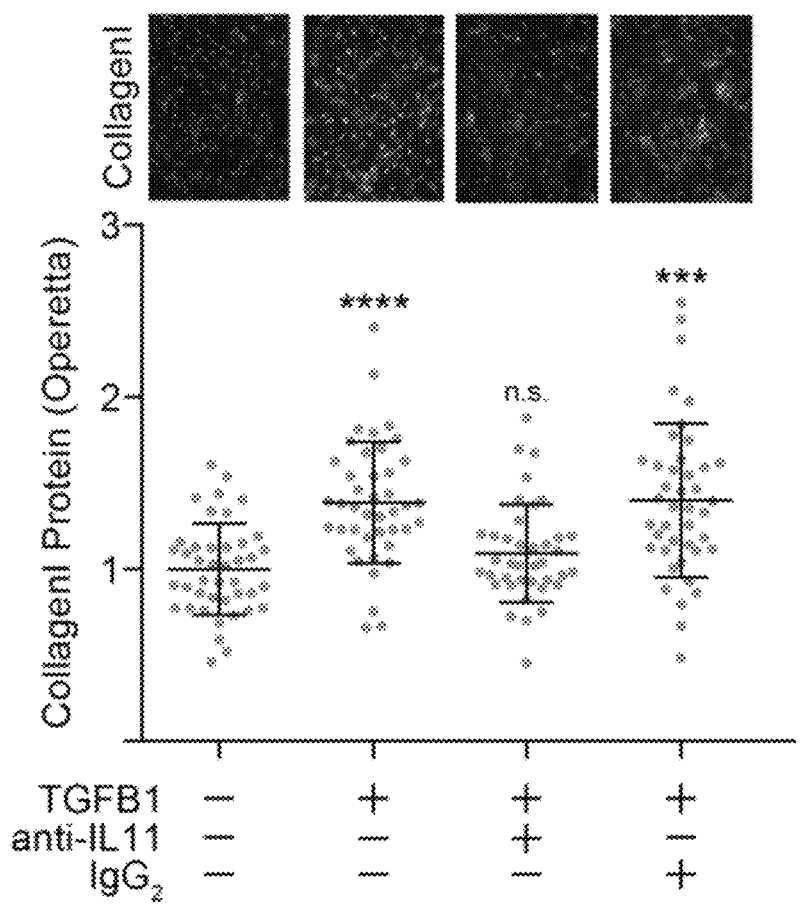
FIGS. 8A and 8B. Graphs and images showing the effect of neutralisation of IL-11 on collagen production triggered by TGFβ1. Collagen production by cardiac fibroblasts with or without stimulation with TGFβ1, and in the presence/absence of neutralising anti-IL-11 antibody or isotype control IgG, as determined by (FIG. 8A) Operetta assay or (FIG. 8B) Sirius Red staining. [Mean±SD, Dunnett]*$P<0.05$,  $P<0.01$, * $P<0.001$ or **** $P<0.0001$.
Figure 8B:
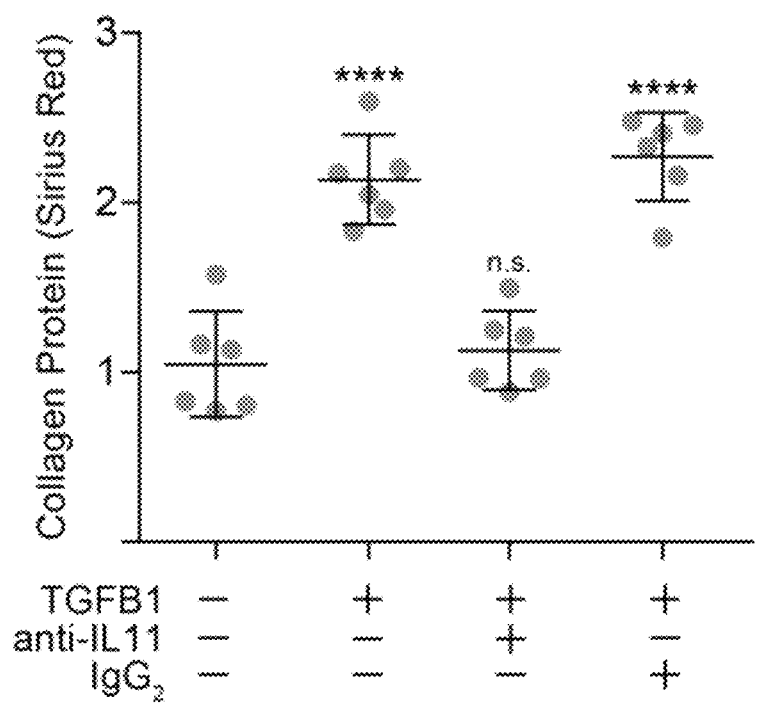

The results are shown in FIGS. 8A and 8B, and confirm the anti-fibrotic effect of inhibition of IL-11/IL-11R signalling using a neutralising antibody.

Next, the ability of several other IL-11/IL-11R antagonists to inhibit fibrosis was analysed in vitro using the atrial fibroblast, TGFβ1-induced myofibroblast transition assay described herein above.

Briefly, human atrial fibroblasts cells were cultured in vitro, stimulated for 24 h with TGFβ1 (5 ng/ml) or left unstimulated, in the presence/absence of: (i) neutralising anti-IL-11 antibody, (ii) a IL-11RA-gp130 fusion protein (iii) neutralising anti-IL-11Rα antibody, (iv) treatment with siRNA directed against IL-11 or (v) treatment with siRNA directed against IL-11RA. The proportion of activated fibroblasts (myofibroblasts) was analysed by evaluating αSMA content as described above.

Figure 9:
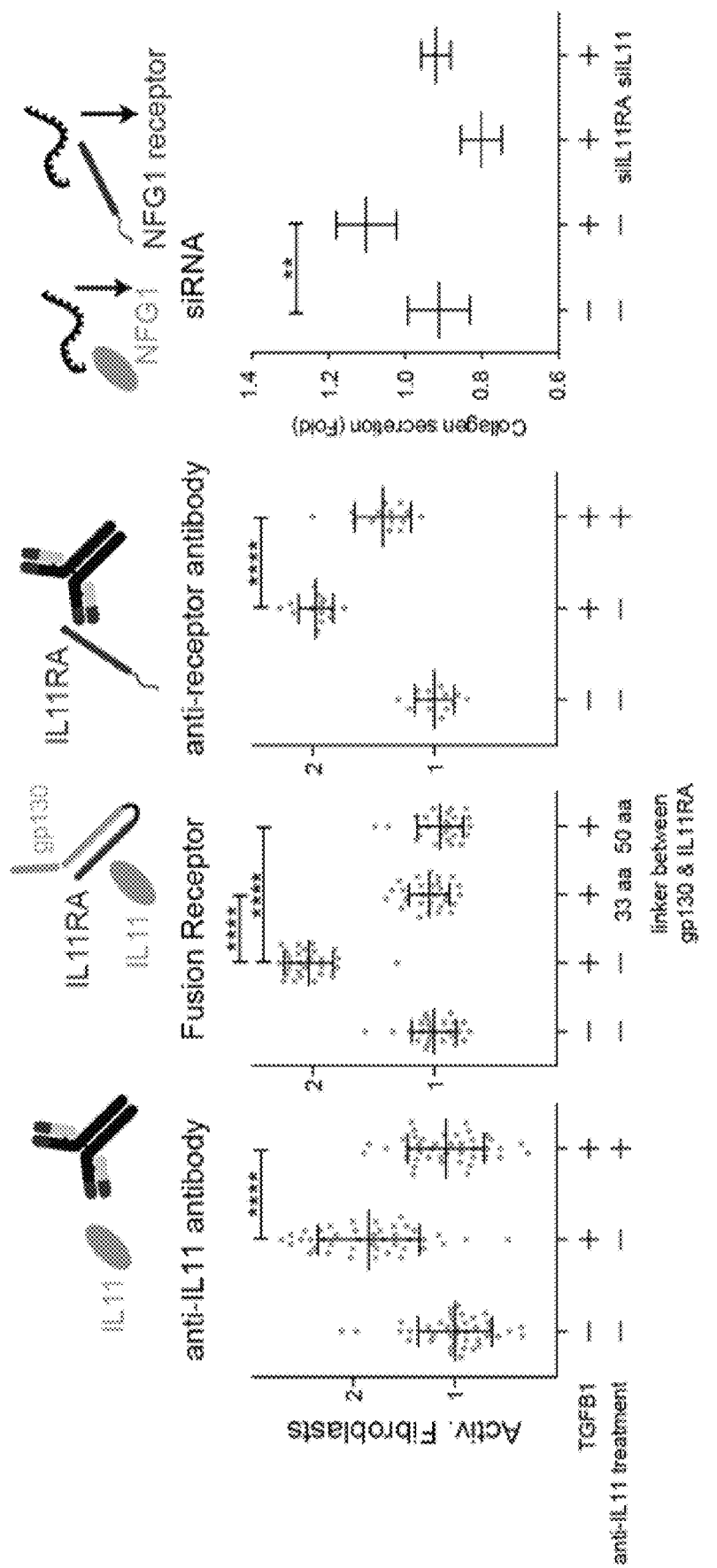
FIG. 9. Graphs showing the ability of various IL-11 and IL-11Rα antagonists to inhibit fibrosis. Human atrial fibroblasts were treated with neutralizing antibody against IL-11, neutralizing antibody against IL-11Rα, decoy IL-11 receptor molecule that binds to IL-11, siRNA that downregulates IL-11 expression or siRNA that downregulates IL-11RA expression and the effect on the TGFβ1-driven pro-fibrotic response in fibroblasts in vitro was analysed. [Mean±SD, Dunnett]*$P<0.05$,  $P<0.01$, * $P<0.001$ or **** $P<0.0001$.
Figure 10A:
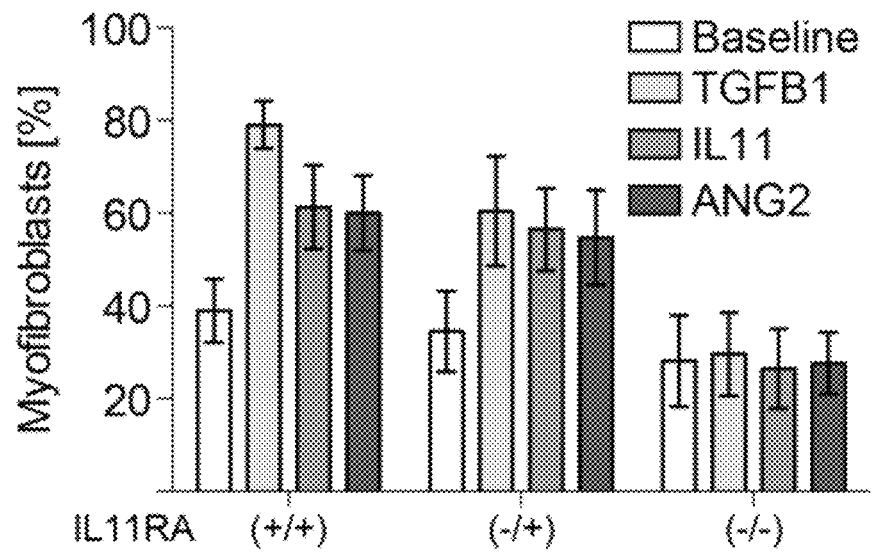
FIGS. 10A to 10D. Bar charts showing the response of fibroblasts from IL-11RA knockout mice to pro-fibrotic treatment. Fibroblasts derived from IL-11RA WT (+/+), Heterozygous (+/−) and Homozygous null (−/−) mice were incubated for 24 h with TGFβ1, IL-11 or AngII (5 ng/ml).
Figure 10B:
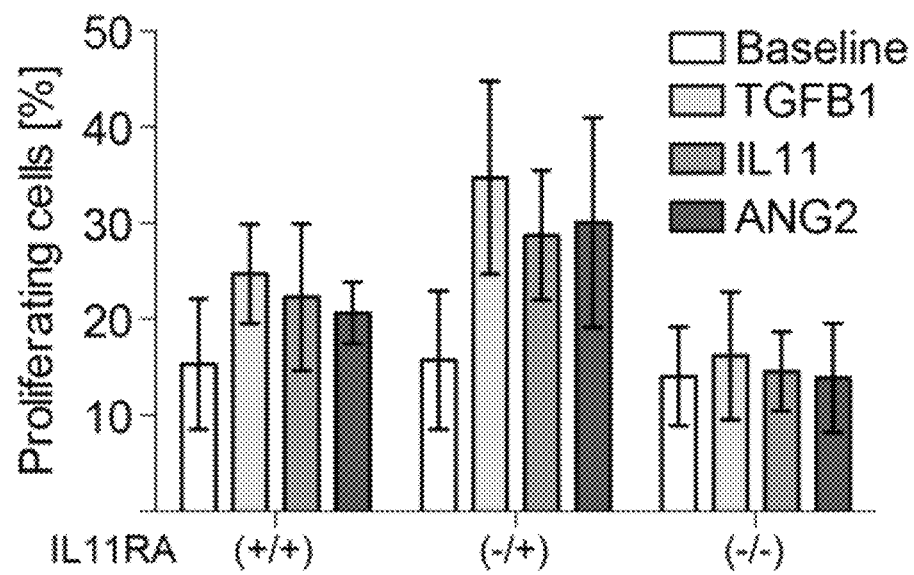
Figure 10C:
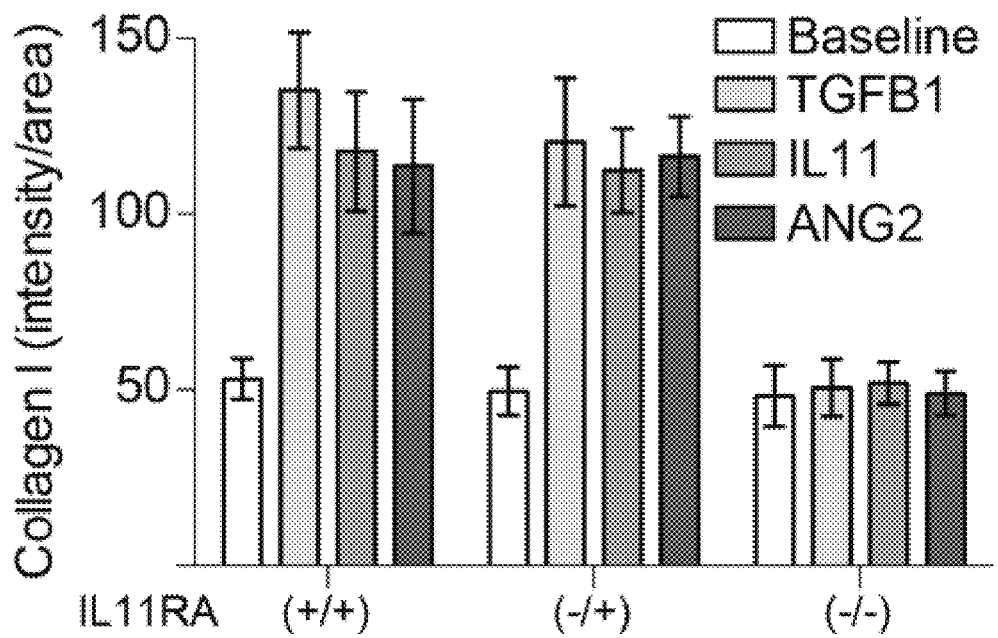
Figure 10D:
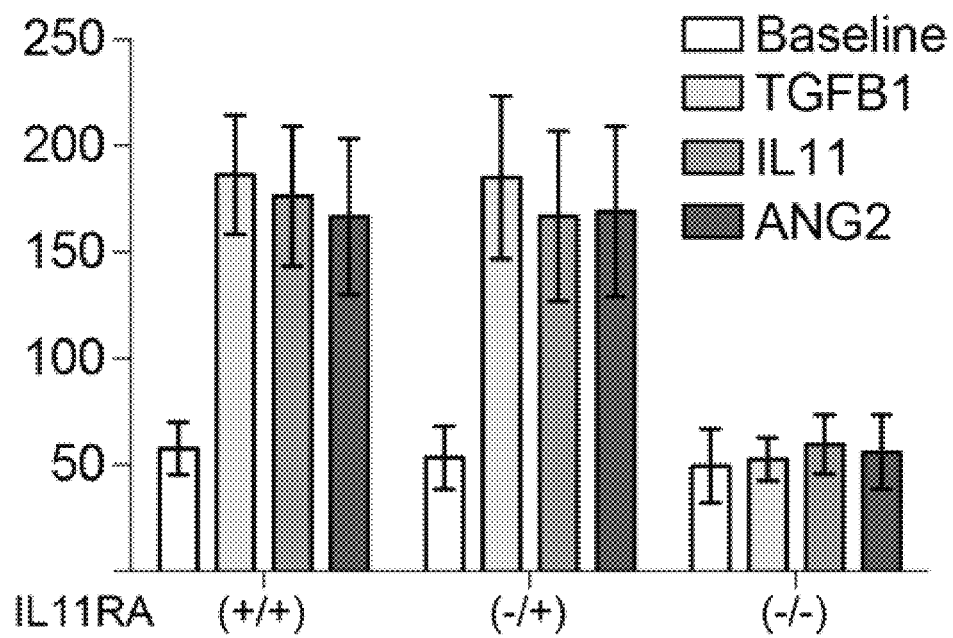

The results are shown in FIG. 9. Each of the antagonists of IL-11/IL-11R signalling was found to be able to abrogate TGFβ1-mediated profibrotic response.

Example 3: In Vivo Confirmation of a Profibrotic Role for IL-11/IL-11R Signalling 3.1 In Vitro Studies Using Cells Derived from IL-11RA Gene Knock-Out Mice All mice were bred and housed in the same room and provided food and water ad libitum. Mice lacking functional alleles for IL-11Rα (IL-11RA1 KO mice) were on C57Bl/6 genetic background. Mice were of 9-11 weeks of age and the weight of animals did not differ significantly.

To further confirm the anti-fibrotic effect of inhibition of IL-11/IL-11R signalling, primary fibroblasts were generated from IL-11RA gene knock-out mice and incubated with primary fibroblast cells harvested from IL-11RA+/+(i.e. wildtype), IL-11RA+/−(i.e. heterozygous knockout) and IL-11RA−/− (i.e. homozygous knockout) animals with TGFβ1, IL-11 or AngII. Activation and proliferation of fibroblasts and ECM production was analysed.

Fibroblasts derived from IL-11RA+/+, IL-11RA+/− and IL-11RA−/− mice were incubated for 24 hours with TGFβ1, IL-11 or AngII (5 ng/ml). Following incubation, cells were stained for αSMA content to estimate the fraction of myofibroblasts, for EdU to identify the fraction of proliferating cells, and for collagen and periostin to estimate ECM production. Fluorescence was measured using the Operetta platform.

The results are shown in FIGS. 10A to 10D. IL-11RA−/− mice were found not to respond to pro-fibrotic stimuli. These results suggested that IL-11/IL-11R signalling is also required for AngII-induced fibrosis.

Next, it was investigated whether this was also true for other pro-fibrotic cytokines.

Briefly, fibroblasts were cultured in vitro in the presence/absence of various different pro-fibrotic factors (ANG2, ET-1 or PDGF), and in the presence/absence of neutralising anti-IL-11 antibody or pan anti-TGFβ antibody. After 24 hours, collagen production by the cells was determined by analysis using the Operetta system as described above, and myofibroblast generation was determined by analysis of αSMA expression as described above.

Figure 11A:
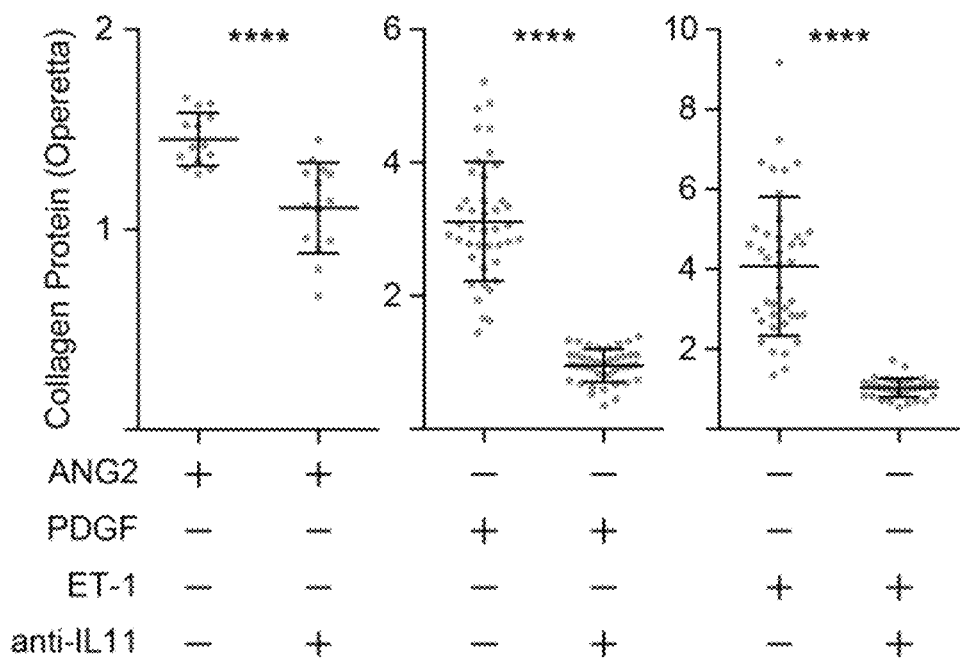
FIGS. 11A and 11B. Graphs showing the effect of IL-11 neutralisation on fibrosis in response to various pro-fibrotic stimuli. Fibroblasts were cultured in vitro in the presence/ absence of various different pro-fibrotic factors, and in the presence/absence of neutralising anti-IL-11 antibody or pan anti-TGFβ antibody (FIG. 11A) Collagen production and (FIG. 11B) myofibroblast generation as determined by analysis of αSMA expression. [Mean±SD, Dunnett] *$P<0.05$,  $P<0.01$, * $P<0.001$ or **** $P<0.0001$.
Figure 11B:
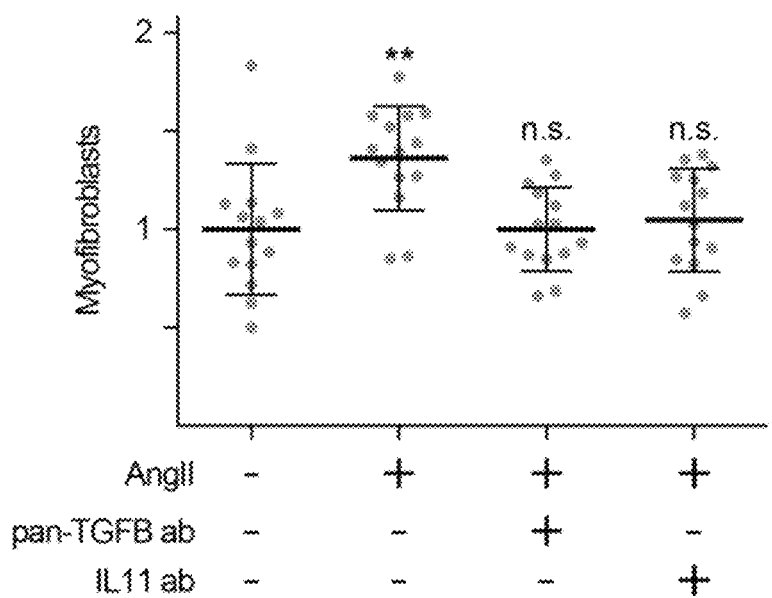
Figure 12A:
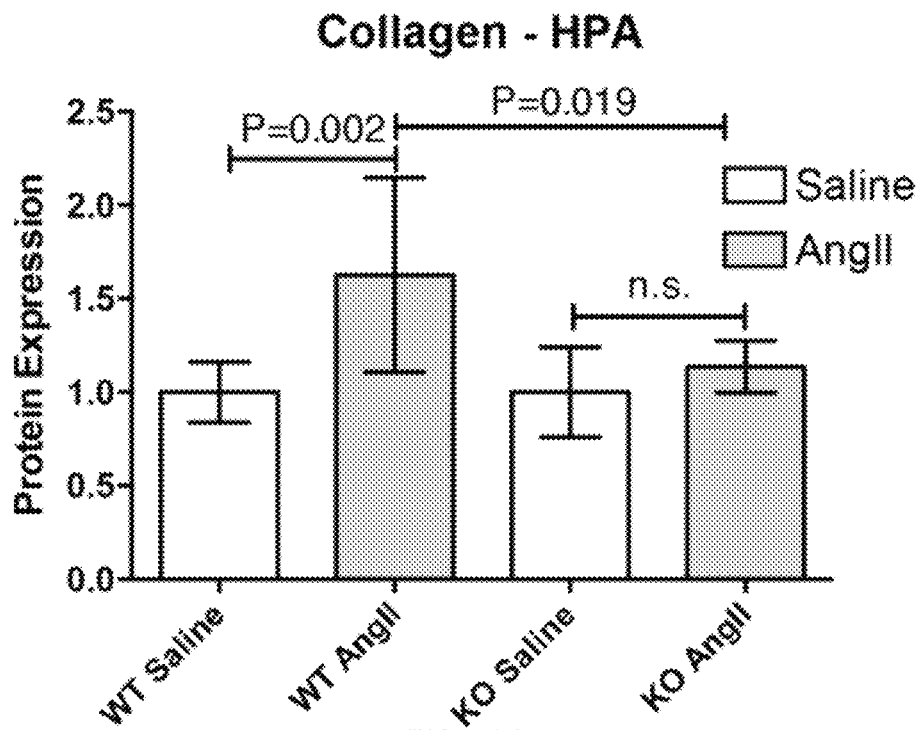
FIGS. 12A to 12D. Bar charts showing expression of markers of fibrosis in the atrium and heart of WT and IL-11RA (−/−) animals following treatment with AngII treatment.
Figure 12B:
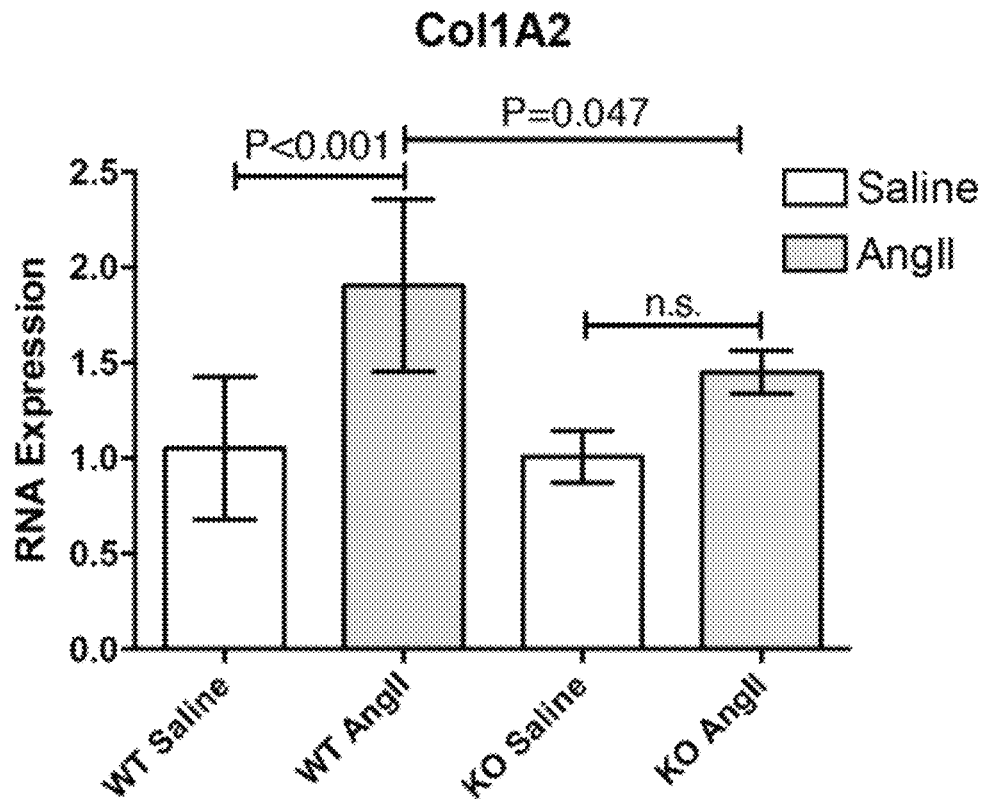
Figure 12C:
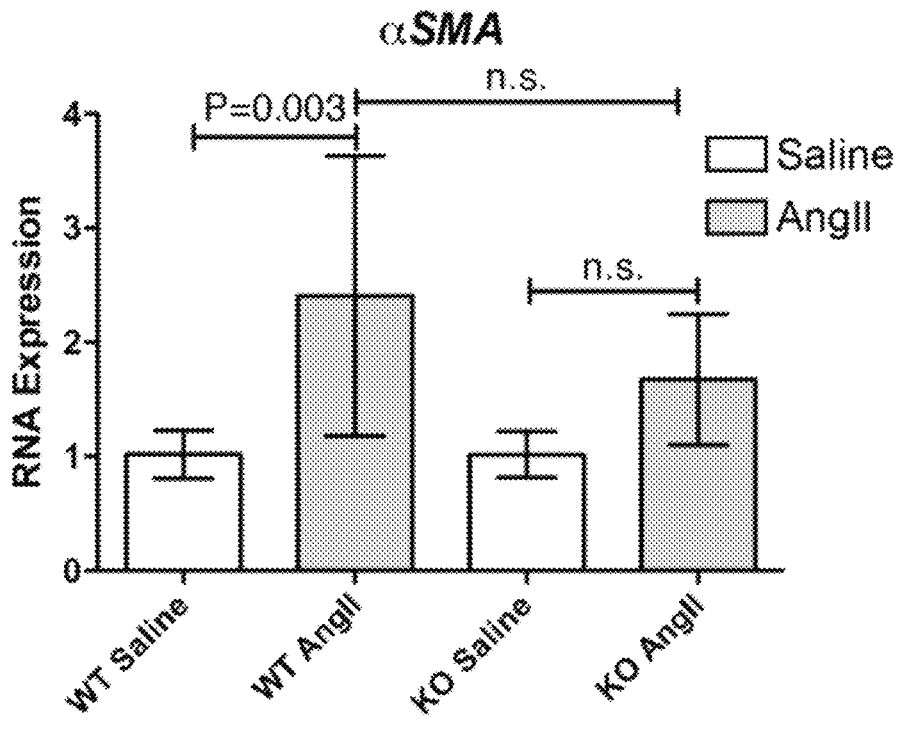
Figure 12D:
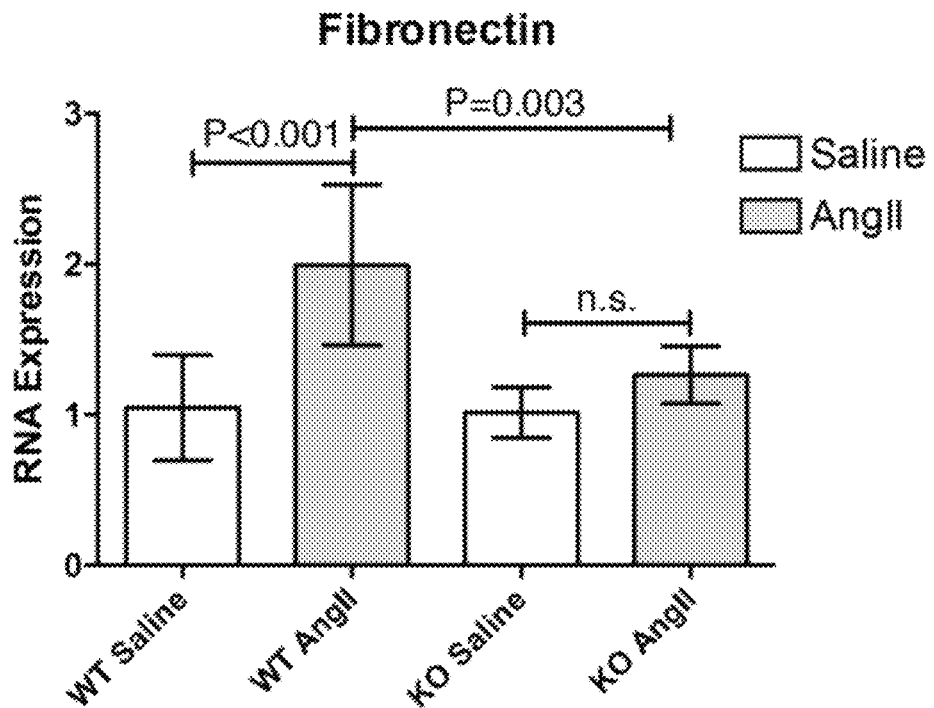

The results are shown in FIGS. 11A and 11B. IL-11/IL-11R signalling was found to be required for fibrosis downstream of various profibrotic stimuli, and was thus identified as a central mediator of fibrosis induced by a variety of different profibrotic factors.

In a further experiment, the role of IL-11 signalling was investigated in lung fibrosis, using an in vitro scratch assay of migration of lung fibroblasts. In response to pro-fibrotic stimuli, fibroblasts are activated and migrate within the fibrotic niche in the body. The migration rate of cells is a measure of cell-cell and cell-matrix interactions and a model for wound healing in vivo (Liang et al., 2007; Nat Protoc. 2(2):329-33).

Fibroblasts derived from lung tissue from both wild type (WT) and also homozygous IL-11RA (−/−) knockout mice were grown at low passage on a plastic surface until they formed a uniform cell monolayer. A scratch was then created in the cell layer, and cell migration close to the scratch was monitored, either in the absence of stimulation, or in the presence of TGFβ1 or IL-11. Images captured at images at the two time points of immediately after creating the scratch and at 24 h were used to determine the area covered by cells, and the rate of migration was compared between WT and KO fibroblasts. Cell migration (area in the scratch covered by cells after 24 h) was normalized to the migration rate of WT cells without stimulus.

Figure 31:
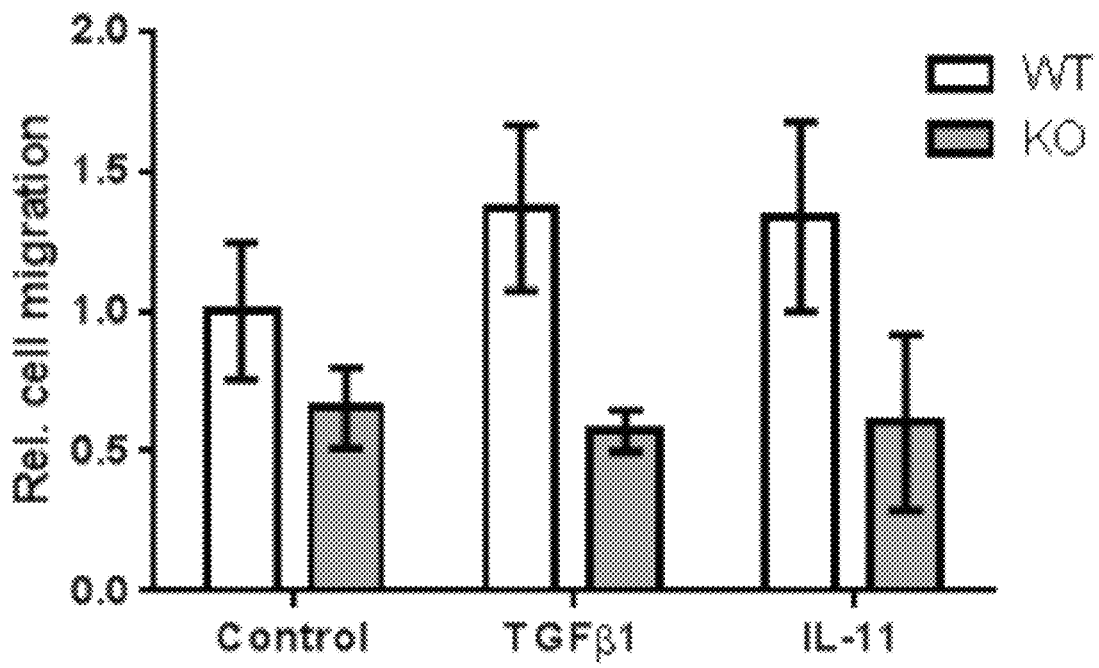
FIG. 31. Bar chart showing lung fibroblast cell migration with and without IL-11 signalling. Migration of lung fibroblasts from IL-11RA+/+(WT) and IL-11RA−/− (KO) animals was analysed in an in vitro scratch assay without stimulus, or in the presence of TGFβ1 or IL-11.

The results are shown in FIG. 31. Lung fibroblasts derived from WT mice were shown to migrate faster in the presence of TGFβ1 and IL-11, indicating a pro-fibrotic effect of both cytokines in lung fibroblasts. Cells lacking IL-11 signalling derived from KO mice migrated more slowly as compared to WT cells. They also did not migrate faster in the presence of TGFβ1. The scratch assay revealed that lung fibroblasts lacking IL-11 signalling have a decrease cell migration rate both in the presence of TGFβ1 or IL-11, and at baseline. Thus, inhibition of IL-11 signalling is anti-fibrotic in the lung.

3.2 Heart Fibrosis

The efficacy of IL-11 inhibition to treat fibrotic disorders was investigated in vivo. A mouse model for cardiac fibrosis, in which fibrosis is induced by treatment with AngII, was used to investigate whether IL-11RA−/− mice were protected from cardiac fibrosis.

Briefly, a pump was implanted, and wildtype (WT) IL-11RA(+/+) and knockout (KO) IL-11RA(−/−) mice were treated with AngII (2 mg/kg/day) for 28 days. At the end of the experiment, collagen content was assessed in the atria of the mice using a calorimetric hydroxyproline-based assay kit, and the level of RNA expression of the markers or fibrosis Col1A2, αSMA (ACTA2) and fibronectin (Fn1) were analysed by qPCR.

The results are shown in FIGS. 12A to 12D. The IL-11RA−/− mice were found to be protected from the profibrotic effects of AngII.

3.3 Kidney Fibrosis

A mouse model for kidney fibrosis was established in wildtype (WT) IL-11RA(+/+) and knockout (KO) IL-11RA (−/−) mice by intraperitoneal injection of folic acid (180 mg/kg) in vehicle (0.3M $NaHCO_3$); control mice were administered vehicle alone.

Kidneys were removed 28 days post-injection, weighed and either fixed in 10% neutral-buffered formalin for Masson's trichrome and Sirius staining or snap-frozen for collagen assay, RNA, and protein studies.

Total RNA was extracted from the snap-frozen kidney using TRIZOL™ reagent (Invitrogen) and QIAGEN TISSUELYZER™ method followed by RNEASY™ column (Qiagen) purification. The cDNA was prepared using ISCRIPT™ cDNA synthesis kit, in which each reaction contained 1 μg of total RNA, as per the manufacturer's instructions. Quantitative RT-PCR gene expression analysis was performed on triplicate samples with either TAQMAN™ (Applied Biosystems) or fast SYBR™ green (Qiagen) technology using STEPONEPLUS™ (Applied Biosystem) over 40 cycles. Expression data were normalized to GAPDH mRNA expression level and we used the 2-ΔΔCt method to calculate the fold-change. The snap-frozen kidneys were subjected to acid hydrolysis by heating in 6M HCl at a concentration of 50 mg/ml (95° C., 20 hours). The amount of total collagen in the hydrolysate was quantified based on the colorimetric detection of hydroxyproline using QUICKZYME™ Total Collagen assay kit (Quickzyme Biosciences) as per the manufacturer's instructions.

Figure 15:
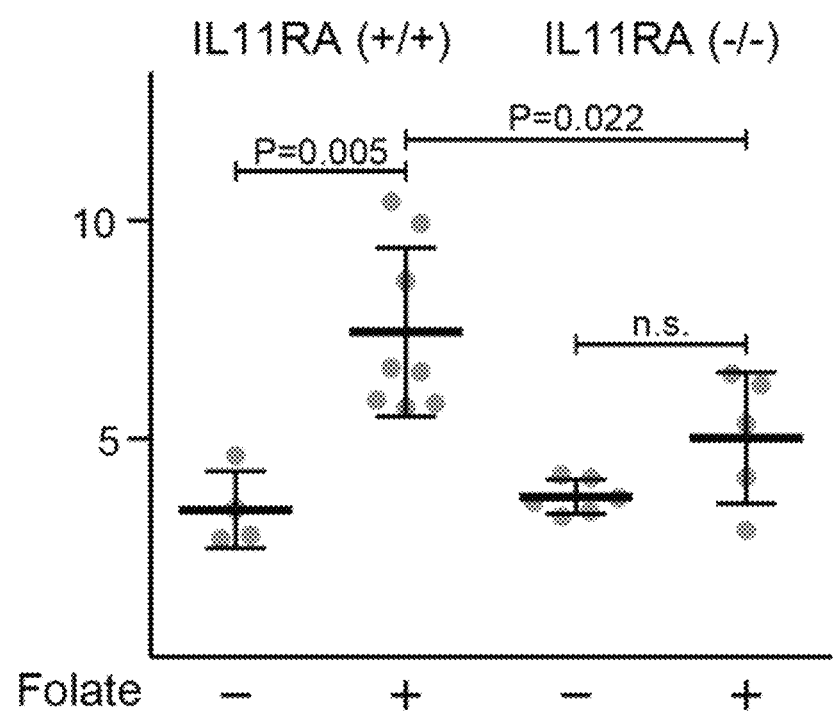
FIG. 15. Graphs showing the effect of IL-11RA knockout on folate-induced kidney fibrosis as measured by collagen content in kidney tissue.

The results of the analysis are shown in FIG. 15. Folate-induced kidney fibrosis is shown to be dependent on IL-11 mediated signalling. A significant increase in collagen content in kidney tissue was observed in IL-11RA+/+ mice, indicative of kidney fibrosis. No significant increase in collagen content was observed in IL-11RA-/- mice. Animals deficient for IL-11 signalling had significantly less collagen deposition in kidneys after toxic injury as compared to wild type animals.

3.4 Lung Fibrosis

Figure 13A:
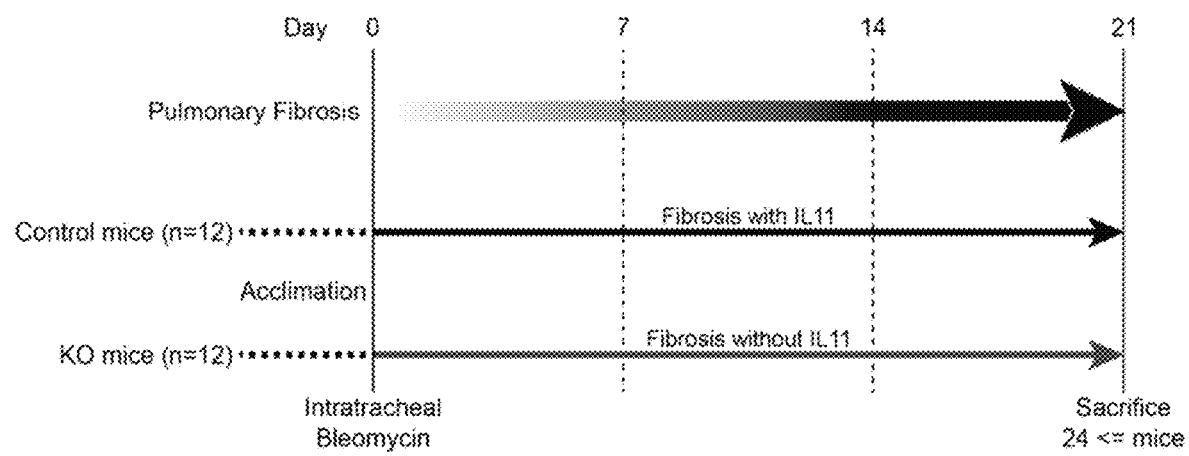
FIGS. 13A to 13C. Schematics of the experimental procedures for analysing fibrosis in (FIG. 13A) lung, (FIG. 13B) skin and (FIG. 13C) eye for IL-11RA−/− mice as compared to IL-11RA+/+ mice.
Figure 13B:
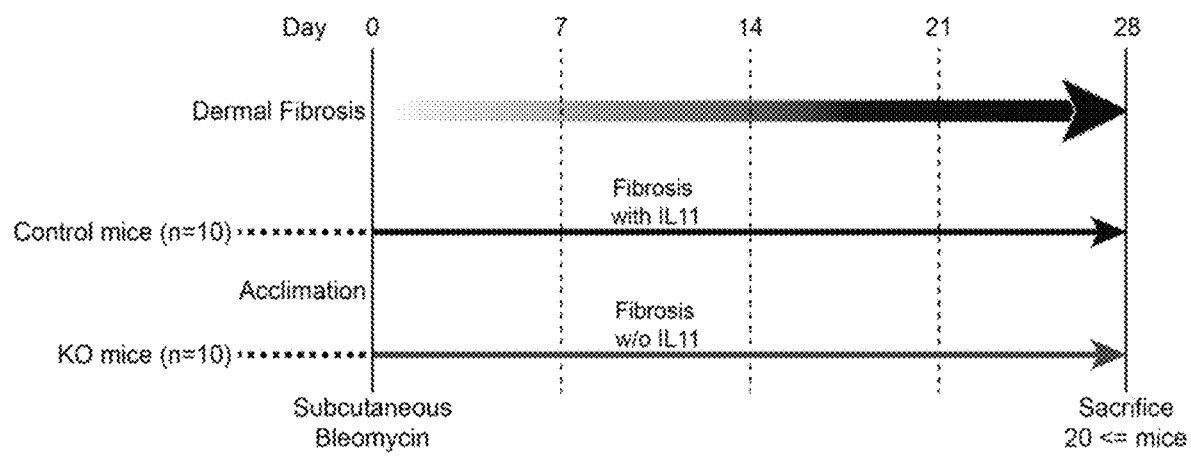
Figure 13C:
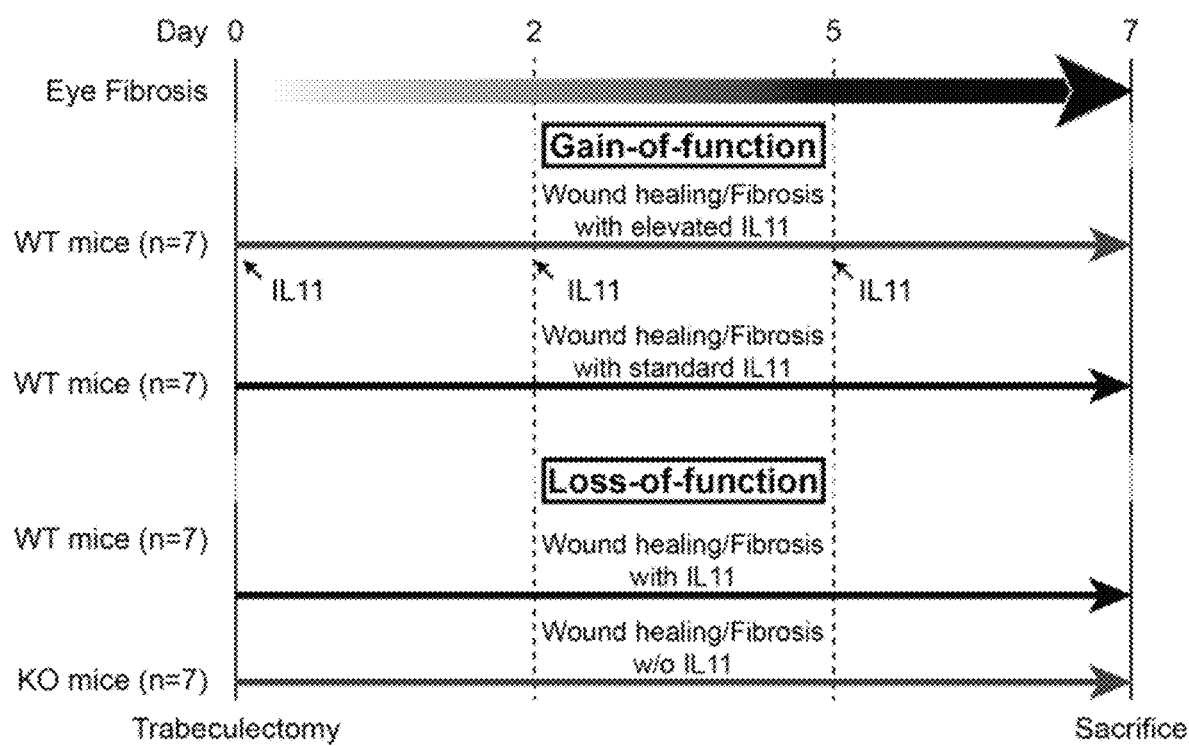

IL-11 is confirmed as a key mediator of fibrosis in the lung, skin and eye in further in vivo models using the IL-11RA-/- knockout mice. Schematics of the experiments are shown in FIGS. 13A to 13C.

To analyse pulmonary fibrosis, IL-11RA-/- mice and IL-11RA+/+ mice are treated by intratracheal administration of bleomycin on day 0 to establish a fibrotic response in the lung (pulmonary fibrosis). Fibrosis of the lung develops by 21 days, at which point animals are sacrificed and analysed for differences in fibrosis markers between animals with and without IL-11 signalling. IL-11RA-/- mice have a reduced fibrotic response in lung tissue as compared to IL-11RA+/+ mice, as evidenced by reduced expression of markers of fibrosis.

3.5 Skin Fibrosis

To analyse fibrosis of the skin, IL-11RA-/- mice and IL-11RA+/+ mice are treated by subcutaneous administration of bleomycin on day 0 to establish a fibrotic response in the skin. Fibrosis of the skin develops by 28 days, at which point animals are sacrificed and analysed for differences in fibrosis markers between animals with and without IL-11 signalling. IL-11RA-/- mice have a reduced fibrotic response in skin tissue as compared to IL-11RA+/+ mice, as evidenced by reduced expression of markers of fibrosis.

3.6 Eye Fibrosis

To analyse fibrosis in the eye, IL-11RA-/- mice and IL-11RA+/+ mice underwent trabeculectomy (filtration surgery) on day 0 to initiate a wound healing response in the eye. This mouse model of glaucoma filtration surgery has been shown to be an efficient model to evaluate the wound healing response in the eye (Khaw et al. 2001, Curr Opin Ophthalmol 12, 143-148; Seet et al. 2011, Mol. Med. 17, 557-567) and has successfully shown the beneficial effect of fibrotic modulators in vivo (Mead et al. 2003, Invest. Ophthalmol. Vis. Sci. 44, 3394-3401; Wong et al. 2003 Invest. Ophthalmol. Vis. Sci. 44, 1097-1103; Wong et al. 2005, Invest. Ophthalmol. Vis. Sci. 46, 2018-2022).

Briefly, the conjunctiva was dissected to expose the underlying sclera, after which an incision was made through the sclera into the anterior chamber of the eye using a 30-gauge needle. The created fistula allowed aqueous humor to exit into and underneath the conjunctiva. The dissected conjunctiva was then secured and closed at the limbus by a 10-0 (0.2 metric) Ethilon black monofilament nylon scleral suture. Fucithalmic ointment was instilled at the end of the procedure. The surgery was performed under anaesthesia by intraperitoneal injection of a 0.1 ml ketamine/xylazine mixture, as well as topical application of one drop per eye of 1% xylocaine. Fucithalmic ointment was instilled post-surgery to prevent infection. Surgery was performed with 70% propyl alcohol sterilized surgical scissors and forceps and sterile needles.

The accumulated fluid underneath the sutured conjunctiva was observed as a conjunctival bleb. Mice were euthanized on day 7 post-surgery for analyses. For qualitative immune-histological analyses, eyes from mice will be harvested by enucleation and then sectioned. Maturation of collagen fibres was evaluated with using the picro-sirius red/polarization light technique (Szendröi et al. 1984, Acta Morphol Hung 32, 47-55); orange-red indicated mature collagen, and yellow/green indicated newly formed immature collagen.

Figures 27, 28A:
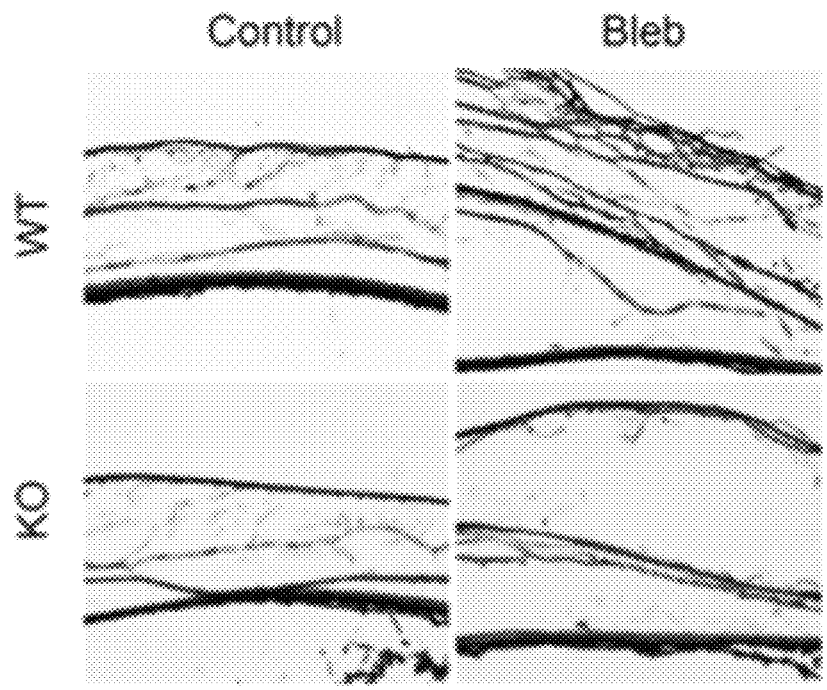
FIG. 27. Table summarising the fold-change data of FIGS. 24 to 26 for the anti-IL-11Rα antibodies. Antibody candidates numbered 1 to 17 correspond to clone designations as indicated in FIG. 23. Industry standard is monoclonal mouse anti-IL-11 IgG2A; Clone #22626; Catalog No. MAB218; R&D Systems, MN, USA.
FIGS. 28A and 28B. Photographs showing the effect of IL-11RA knockout on wound healing and fibrosis in the eye following trabeculectomy (filtration surgery).
Figure 28B:
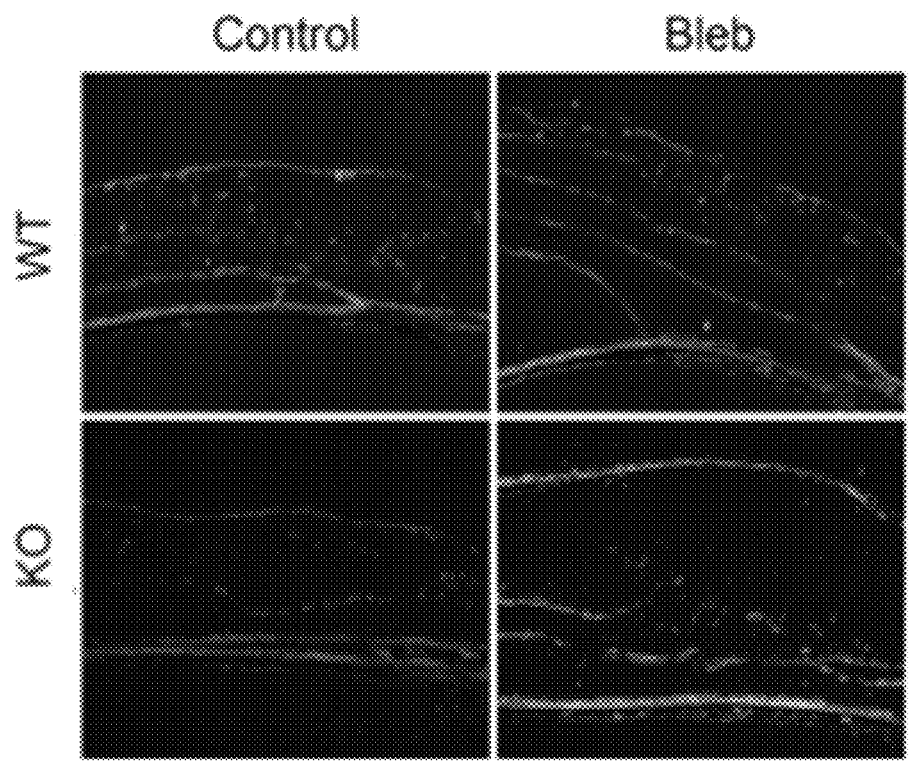
Figure 29A:
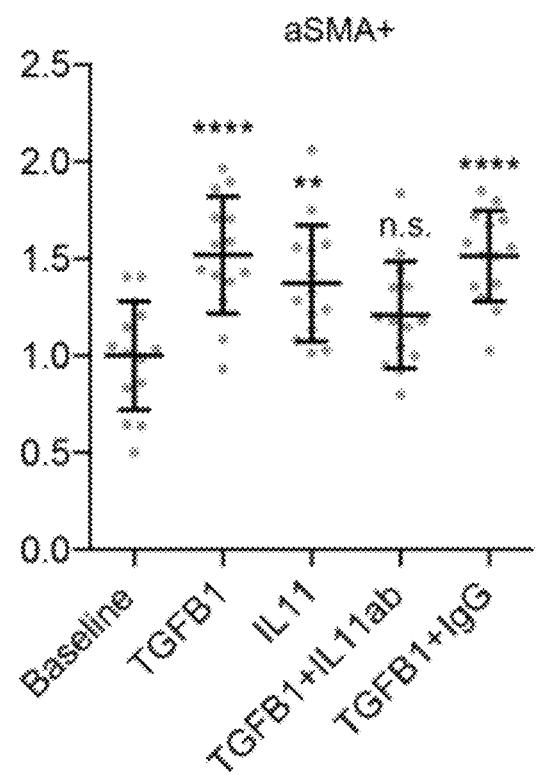
FIGS. 29A to 29D. Graphs showing that IL-11 is required for the pro-fibrotic effects of TGFβ1 in liver fibroblasts. Activation and proliferation of primary human liver fibroblasts, with or without stimulation with TGFβ1, and in the presence/absence of neutralising anti-IL-11 antibody or isotype control IgG, as measured by analysis of the proportion of (FIG. 29A) α-SMA positive cells, and (FIG. 29B) EdU positive cells, (FIG. 29C) Collagen positive cells and (FIG. 29D) Periostin positive cells as compared to the unstimulated cells (Baseline). [Mean±SD, Dunnett]*P<0.05,  P<0.01, * P<0.001 or **** P<0.0001.
Figure 29B:
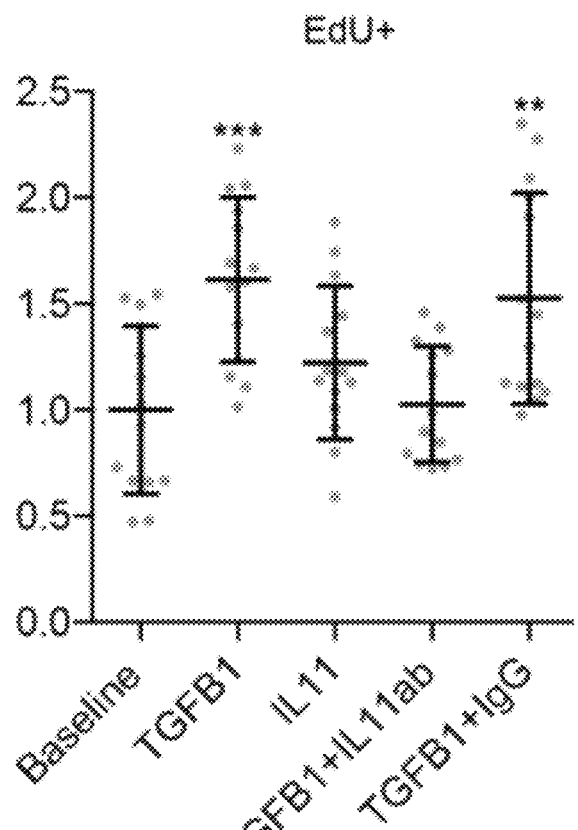
Figure 29C:
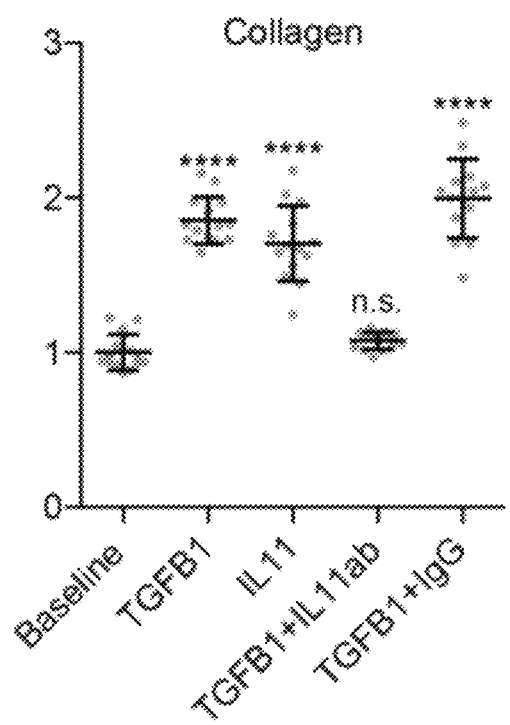
Figure 29D:
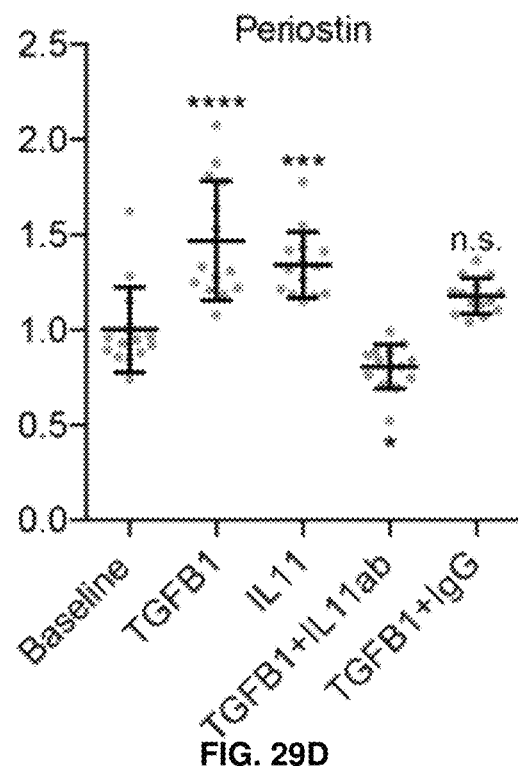

The results of the experiment are shown in FIGS. 28A and 28B. IL-11RA-/- mice were found to have a reduced fibrotic response in eye tissue as compared to IL-11RA+/+ mice.

3.7 Other Tissues

The effect of IL-11RA knockout on fibrosis is also analysed in mouse models of fibrosis for other tissues, such as the liver, bowel, and is also analysed in a model relevant to multiorgan (i.e. systemic) fibrosis. The fibrotic response is measured and compared between the IL-11RA-/- mice and IL-11RA+/+ mice. IL-11RA-/- mice have a reduced fibrotic response as compared to IL-11RA+/+ mice, as evidenced by reduced expression of markers of fibrosis.

Example 4: Analysis of the Molecular Mechanisms Underlying IL-11-Mediated Induction of Fibrosis The canonical mode of action of IL-11 is thought to be regulation of RNA expression via STAT3-mediated transcription (Zhu et al., 2015 PLoS ONE 10, e0126296), and also through activation of ERK.

STAT3 activation is observed following stimulation with IL-11. However, when fibroblasts are incubated with TGFβ1, only activation of the canonical SMAD pathway and ERK pathways is seen, and activation of STAT3 is not observed, even in spite of the fact that IL-11 is secreted in response to TGFβ1. Only ERK activation is common to both TGFβ1 and IL-11 signal transduction.

Cross-talk between TGFβ1 and IL-6 signalling has previously been described, wherein TGFβ1 blocks the activation of STAT3 by IL-6 (Walia et al., 2003 FASEB J. 17, 2130-2132). Given the close relationship between IL-6 and IL-11, similar cross-talk may be observed for IL-11 mediated signalling.

The inventors investigated by RNA-seq analysis whether regulation of RNA abundance was the underlying mechanism for the increased expression of fibrosis marker proteins in response to IL-11, which would suggest STAT3 as the underlying signalling pathway for IL-11 mediated profibrotic processes. Fibroblasts were incubated for 24 hours either without stimulus, or in the presence of TGFβ1, IL-11 or TGFβ1 and IL-11

Figure 14A:
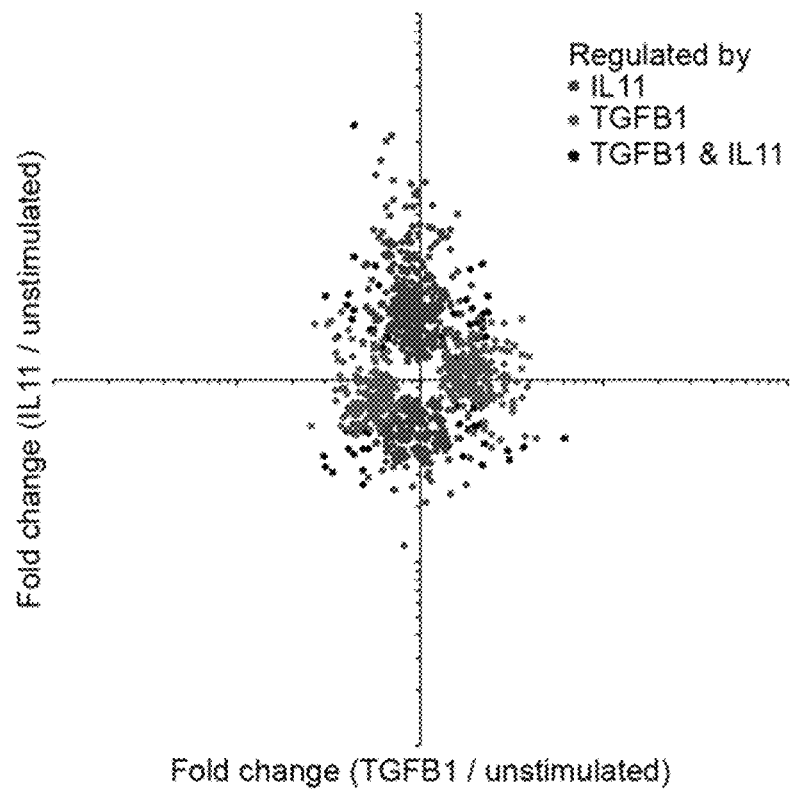
FIGS. 14A and 14B. Scatterplots showing fold change in gene expression.
Figure 14B:
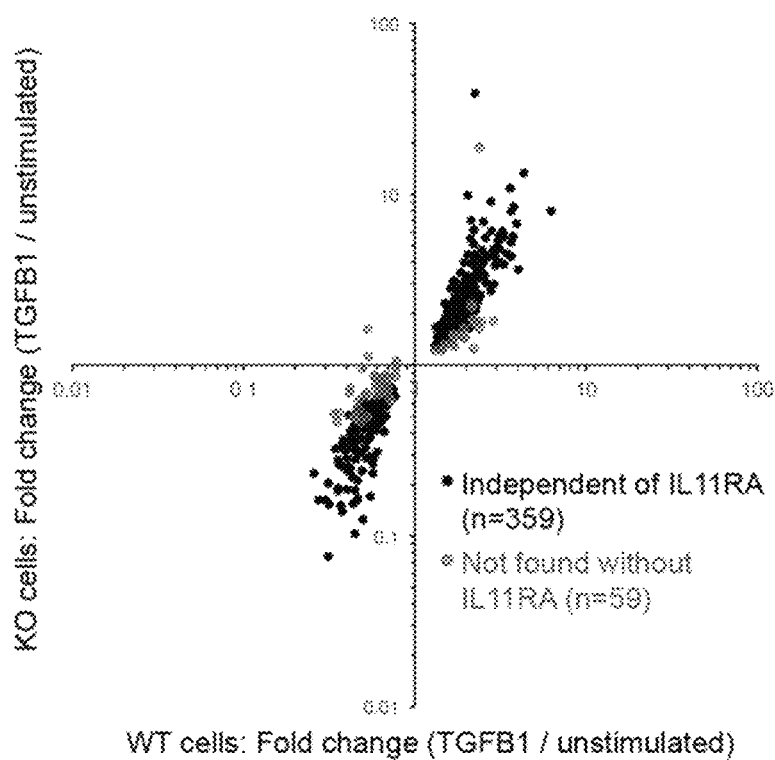

The results are shown in FIG. 14A. TGFβ1 induced the expression of collagen, ACTA2 (αSMA) and other fibrosis marker at the RNA level. However, IL-11 did not regulate the expression of these genes, but a different set of genes.

Gene ontology analysis suggests that a pro-fibrotic effect in fibroblasts is driven by IL-11-regulated RNA expression. Both TGFβ1 and IL-11 regulate an almost completely different set of genes on the RNA level.

Whilst TGFβ1 increases IL-11 secretion, the target genes of IL-11 are not regulated when both TGFβ1 and IL-11 are present. This suggests that TGFβ1 upregulates IL-11 and simultaneously blocks the canonical IL-11-driven regulation of RNA expression via STAT3, similar to what is known about the interaction of TGFβ1 and IL-6 pathways (Walia et al., 2003 FASEB J. 17, 2130-2132).

We also analysed whether RNA expression differences induced by TGFβ1 are dependent on IL-11 signalling, by analysing changes in RNA expression in fibroblasts obtained from IL-11RA−/− mice as compared to IL-11RA+1+ mice. RNA expression regulated by TGFβ1 is still observed when IL-11RA knockout cells were stimulated with TGFβ1, and RNA levels of αSMA, collagen etc. were still upregulated in the absence of IL-11 signalling (in IL-11RA−/− fibroblasts). When the pro-fibrotic effect of IL-11 and the anti-fibrotic effect of IL-11 inhibition was investigated in vitro, reduced expression of markers of fibrosis was only observed at the protein level, not at the transcriptional level as determined by qPCR.

The activation of non-canonical pathways (e.g. ERK signal transduction) is known to be crucial for the pro-fibrotic action of TGFβ1 (Guo and Wang, 2008 Cell Res 19, 71-88). It is likely that non-canonical pathways are likely to be important for signalling for all known pro-fibrotic cytokines, and that IL-11 is a post-transcriptional regulator which is essential for fibrosis.

Example 5: Anti-Human IL-11Rα Antibodies

Mouse monoclonal antibodies directed against human IL-11Rα protein were generated as follows.

cDNA encoding the amino acid for human IL-11Rα was cloned into expression plasmids (Aldevron GmbH, Freiburg, Germany).

Mice were immunised by intradermal application of DNA-coated gold-particles using a hand-held device for particle-bombardment ("gene gun"). Serum samples were collected from mice after a series of immunisations, and tested in flow cytometry on HEK cells which had been transiently transfected with human IL-11Rα expression plasmids (cell surface expression of human IL-11Rα by transiently transfected HEK cells was confirmed with anti-tag antibodies recognising a tag added to the N-terminus of the IL-11Rα protein).

Antibody-producing cells were isolated from the mice and fused with mouse myeloma cells (Ag8) according to standard procedures.

Hybridomas producing antibodies specific for IL-11Rα were identified by screening for ability to bind to IL-11Rα expressing HEK cells by flow cytometry.

Cell pellets of positive hybridomas cells were prepared using an RNA protection agent (RNAlater, cat. #AM7020 by ThermoFisher Scientific) and further processed for sequencing of the variable domains of the antibodies.

Sequencing was performed using BigDye® Terminator v3.1 Cycle Sequencing kit (Life Technologies®) according to the manufacturer's instructions. All data was collected using a 3730xl DNA Analyzer system and Unified Data Collection software (Life Technologies®). Sequence assembly was performed using CodonCode Aligner (CodonCode Corporation). Mixed base calls were resolved by automatically assigning the most prevalent base call to the mixed base calls. Prevalence was determined by both frequency of a base call and the individual quality of the base calls.

In total, 17 mouse monoclonal anti-human IL-11Rα antibody clones were generated (FIG. 23); clones BSO-1E3, BSO-2C1, BSO-2E5, BSO-4G3, BSO-5E5, BSO-7G9, BSO-9A7, BSO-10D11, BSO-13B10, BSW-1D3, BSW-1F6, BSW-4G5, BSW-6H3, BSW-7E9, BSW-7G8, BSW-7H8, and BSW-8B7.

The VL and VH domain sequences were determined for antibody clones BSO-1E3, BSO-2E5, BSO-4G3, BSO-5E5, BSO-7G9, BSO-9A7, BSO-10D11, and BSO-13B10 are shown in FIGS. 16 and 17, as are LC-CDRs 1-3 and HC-CDRs 1-3 as determined by analysis using VBASE2 software (http://www.vbase2.org/; Retter et al., Nucl. Acids Res. (2005) 33 (suppl 1): D671-D674).

Two VH and VL sequences were obtained for BSO-1E3 (BSO-1E3_1 and BSO-1E3_2).

Example 6: Functional Characterisation of Anti-Human IL-11Rα Antibodies 6.1 Ability to Inhibit Human IL-11/IL-11R Mediated Signalling To investigate the ability of the anti-IL-11Rα antibodies to neutralise human IL-11/IL-11R mediated signalling, cardiac atrial human fibroblasts were cultured in wells of 96-well plates in the presence of TGFβ1 (5 ng/ml) for 24 hours, in the presence or absence of the anti-IL-11Rα antibodies. This profibrotic stimulus promotes the expression of IL-11, which in turn drives the transition of quiescent fibroblasts to activated, αSMA-positive fibroblasts. It has previously been shown that neutralising IL-11 prevents TGFβ1-induced transition to activated, αSMA-positive fibroblasts.

Anti-IL-11Rα antibodies (2 µg/ml) were added to fibroblast cultures that were stimulated with TGFβ1, and at the end of the 24 hour culture period, the percentage of αSMA-positive fibroblasts was determined. The percentages were normalised based on the percentage of αSMA-positive fibroblasts observed in cultures of fibroblasts which had not been stimulated with TGFβ1.

Expression of αSMA was analysed with the Operetta High-Content Imaging System in an automated high-throughput fashion.

Figures 23, 24:
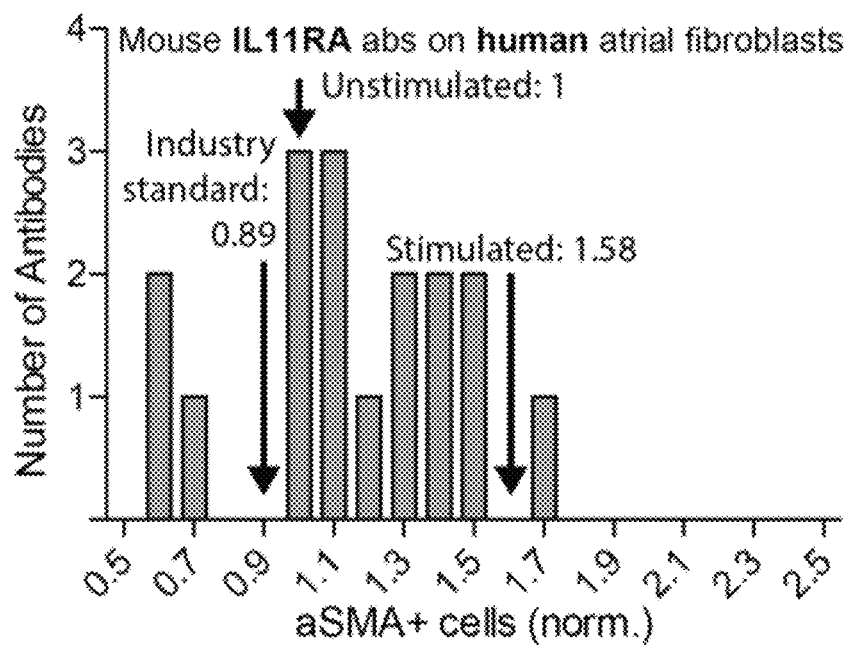
FIG. 23. Table summarising the 17 anti-human IL-11 antibody clones.
FIG. 24. Bar chart showing inhibition by the anti-IL-11Rα antibodies of signalling mediated by IL-11 in vitro in human atrial fibroblasts, as determined by fold change in the percentage of αSMA positive cells as compared to control (unstimulated) fibroblasts, following stimulation with TGFβ1, in the presence of the anti-IL-11Rα antibodies.

The results are shown in FIGS. 24 and 27. Stimulation with TGFβ1 resulted in a 1.58 fold increase in the number of αSMA-positive, activated fibroblasts at the end of the 24 hour culture period in the absence of anti-IL-11Rα antibodies.

A commercial monoclonal mouse anti-IL-11 antibody (Monoclonal Mouse IgG2A; Clone #22626; Catalog No. MAB218; R&D Systems, MN, USA) was included as a control. This antibody was found to be able to reduce the percentage of activated fibroblasts to 0.89 fold of the percentage of activated fibroblasts in unstimulated cultures (i.e. in the absence of stimulation with TGFβ1).

The anti-IL-11Rα antibodies were found to be able to inhibit IL-11/IL-11R signalling in human fibroblasts, and several were able to inhibit IL-11/IL-11R signalling to a greater extent than the monoclonal mouse anti-IL-11 antibody: BSO-1E3, BSO-5E5 and BSO-13B10.

6.2 Ability to Inhibit Mouse IL-11 Mediated Signalling

The ability of the anti-IL-11Rα antibodies to inhibit mouse IL-11-mediated signalling was also investigated, following the same procedure as described in section 6.1 above, but using mouse atrial fibroblasts instead of human atrial fibroblasts.

Figure 25:
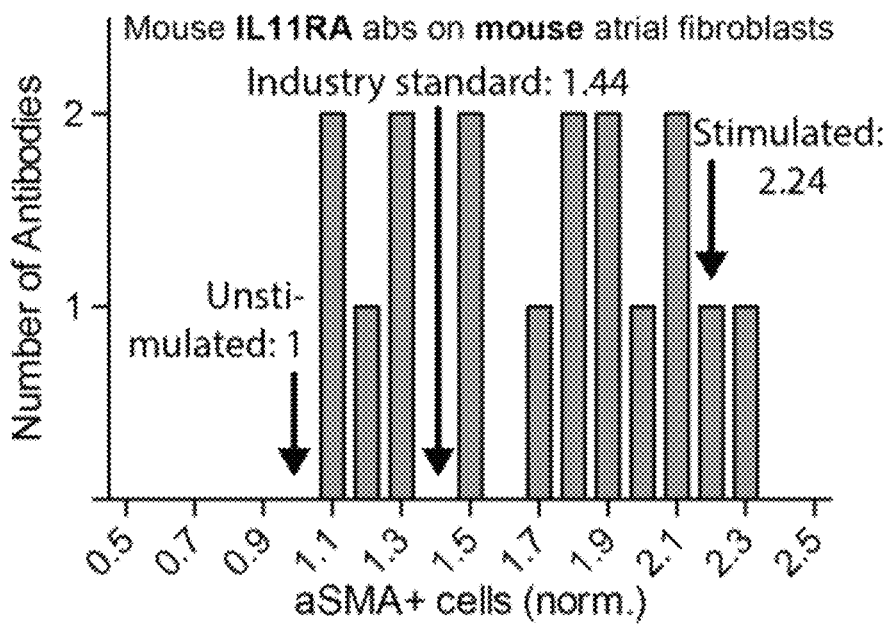
FIG. 25. Bar chart showing inhibition by the anti-IL-11Rα antibodies of signalling mediated by IL-11 in vitro in mouse atrial fibroblasts, as determined by fold change in the percentage of αSMA positive cells as compared to control (unstimulated) fibroblasts, following stimulation with TGFβ1, in the presence of the anti-IL-11Rα antibodies.

The results are shown in FIGS. 25 and 27. Stimulation with TGFβ1 resulted in a 2.24 fold increase in the number of αSMA-positive, activated fibroblasts at the end of the 24 hour culture period in the absence of anti-IL-11Rα antibodies.

The commercial monoclonal mouse anti-IL-11 antibody (Monoclonal Mouse IgG2A; Clone #22626; Catalog No. MAB218; R&D Systems, MN, USA) was included as a control. This antibody was found to be able to reduce the percentage of activated fibroblasts to 1.44 fold of the percentage of activated fibroblasts in unstimulated cultures (i.e. in the absence of stimulation with TGFβ1).

The anti-IL-11Rα antibodies were found to be able to inhibit IL-11/IL-11R signalling in mouse fibroblasts, and several were able to inhibit IL-11/IL-11R signalling to a greater extent than the monoclonal mouse anti-IL-11 antibody: BSO-1E3, BSO-2C1, BSO-5E5, BSO-9A7 and BSO-13B10.

6.3 Ability to Inhibit IL-11 Trans Signaling, by IL-11 in Complex with IL-11Rα

Trans signalling is recognised as a major aspect of IL-6 signalling, where a complex of IL-6 and soluble IL-6Ra can activate cells that express gp130, but lack the IL-6 receptor (Hunter and Jones, 2015 Nature Immunology 16, 448-457).

It has recently been suggested that trans signalling by a complex of IL-11 and soluble IL-11RA is also important for IL-11 biology (Lokau et al., Cell Reports (2016) 14, 1761-1773). Using a recombinant fusion protein of IL-11 and IL-11Rα (as described in Pflanz et al., Febs Lett (1999) 450: 117-122), anti-IL-11 antibodies were screened for the ability to inhibit trans signalling mediated by IL-11:IL-11Rα complex.

Importantly, antibodies which are capable of inhibiting both classical IL-11 mediated signalling and IL-11 trans signalling by IL-11:IL-11Rα complex are able to inhibit all known modes of IL-11/IL-11R signalling.

The IL-11:IL-11Rα fusion protein (hereafter referred to as hyper IL-11) consists of the extracellular domain of the IL-11 receptor alpha (IL-11Rα) linked to IL-11.

Figure 32A:
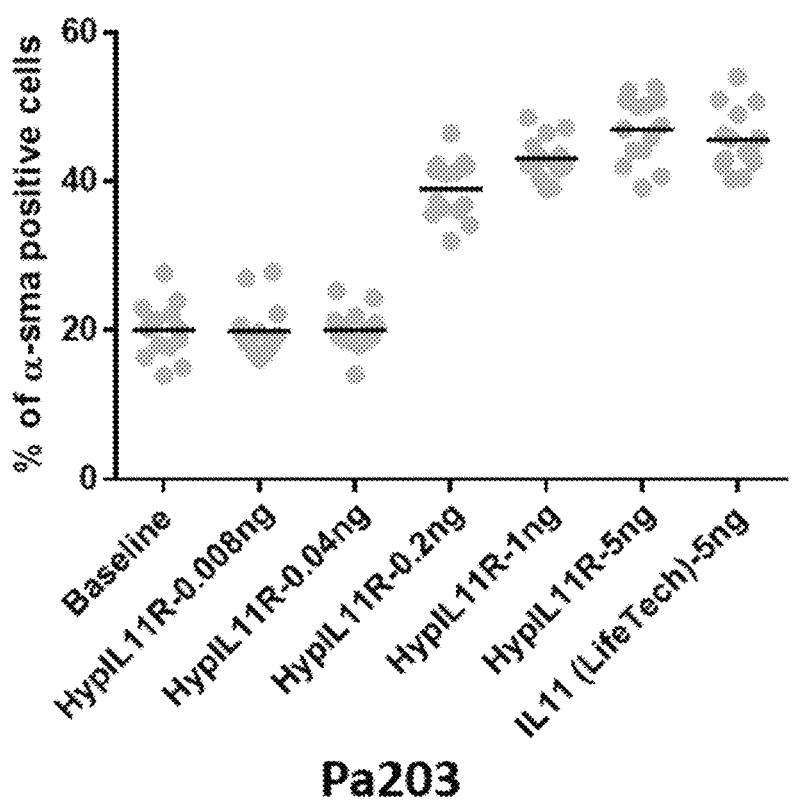
FIGS. 32A and 32B. Graphs showing fibroblast activation in response to hyper IL-11. Cells were stimulated with the indicated amount (in ng/ml) of hyper IL-11 or recombinant IL-11, and fibroblast activation was measured by analysis of the percentage of α-SMA positive cells.
Figure 32B:
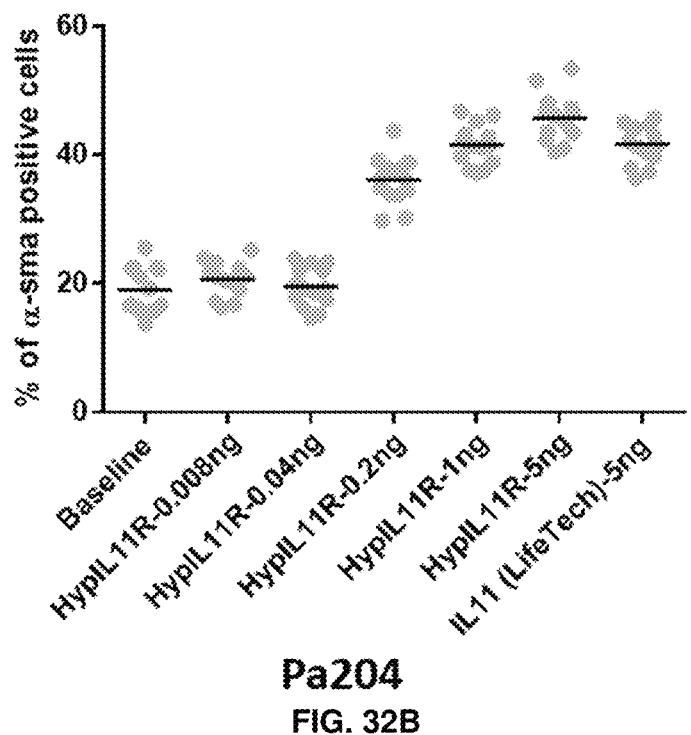

Hyper IL-11 was found to be a more potent activator of human fibroblasts than recombinant IL-11 protein. Briefly, in two separate experiments human fibroblasts were cultured without stimulation (Baseline), in the presence of different amounts of hyper IL-11 (0.008 ng/ml, 0.04 ng/ml, 0.2 ng/ml, 1 ng/ml and 5 ng/ml), or 5 ng/ml recombinant human IL-11 obtained from a commercial source, and fibroblast activation was analysed by determining the percentage of αSMA-positive cells as described herein. The results are shown in (FIGS. 32A and 32B). Hyper-IL-11 activated fibroblasts in a dose-dependent fashion, and was a more potent activator than IL-11.

The IL-11:IL-11Rα fusion protein was prepared as follows:
DNA encoding IL-11:IL-11Rα fusion protein (i.e. SEQ ID NO:98) was cloned into pTT5 vector, and transfected into 293-6E cells in culture in serum-free FREESTYLE™ 293 Expression Medium (Thermo Fisher Scientific).
Cells were maintained in Erlenmeyer Flasks (Corning Inc.) at 37° C. with 5% CO2 on an orbital shaker (VWR Scientific).
Cell culture supernatants were collected on day 6 were used for purification.
Cell culture supernatant was loaded onto an affinity purification column.
After washing and elution with appropriate buffer, the eluted fractions were pooled and buffer exchanged to final formulation buffer.
The purified IL-11:IL-11Rα fusion protein was analyzed by SDS-PAGE, Western blot to confirm molecular weight and purity.

DNA encoding IL-11: IL-11Rα fusion protein (SEQ ID NO: 98):
GAATTCCCGCCGCCACCATGGGCTGGTCCTGCATCATCCTGTTTCTGGTG
GCCACAGCCACCGGCGTGCACTCTCCACAGGCTTGGGGACCTCCAGGCGT
GCAGTATGGCCAGCCTGGCAGATCCGTGAAGCTGTGCTGTCCTGGCGTGA
CAGCTGGCGACCCTGTGTCCTGGTTCAGAGATGGCGAGCCCAAGCTGCTG
CAGGGCCCAGATTCTGGACTGGGCCACGAACTGGTGCTGGCCCAGGCCGA
TTCTACCGACGAGGGCACCTACATCTGCCAGACCCTGGATGGCGCCCTGG
GCGGAACAGTGACACTGCAGCTGGGCTACCCTCCCGCCAGACCTGTGGTG
TCTTGTCAGGCCGCCGACTACGAGAACTTCAGCTGCACATGGTCCCCCAG
CCAGATCAGCGGCCTGCCCACCAGATACCTGACCAGCTACCGGAAGAAAA
CCGTGCTGGGCGCCGACAGCCAGAGAAGAAGCCCTTCTACAGGCCCCTGG
CCCTGCCCTCAGGATCCTCTGGGAGCTGCCAGATGTGTGGTGCACGGCGC
CGAGTTCTGGTCCCAGTACCGGATCAACGTGACCGAAGTGAACCCCCTGG
GCGCCTCCACAAGACTGCTGGATGTGTCCCTGCAGAGCATCCTGCGGCCC
GATCCTCCACAGGGCCTGAGAGTGGAAAGCGTGCCCGGCTACCCCAGAAG
GCTGAGAGCCAGCTGGACATACCCCGCCTCTTGGCCTTGCCAGCCCCACT
TCCTGCTGAAGTTTCGGCTGCAGTACCGGCCAGCCCAGCACCCTGCTTGG
AGCACAGTGGAACCTGCCGGCCTGGAAGAAGTGATCACAGACGCCGTGGC
CGGACTGCCTCATGCTGTGCGGGTGTCCGCCAGAGACTTTCTGGATGCCG
GCACCTGGTCTACCTGGTCCCCAGAAGCCTGGGGCACACCTTCTACTGGC
GGACCTGCTGGACAGTCTGGCGGAGGCGGAGGAAGTGGCGGAGGATCAGG
GGGAGGATCTGTGCCTGGACCTCCTCCAGGACCCCCTAGAGTGTCCCCAG
ATCCTAGGGCCGAGCTGGACTCTACCGTGCTGCTGACCAGATCCCTGCTG
GCCGACACAAGGCAGCTGGCTGCCCAGCTGAGAGACAAGTTCCCCGCCGA
CGGCGACCACAACCTGGATAGCCTGCCTACCCTGGCCATGTCTGCTGGCG
CACTGGGGGCTCTGCAGCTGCCTGGGGTGCTGACTAGACTGAGAGCCGAC
CTGCTGAGCTACCTGCGGCATGTGCAGTGGCTGAGAAGGGCTGGCGGCAG
CAGCCTGAAAACCCTGGAACCTGAGCTGGGCACACTGCAGGCCAGACTGG
ACAGACTGCTGCGCAGACTGCAGCTGCTGATGAGCAGACTGGCTCTGCCC
CAGCCTCCTCCTGACCCTCCTGCTCCTCCACTGGCTCCTCCAAGCTCTGC
TTGGGGCGGAATTAGAGCCGCCCACGCCATTCTGGGAGGCCTGCACCTGA
CACTGGATTGGGCAGTGCGGGCCTGCTGCTGCTGAAAACCAGACTGCAC
CACCACCATCACCACTGATAAGCTT Amino acid sequence of IL-11: IL-11Rα fusion protein (SEQ ID NO: 99):
MGWSCIILFLVATATGVHSPQAWGPPGVQYGQPGRSVKLCCPGVTAGDPV

SWFRDGEPKLLQGPDSGLGHELVLAQADSTDEGTYICQTLDGALGGTVTL

QLGYPPARPVVSCQAADYENFSCTWSPSQISGLPTRYLTSYRKKTVLGAD

SQRRSPSTGPWPCPQDPLGAARCVVHGAEFWSQYRINVTEVNPLGASTRL

LDVSLQSILRPDPPQGLRVESVPGYPRRLRASWTYPASWPCQPHFLLKFR

LQYRPAQHPAWSTVEPAGLEEVITDAVAGLPHAVRVSARDFLDAGTWSTW

SPEAWGTPSTGGPAGQSGGGGSGGGSGGGSVPGPPPGPPRVSPDPRAEL

-continued

```
DSTVLLTRSLLADTRQLAAQLRDKFPADGDHNLDSLPTLAMSAGALGALQ

LPGVLTRLRADLLSYLRHVQWLRRAGGSSLKTLEPELGTLQARLDRLLRR

LQLLMSRLALPQPPPDPPAPPLAPPSSAWGGIRAAHAILGGLHLTLDWAV

RGLLLLKTRLHHHHHH
```

Figure 33:
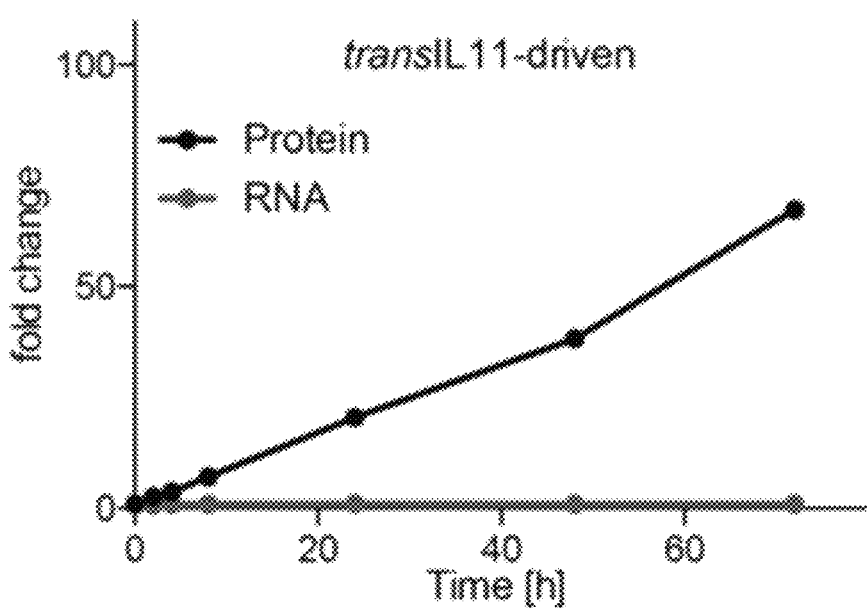
FIG. 33. Graph showing induction of IL-11 secretion in primary fibroblasts by hyper IL-11. Cells were stimulated with hyper IL-11, and IL-11RNA and native IL-11 protein levels were measured in the cell culture supernatant by ELISA at the indicated time points.

Fibroblasts cultured in vitro and stimulated with hyper IL-11 were shown to upregulate IL-11 protein expression, as determined by ELISA (FIG. 33). Interestingly, an increase in IL-11 RNA level was not detected in response to stimulation with hyper IL-11. Unlike TGFB1, which increases IL-11 expression at both the RNA and the protein level, hyper IL-11 seems to upregulate IL-11 expression only post-transcriptionally, at the protein level.

The ability of the mouse anti-IL-11Rα antibodies to inhibit signalling mediated by hyper IL-11 was investigated.

Human atrial fibroblasts were incubated for 24 h with hyper IL-11 (0.2 ng/ml) in the presence anti-IL-11Rα antibodies (2 µg/ml) or isotype control antibody. Following incubation, cell culture supernatant was analysed for MMP2. Stimulation with hyper IL-11 results in an increase in the secretion of MMP2 as compared to non-stimulated cultures.

Figure 26:
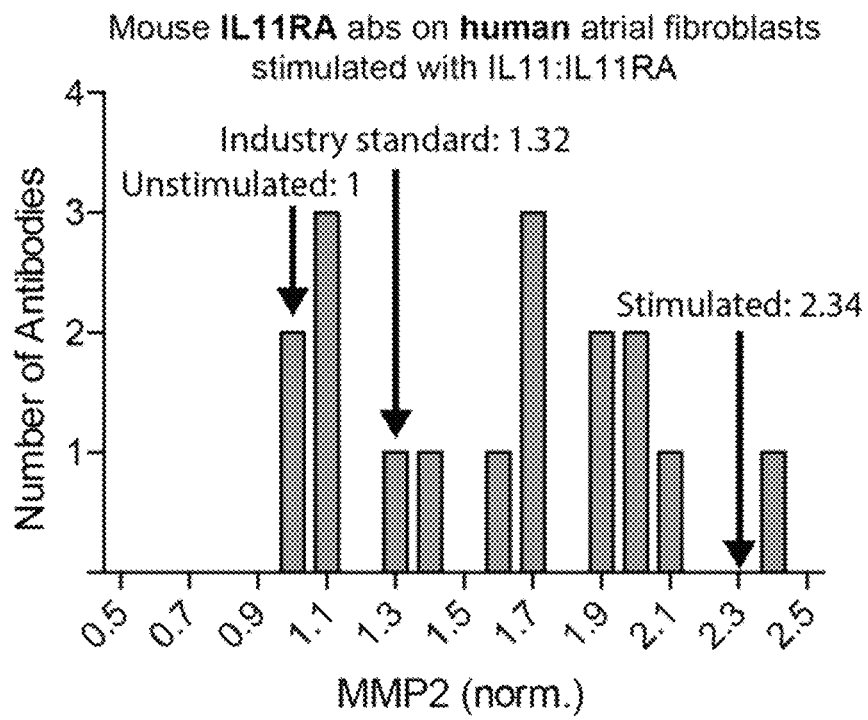
FIG. 26. Bar chart showing inhibition by the anti-IL-11Rα antibodies of IL-11 trans signalling mediated by hyper IL-11 in vitro in human atrial fibroblasts, as determined by fold change in the amount of MMP2 in the cell culture supernatant as compared to control (unstimulated) fibroblasts, following stimulation with hyper IL-11, in the presence of the anti-IL-11Rα antibodies.

The results of the experiments are shown in FIGS. 26 and 27. The anti-IL-11Rα antibodies were found to be capable of neutralising signalling mediated by hyper IL-11 (i.e. IL-11 trans signalling), and several were found to be capable of inhibiting trans signalling to a greater extent than the commercial monoclonal mouse anti-IL-11 antibody (Monoclonal Mouse IgG2A; Clone #22626; Catalog No. MAB218; R&D Systems, MN, USA): BSO-1E3 (RA1), BSO-2E5 (RA3), BSO-5E5 (RA5), BSO-9A7 (RA7), BSO-13B10 (RA9) and BSW-1F6 (RA11).

Clones BSO-1E3 (RA1), BSO-5E5 (RA5), BSO-9A7 (RA7), BSO-13B10 (RA9) were identified as promising candidates for further development (highlighted in FIG. 27), showing good ability to inhibit both human and mouse IL-11/IL-11R signalling, and good inhibition of IL-11 trans signalling.

6.4 Screening for Ability to Bind IL-11Rα

The mouse hybridomas producing anti-human IL-11Rα antibodies were sub-cloned, and cell culture supernatant from the subcloned hybridomas was analysed by "mix-and-measure" iQue assay for (i) ability to bind to human IL-11Rα, and (ii) cross reactivity for antigen other than IL-11Rα.

Briefly, labelled control cells (not expressing IL-11Rα at the cell surface) and unlabelled target cells expressing human IL-11Rα at their surface (following transient transfection with a plasmid encoding a FLAG-tagged human IL-11Rα) were mixed together with the cell culture supernatant (containing mouse-anti-IL-11Rα antibodies) and secondary detection antibodies (fluorescently-labelled anti-mouse IgG antibody).

The cells were then analysed using the HTFC Screening System (iQue) for the two labels (i.e. the cell label and the label on the secondary antibody). Detection of the secondary antibody on the unlabelled, IL-11Rα expressing cells indicated ability of the mouse-anti-IL-11Rα antibodies to bind to IL-11Rα. Detection of the secondary antibody on the labelled, control cells indicated cross-reactivity of the mouse-anti-IL-11Rα antibodies for target other than IL-11Rα.

As a positive control condition, labelled and unlabelled cells were incubated with a mouse anti-FLAG tag antibody as the primary antibody.

Figures 34A, 34B:
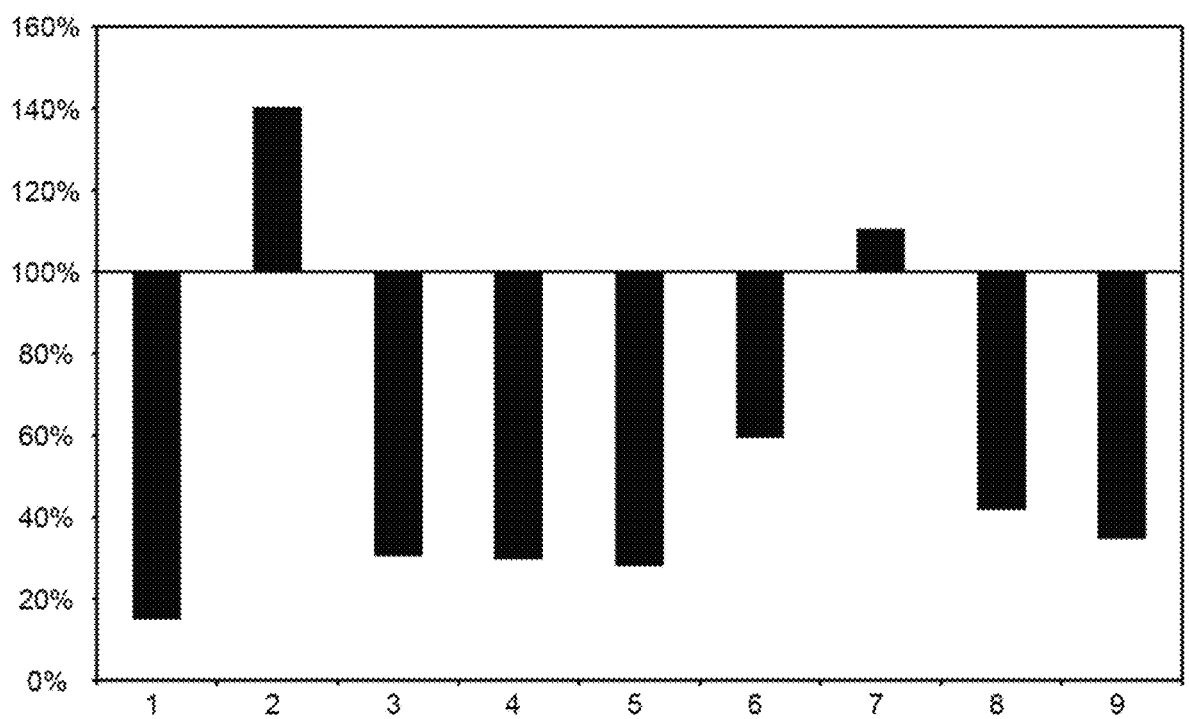
FIGS. 34A and 34B. Table and bar chart showing binding of mouse-anti-IL-11Rα antibodies to human IL-11Rα, as determined by iQue analysis (FIG. 34A) Table summarising the results of the experiments.

The results are shown in FIGS. 34A and 34B. The majority of the subcloned hybridomas expressed antibody which was able to bind to human IL-11Rα, and which recognised this target with high specificity. The antibody produced by subclone BSO-1E3 was found not to bind to human IL-11Rα.

Antibodies BSO-2C1 and BSO-9A7 displayed stronger signal for binding to IL-11Rα than signal for the positive control anti-tag antibody for the tag, indicating that these antibodies bind to IL-11Rα with very high affinity.

6.5 Analysis of Antibody Affinity for Human IL-11Rα

The anti-human IL-11Rα antibodies are analysed for their affinity of binding to human IL-11Rα by ELISA assay.

Recombinant human IL-11Rα is obtained from Genscript and Horseradish peroxidase (HRP)-conjugated anti-human IgG (Fc-specific) antibody is obtained from Sigma. Corning 96-well ELISA plates are obtained from Sigma. Pierce 3,3',5,5'-tetramethylbenzidine (TMB) ELISA substrate kit is obtained from Life Technologies (0.4 g/mL TMB solution, 0.02% hydrogen peroxide in citric acid buffer). Bovine serum albumin and sulphuric acid is obtained from Sigma. Wash buffer comprises 0.05% Tween-20 in phosphate buffered saline (PBS-T). Purified IgG controls are purchased from Life Technologies. Tecan Infinite 200 PRO NanoQuant is used to measure absorbance.

Criss-cross serial dilution analysis was performed as described by Hornbeck et al., (2015) Curr Protoc Immunol 110, 2.1.1-23) to determine the optimal concentration of coating antigen, primary and secondary antibodies.

An indirect ELISA is performed to assess the binding affinity of the mouse anti-IL-11Rα antibodies at 50% of effective concentration ($EC_{50}$) as previously described (Unverdorben et al., (2016) MAbs 8, 120-128.). ELISA plates are coated with 1 µg/mL of recombinant human IL-11Rα overnight at 4° C., and remaining binding sites are blocked with 2% BSA in PBS. The antibodies are diluted in 1% BSA in PBS, titrated to obtain working concentrations of 800, 200, 50, 12.5, 3.125, 0.78, 0.195, and 0.049 ng/mL, and incubated in duplicates for 2 hours at room temperature. Detection of antigen-antibody binding is performed with 15.625 ng/mL of HRP-conjugated anti-mouse IgG antibody. Following 2 hours of incubation with the detection antibody, 100 µl of TMB substrate is added for 15 mins and chromogenic reaction stopped with 100 µl of 2 M $H_2SO_4$. Absorbance reading is measured at 450 nm with reference wavelength correction at 570 nm. Data are fitted with GraphPad Prism software with log transformation of antibody concentrations followed by non-linear regression analysis with the asymmetrical (five-parameter) logistic dose-response curve to determine individual EC50 values.

6.6 Ability to Inhibit Human IL-11/IL-11R Signalling in a Variety of Tissues

Ability of the antibodies to neutralise IL-11/IL-11R signalling and trans signalling in fibroblasts obtained from a variety of different tissues is investigated, essentially as described in sections 6.1 and 6.3 except that instead of cardiac atrial human fibroblasts, human fibroblasts derived from liver, lung, kidney, eye, skin, pancreas, spleen, bowel, brain, and bone marrow are used for the experiments.

Anti-IL-11Rα antibodies are demonstrated to be capable of neutralising IL-11/IL-11R signalling in fibroblasts derived from the various different tissues, as determined by observation of a relative decrease in the proportion of αSMA-positive fibroblasts at the end of the 24 h culture period in the presence of the anti-IL-11Rα antibodies as compared to culture in the absence of the antibodies.

Example 7: Chimeric and Humanised Versions of the Mouse Anti-Human IL-11 Antibodies Mouse/human chimeric and humanised versions of the mouse monoclonal anti-human IL-11Rα antibodies of Example 5 are prepared according to standard methods.

7.1 Mouse/Human Chimeric Antibodies

Mouse/human chimeric antibodies are prepared from the mouse monoclonal anti-human IL-11Rα antibodies as described in Human Monoclonal Antibodies: Methods and Protocols, Michael Steinitz (Editor), Methods in Molecular Biology 1060, Springer Protocols, Humana Press (2014), in Chapter 8 thereof.

Briefly, the DNA sequences encoding the VH and VL of hybridomas producing the mouse anti-human IL-11Rα antibodies are determined, and combined with DNA sequence encoding human immunoglobulin constant regions to produce a mouse/human chimeric antibody sequence, from which a chimeric mouse/human antibody is expressed in mammalian cells.

7.2 Humanised Antibodies

Humanised antibodies are prepared from the mouse monoclonal anti-human IL-11Rα antibodies as described in Human Monoclonal Antibodies: Methods and Protocols, Michael Steinitz (Editor), Methods in Molecular Biology 1060, Springer Protocols, Humana Press (2014), in Chapter 7 thereof, in particular at section 3.1 of Chapter 7 entitled 'Antibody Humanization'.

Briefly, the DNA sequences encoding the VH and VL of hybridomas producing the mouse anti-human IL-11Rα antibodies are determined, and inserted into DNA sequence encoding human antibody variable region framework regions and immunoglobulin constant regions, to produce a humanised antibody sequence, from which a humanised antibody is expressed in mammalian cells.

Example 8: Further Biochemical Analysis of Anti-IL-11Rα Antibodies

The antibodies described above are subjected to further biochemical analysis.

The antibodies are analysed by BIAcore, Biolayer interferometry (BLI) and MicroScale Thermophoresis (MST) analysis to determine the affinity of binding to human IL-11Rα.

BIAcore determination of antibody affinity by surface plasmon resonance (SPR) analysis is performed as described in Rich et al., Anal Biochem. 2008 Feb. 1; 373(1):112-20.

Biolayer interferometry analysis of antibody affinity is performed as described in Concepcion et al., Comb Chem High Throughput Screen. 2009 September; 12(8):791-800.

MicroScale Thermophoresis analysis of antibody affinity is performed as described in Jerabek-Willemsen et al., Assay Drug Dev Technol. 2011 August; 9(4): 342-353.

Aggregation of the antibodies is analysed by size exclusion chromatography (SEC), as described in Iacob et al., J Pharm Sci. 2013 December; 102(12): 4315-4329.

Hydophobicity of the antibodies is analysed by Hydrophobic interaction chromatography (HIC) as described in Haverick et al., MAbs. 2014 July-August; 6(4):852-8.

The melting temperature of the antibodies is analysed by Differential scanning fluorimetry (DSF) as described in Menzen and Friess, J Pharm Sci. 2013 February; 102(2): 415-28.

Example 9: Inhibition of Fibrosis In Vivo Using Anti-IL-11Rα Antibodies

The therapeutic utility of the anti-human IL-11Rα antibodies is demonstrated in vivo in mouse models of fibrosis for various different tissues. The mice used in the experiments are wildtype (i.e. IL-11RA+/+) mice.

9.1 Heart Fibrosis

A pump is implanted, and mice are treated with AngII (2 mg/kg/day) for 28 days.

Neutralising anti-IL-11Rα antibodies, or control antibodies, are administered to different groups of mice by intravenous injection. At the end of the experiment, collagen content is assessed in the atria of the mice using a calorimetric hydroxyproline-based assay kit, and the level of RNA expression of the markers or fibrosis Col1A2, αSMA (ACTA2) and fibronectin (Fn1) were analysed by qPCR.

Mice treated with neutralising anti-IL-11Rα antibodies have a reduced fibrotic response in heart tissue as compared to mice treated with control antibodies, as evidenced by reduced expression of markers of fibrosis.

9.2 Kidney Fibrosis

A mouse model for kidney fibrosis is established, in which fibrosis is induced by intraperitoneal injection of folic acid (180 mg/kg) in vehicle (0.3M $NaHCO_3$); control mice were administered vehicle alone.

Neutralising anti-IL-11Rα antibodies, or control antibodies, are administered to different groups of mice by intravenous injection. Kidneys are removed at day 28, weighed and either fixed in 10% neutral-buffered formalin for Masson's trichrome and Sirius staining or snap-frozen for collagen assay, RNA, and protein studies.

Total RNA is extracted from the snap-frozen kidney using TRIZOL™ reagent (Invitrogen) and QIAGEN TISSUELYZER™ method followed by RNEASY™ column (Qiagen) purification. The cDNA is prepared using ISCRIPT™ cDNA synthesis kit, in which each reaction contained 1 µg of total RNA, as per the manufacturer's instructions. Quantitative RT-PCR gene expression analysis is performed on triplicate samples with either TAQMAN™ (Applied Biosystems) or fast SYBR™ green (Qiagen) technology using STEPONEPLUS™ (Applied Biosystem) over 40 cycles. Expression data are normalized to GAPDH mRNA expression level and the 2-ΔΔCt method is used to calculate the fold-change. The snap-frozen kidneys are subjected to acid hydrolysis by heating in 6M HCl at a concentration of 50 mg/ml (95° C., 20 hours). The amount of total collagen in the hydrolysate is quantified based on the colorimetric detection of hydroxyproline using QUICKZYME™ Total Collagen assay kit (Quickzyme Biosciences) as per the manufacturer's instructions.

Mice treated with neutralising anti-IL-11Rα antibodies have a reduced fibrotic response in kidney tissue as compared to mice treated with control antibodies, as evidenced by reduced expression of markers of fibrosis.

9.3 Lung Fibrosis

Mice are treated by intratracheal administration of bleomycin on day 0 to establish a fibrotic response in the lung (pulmonary fibrosis).

Neutralising anti-IL-11Rα antibodies, or control antibodies, are administered to different groups of mice by intravenous injection. Mice are sacrificed at day 21, and analysed for differences in fibrosis markers.

Mice treated with neutralising anti-IL-11Rα antibodies have a reduced fibrotic response in lung tissue as compared to mice treated with control antibodies, as evidenced by reduced expression of markers of fibrosis.

9.4 Skin Fibrosis

Mice are treated by subcutaneous administration of bleomycin on day 0 to establish a fibrotic response in the skin.

Neutralising anti-IL-11Rα antibodies, or control antibodies, are administered to different groups of mice by intravenous injection. Mice are sacrificed at day 21, and analysed for differences in fibrosis markers.

Mice treated with neutralising anti-IL-11Rα antibodies have a reduced fibrotic response in skin tissue as compared to mice treated with control antibodies, as evidenced by reduced expression of markers of fibrosis.

9.5 Eye Fibrosis

Mice undergo trabeculectomy procedure as described in Example 3.6 above to initiate a wound healing response in the eye.

Neutralising anti-IL-11Rα antibodies, or control antibodies, are administered to different groups of mice by intravenous injection, and fibrosis is monitored in the eye tissue.

Mice treated with neutralising anti-IL-11Rα antibodies have a reduced fibrotic response in eye tissue as compared to mice treated with control antibodies, as evidenced by reduced expression of markers of fibrosis.

9.6 Other Tissues

The effect of treatment with neutralising anti-IL-11Rα antibodies on fibrosis is also analysed in mouse models of fibrosis for other tissues, such as the liver, kidney, bowel, and is also analysed in a model relevant to multiorgan (i.e. systemic) fibrosis.

The fibrotic response is measured and compared between mice treated with neutralising anti-IL-11Rα antibodies and mice treated with control antibodies. Mice treated with neutralising anti-IL-11Rα antibodies have a reduced fibrotic response as compared to mice treated with control antibodies, as evidenced by reduced expression of markers of fibrosis.

Example 10: Treatment of Cancer In Vivo Using Anti-IL-11Rα Antibodies

The effect of treatment with neutralising anti-IL-11Rα antibodies on cancer is analysed in mouse models of cancer.

Models of breast, lung, and gastrointestinal cancers are established in mice, the mice are treated by administration of neutralising anti-IL-11Rα antibodies, or control antibodies, and the development/progression of cancer is monitored.

An anti-cancer effect is observed for the neutralising anti-IL-11Rα antibodies, as evidenced by reduced symptoms of cancer and/or increased survival as compared to mice treated with control antibodies.

Example 11: Treatment of AMD Using Anti-IL-11Rα Antibodies

The effect of treatment with neutralising anti-IL-11Rα antibodies is investigated in wet age-related macular degeneration (AMD).

Neutralising anti-IL-11Rα antibody is administered to subjects having wet AMD. In some treatment conditions, subjects are administered with VEGF antagonist therapy (e.g. ranibizumab, bevacizumab, pegaptanib, brolucizumab or aflibercept), PDGF antagonist therapy (e.g. pegpleranib), or are treated by laser coagulation therapy in addition to treatment with anti-IL-11Rα antibody.

A reduction in wet AMD pathology and/or improvement in the symptoms of wet AMD is observed in subjects treated with anti-IL-11Rα antibody as compared to subjects not treated with anti-IL-11Rα antibody.

Example 12: Inhibition of Kidney Fibrosis Using Anti-IL-11Rα Antibodies 10-12 week old littermate mice of similar weight had kidney fibrosis induced by intraperitoneal (i.p.) injection of folic acid (180 mg kg$^{-1}$) in vehicle (0.3 M NaHCO$_3$); control mice were administered vehicle alone.

Anti-IL11Ra antibody clone BSO-9A7 was administered one day after folic acid treatment and then 3 times per week at a dose of 20 mg/kg. Mice were euthanized 28 days post-injection.

The mouse plasma levels of urea and creatinine were quantified using urea assay kit (ab83362, Abcam) and creatinine assay kit (ab65340, Abcam), respectively according to the manufacturer's instructions. The amount of total collagen in the kidney was quantified on the basis of colourimetric detection of hydroxyproline using a QUICKZYME™ Total Collagen assay kit (Quickzyme Biosciences). All colourimetric assays were performed according to the manufacturer's instructions.

Tissues were paraffin-embedded, and kidneys were sectioned at 3 μm. For paraffin sections, tissues were fixed for 24 h, at room temperature in 10% neutral-buffered formalin (Sigma-Aldrich), dehydrated and embedded in paraffin. For cryosections, freshly dissected organs were embedded with Tissue-Tek Optimal Cutting Temperature compound (VWR International). Cryomoulds were then frozen in a metal beaker with isopentane cooled in liquid nitrogen and sections were stored in –80° C. Total collagen was stained with Masson's trichrome stain kit (HT15, Sigma-Aldrich) according to the manufacturer's instructions. Images of the sections were captured and blue-stained fibrotic areas were semi-quantitatively determined with ImageJ software (version 1.49). For immunohistochemistry, the tissue sections were incubated with anti-ACTA2 antibody (ab5694, Abcam). Primary antibody staining was visualized using an IMMPRESS™ HRP Anti-Rabbit IgG Polymer Detection kit (Vector Laboratories) with IMMPACT™ DAB Peroxidase Substrate (Vector Laboratories) as the chromogen. The sections were then counterstained with Mayer's haematoxylin (Merck).

Figure 35A:
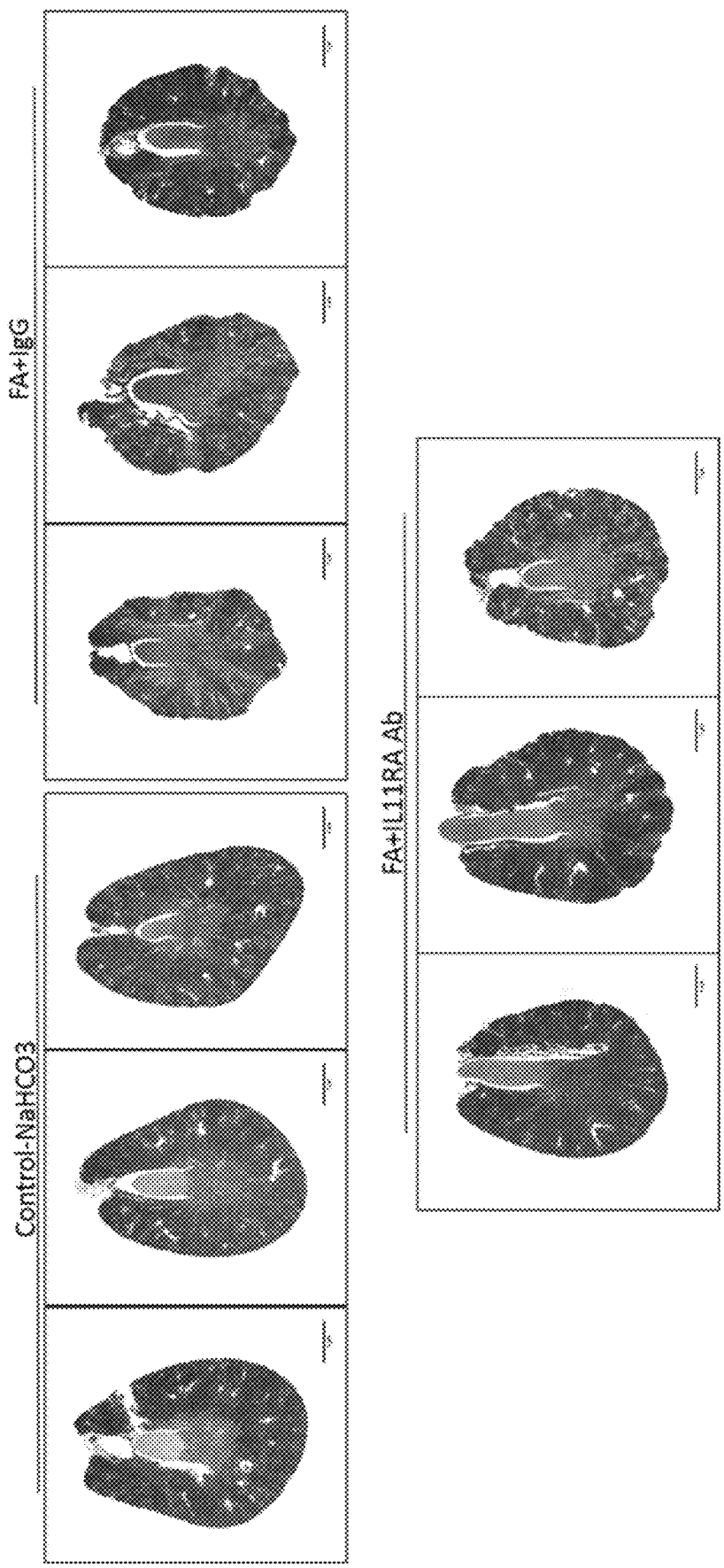
FIGS. 35A and 35B. Images and graph showing the results of histological analysis of kidney sections from mice subjected to different treatments in a mouse model of kidney fibrosis. Kidney fibrosis was induced by intraperitoneal (IP) injection of folic acid (FA, 180 mg/kg) in vehicle (0.3M NaHCO$_3$) mice; control mice were administered vehicle alone. Mice were administered isotype control IgG2 (20 mg/kg, 3× per week, intraperitoneal), anti-IL-11Rα antibody (20 mg/kg, 3× per week, intraperitoneally) from day 1 post folic acid injury and for the duration of the experiment. Animals were sacrificed 28 days after folic acid-induced kidney damage and analysed for fibrosis histologically using Masson's Trichrome stain.
Figure 35B:
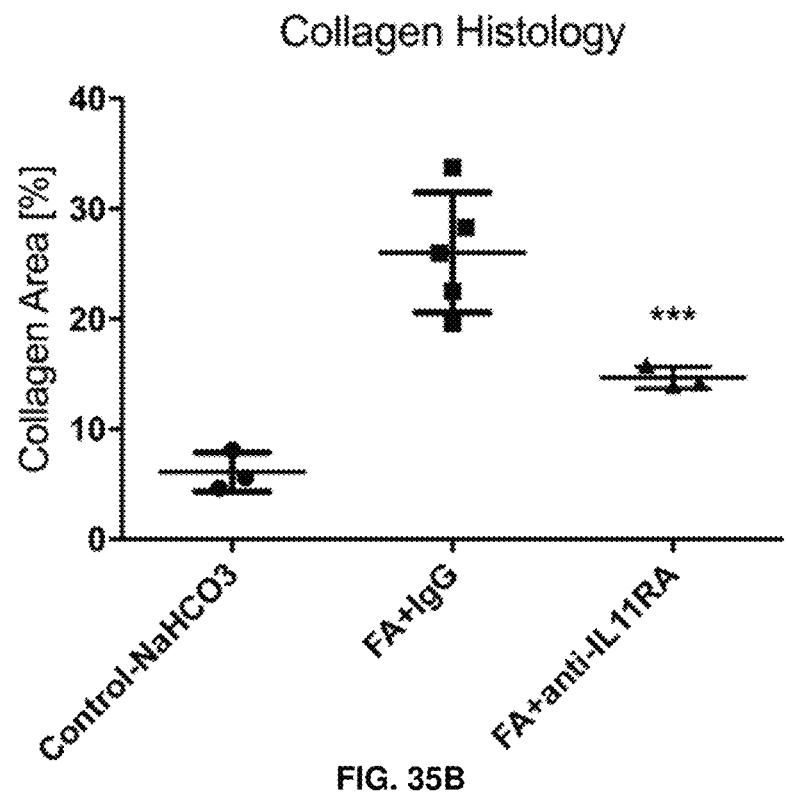

FIGS. 35A and 35B show that mice treated with anti-IL11Ra antibody were found to have significantly reduced staining for collagen, indicating that anti-IL11Ra antibody treatment had inhibited kidney fibrosis.

Figure 36:
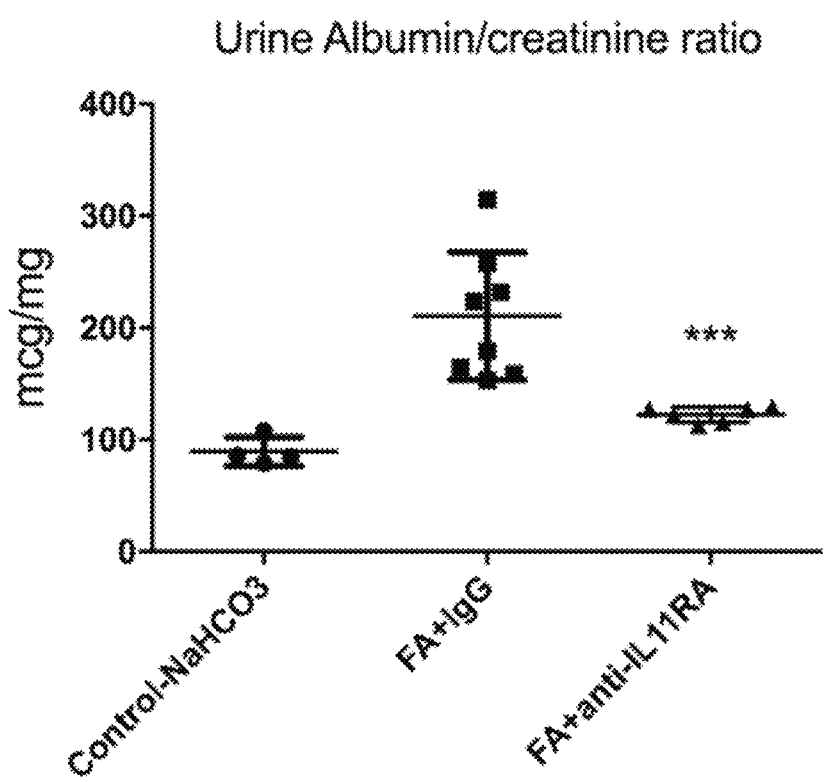
FIG. 36. Graph showing the urinary albumin/creatine ratio in mice subjected to different treatments in a mouse model of kidney fibrosis. Kidney fibrosis was induced by intraperitoneal (IP) injection of folic acid (FA, 180 mg/kg) in vehicle (0.3M NaHCO$_3$) mice; control mice were administered vehicle alone. FA treated mice were administered isotype control IgG2 (20 mg/kg, 3× per week, intraperitoneal) or anti-IL11Ra antibody (20 mg/kg, 3× per week, intraperitoneal) from day 1 post folic acid injury and for the duration of the experiment. Mice were placed in metabolic cages and urinary creatinine and albumin measured using commercial assays (Abcam) according to the manufacturer's instructions. ***, P<0.001 compared to FA+IgG, ANOVA.

FIG. 36 shows that the urinary albumin/creatine ratio was significantly reduced by treatment with anti-IL11Ra antibody, indicating a reduced level of kidney damage in mice treated with anti-IL-11Ra antibody.

In another experiment a mouse model of acute renal injury was induced by unilateral ureteric obstruction (UUO). Briefly, mice were treated by sham operation or ureteric obstruction of one ureter. Mice received IgG, anti-IL-11Ra antibody clone BSO-9A7 (20 mg/kg; on surgical days –1, 1, 3, 5) and injured kidneys ('UUO') or contralateral uninjured kidneys (Con) were harvested on day 7 post surgery.

Semi-quantitative assessment of tubular injury was performed by histological analysis of casts, tubular atrophy or tubular expansion blinded to experimental conditions (Tubular injury score: 0, none; 1, minimal; 2, mild; 3, moderate; 4, severe).

Figure 37A:
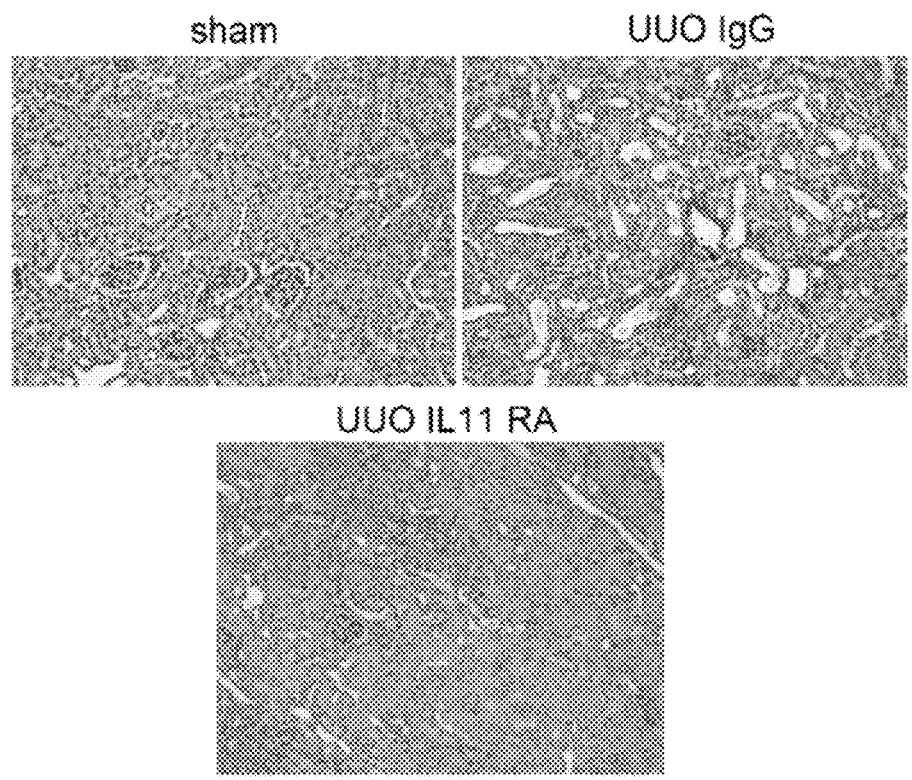
FIGS. 37A and 37B. Images and graph showing the results of histological analysis of kidney sections from mice subjected to different treatments in a mouse model of acute renal injury.
Figure 37B:
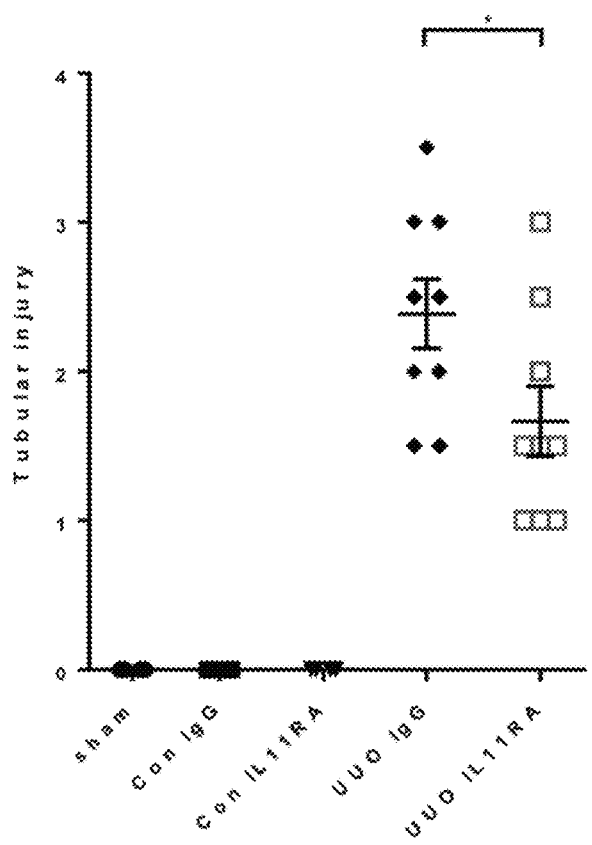

FIGS. 37A and 37B show that treatment with anti-IL-11Ra antibody reduced tubular damage in a mouse model of acute renal injury.

Example 13: IL-11 and Liver Fibrosis

Protein expression of IL-11 in healthy and diseased livers was confirmed by western blots in matched samples of human livers. Matched frozen liver samples were prepared for western blotting and levels of IL11 determined using Human IL-11 Antibody Monoclonal Mouse IgG2A Clone #22626, catalog number MAB218 from R&D Systems. Film images were generated.

Figure 38:
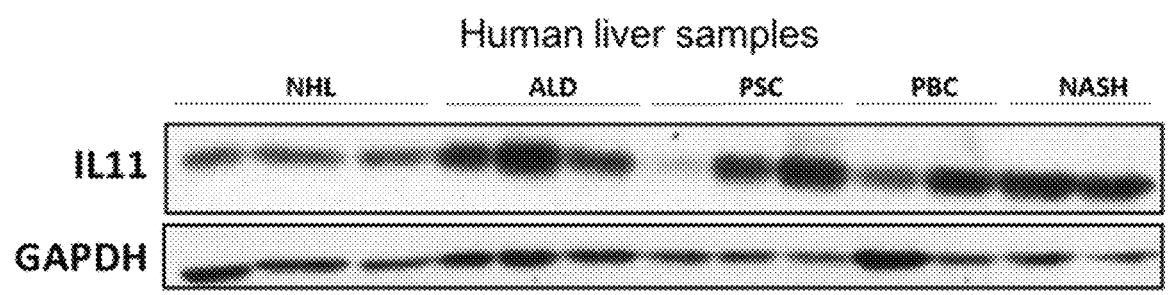
FIG. 38. Image showing the results of ELISA western blot for IL-11 of human liver samples. Liver samples obtained from patients undergoing liver surgery were used for western blot analysis. Blotting of GAPDH was used as a loading control. Samples from normal human liver (NHL) had low levels of IL-11 protein, whereas samples from patients with fibrotic liver diseases including alcoholic liver disease (ALD), primary sclerosing cholangitis (PSC), primary biliary cirrhosis (PBC) or non-alcoholic steatohepatitis (NASH) had higher levels of IL-11.

The results are shown in FIG. 38. Increased expression of IL-11 was detected in most diseased tissue as compared to normal healthy livers.

To determine whether IL-11 expression changed with disease, an ELISA was performed on media from Precision Cut Liver Slices (PCLS) was performed using Human IL-11 DuoSet 15 plate kit, catalog number DY218 from R&D Systems.

Human PCLS were cut and incubated with media treatments after a 24 h rest period for acclimatisation to media plates. Samples were treated with media only (control), media with LPS, a combination of profibrogenic stimuli inducing TGFβ1, or a combination of profibrogenic stimuli inducing TGFβ1 and the TGFβ1 inhibitor ALK5.

Figure 39:
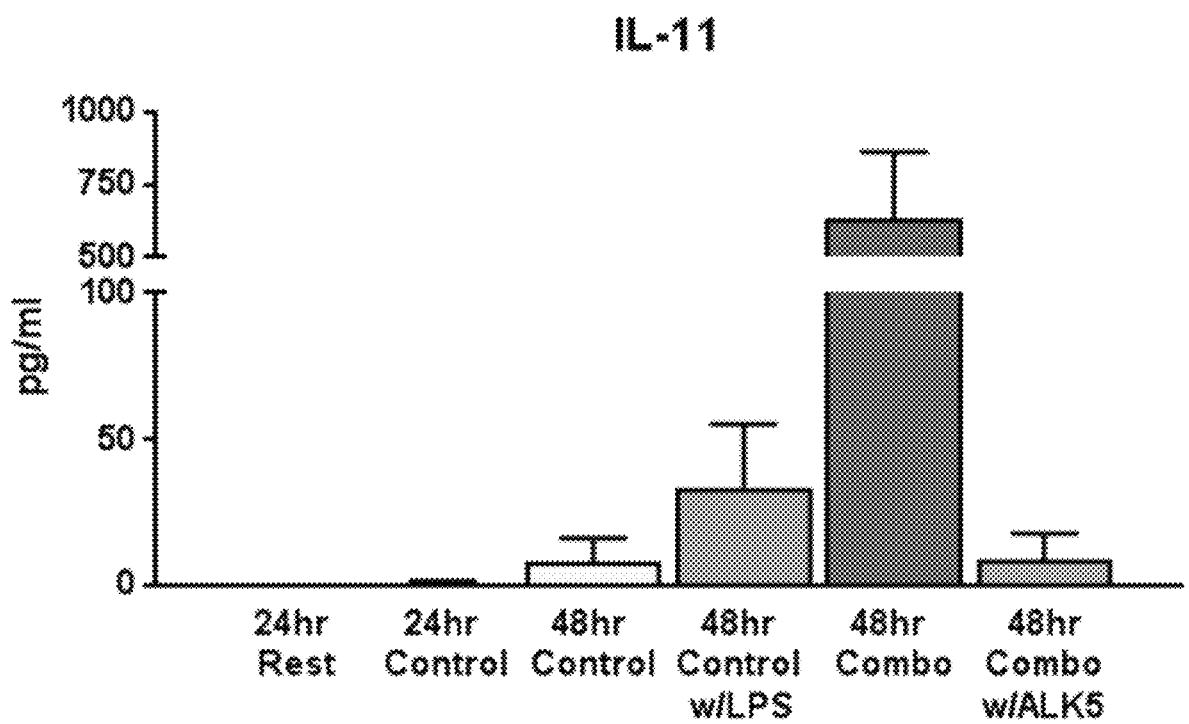
FIG. 39. Bar chart showing the results of ELISA analysis of secretion of IL-11 by human PCLS subjected to different treatments.

The results are shown in FIG. 39. The profibrogenic stimuli induced upregulation of IL-11 protein expression, and ALK5 inhibitor was found to inhibit TGFβ1 receptor signalling, which reduced the expression of IL-11 protein down to control levels.

Example 14: Inhibition of Heart Fibrosis Using Anti-IL-11Rα Antibodies

The anti-fibrotic effect of anti-IL-11Ra antibody treatment was analysed in a mouse model of cardiac fibrosis.

Briefly, transverse aortic constriction (TAC) was performed in male mice as described previously (Tarnavski, O. et al. Mouse cardiac surgery: comprehensive techniques for the generation of mouse models of human diseases and their application for genomic studies. Physiol. Genomics 16, 349-360 (2004)). Age-matched mice underwent a sham operative procedure without TAC. Trans-thoracic two-dimensional Doppler echocardiography was used to confirm increased pressure gradients (>40 mm Hg), indicative of successful TAC.

Mice were euthanized at 2 weeks post-TAC for histological and molecular assessment. Anti-IL-11Ra antibody clone BSO-9A7 or control IgG antibody were administered intraperitoneally 3 times per week at a dose of 20 mg/kg. After two weeks hearts were harvested and assessed for fibrosis extent using Masson's Trichrome stain kit (HT15, Sigma-Aldrich), in accordance with the manufacturer's instructions. The amount of total collagen in the heart was quantified on the basis of colourimetric detection of hydroxyproline using a QUICKZYME™ Total Collagen assay kit (Quickzyme Biosciences).

Figure 40A:
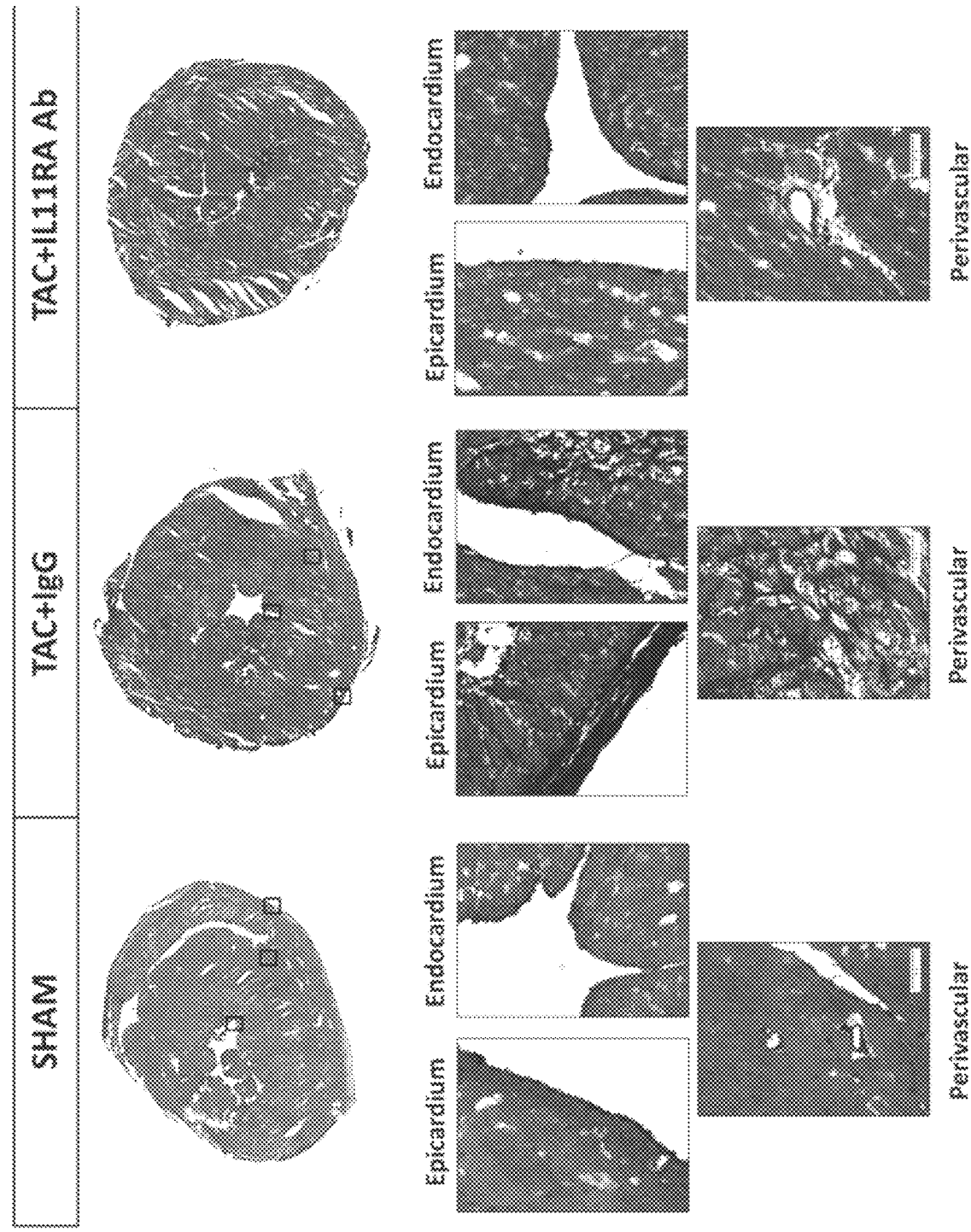
FIGS. 40A and 40B. Images and bar chart showing the results of histological analysis of heart fibrosis in mice subjected to different treatments in a mouse model of cardiac fibrosis. Mice (C57B16, male, 8-12 weeks old) were subjected to fibrosis-inducing transverse aortic constriction (TAC) or sham operations. TAC-treated animals received either control antibody (20 mg/kg, 3×/week, intraperitoneal) or neutralizing anti-IL-11Rα antibody (20 mg/kg, 3×/week, intraperitoneal). After two weeks hearts were harvested and assessed for fibrosis extent using Masson's Trichrome stain (FIG. 40A).
Figure 40B:
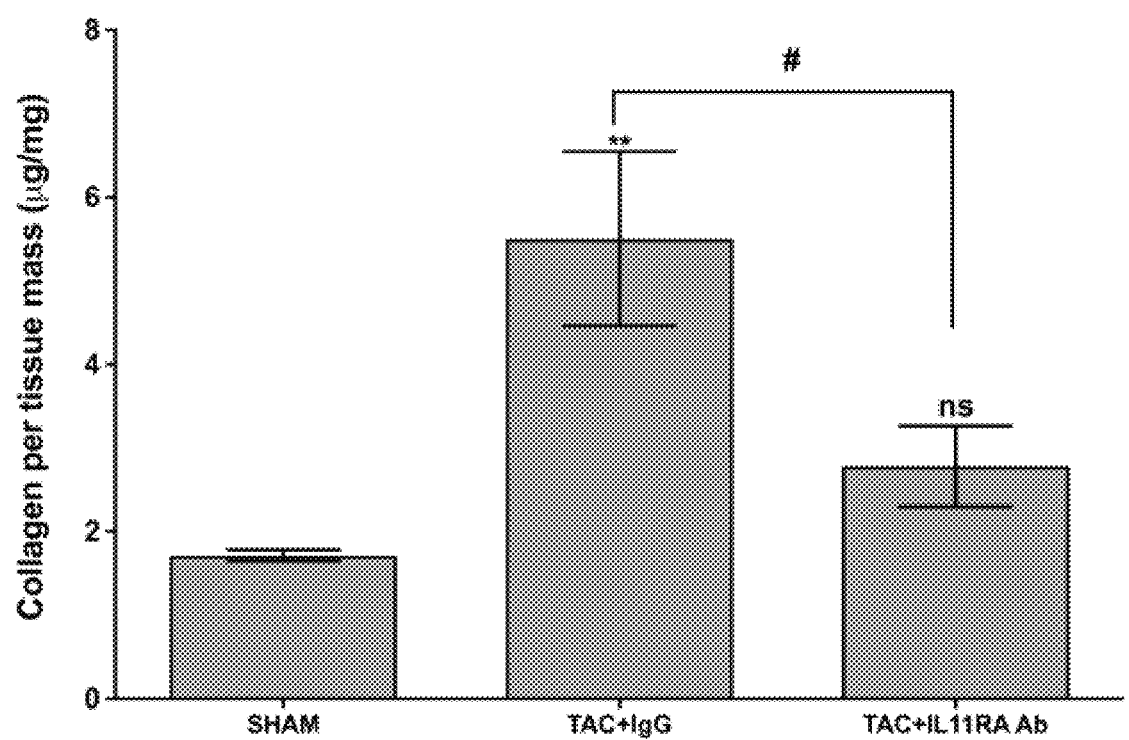

The results of the analysis is shown in FIGS. 40A and 40B. Mice treated with neutralising anti-IL-11Ra antibody were found to have reduced levels of collagen in the heart as compared to mice treated with IgG control antibody (FIG. 40A), and reduced level of fibrosis in the epicardium, endocardium and in perivascular regions as compared to mice treated with IgG control antibody (FIG. 40B).

The invention claimed is:

1. An antibody or antigen binding fragment, which is capable of binding to IL-11Rα, comprising a light chain variable region sequence and a heavy chain variable region sequence, wherein:

the light chain variable region sequence comprises the following CDRS:

```
                            (SEQ ID NO: 33)
LC-CDR1: QSISNN;

(SEQ ID NO: 34)
LC-CDR2: YAS;
and (SEQ ID NO: 35)
LC-CDR3: QQRYSWPLT,
``` or a variant comprising 1 amino acid substitution in the sequence QQRYSWPLT (SEQ ID NO: 35); and the heavy chain variable region sequence comprises the following CDRs:

```
                            (SEQ ID NO: 60)
HC-CDR1: GYTFTNYW;

(SEQ ID NO: 61)
HC-CDR2: IGPSDSKT;
and (SEQ ID NO: 62)
HC-CDR3: ARGDYVLFTY.
```

2. The antibody or antigen binding fragment according to claim 1, wherein:

the light chain variable region sequence has at least 80% sequence identity to the light chain variable region sequence of SEQ ID NO: 7, and the heavy chain variable region sequence has at least 80% sequence identity to the heavy chain variable region sequence of SEQ ID NO: 16.

3. The antibody or antigen binding fragment according to claim 1, wherein the light chain variable region sequence comprises the following CDRs:

```
                            (SEQ ID NO: 33)
i) LC-CDR1: QSISNN;

(SEQ ID NO: 34)
ii) LC-CDR2: YAS;
and (SEQ ID NO: 35)
iii) LC-CDR3: QQRYSWPLT;
``` and wherein the heavy chain variable region sequence comprises the following CDRs:

```
                            (SEQ ID NO: 60)
iv) HC-CDR1: GYTFTNYW;

(SEQ ID NO: 61)
v) HC-CDR2: IGPSDSKT;
and (SEQ ID NO: 62)
vi) HC-CDR3: ARGDYVLFTY.
```

4. The antibody or antigen binding fragment according to claim 1, which is capable of inhibiting IL-11 trans signalling.

5. The antibody or antigen binding fragment according to claim 1, wherein the antibody or antigen binding fragment is a humanised antibody or antigen binding fragment.

6. The antibody or antigen binding fragment according claim 1, conjugated to a drug moiety or a detectable moiety.

7. A method for producing an antibody or antigen binding fragment according to claim 1, comprising culturing a cell comprising a nucleic acid or vector encoding the antibody or antigen binding fragment according to claim 1 under conditions suitable for the expression of the antibody or antigen binding fragment.

8. The method of claim 7, further comprising isolating the antibody or antigen binding fragment from the cell, thereby producing an isolated antibody or antigen binding fragment.

9. The method of claim 8, further comprising mixing the isolated antibody or antigen binding fragment with a pharmaceutically acceptable carrier, adjuvant, excipient or diluent.

10. A method of treating fibrosis or a disease/disorder characterised by fibrosis, comprising administering an antibody or antigen binding fragment to a subject suffering from fibrosis or a disease/disorder characterised by fibrosis, wherein the antibody or antigen binding fragment is capable of binding to IL-11Rα, and comprises a light chain variable region sequence and a heavy chain variable region sequence, wherein:

the light chain variable region sequence comprises the following CDRs:

```
                            (SEQ ID NO: 33)
LC-CDR1: QSISNN;

(SEQ ID NO: 34)
LC-CDR2: YAS;
and (SEQ ID NO: 35)
LC-CDR3: QQRYSWPLT,
``` or a variant comprising 1 amino acid substitution in the sequence QQRYSWPLT (SEQ ID NO: 35); and the heavy chain variable region sequence comprises the following CDRs:

```
                            (SEQ ID NO: 60)
HC-CDR1: GYTFTNYW;

(SEQ ID NO: 61)
HC-CDR2: IGPSDSKT;
and (SEQ ID NO: 62)
HC-CDR3: ARGDYVLFTY.
```

11. The method according to claim 10, wherein:

the light chain variable region sequence has at least 80% sequence identity to the light chain variable region sequence of SEQ ID NO: 7, and the heavy chain variable region sequence has at least 80% sequence identity to the heavy chain variable region sequence of SEQ ID NO: 16.

12. The method according to claim 10, wherein the light chain variable region sequence comprises the following CDRs:

```
                                      (SEQ ID NO: 33)
    i) LC-CDR1: QSISNN;

(SEQ ID NO: 34)
   ii) LC-CDR2: YAS;
and (SEQ ID NO: 35)
  iii) LC-CDR3: QQRYSWPLT;
``` and wherein the heavy chain variable region sequence comprises the following CDRs:

```
                                      (SEQ ID NO: 60)
   iv) HC-CDR1: GYTFTNYW;

(SEQ ID NO: 61)
    v) HC-CDR2: IGPSDSKT;
and (SEQ ID NO: 62)
   vi) HC-CDR3: ARGDYVLFTY.
```

13. The method according to claim 10, wherein the antibody or antigen binding fragment is capable of inhibiting IL-11 trans signalling.

14. The method according to claim 10, wherein the antibody or antigen binding fragment is a humanised antibody or antigen binding fragment.

15. The method according to claim 10, wherein the antibody or antigen binding fragment is conjugated to a drug moiety or a detectable moiety.

\* \* \* \* \*

SEQUENCE LISTING

```
<160> NUMBER OF SEQ ID NOS: 99

<210> SEQ ID NO 1
<211> LENGTH: 112
<212> TYPE: PRT
<213> ORGANISM: Artificial Sequence
<220> FEATURE:
<223> OTHER INFORMATION: BSO-1E3_1

<400> SEQUENCE: 1

Asp Val Val Met Thr Gln Ile Pro Leu Ser Leu Ser Val Ser Met Lys
1               5                   10                  15

Phe Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

<210> SEQ ID NO 2
<211> LENGTH: 107
<212> TYPE: PRT
<213> ORGANISM: Artificial Sequence
```

```
<220> FEATURE:
<223> OTHER INFORMATION: BSO-1E3_2

<400> SEQUENCE: 2

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 3
<211> LENGTH: 107
<212> TYPE: PRT
<213> ORGANISM: Artificial Sequence
<220> FEATURE:
<223> OTHER INFORMATION: BSO-2E5

<400> SEQUENCE: 3

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ala Ser Leu Glu Ser Gly Val Pro Lys Arg Phe Ser Gly
    50                  55                  60

Ser Arg Ser Gly Ser Asp Tyr Ser Leu Thr Ile Ser Arg Leu Glu Ser
65                  70                  75                  80

Glu Asp Phe Val Asp Tyr Tyr Cys Gln Gln Tyr Ala Ser Ser Pro Pro
                85                  90                  95

Thr Phe Gly Ala Gly Thr Lys Leu Glu Leu Lys
            100                 105

<210> SEQ ID NO 4
<211> LENGTH: 111
<212> TYPE: PRT
<213> ORGANISM: Artificial Sequence
<220> FEATURE:
<223> OTHER INFORMATION: BSO-4G3

<400> SEQUENCE: 4

Asp Ile Val Leu Thr Gln Ser Pro Ala Ser Leu Ala Val Ser Leu Gly
1               5                   10                  15

Gln Ser Val Thr Ile Ser Cys Arg Ala Ser Glu Ser Val Glu Tyr Ser
            20                  25                  30

Gly Thr Thr Leu Met Gln Trp Tyr Gln Gln Lys Pro Gly Gln Pro Pro
        35                  40                  45

Lys Leu Leu Ile Tyr Gly Ala Ser Asn Val Glu Ser Gly Val Pro Ala
    50                  55                  60
```

```
Arg Phe Ser Gly Ser Gly Ser Gly Thr Asp Phe Ser Leu Asn Ile His
 65                  70                  75                  80

Pro Val Glu Glu Asp Asp Ile Ala Met Tyr Phe Cys Gln Gln Ser Arg
                 85                  90                  95

Lys Val Pro Tyr Thr Phe Gly Ser Gly Thr Lys Leu Glu Ile Lys
                100                 105                 110
```

<210> SEQ ID NO 5
<211> LENGTH: 113
<212> TYPE: PRT
<213> ORGANISM: Artificial Sequence
<220> FEATURE:
<223> OTHER INFORMATION: BSO-5E5

<400> SEQUENCE: 5

```
Asp Ile Val Met Ser Gln Ser Pro Ser Ser Leu Pro Val Ser Val Gly
 1                   5                  10                  15

Glu Asn Val Thr Met Ser Cys Lys Ser Ser Gln Ser Leu Leu Tyr Gly
                 20                  25                  30

Ser Asn Gln Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Phe Cys Gln Gln
                 85                  90                  95

Tyr Tyr Ser Tyr Pro Arg Thr Phe Gly Gly Gly Thr Lys Leu Glu Ile
                100                 105                 110

Lys
```

<210> SEQ ID NO 6
<211> LENGTH: 112
<212> TYPE: PRT
<213> ORGANISM: Artificial Sequence
<220> FEATURE:
<223> OTHER INFORMATION: BSO-7G9

<400> SEQUENCE: 6

```
Asp Val Val Met Thr Gln Thr Pro Leu Ser Leu Pro Val Ser Leu Gly
 1                   5                  10                  15

Asp Gln Ala Ser Ile Ser Cys Arg Ser Ser Gln Ser Leu Val His Ser
                 20                  25                  30

Asn Gly Asn Thr Tyr Leu His Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Leu Thr Phe Gly Ala Gly Thr Lys Leu Glu Leu Lys
                100                 105                 110
```

<210> SEQ ID NO 7
<211> LENGTH: 107
<212> TYPE: PRT
<213> ORGANISM: Artificial Sequence
<220> FEATURE:

<223> OTHER INFORMATION: BSO-9A7

<400> SEQUENCE: 7

Asp Ile Val Leu Thr Gln Ser Pro Ala Thr Leu Ser Met Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Phe Asn Ser Val Glu Thr
65                  70                  75                  80

Glu Asp Phe Gly Val Tyr Phe Cys Gln Gln Arg Tyr Ser Trp Pro Leu
                85                  90                  95

Thr Phe Gly Ala Gly Thr Lys Leu Glu Met Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: BSO-10D11

<400> SEQUENCE: 8

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Ala Tyr
            20                  25                  30

Leu Ser Trp Leu Gln Gln Lys Pro Asp Gly Thr Ile Lys Arg Leu Ile
        35                  40                  45

Tyr Ser Thr Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Phe Cys Leu Gln Tyr Ala Ser Ser Pro Leu
                85                  90                  95

Thr Phe Gly Ala Gly Thr Lys Leu Glu Leu Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: BSO-13B10

<400> SEQUENCE: 9

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Ser Asn
            20                  25                  30

Val Ala Trp Tyr Gln Gln Lys Ala Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser

```
                65                  70                  75                  80
Glu Asp Leu Ala Glu Tyr Phe Cys Gln Gln Tyr Asn Ser Tyr Pro Leu
                    85                  90                  95

Thr Phe Gly Ala Gly Thr Lys Leu Glu Leu Lys
                100                 105

<210> SEQ ID NO 10
<211> LENGTH: 119
<212> TYPE: PRT
<213> ORGANISM: Artificial Sequence
<220> FEATURE:
<223> OTHER INFORMATION: BSO-1E3_1

<400> SEQUENCE: 10

Gln Val Gln Leu Gln Gln Pro Gly Ala Glu Leu Val Thr Pro Gly Ala
1               5                   10                  15

Ser Val Lys Leu Ser Cys Lys Ala Ser Gly Phe Thr Phe Thr Asn Asn
                20                  25                  30

Trp Met His Trp Val Lys Gln Arg Pro Gly Gln Gly Leu Glu Trp Ile
            35                  40                  45

Gly Met Ile His Pro Asn Ser Gly Ile Thr Asn Ile Asn Glu Lys Phe
        50                  55                  60

Lys Asn Lys Ala Thr Val Thr Val Asp Lys Ser Ser Ser Thr Val Tyr
65                  70                  75                  80

Ile Gln Leu Ser Ser Leu Thr Ser Glu Asp Ser Ala Val Tyr Tyr Cys
                85                  90                  95

Arg Ser Asp Gly Thr Tyr Glu Tyr Phe Asp Tyr Trp Gly Gln Gly
                100                 105                 110

Thr Pro Leu Thr Val Ser Ser
        115

<210> SEQ ID NO 11
<211> LENGTH: 117
<212> TYPE: PRT
<213> ORGANISM: Artificial Sequence
<220> FEATURE:
<223> OTHER INFORMATION: BSO-1E3_2

<400> SEQUENCE: 11

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Asn Phe Asn Asp Tyr
                20                  25                  30

Tyr Ile Asn Trp Val Asn Gln Arg Pro Gly Gln Gly Leu Glu Trp Ile
            35                  40                  45

Gly Trp Ile Phe Pro Gly Arg Ile Ile Thr Tyr Tyr Asn Glu Lys Phe
        50                  55                  60

Lys Gly Lys Ala Thr Leu Thr Val Asp Thr Ser Ser Asn Thr Ala Tyr
65                  70                  75                  80

Met Leu Leu Ser Ser Leu Thr Ser Glu Asp Ser Ala Val Tyr Phe Cys
                85                  90                  95

Ala Arg Gly Val Gly Glu Gly Phe Asp Tyr Trp Gly Gln Gly Thr Thr
                100                 105                 110

Leu Thr Val Ser Ser
        115

<210> SEQ ID NO 12
<211> LENGTH: 113
```

```
<212> TYPE: PRT
<213> ORGANISM: Artificial Sequence
<220> FEATURE:
<223> OTHER INFORMATION: BSO-2E5

<400> SEQUENCE: 12

Gln Gly Gln Val Gln Gln Ser Gly Ala Glu Leu Val Lys Pro Gly Ala
1               5                   10                  15

Ser Val Lys Leu Ser Cys Lys Thr Ser Gly Phe Thr Phe Ser Thr Ser
                20                  25                  30

Tyr Ile Ser Trp Leu Lys Gln Lys Pro Arg Gln Ser Leu Glu Trp Ile
            35                  40                  45

Ala Trp Ile Tyr Ala Gly Thr Gly Ser Thr Ser Tyr Asn Gln Lys Phe
    50                  55                  60

Thr Gly Lys Ala Gln Leu Thr Val Asp Thr Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg His Trp Ala Tyr Trp Gly Gln Gly Thr Leu Val Thr Val Ser
            100                 105                 110

Ala

<210> SEQ ID NO 13
<211> LENGTH: 115
<212> TYPE: PRT
<213> ORGANISM: Artificial Sequence
<220> FEATURE:
<223> OTHER INFORMATION: BSO-4G3

<400> SEQUENCE: 13

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
                20                  25                  30

Ala Met Ser Trp Val Arg Gln Thr Pro Glu Lys Arg Leu Glu Trp Val
            35                  40                  45

Ala Ala Ile Lys Ser Asn Gly Gly Ser Thr Tyr Tyr Pro Asp Thr Val
    50                  55                  60

Lys Asp Arg Phe Thr Ile Ser Arg Asp Asn Ala Lys Asn Thr Leu Tyr
65                  70                  75                  80

Leu Gln Met Ser Ser Leu Arg Pro Glu Asp Thr Ala Leu Tyr Tyr Cys
                85                  90                  95

Ala His Gly Leu Leu Phe Ala His Trp Gly Gln Gly Thr Leu Val Thr
            100                 105                 110

Val Ser Ala
        115

<210> SEQ ID NO 14
<211> LENGTH: 122
<212> TYPE: PRT
<213> ORGANISM: Artificial Sequence
<220> FEATURE:
<223> OTHER INFORMATION: BSO-5E5

<400> SEQUENCE: 14

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asp
                20                  25                  30
```

```
Tyr Tyr Trp Asn Trp Ile Arg Gln Phe Pro Gly Asn Lys Leu Glu Trp
            35                  40                  45

Met Gly Tyr Ile Ser Tyr Asp Ser Ser Asn Tyr Asn Pro Ser Leu
 50                  55                  60

Lys Asn Arg Ile Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                 85                  90                  95

Ala Ser Val Gly Tyr Tyr Val Ser Asp Trp Tyr Phe Asp Val Trp
                100                 105                 110

Gly Thr Gly Thr Thr Val Thr Val Ser Ser
                115                 120
```

<210> SEQ ID NO 15
<211> LENGTH: 122
<212> TYPE: PRT
<213> ORGANISM: Artificial Sequence
<220> FEATURE:
<223> OTHER INFORMATION: BSO-7G9

<400> SEQUENCE: 15

```
Gln Val Gln Leu Gln Gln Pro Gly Ala Glu Leu Val Lys Pro Gly Ala
 1               5                  10                  15

Ser Val Arg Leu Ser Cys Lys Ala Ser Gly Tyr Thr Phe Thr Ser Tyr
                 20                  25                  30

Trp Met His Trp Val Lys Gln Arg Pro Gly Gln Gly Leu Glu Trp Ile
            35                  40                  45

Gly Met Ile His Pro Asn Ser Gly Tyr Thr Asn Tyr Asn Glu Lys Phe
 50                  55                  60

Lys Ile Lys Ala Thr Leu Thr Val Asp Lys Ser Ser Thr Ala His
 65                  70                  75                  80

Met Gln Leu Ser Ser Leu Thr Ser Glu Asp Ser Ala Val Tyr His Cys
                 85                  90                  95

Ala Arg Gly Gly Tyr Asp Gly Ser Tyr Gly Pro Trp Phe Ala Tyr Trp
                100                 105                 110

Gly Gln Gly Thr Leu Val Thr Val Ser Ala
                115                 120
```

<210> SEQ ID NO 16
<211> LENGTH: 117
<212> TYPE: PRT
<213> ORGANISM: Artificial Sequence
<220> FEATURE:
<223> OTHER INFORMATION: BSO-9A7

<400> SEQUENCE: 16

```
Gln Val Gln Leu Gln Gln Pro Gly Ala Glu Leu Val Arg Pro Gly Ser
 1               5                  10                  15

Ser Val Lys Leu Ser Cys Lys Ala Ser Gly Tyr Thr Phe Thr Asn Tyr
                 20                  25                  30

Trp Met His Trp Leu Lys Gln Arg Pro Val Gln Gly Leu Glu Trp Ile
            35                  40                  45

Gly Asn Ile Gly Pro Ser Asp Ser Lys Thr His Tyr Asn Gln Lys Phe
 50                  55                  60

Lys Asp Lys Ala Thr Leu Thr Val Asp Lys Ser Ser Ser Thr Ala Tyr
 65                  70                  75                  80

Met Gln Leu Asn Ser Leu Thr Ser Glu Asp Ser Ala Val Tyr Tyr Cys
```

```
                    85                  90                  95
Ala Arg Gly Asp Tyr Val Leu Phe Thr Tyr Trp Gly Gln Gly Thr Leu
                100                 105                 110
Val Thr Val Ser Ala
        115

<210> SEQ ID NO 17
<211> LENGTH: 121
<212> TYPE: PRT
<213> ORGANISM: Artificial Sequence
<220> FEATURE:
<223> OTHER INFORMATION: BSO-10D11

<400> SEQUENCE: 17

Gln Val Gln Leu Gln Gln Ser Gly Thr Glu Leu Val Arg Pro Gly Thr
1               5                   10                  15

Ser Val Lys Met Ser Cys Lys Ala Ala Gly Tyr Thr Phe Thr Asp Tyr
                20                  25                  30

Trp Ile Gly Trp Ile Lys Gln Arg Pro Gly His Gly Leu Glu Trp Ile
            35                  40                  45

Gly Asp Ile Phe Pro Gly Gly Asp Tyr Thr Lys Cys Ser Glu Arg Phe
        50                  55                  60

Lys Gly Lys Ala Lys Leu Thr Ala Asp Thr Ser Ser Thr Ala Tyr
65                  70                  75                  80

Met Gln Leu Ser Arg Leu Thr Ser Glu Asp Ser Ala Ile Tyr Tyr Cys
                85                  90                  95

Ala Arg Arg Ser Thr Thr Ile Arg Phe Gly Ala Met Asp Asn Trp Gly
                100                 105                 110

Gln Gly Thr Ser Val Thr Val Ser Ser
        115                 120

<210> SEQ ID NO 18
<211> LENGTH: 118
<212> TYPE: PRT
<213> ORGANISM: Artificial Sequence
<220> FEATURE:
<223> OTHER INFORMATION: BSO-13B10

<400> SEQUENCE: 18

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Phe
                20                  25                  30

Ser Ile Ser Trp Val Arg Gln Pro Pro Gly Lys Gly Leu Glu Trp Leu
            35                  40                  45

Gly Gly Ile Trp Thr Gly Gly Gly Thr Asn Tyr Asn Ser Ala Leu Lys
        50                  55                  60

Pro Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Asn Ser Asn Tyr Pro Ser Gly Phe Ala Tyr Trp Gly Gln Gly Thr
                100                 105                 110

Leu Val Thr Val Ser Ala
        115

<210> SEQ ID NO 19
<211> LENGTH: 11
```

```
<212> TYPE: PRT
<213> ORGANISM: Artificial Sequence
<220> FEATURE:
<223> OTHER INFORMATION: BSO-1E3_1 CDR1 Light Chain

<400> SEQUENCE: 19

Gln Ser Leu Val His Ser Asn Gly Asn Thr Tyr
1               5                   10

<210> SEQ ID NO 20
<211> LENGTH: 3
<212> TYPE: PRT
<213> ORGANISM: Artificial Sequence
<220> FEATURE:
<223> OTHER INFORMATION: BSO-1E3_1 CDR2 Light Chain

<400> SEQUENCE: 20

Lys Val Ser
1

<210> SEQ ID NO 21
<211> LENGTH: 9
<212> TYPE: PRT
<213> ORGANISM: Artificial Sequence
<220> FEATURE:
<223> OTHER INFORMATION: BSO-1E3_1 CDR3 Light Chain

<400> SEQUENCE: 21

Ser Gln Ser Thr His Val Pro Leu Thr
1               5

<210> SEQ ID NO 22
<211> LENGTH: 6
<212> TYPE: PRT
<213> ORGANISM: Artificial Sequence
<220> FEATURE:
<223> OTHER INFORMATION: BSO-1E3_2 CDR1 Light Chain

<400> SEQUENCE: 22

Glu Asn Val Gly Thr Tyr
1               5

<210> SEQ ID NO 23
<211> LENGTH: 3
<212> TYPE: PRT
<213> ORGANISM: Artificial Sequence
<220> FEATURE:
<223> OTHER INFORMATION: BSO-1E3_2 CDR2 Light Chain

<400> SEQUENCE: 23

Gly Ala Ser
1

<210> SEQ ID NO 24
<211> LENGTH: 9
<212> TYPE: PRT
<213> ORGANISM: Artificial Sequence
<220> FEATURE:
<223> OTHER INFORMATION: BSO-1E3_2 CDR3 Light Chain

<400> SEQUENCE: 24

Gly Gln Gly Tyr Ser Tyr Pro Tyr Thr
1               5

<210> SEQ ID NO 25
<211> LENGTH: 6
<212> TYPE: PRT
```

```
<213> ORGANISM: Artificial Sequence
<220> FEATURE:
<223> OTHER INFORMATION: BSO-2E5 CDR1 Light Chain

<400> SEQUENCE: 25

Gln Asp Ile Gly Ser Ser
1               5

<210> SEQ ID NO 26
<211> LENGTH: 3
<212> TYPE: PRT
<213> ORGANISM: Artificial Sequence
<220> FEATURE:
<223> OTHER INFORMATION: BSO-2E5 CDR2 Light Chain

<400> SEQUENCE: 26

Ala Thr Ala
1

<210> SEQ ID NO 27
<211> LENGTH: 9
<212> TYPE: PRT
<213> ORGANISM: Artificial Sequence
<220> FEATURE:
<223> OTHER INFORMATION: BSO-2E5 CDR3 Light Chain

<400> SEQUENCE: 27

Gln Gln Tyr Ala Ser Ser Pro Pro Thr
1               5

<210> SEQ ID NO 28
<211> LENGTH: 10
<212> TYPE: PRT
<213> ORGANISM: Artificial Sequence
<220> FEATURE:
<223> OTHER INFORMATION: BSO-4G3 CDR1 Light Chain

<400> SEQUENCE: 28

Glu Ser Val Glu Tyr Ser Gly Thr Thr Leu
1               5                   10

<210> SEQ ID NO 29
<211> LENGTH: 9
<212> TYPE: PRT
<213> ORGANISM: Artificial Sequence
<220> FEATURE:
<223> OTHER INFORMATION: BSO-4G3 CDR3 Light Chain

<400> SEQUENCE: 29

Gln Gln Ser Arg Lys Val Pro Tyr Thr
1               5

<210> SEQ ID NO 30
<211> LENGTH: 12
<212> TYPE: PRT
<213> ORGANISM: Artificial Sequence
<220> FEATURE:
<223> OTHER INFORMATION: BSO-5E5 CDR1 Light Chain

<400> SEQUENCE: 30

Gln Ser Leu Leu Tyr Gly Ser Asn Gln Lys Asn Tyr
1               5                   10

<210> SEQ ID NO 31
<211> LENGTH: 3
<212> TYPE: PRT
<213> ORGANISM: Artificial Sequence
```

```
<220> FEATURE:
<223> OTHER INFORMATION: BSO-5E5 CDR2 Light Chain

<400> SEQUENCE: 31

Trp Ala Ser
1

<210> SEQ ID NO 32
<211> LENGTH: 9
<212> TYPE: PRT
<213> ORGANISM: Artificial Sequence
<220> FEATURE:
<223> OTHER INFORMATION: BSO-5E5 CDR3 Light Chain

<400> SEQUENCE: 32

Gln Gln Tyr Tyr Ser Tyr Pro Arg Thr
1               5

<210> SEQ ID NO 33
<211> LENGTH: 6
<212> TYPE: PRT
<213> ORGANISM: Artificial Sequence
<220> FEATURE:
<223> OTHER INFORMATION: BSO-9A7 CDR1 Light Chain

<400> SEQUENCE: 33

Gln Ser Ile Ser Asn Asn
1               5

<210> SEQ ID NO 34
<211> LENGTH: 3
<212> TYPE: PRT
<213> ORGANISM: Artificial Sequence
<220> FEATURE:
<223> OTHER INFORMATION: BSO-9A7 CDR2 Light Chain

<400> SEQUENCE: 34

Tyr Ala Ser
1

<210> SEQ ID NO 35
<211> LENGTH: 9
<212> TYPE: PRT
<213> ORGANISM: Artificial Sequence
<220> FEATURE:
<223> OTHER INFORMATION: BSO-9A7 CDR3 Light Chain

<400> SEQUENCE: 35

Gln Gln Arg Tyr Ser Trp Pro Leu Thr
1               5

<210> SEQ ID NO 36
<211> LENGTH: 6
<212> TYPE: PRT
<213> ORGANISM: Artificial Sequence
<220> FEATURE:
<223> OTHER INFORMATION: BSO-10D11 CDR1 Light Chain

<400> SEQUENCE: 36

Gln Glu Ile Ser Ala Tyr
1               5

<210> SEQ ID NO 37
<211> LENGTH: 3
<212> TYPE: PRT
<213> ORGANISM: Artificial Sequence
<220> FEATURE:
```

<223> OTHER INFORMATION: BSO-10D11 CDR2 Light Chain

<400> SEQUENCE: 37

Ser Thr Ser
1

<210> SEQ ID NO 38
<211> LENGTH: 9
<212> TYPE: PRT
<213> ORGANISM: Artificial Sequence
<220> FEATURE:
<223> OTHER INFORMATION: BSO-10D11 CDR3 Light Chain

<400> SEQUENCE: 38

Leu Gln Tyr Ala Ser Ser Pro Leu Thr
1               5

<210> SEQ ID NO 39
<211> LENGTH: 6
<212> TYPE: PRT
<213> ORGANISM: Artificial Sequence
<220> FEATURE:
<223> OTHER INFORMATION: BSO-13B10 CDR1 Light Chain

<400> SEQUENCE: 39

Gln Asn Val Gly Ser Asn
1               5

<210> SEQ ID NO 40
<211> LENGTH: 3
<212> TYPE: PRT
<213> ORGANISM: Artificial Sequence
<220> FEATURE:
<223> OTHER INFORMATION: BSO-13B10 CDR2 Light Chain

<400> SEQUENCE: 40

Ser Ala Ser
1

<210> SEQ ID NO 41
<211> LENGTH: 9
<212> TYPE: PRT
<213> ORGANISM: Artificial Sequence
<220> FEATURE:
<223> OTHER INFORMATION: BSO-13B10 CDR3 Light Chain

<400> SEQUENCE: 41

Gln Gln Tyr Asn Ser Tyr Pro Leu Thr
1               5

<210> SEQ ID NO 42
<211> LENGTH: 8
<212> TYPE: PRT
<213> ORGANISM: Artificial Sequence
<220> FEATURE:
<223> OTHER INFORMATION: BSO-1E3_1 CDR1 Heavy Chain

<400> SEQUENCE: 42

Gly Phe Thr Phe Thr Asn Asn Trp
1               5

<210> SEQ ID NO 43
<211> LENGTH: 8
<212> TYPE: PRT
<213> ORGANISM: Artificial Sequence
<220> FEATURE:
<223> OTHER INFORMATION: BSO-1E3_1 CDR2 Heavy Chain

<400> SEQUENCE: 43

Ile His Pro Asn Ser Gly Ile Thr
1               5

<210> SEQ ID NO 44
<211> LENGTH: 12
<212> TYPE: PRT
<213> ORGANISM: Artificial Sequence
<220> FEATURE:
<223> OTHER INFORMATION: BSO-1E3_1 CDR3 Heavy Chain

<400> SEQUENCE: 44

Arg Ser Asp Gly Thr Tyr Glu Gly Tyr Phe Asp Tyr
1               5                   10

<210> SEQ ID NO 45
<211> LENGTH: 8
<212> TYPE: PRT
<213> ORGANISM: Artificial Sequence
<220> FEATURE:
<223> OTHER INFORMATION: BSO-1E3_2 CDR1 Heavy Chain

<400> SEQUENCE: 45

Gly Tyr Asn Phe Asn Asp Tyr Tyr
1               5

<210> SEQ ID NO 46
<211> LENGTH: 8
<212> TYPE: PRT
<213> ORGANISM: Artificial Sequence
<220> FEATURE:
<223> OTHER INFORMATION: BSO-1E3_2 CDR2 Heavy Chain

<400> SEQUENCE: 46

Ile Phe Pro Gly Arg Ile Ile Thr
1               5

<210> SEQ ID NO 47
<211> LENGTH: 10
<212> TYPE: PRT
<213> ORGANISM: Artificial Sequence
<220> FEATURE:
<223> OTHER INFORMATION: BSO-1E3_1 CDR3 Heavy Chain

<400> SEQUENCE: 47

Ala Arg Gly Val Gly Glu Gly Phe Asp Tyr
1               5                   10

<210> SEQ ID NO 48
<211> LENGTH: 8
<212> TYPE: PRT
<213> ORGANISM: Artificial Sequence
<220> FEATURE:
<223> OTHER INFORMATION: BSO 2E5 CDR1 Heavy Chain

<400> SEQUENCE: 48

Gly Phe Thr Phe Ser Thr Ser Tyr
1               5

<210> SEQ ID NO 49
<211> LENGTH: 8
<212> TYPE: PRT
<213> ORGANISM: Artificial Sequence
<220> FEATURE:
<223> OTHER INFORMATION: BSO-2E5 CDR2 Heavy Chain

<400> SEQUENCE: 49

Ile Tyr Ala Gly Thr Gly Ser Thr
1               5

<210> SEQ ID NO 50
<211> LENGTH: 6
<212> TYPE: PRT
<213> ORGANISM: Artificial Sequence
<220> FEATURE:
<223> OTHER INFORMATION: BSO-2E5 CDR3 Heavy Chain

<400> SEQUENCE: 50

Ala Arg His Trp Ala Tyr
1               5

<210> SEQ ID NO 51
<211> LENGTH: 8
<212> TYPE: PRT
<213> ORGANISM: Artificial Sequence
<220> FEATURE:
<223> OTHER INFORMATION: BSO-4G3 CDR1 Heavy Chain

<400> SEQUENCE: 51

Gly Phe Thr Phe Ser Thr Tyr Ala
1               5

<210> SEQ ID NO 52
<211> LENGTH: 8
<212> TYPE: PRT
<213> ORGANISM: Artificial Sequence
<220> FEATURE:
<223> OTHER INFORMATION: BSO-4G3 CDR2 Heavy Chain

<400> SEQUENCE: 52

Ile Lys Ser Asn Gly Gly Ser Thr
1               5

<210> SEQ ID NO 53
<211> LENGTH: 8
<212> TYPE: PRT
<213> ORGANISM: Artificial Sequence
<220> FEATURE:
<223> OTHER INFORMATION: BSO-4G3 CDR3 Heavy Chain

<400> SEQUENCE: 53

Ala His Gly Leu Leu Phe Ala His
1               5

<210> SEQ ID NO 54
<211> LENGTH: 9
<212> TYPE: PRT
<213> ORGANISM: Artificial Sequence
<220> FEATURE:
<223> OTHER INFORMATION: BSO-5E5 CDR1 Heavy Chain

<400> SEQUENCE: 54

Gly Tyr Ser Ile Thr Ser Asp Tyr Tyr
1               5

<210> SEQ ID NO 55
<211> LENGTH: 7
<212> TYPE: PRT
<213> ORGANISM: Artificial Sequence
<220> FEATURE:
<223> OTHER INFORMATION: BSO-5E5 CDR2 Heavy Chain

<400> SEQUENCE: 55

```
Ile Ser Tyr Asp Ser Ser Asn
1               5

<210> SEQ ID NO 56
<211> LENGTH: 15
<212> TYPE: PRT
<213> ORGANISM: Artificial Sequence
<220> FEATURE:
<223> OTHER INFORMATION: BSO-5E5 CDR3 Heavy Chain

<400> SEQUENCE: 56

Ala Ser Val Gly Tyr Tyr Val Ser Asp Trp Tyr Phe Asp Val
1               5                   10                  15

<210> SEQ ID NO 57
<211> LENGTH: 8
<212> TYPE: PRT
<213> ORGANISM: Artificial Sequence
<220> FEATURE:
<223> OTHER INFORMATION: BSO-7G9 CDR1 Heavy Chain

<400> SEQUENCE: 57

Gly Tyr Thr Phe Thr Ser Tyr Trp
1               5

<210> SEQ ID NO 58
<211> LENGTH: 8
<212> TYPE: PRT
<213> ORGANISM: Artificial Sequence
<220> FEATURE:
<223> OTHER INFORMATION: BSO-7G9 CDR2 Heavy Chain

<400> SEQUENCE: 58

Ile His Pro Asn Ser Gly Tyr Thr
1               5

<210> SEQ ID NO 59
<211> LENGTH: 15
<212> TYPE: PRT
<213> ORGANISM: Artificial Sequence
<220> FEATURE:
<223> OTHER INFORMATION: BSO-7G9 CDR3 Heavy Chain

<400> SEQUENCE: 59

Ala Arg Gly Gly Tyr Asp Gly Ser Tyr Gly Pro Trp Phe Ala Tyr
1               5                   10                  15

<210> SEQ ID NO 60
<211> LENGTH: 8
<212> TYPE: PRT
<213> ORGANISM: Artificial Sequence
<220> FEATURE:
<223> OTHER INFORMATION: BSO-9A7 CDR1 Heavy Chain

<400> SEQUENCE: 60

Gly Tyr Thr Phe Thr Asn Tyr Trp
1               5

<210> SEQ ID NO 61
<211> LENGTH: 8
<212> TYPE: PRT
<213> ORGANISM: Artificial Sequence
<220> FEATURE:
<223> OTHER INFORMATION: BSO-9A7 CDR2 Heavy Chain

<400> SEQUENCE: 61
```

Ile Gly Pro Ser Asp Ser Lys Thr
1               5

<210> SEQ ID NO 62
<211> LENGTH: 10
<212> TYPE: PRT
<213> ORGANISM: Artificial Sequence
<220> FEATURE:
<223> OTHER INFORMATION: BSO-9A7 CDR3 Heavy Chain

<400> SEQUENCE: 62

Ala Arg Gly Asp Tyr Val Leu Phe Thr Tyr
1               5                   10

<210> SEQ ID NO 63
<211> LENGTH: 8
<212> TYPE: PRT
<213> ORGANISM: Artificial Sequence
<220> FEATURE:
<223> OTHER INFORMATION: BSO-10D11 CDR1 Heavy Chain

<400> SEQUENCE: 63

Gly Tyr Thr Phe Thr Asp Tyr Trp
1               5

<210> SEQ ID NO 64
<211> LENGTH: 8
<212> TYPE: PRT
<213> ORGANISM: Artificial Sequence
<220> FEATURE:
<223> OTHER INFORMATION: BSO-10D11 CDR2 Heavy Chain

<400> SEQUENCE: 64

Ile Phe Pro Gly Gly Asp Tyr Thr
1               5

<210> SEQ ID NO 65
<211> LENGTH: 14
<212> TYPE: PRT
<213> ORGANISM: Artificial Sequence
<220> FEATURE:
<223> OTHER INFORMATION: BSO-10D11 CDR3 Heavy Chain

<400> SEQUENCE: 65

Ala Arg Arg Ser Thr Thr Ile Arg Phe Gly Ala Met Asp Asn
1               5                   10

<210> SEQ ID NO 66
<211> LENGTH: 8
<212> TYPE: PRT
<213> ORGANISM: Artificial Sequence
<220> FEATURE:
<223> OTHER INFORMATION: BSO-13B10 CDR1 Heavy Chain

<400> SEQUENCE: 66

Gly Phe Ser Leu Thr Ser Phe Ser
1               5

<210> SEQ ID NO 67
<211> LENGTH: 7
<212> TYPE: PRT
<213> ORGANISM: Artificial Sequence
<220> FEATURE:
<223> OTHER INFORMATION: BSO-13B10 CDR2 Heavy Chain

<400> SEQUENCE: 67

Ile Trp Thr Gly Gly Gly Thr

<210> SEQ ID NO 68
<211> LENGTH: 12
<212> TYPE: PRT
<213> ORGANISM: Artificial Sequence
<220> FEATURE:
<223> OTHER INFORMATION: BSO-13B10 CDR3 Heavy Chain

<400> SEQUENCE: 68

Ala Arg Asn Ser Asn Tyr Pro Ser Gly Phe Ala Tyr
1               5                   10

<210> SEQ ID NO 69
<211> LENGTH: 6
<212> TYPE: PRT
<213> ORGANISM: Artificial Sequence
<220> FEATURE:
<223> OTHER INFORMATION: BSO-9A7, BSO-10D11, BSO-13B10, BSO-2E5 LC-CDR1-
      1 Family consensus
<220> FEATURE:
<221> NAME/KEY: MISC_FEATURE
<222> LOCATION: (2)..(2)
<223> OTHER INFORMATION: X = N, S, E or D
<220> FEATURE:
<221> NAME/KEY: MISC_FEATURE
<222> LOCATION: (3)..(3)
<223> OTHER INFORMATION: X = I or V
<220> FEATURE:
<221> NAME/KEY: MISC_FEATURE
<222> LOCATION: (4)..(4)
<223> OTHER INFORMATION: X = G or S
<220> FEATURE:
<221> NAME/KEY: MISC_FEATURE
<222> LOCATION: (5)..(5)
<223> OTHER INFORMATION: X = S, N or A
<220> FEATURE:
<221> NAME/KEY: MISC_FEATURE
<222> LOCATION: (6)..(6)
<223> OTHER INFORMATION: X = N, Y or S

<400> SEQUENCE: 69

Gln Xaa Xaa Xaa Xaa Xaa
1               5

<210> SEQ ID NO 70
<211> LENGTH: 12
<212> TYPE: PRT
<213> ORGANISM: Artificial Sequence
<220> FEATURE:
<223> OTHER INFORMATION: BSO-5E5, BSO-1E3_1, BSO-7G9 LC-CDR1-2 Family
      Consensus
<220> FEATURE:
<221> NAME/KEY: MISC_FEATURE
<222> LOCATION: (4)..(4)
<223> OTHER INFORMATION: X = Absent or L
<220> FEATURE:
<221> NAME/KEY: MISC_FEATURE
<222> LOCATION: (5)..(5)
<223> OTHER INFORMATION: X = V or Y
<220> FEATURE:
<221> NAME/KEY: MISC_FEATURE
<222> LOCATION: (6)..(6)
<223> OTHER INFORMATION: X = H or G
<220> FEATURE:
<221> NAME/KEY: MISC_FEATURE
<222> LOCATION: (9)..(9)
<223> OTHER INFORMATION: X = G or Q
<220> FEATURE:
<221> NAME/KEY: MISC_FEATURE
<222> LOCATION: (10)..(10)
<223> OTHER INFORMATION: X = N or K
<220> FEATURE:
<221> NAME/KEY: MISC_FEATURE
<222> LOCATION: (11)..(11)
<223> OTHER INFORMATION: X = T or N

<400> SEQUENCE: 70

Gln Ser Leu Xaa Xaa Xaa Ser Asn Xaa Xaa Xaa Tyr
1               5                   10

<210> SEQ ID NO 71
<211> LENGTH: 3
<212> TYPE: PRT
<213> ORGANISM: Artificial Sequence
<220> FEATURE:
<223> OTHER INFORMATION: BSO-4G3, BSO-1E3_2, BSO-5E5, BSO-9A7, BSO-13B10
      LC-CDR2-1 Family Consensus
<220> FEATURE:
<221> NAME/KEY: MISC_FEATURE
<222> LOCATION: (1)..(1)
<223> OTHER INFORMATION: X = G, W, Y or S

<400> SEQUENCE: 71

Xaa Ala Ser
1

<210> SEQ ID NO 72
<211> LENGTH: 3
<212> TYPE: PRT
<213> ORGANISM: Artificial Sequence
<220> FEATURE:
<223> OTHER INFORMATION: BSO-10D11, BSO-1E3_1, BSO-7G9 LC-CDR2-2 Family
      Consensus
<220> FEATURE:
<221> NAME/KEY: MISC_FEATURE
<222> LOCATION: (1)..(1)
<223> OTHER INFORMATION: X = S or K
<220> FEATURE:
<221> NAME/KEY: MISC_FEATURE
<222> LOCATION: (2)..(2)
<223> OTHER INFORMATION: X = T or V

<400> SEQUENCE: 72

Xaa Xaa Ser
1

<210> SEQ ID NO 73
<211> LENGTH: 9
<212> TYPE: PRT
<213> ORGANISM: Artificial Sequence
<220> FEATURE:
<223> OTHER INFORMATION: BSO-1E3_1, BSO-7G9, BSO-1E3_2, BSO-2E5, BSO-
      4G3, BSO-5E5, BSO-9A7, BSO-10D11, BSo-13B10 LC-CDR3-1 Family
      Consensus
<220> FEATURE:
<221> NAME/KEY: MISC_FEATURE
<222> LOCATION: (1)..(1)
<223> OTHER INFORMATION: X = Q, S, G or L
<220> FEATURE:
<221> NAME/KEY: MISC_FEATURE
<222> LOCATION: (3)..(3)
<223> OTHER INFORMATION: X = Y, S, G or R
<220> FEATURE:
<221> NAME/KEY: MISC_FEATURE
<222> LOCATION: (4)..(4)
<223> OTHER INFORMATION: X = Y, A, T, N or R
<220> FEATURE:
<221> NAME/KEY: MISC_FEATURE
<222> LOCATION: (5)..(5)
<223> OTHER INFORMATION: X = S, H or K
<220> FEATURE:
<221> NAME/KEY: MISC_FEATURE
<222> LOCATION: (6)..(6)
<223> OTHER INFORMATION: X = V, Y, S or W
<220> FEATURE:
<221> NAME/KEY: MISC_FEATURE
<222> LOCATION: (8)..(8)
<223> OTHER INFORMATION: X = L, Y, R or P

<400> SEQUENCE: 73

Xaa Gln Xaa Xaa Xaa Xaa Pro Xaa Thr
1               5

<210> SEQ ID NO 74
<211> LENGTH: 8
<212> TYPE: PRT
<213> ORGANISM: Artificial Sequence
<220> FEATURE:
<223> OTHER INFORMATION: BSO-7G9, BSO-9A7, BSO-10D11 HC-CDR1-1 Family
      Consensus
<220> FEATURE:
<221> NAME/KEY: MISC_FEATURE
<222> LOCATION: (6)..(6)
<223> OTHER INFORMATION: X = S, N or D

<400> SEQUENCE: 74

Gly Tyr Thr Phe Thr Xaa Tyr Trp
1               5

<210> SEQ ID NO 75
<211> LENGTH: 8
<212> TYPE: PRT
<213> ORGANISM: Artificial Sequence
<220> FEATURE:
<223> OTHER INFORMATION: BSO-2E5, BSO-4G3, BSO-1E3_1 HC-CDR1-2 Family
      Consensus
<220> FEATURE:
<221> NAME/KEY: MISC_FEATURE
<222> LOCATION: (5)..(5)
<223> OTHER INFORMATION: X = S or T
<220> FEATURE:
<221> NAME/KEY: MISC_FEATURE
<222> LOCATION: (6)..(6)
<223> OTHER INFORMATION: X = T or N
<220> FEATURE:
<221> NAME/KEY: MISC_FEATURE
<222> LOCATION: (7)..(7)
<223> OTHER INFORMATION: X = S, Y or N
<220> FEATURE:
<221> NAME/KEY: MISC_FEATURE
<222> LOCATION: (8)..(8)
<223> OTHER INFORMATION: X = Y, A or W

<400> SEQUENCE: 75

Gly Phe Thr Phe Xaa Xaa Xaa Xaa
1               5

<210> SEQ ID NO 76
<211> LENGTH: 9
<212> TYPE: PRT
<213> ORGANISM: Artificial Sequence
<220> FEATURE:
<223> OTHER INFORMATION: BSO-5E5, BSO-1E3_2 HC-CDR1-3 Family Consensus
<220> FEATURE:
<221> NAME/KEY: MISC_FEATURE
<222> LOCATION: (3)..(3)
<223> OTHER INFORMATION: X = S or N
<220> FEATURE:
<221> NAME/KEY: MISC_FEATURE
<222> LOCATION: (4)..(4)
<223> OTHER INFORMATION: X = I or F
<220> FEATURE:
<221> NAME/KEY: MISC_FEATURE
<222> LOCATION: (5)..(5)
<223> OTHER INFORMATION: X = T or N
<220> FEATURE:
<221> NAME/KEY: MISC_FEATURE
<222> LOCATION: (6)..(6)
<223> OTHER INFORMATION: X = Absent or S

<400> SEQUENCE: 76

Gly Tyr Xaa Xaa Xaa Xaa Asp Tyr Tyr
1               5

<210> SEQ ID NO 77
<211> LENGTH: 8
<212> TYPE: PRT
<213> ORGANISM: Artificial Sequence
<220> FEATURE:
<223> OTHER INFORMATION: BSO-1E3_1, BSO-4G3, BSO-2E5, BSO-7G9 HC-CDR2-1
      Family Consensus
<220> FEATURE:
<221> NAME/KEY: MISC_FEATURE
<222> LOCATION: (2)..(2)
<223> OTHER INFORMATION: X = H, K or Y
<220> FEATURE:
<221> NAME/KEY: MISC_FEATURE
<222> LOCATION: (3)..(3)
<223> OTHER INFORMATION: X = P, S or A
<220> FEATURE:
<221> NAME/KEY: MISC_FEATURE
<222> LOCATION: (4)..(4)
<223> OTHER INFORMATION: X = N or G
<220> FEATURE:
<221> NAME/KEY: MISC_FEATURE
<222> LOCATION: (5)..(5)
<223> OTHER INFORMATION: X = S, G or T
<220> FEATURE:
<221> NAME/KEY: MISC_FEATURE
<222> LOCATION: (7)..(7)
<223> OTHER INFORMATION: X = S, I or Y

<400> SEQUENCE: 77

Ile Xaa Xaa Xaa Xaa Gly Xaa Thr
1               5

<210> SEQ ID NO 78
<211> LENGTH: 8
<212> TYPE: PRT
<213> ORGANISM: Artificial Sequence
<220> FEATURE:
<223> OTHER INFORMATION: BSO-1E3_2, BSO-10D11 HC-CDR2-2 Family Consensus
<220> FEATURE:
<221> NAME/KEY: MISC_FEATURE
<222> LOCATION: (5)..(5)
<223> OTHER INFORMATION: X = R or G
<220> FEATURE:
<221> NAME/KEY: MISC_FEATURE
<222> LOCATION: (6)..(6)
<223> OTHER INFORMATION: X = I or D
<220> FEATURE:
<221> NAME/KEY: MISC_FEATURE
<222> LOCATION: (7)..(7)
<223> OTHER INFORMATION: X = I or Y

<400> SEQUENCE: 78

Ile Phe Pro Gly Xaa Xaa Xaa Thr
1               5

<210> SEQ ID NO 79
<211> LENGTH: 15
<212> TYPE: PRT
<213> ORGANISM: Artificial Sequence
<220> FEATURE:
<223> OTHER INFORMATION: BSO-7G9, BSO-1E3_2, BSO-9A7 HC-CDR3-1 Family
      Consensus
<220> FEATURE:
<221> NAME/KEY: MISC_FEATURE
<222> LOCATION: (4)..(4)
<223> OTHER INFORMATION: X = Absent, D or G
<220> FEATURE:
<221> NAME/KEY: MISC_FEATURE

```
<222> LOCATION: (5)..(5)
<223> OTHER INFORMATION: X = Absent or Y
<220> FEATURE:
<221> NAME/KEY: MISC_FEATURE
<222> LOCATION: (6)..(6)
<223> OTHER INFORMATION: X = V or D
<220> FEATURE:
<221> NAME/KEY: MISC_FEATURE
<222> LOCATION: (7)..(7)
<223> OTHER INFORMATION: X = G or L
<220> FEATURE:
<221> NAME/KEY: MISC_FEATURE
<222> LOCATION: (8)..(8)
<223> OTHER INFORMATION: X = Absent, E or S
<220> FEATURE:
<221> NAME/KEY: MISC_FEATURE
<222> LOCATION: (9)..(9)
<223> OTHER INFORMATION: X = Absent or Y
<220> FEATURE:
<221> NAME/KEY: MISC_FEATURE
<222> LOCATION: (10)..(10)
<223> OTHER INFORMATION: X = Absent or G
<220> FEATURE:
<221> NAME/KEY: MISC_FEATURE
<222> LOCATION: (11)..(11)
<223> OTHER INFORMATION: X = Absent or P
<220> FEATURE:
<221> NAME/KEY: MISC_FEATURE
<222> LOCATION: (12)..(12)
<223> OTHER INFORMATION: X = Absent or W
<220> FEATURE:
<221> NAME/KEY: MISC_FEATURE
<222> LOCATION: (14)..(14)
<223> OTHER INFORMATION: X = D, T or A

<400> SEQUENCE: 79

Ala Arg Gly Xaa Xaa Xaa Xaa Xaa Xaa Xaa Xaa Phe Xaa Tyr
1               5                   10                  15

<210> SEQ ID NO 80
<211> LENGTH: 336
<212> TYPE: DNA
<213> ORGANISM: Artificial Sequence
<220> FEATURE:
<223> OTHER INFORMATION: BSO-1E3_1

<400> SEQUENCE: 80
gatgttgtga tgacccaaat tccactctcc ctgtctgtca gtatgaagtt ccaagcctcc      60
atctcttgca gatctagtca gagccttgta cacagtaatg aaacaccta tttacattgg     120 tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttccg    300
ctcacgttcg gtgctgggac caagctggag ctgaaa                              336

<210> SEQ ID NO 81
<211> LENGTH: 321
<212> TYPE: DNA
<213> ORGANISM: Artificial Sequence
<220> FEATURE:
<223> OTHER INFORMATION: BSO-1ES_2

<400> SEQUENCE: 81
aacattgtaa tgacccaatc tcccaaatcc atgtccatgt cagtaggaga gagggtcacc      60
ttgagctgca aggccagtga gaatgtgggt acttatgtat cctggtatca acagaaacca    120
gagcagtctc ctaaactgct gatatacggg gcatccaacc ggtacactgg ggtcccgat     180 cgcttcacag gcagtggatc tgcaacagat ttcactctga ccatcagcag tgtgcaggct    240
```

```
gaagaccttg cagattatca ctgtggacag ggttacagct atccgtacac gttcggaggg    300
gggaccaagc tggaaataaa a                                              321
```

<210> SEQ ID NO 82
<211> LENGTH: 321
<212> TYPE: DNA
<213> ORGANISM: Artificial Sequence
<220> FEATURE:
<223> OTHER INFORMATION: BSO-2E5

<400> SEQUENCE: 82

```
gacatccaga tgacccagtc tccatcctcc ttatctgcct ctctgggaga aagagtcagt     60
ctcacttgtc gggcaagtca ggacattggt agtagcttaa actggcttca gcaggaacca    120
gatggaacta ttaaacgcct gatctacgcc acagccagtt tagaatctgg tgtccccaaa    180
aggttcagtg gcagtaggtc tgggtcagac tattctctca ccatcagcag acttgagtct    240
gaagattttg tagactatta ctgtcaacaa tatgctagct cctcccac gttcggtgct      300 gggaccaagc tggagctgaa a                                              321
```

<210> SEQ ID NO 83
<211> LENGTH: 333
<212> TYPE: DNA
<213> ORGANISM: Artificial Sequence
<220> FEATURE:
<223> OTHER INFORMATION: BSO-4G3

<400> SEQUENCE: 83

```
gacattgtgc tcacccaatc tccagcttct ttggctgtgt ctctagggca gagtgtcacc     60
atctcctgca gagccagtga aagtgttgaa tattctggca ctactttaat gcagtggtac    120
caacagaaac caggacagcc acccaaactc ctcatctatg gtgcatccaa cgtagaatct    180
ggggtccctg ccaggtttag tggcagtggg tctgggacag acttcagcct caacatccat    240
cctgtggagg aggatgatat tgcaatgtat ttctgtcagc aaagtaggaa ggttccgtat    300
acgttcggat cggggaccaa gctggaaata aaa                                 333
```

<210> SEQ ID NO 84
<211> LENGTH: 339
<212> TYPE: DNA
<213> ORGANISM: Artificial Sequence
<220> FEATURE:
<223> OTHER INFORMATION: BSO-5E5

<400> SEQUENCE: 84

```
gacattgtga tgtcacagtc tccatcctcc ctacctgtgt cagttggaga gaatgttact     60
atgagctgca agtccagtca gagccttta tatggtagca tcaaaagaa ctacttggcc      120 tggtaccagc agaaaccagg gcagtctcct aaactgctga tttactgggc atccactagg    180
gaatctgggg tccctgatcg cttcacaggc agtggatctg gacagatttc actctcacc    240 atcagcagtg tgaaggctga agacctggca gtttatttct gtcagcaata ttatagctat    300
cctcggacgt tcggtggagg caccaagctg gaaatcaaa                           339
```

<210> SEQ ID NO 85
<211> LENGTH: 336
<212> TYPE: DNA
<213> ORGANISM: Artificial Sequence
<220> FEATURE:
<223> OTHER INFORMATION: BSO-7G9

<400> SEQUENCE: 85

```
gatgttgtga tgacccaaac tccactctcc ctgcctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaagtac acatgttccg   300
ctcacgttcg gtgctgggac caagctggag ctgaaa                             336
```

<210> SEQ ID NO 86
<211> LENGTH: 321
<212> TYPE: DNA
<213> ORGANISM: Artificial Sequence
<220> FEATURE:
<223> OTHER INFORMATION: BSO-9A7

<400> SEQUENCE: 86

```
gatattgtgc taactcagtc tccagccacc ctgtctatga ctccaggaga tagcgtcagt    60
ctttcctgca gggccagcca agtattagc aacaacctac actggtatca acaaaaatca   120
catgagtctc caaggcttct catcaagtat gcttcccagt ccatctctgg gatccctcc   180 aggttcagtg gcagtggatc ggggacagat tcactctca gtttcaacag tgtggagact   240
gaagattttg gagtgtattt ctgtcaacag agatacagct ggcctctcac gttcggtgct   300
gggaccaagc tggaaatgaa a                                             321
```

<210> SEQ ID NO 87
<211> LENGTH: 321
<212> TYPE: DNA
<213> ORGANISM: Artificial Sequence
<220> FEATURE:
<223> OTHER INFORMATION: BSO-10D11

<400> SEQUENCE: 87

```
gacatccaga tgacccagtc tccatcctcc ttatctgcct ctctgggaga aagagtcagt    60
ctcacttgtc gggcaagtca ggaaattagt gcttacttaa gctggcttca gcagaaacca   120
gatggaacta ttaaacgcct gatctacagc acatccactt tagattctgg tgtcccaaaa   180
aggttcagtg gcagtaggtc tgggtcagat tattctctca ccatcagcag ccttgagtct   240
gaagattttg cagactattt ctgtctccaa tatgctagtt ctccgctcac gttcggtgct   300
gggaccaagc tggagctgaa a                                             321
```

<210> SEQ ID NO 88
<211> LENGTH: 321
<212> TYPE: DNA
<213> ORGANISM: Artificial Sequence
<220> FEATURE:
<223> OTHER INFORMATION: BSO-13B10

<400> SEQUENCE: 88

```
gacattgtga tgacccagtc tcaaaaattc atgtccacat cagtaggaga cagggtcagc    60
gtcacctgca aggccagtca gaatgtgggt agtaatgtag cctggtatca acagaaagca   120
gggcaatctc ctaaagcact gatttactcg gcatcctacc ggtacagtgg agtccctgat   180
cgcttcacag gcagtggatc tgggacagat ttcactctca ccatcagcaa tgtgcagtct   240
gaagacttgg cagagtattt ctgtcagcaa tataacagct atccgctcac gttcggtgct   300
gggaccaagc tggagctgaa a                                             321
```

<210> SEQ ID NO 89
<211> LENGTH: 357
<212> TYPE: DNA
<213> ORGANISM: Artificial Sequence
<220> FEATURE:
<223> OTHER INFORMATION: BSO-1E3_1

<400> SEQUENCE: 89

```
caggtccaac tgcagcagcc tggggctgaa ctggtcacgc tggggcttc  agtgaagttg      60
tcctgcaagg cttctggctt cactttcacc aacaactgga tgcactgggt gaagcagaga     120
cctggacaag gccttgagtg gattggaatg attcatccta atagtgggat tactaacatc     180
aatgagaagt tcaagaacaa ggccacagtg actgtagaca aatcctccag cacagtctac     240
atacaactca gcagcctgac atctgaggac tctgcggtct attactgtcg ctccgatggt     300
acctacgagg gctactttga ctactggggc caaggcaccc tctcacagt  ctcctca       357
```

<210> SEQ ID NO 90
<211> LENGTH: 351
<212> TYPE: DNA
<213> ORGANISM: Artificial Sequence
<220> FEATURE:
<223> OTHER INFORMATION: BSO-1E3_2

<400> SEQUENCE: 90

```
caggtccaac tacagcagtc tggacctgaa ctggtgaagc ctggggcttc agtgaagata      60
tcctgcaagg cttctggcta caatttcaat gactactata aaactgggt  gaaccagagg     120
cctggacagg gacttgagtg gattggatgg attttttcctg gaagaattat tacttactac    180
aatgagaaat tcaagggcaa ggccacactt actgtagaca catcctccaa cacagcctac     240
atgttgctca gcagcctgac ctctgaggac tctgcggtct atttctgtgc aagagggta     300
ggagagggct ttgactactg gggccaaggc accactctca cagtctcctc a             351
```

<210> SEQ ID NO 91
<211> LENGTH: 339
<212> TYPE: DNA
<213> ORGANISM: Artificial Sequence
<220> FEATURE:
<223> OTHER INFORMATION: BSO-2E5

<400> SEQUENCE: 91

```
cagggtcagg tgcagcagtc tggagctgag ctggtgaagc ctggggcttc agtgaagctg      60
tcctgcaaga cttctggctt caccttcagt actagttata aagttggtt  gaagcagaag     120
cctcgacaga gtcttgagtg gattgcatgg atttatgctg aactggtag  tactagctat     180
aatcagaaat tcacaggcaa ggcccaactg actgtagaca catcctccag cacagcctac     240
atgcaactca gcagcctgac atctgaggac tctgccatct attactgtgc aagacactgg     300
gcttactggg gccaagggac tctggtcact gtctctgca                            339
```

<210> SEQ ID NO 92
<211> LENGTH: 345
<212> TYPE: DNA
<213> ORGANISM: Artificial Sequence
<220> FEATURE:
<223> OTHER INFORMATION: BSO-4G3

<400> SEQUENCE: 92

```
gaggtgcagc tggtggagtc tgggggaggc ttagtgaagc ctggcgggtc cctgaaactc      60
```

```
tcctgtgcag cctctggatt cactttcagt acctatgcca tgtcttgggt tcgccagact    120
ccagagaaga ggctggagtg ggtcgcagcc attaaaagta atggtggtag cacctactat    180
ccagacactg tgaaggaccg attcaccatt tccagagaca atgccaagaa caccctgtac    240
ctgcaaatga gcagtctgag gcctgaggac acagccttgt attactgtgc acatggtctc    300
ctgtttgctc actggggcca agggactctg gtcactgtct ctgca                    345
```

```
<210> SEQ ID NO 93
<211> LENGTH: 366
<212> TYPE: DNA
<213> ORGANISM: Artificial Sequence
<220> FEATURE:
<223> OTHER INFORMATION: BSO-5E5
<220> FEATURE:
<221> NAME/KEY: misc_feature
<222> LOCATION: (352)..(352)
<223> OTHER INFORMATION: n is a, c, g, or t

<400> SEQUENCE: 93
gatgtacagc ttcaggagtc aggacctggc ctcgtgaaac cttctcagtc tctgtctctc     60
acctgctctg tcactggcta ctccatcacc agtgattatt actggaactg gatccggcag    120
tttccaggaa acaaactgga atggatggc tacataagct acgatagtag caataactac     180
aacccatctc tcaaaaatcg aatctccatc actcgtgaca catctaagaa ccagtttttc    240
ctgaagttga attctgtgac tactgaggac acagccacat tattactgtgc ttcagtgggt   300 tattactacg ttagtgactg gtacttcgat gtctggggca cagggaccac gntcaccgtc    360
tcctca                                                               366
```

```
<210> SEQ ID NO 94
<211> LENGTH: 366
<212> TYPE: DNA
<213> ORGANISM: Artificial Sequence
<220> FEATURE:
<223> OTHER INFORMATION: BSO-7G9

<400> SEQUENCE: 94
caggtccaac tgcagcagcc tggggctgag ctggtaaagc ctggggcttc agtgaggttg     60
tcctgcaagg cttctggcta cactttcacc agctactgga tgcactgggt gaagcagagg    120
cctggacaag gccttgagtg gattggaatg attcatccta atagtggtta tactaattac    180
aatgagaagt tcaagatcaa ggccacactg actgtagaca aatcctccag cacagcccac    240
atgcaactca gcagcctgac atctgaggat tctgcggtct atcactgtgc aagagggggg    300
tatgatggtt cctacgggcc ctggtttgct tactggggcc aagggactct ggtcactgtc    360
tctgca                                                               366
```

```
<210> SEQ ID NO 95
<211> LENGTH: 351
<212> TYPE: DNA
<213> ORGANISM: Artificial Sequence
<220> FEATURE:
<223> OTHER INFORMATION: BSO-9A7

<400> SEQUENCE: 95
caggtccaac tgcagcagcc tggggctgag ctggtgaggc ctgggtcttc agtgaagctg     60
tcctgcaagg cttctggcta caccttcacc aactactgga tgcattggtt gaagcagagg    120
cctgtacaag gccttgagtg gattggtaac attggcccct ctgatagtaa aactcactac    180
aatcaaaaat tcaaggacaa ggccacattg actgtagaca aatcctccag cacagcctac    240
```

```
atgcaactca acagcctgac atctgaggac tctgcggtct attactgtgc aagggggtgat    300 tacgtcctgt ttacttactg gggccaaggg actctggtca ctgtctctgc a              351
```

<210> SEQ ID NO 96
<211> LENGTH: 363
<212> TYPE: DNA
<213> ORGANISM: Artificial Sequence
<220> FEATURE:
<223> OTHER INFORMATION: BSO-10D11

<400> SEQUENCE: 96

```
caggtccagc tgcagcagtc tggaactgag ctggtaaggc ctgggacttc agtgaagatg      60
tcctgcaagg ctgctggata caccttcact gactactgga taggttggat aaagcagagg    120
cctggacatg gccttgagtg gattggagat attttccctg aggtgattta ctactaagtgc   180 agtgagaggt tcaagggcaa ggccaaactg actgcagaca catcctccag cactgcctac    240
atgcagctca gcagactgac atctgaggac tctgccatct attactgtgc aagaaggagt    300
actacgatac gcttcgggggc tatggacaac tgggggtcaag aacctcagt caccgtctcc    360 tca                                                                  363
```

<210> SEQ ID NO 97
<211> LENGTH: 354
<212> TYPE: DNA
<213> ORGANISM: Artificial Sequence
<220> FEATURE:
<223> OTHER INFORMATION: BSO-13B10

<400> SEQUENCE: 97

```
caggtgcagc tgaaggagtc aggacctggc ctggtggcgc cctcacagag cctgtccatc      60
acatgcactg tctctggggtt ctcattaacc agcttttcta taagctgggt tcgccagcca   120
ccaggaaagg gtctggagtg gcttggagga atatggactg gtggaggcac aaattataat    180
tcagctctca aacccagact gagcatcagc aaagacaact ccaagagtca gttttctta    240 aaaatgaaca gtctgcaaac tgatgacaca gccaggtact actgtgccag aaatagtaac    300 taccccttccg ggtttgctta ctggggccaa gggactctgg tcactgtctc tgca           354
```

<210> SEQ ID NO 98
<211> LENGTH: 1575
<212> TYPE: DNA
<213> ORGANISM: Artificial Sequence
<220> FEATURE:
<223> OTHER INFORMATION: IL-11:IL-11Ralpha fusion protein

<400> SEQUENCE: 98

```
gaattcccgc cgccaccatg ggctggtcct gcatcatcct gtttctggtg gccacagcca     60
ccggcgtgca ctctccacag gcttgggggac ctccaggcgt gcagtatggc cagcctggca   120
gatccgtgaa gctgtgctgt cctggcgtga cagctggcga ccctgtgtcc tggttcagag   180
atggcgagcc caagctgctg cagggcccag attctggact gggccacgaa ctggtgctgg   240
cccaggccga ttctaccgac gagggcacct acatctgcca gaccctggat ggcgccctgg   300
gcggaacagt gacactgcag ctgggctacc ctccccgcca acctgtggtg tcttgtcagg   360
ccgccgacta cgaaaacttc agctgcacat ggtcccccag ccagatcagc ggcctgccca   420
ccagatacct gaccagctac cggaagaaaa ccgtgctggg cgccgacagc cagagaagaa   480
gcccttctac aggcccctgg ccctgccctc aggatcctct gggagctgcc agatgtgtgg   540
```

```
tgcacggcgc cgagttctgg tcccagtacc ggatcaacgt gaccgaagtg aaccccctgg      600
gcgcctccac aagactgctg gatgtgtccc tgcagagcat cctgcggccc gatcctccac      660
agggcctgag agtggaaagc gtgcccggct accccagaag gctgagagcc agctggacat      720
accccgcctc ttggccttgc cagccccact tcctgctgaa gtttcggctg cagtaccggc      780
cagcccagca ccctgcttgg agcacagtgg aacctgccgg cctggaagaa gtgatcacag      840
acgccgtggc cggactgcct catgctgtgc gggtgtccgc cagagacttt ctggatgccg      900
gcacctggtc tacctggtcc ccagaagcct ggggcacacc ttctactggc ggacctgctg      960
gacagtctgg cggaggcgga ggaagtggcg gaggatcagg gggaggatct gtgcctggac     1020
ctcctccagg acccctaga gtgtccccag atcctagggc cgagctggac tctaccgtgc     1080
tgctgaccag atccctgctg ccgacacaa gcagctggc tgcccagctg agagacaagt     1140
tccccgccga cggcgaccac aacctggata gcctgcctac cctggccatg tctgctggcg     1200
cactgggggc tctgcagctg cctggggtgc tgactagact gagagccgac ctgctgagct     1260
acctgcggca tgtgcagtgg ctgagaaggg ctggcggcag cagcctgaaa acctggaac     1320
ctgagctggg cacactgcag gccagactgg acagactgct gcgcagactg cagctgctga     1380
tgagcagact ggctctgccc cagcctcctc ctgaccctcc tgctcctcca ctggctcctc     1440
caagctctgc ttggggcgga attagagccg cccacgccat tctgggaggc ctgcacctga     1500
cactggattg gcagtgcgg ggcctgctgc tgctgaaaac cagactgcac caccaccatc     1560
accactgata agctt                                                      1575
```

<210> SEQ ID NO 99
<211> LENGTH: 516
<212> TYPE: PRT
<213> ORGANISM: Artificial Sequence
<220> FEATURE:
<223> OTHER INFORMATION: IL-11:IL-11Ralpha fusion protein

<400> SEQUENCE: 99

```
Met Gly Trp Ser Cys Ile Ile Leu Phe Leu Val Ala Thr Ala Thr Gly
1               5                   10                  15

Val His Ser Pro Gln Ala Trp Gly Pro Gly Val Gln Tyr Gly Gln
            20                  25                  30

Pro Gly Arg Ser Val Lys Leu Cys Cys Pro Gly Val Thr Ala Gly Asp
        35                  40                  45

Pro Val Ser Trp Phe Arg Asp Gly Glu Pro Lys Leu Leu Gln Gly Pro
    50                  55                  60

Asp Ser Gly Leu Gly His Glu Leu Val Leu Ala Gln Ala Asp Ser Thr
65                  70                  75                  80

Asp Glu Gly Thr Tyr Ile Cys Gln Thr Leu Asp Gly Ala Leu Gly Gly
                85                  90                  95

Thr Val Thr Leu Gln Leu Gly Tyr Pro Pro Ala Arg Pro Val Val Ser
            100                 105                 110

Cys Gln Ala Ala Asp Tyr Glu Asn Phe Ser Cys Thr Trp Ser Pro Ser
        115                 120                 125

Gln Ile Ser Gly Leu Pro Thr Arg Tyr Leu Thr Ser Tyr Arg Lys Lys
    130                 135                 140

Thr Val Leu Gly Ala Asp Ser Gln Arg Arg Ser Pro Ser Thr Gly Pro
145                 150                 155                 160

Trp Pro Cys Pro Gln Asp Pro Leu Gly Ala Ala Arg Cys Val Val His
                165                 170                 175
```

```
Gly Ala Glu Phe Trp Ser Gln Tyr Arg Ile Asn Val Thr Glu Val Asn
            180                 185                 190

Pro Leu Gly Ala Ser Thr Arg Leu Leu Asp Val Ser Leu Gln Ser Ile
        195                 200                 205

Leu Arg Pro Asp Pro Pro Gln Gly Leu Arg Val Glu Ser Val Pro Gly
    210                 215                 220

Tyr Pro Arg Arg Leu Arg Ala Ser Trp Thr Tyr Pro Ala Ser Trp Pro
225                 230                 235                 240

Cys Gln Pro His Phe Leu Leu Lys Phe Arg Leu Gln Tyr Arg Pro Ala
            245                 250                 255

Gln His Pro Ala Trp Ser Thr Val Glu Pro Ala Gly Leu Glu Glu Val
        260                 265                 270

Ile Thr Asp Ala Val Ala Gly Leu Pro His Ala Val Arg Val Ser Ala
    275                 280                 285

Arg Asp Phe Leu Asp Ala Gly Thr Trp Ser Thr Trp Ser Pro Glu Ala
290                 295                 300

Trp Gly Thr Pro Ser Thr Gly Pro Ala Gly Gln Ser Gly Gly Gly
305                 310                 315                 320

Gly Gly Ser Gly Gly Gly Ser Gly Gly Gly Ser Val Pro Gly Pro Pro
            325                 330                 335

Pro Gly Pro Pro Arg Val Ser Pro Asp Pro Arg Ala Glu Leu Asp Ser
        340                 345                 350

Thr Val Leu Leu Thr Arg Ser Leu Leu Ala Asp Thr Arg Gln Leu Ala
    355                 360                 365

Ala Gln Leu Arg Asp Lys Phe Pro Ala Asp Gly Asp His Asn Leu Asp
    370                 375                 380

Ser Leu Pro Thr Leu Ala Met Ser Ala Gly Ala Leu Gly Ala Leu Gln
385                 390                 395                 400

Leu Pro Gly Val Leu Thr Arg Leu Arg Ala Asp Leu Leu Ser Tyr Leu
            405                 410                 415

Arg His Val Gln Trp Leu Arg Arg Ala Gly Gly Ser Ser Leu Lys Thr
        420                 425                 430

Leu Glu Pro Glu Leu Gly Thr Leu Gln Ala Arg Leu Asp Arg Leu Leu
    435                 440                 445

Arg Arg Leu Gln Leu Leu Met Ser Arg Leu Ala Leu Pro Gln Pro Pro
450                 455                 460

Pro Asp Pro Pro Ala Pro Pro Leu Ala Pro Pro Ser Ser Ala Trp Gly
465                 470                 475                 480

Gly Ile Arg Ala Ala His Ala Ile Leu Gly Gly Leu His Leu Thr Leu
            485                 490                 495

Asp Trp Ala Val Arg Gly Leu Leu Leu Leu Lys Thr Arg Leu His His
        500                 505                 510

His His His His
        515
```